U nited States Patent [19]

Barnett et al.

[11] Patent Number: 5,011,938

[45] Date of Patent: Apr. 30, 1991

[54] 7-SUBSTITUTED BICYCLIC PYRAZOLIDINONES

[75] Inventors: Charles J. Barnett; Richard E. Holmes; Louis N. Jungheim, all of Indianapolis; Sandra K. Sigmund, Carmel; Robert J. Ternansky, Noblesville, all of Ind.

[73] Assignee: Eli Lilly and Company, Indianapolis, Ind.

[21] Appl. No.: 503,574

[22] Filed: Apr. 3, 1990

Related U.S. Application Data

[60] Division of Ser. No. 418,782, Oct. 2, 1989, Pat. No. 4,940,718, which is a continuation of Ser. No. 103,488, Sep. 30, 1987, abandoned, which is a continuation-in-part of Ser. No. 862,906, May 14, 1986, abandoned, which is a continuation-in-part of Ser. No. 729,021, Apr. 30, 1985, abandoned.

[51] Int. Cl.$^5$ ............................................. C07D 231/00
[52] U.S. Cl. ...................................... 548/359; 546/14; 546/199; 548/110; 548/111
[58] Field of Search .................. 546/14, 199; 548/110, 548/111, 359

[56] References Cited

U.S. PATENT DOCUMENTS 4,128,425 12/1978 Greenwald ......................... 548/359
4,512,924 4/1985 Atwood et al. .................. 260/243.3

FOREIGN PATENT DOCUMENTS 86303174.6 11/1986 European Pat. Off. .

Primary Examiner—Robert W. Ramsuer
Attorney, Agent, or Firm—John C. Demeter; Leroy Whitaker

[57] ABSTRACT

7-Substituted bicyclic pyrazolidinone compounds as antimicrobials and the corresponding intermediates, are discussed or provided. The use of the antimicrobial compounds in pharmaceutical compositions and in methods for treating bacterial infections is set forth.

10 Claims, No Drawings

7-SUBSTITUTED BICYCLIC PYRAZOLIDINONES

CROSS-REFERENCE TO RELATED APPLICATIONS

This application is a division of application Ser. No. 07/418,782, filed 10/2/89 which is a continuation of application Ser. No. 07/103,488, filed 9/30/87, now abandoned; which is a continuation-in-part of application Ser. No. 06/862,906, filed 5/14/86, now abandoned; which is a continuation-in-part of application Ser. No. 06/729,021, filed 4/30/85, now abandoned.

SUMMARY OF THE INVENTION

The invention is directed to antimicrobial compounds of the formula

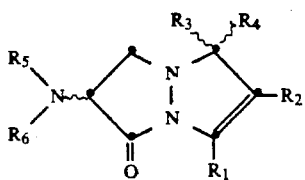

wherein $R_1$, $R_2$, $R_3$, $R_4$, $R_5$ and $R_6$ have the meanings defined below.

Further aspects of the invention include pharmaceutical compositions and methods of treatment of gram-positive and gram-negative bacterial infections comprising the use of the above antimicrobial compounds.

DETAILED DESCRIPTION OF THE INVENTION

I. The Invention in General; Definition of Terms

The present invention embraces compounds of the formula I:

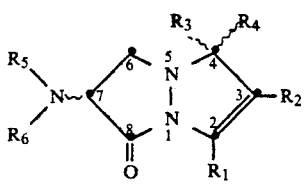

The ring system of the compound in Formula I is a 1,5-diazabicyclo[3.3.0]octa-2-ene ring, often referred to in this Specification as an "unsaturated bicyclic pyrazolidinone" or, more simply, a "bicyclic pyrazolidinone". The numbering system for the ring system is denoted in Formula I.

In the above Formula, the undulating lines connecting $R_3$ and $R_4$ to position 4 and the nitrogen atom to position 7 of the ring system indicate that the stereochemistry at positions 4 and 7 could be independently in the R or S configuration. Furthermore, the Formula represents compounds of the invention in various percentage mixtures of the possible enantiomeric and diastereomeric mixtures.

In the above Formula I:
either $R_1$ or $R_2$ is hydrogen, halo, $C_1$ to $C_6$ alkyl, $C_1$ to $C_6$ substituted alkyl, perfluoro $C_2$ to $C_4$ alkyl, $C_7$ to $C_{12}$ phenylalkyl, $C_7$ to $C_{12}$ substituted phenylalkyl, phenyl, substituted phenyl, a heterocyclic ring, nitro or cyano; a group of the formula $$-CX_3$$

wherein X is fluoro, chloro, bromo or iodo; a group of the formula

wherein Z is 0, 1 or 2 and $R_7$ is $C_1$ to $C_6$ alkyl, $C_1$ to $C_6$ substituted alkyl, $C_2$ to $C_7$ alkenyl, $C_2$ to $C_7$ alkynyl, phenyl, substituted phenyl, $C_7$ to $C_{12}$ phenylalkyl, $C_7$ to $C_{12}$ substituted phenylalkyl, a heterocyclic ring, or (disubstituted)-amino;
a group of the formula $$-COR_8$$

wherein $R_8$ is hydrogen, $C_1$ to $C_6$ alkyl, $C_1$ to $C_6$ substituted alkyl, perfluoro $C_2$ to $C_4$ alkyl, trihalomethyl, $C_7$ to $C_{12}$ phenylalkyl, $C_7$ to $C_{12}$ substituted phenylalkyl, phenyl, substituted phenyl, amino, (monosubstituted)amino or (disubstituted)amino;
a group of the formula

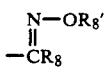

wherein $R_8$ is as defined above and $R_8'$ is hydrogen, $C_1$ to $C_6$ alkyl, $C_2$ to $C_7$ alkenyl, $C_2$ to $C_7$ alkynyl, phenyl, substituted phenyl, $C_7$ to $C_{12}$ phenylalkyl, or $C_7$ to $C_{12}$ substituted phenylalkyl;
a group of the formula $$-COOR_9$$

wherein $R_9$ is hydrogen, an organic or inorganic cation, $C_1$ to $C_6$ alkyl, $C_1$ to $C_6$ substituted alkyl, $C_7$ to $C_{12}$ phenylalkyl, $C_7$ to $C_{12}$ substituted phenylalkyl, phenyl, substituted phenyl, a carboxy-protecting group or a non-toxic, metabolically-labile ester-forming group; a group of the formula $$-PO_3(R_{10})_2$$

wherein $R_{10}$ is hydrogen, an organic or inorganic cation, $C_1$ to $C_6$ alkyl, $C_1$ to $C_6$ substituted alkyl, $C_7$ to $C_{12}$ phenylalkyl, $C_7$ to $C_{12}$ substituted phenylalkyl, phenyl, or substituted phenyl; a group of the formula

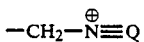

wherein

is a quaternary ammonium group;
a group of the formula $$-CH_2-S-\text{Heterocyclic ring;}$$

a group of the formula $$-OR_{11}$$

wherein $R_{11}$ is hydrogen, $C_1$ to $C_6$ alkyl, $C_1$ to $C_6$ substituted alkyl, $C_7$ to $C_{12}$ phenylalkyl, $C_7$ to $C_{12}$ substituted phenylalkyl, phenyl, substituted phenyl or $C_1$ to $C_7$ acyl; or a group of the formula

—$NR_{12}R_{13}$ wherein $R_{12}$ and $R_{13}$ are the same or different and are hydrogen, $C_1$ to $C_6$ alkyl, $C_1$ to $C_6$ substituted akyl, $C_7$ to $C_{12}$ phenylalkyl, $C_7$ to $C_{12}$ substituted phenylalkyl, phenyl, substituted phenyl, $C_1$ to $C_7$ acyl, or a group of the formula

wherein $R_q$ is $C_1$ to $C_6$ alkyl, $C_7$ to $C_{12}$ arylalkyl or phenyl;

or one of $R_{12}$ and $R_{13}$ is hydrogen and the other is a group of the formula

wherein Nu is (monosubstituted)amino, (disubstituted)amino, $C_1$ to $C_6$ alkylthio, $C_2$ to $C_7$ alkenylthio, $C_1$ to $C_6$ substituted alkylthio, phenylthio, substituted phenylthio, $C_7$ to $C_{12}$ phenylalkylthio, $C_7$ to $C_{12}$ substituted phenylalkylthio, or Nu is a $C_1$ to $C_6$ alkyl alcohol, $C_1$ to $C_6$ substituted alkyl alcohol, phenyl alcohol, substituted phenyl alcohol, $C_7$ to $C_{12}$ phenylalkyl alcohol, or $C_7$ to $C_{12}$ substituted phenyl alcohol;
and the other of $R_1$ or $R_2$ is a group of the formula

—$COOR_{14}$ wherein $R_{14}$ is hydrogen, an organic or inorganic cation, a carboxy-protecting group, or a non-toxic, metabolically-labile ester-forming group;

$R_3$ and $R_4$ are the same or different and are hydrogen, $C_1$ to $C_6$ alkyl, $C_1$ to $C_6$ substituted alkyl, $C_7$ to $C_{12}$ phenylalkyl, $C_7$ to $C_{12}$ substituted phenylalkyl, phenyl, substituted phenyl or a group of the formula

—$COOR_{15}$ wherein $R_{15}$ has the same definition as $R_9$;

$R_5$ and $R_6$ are: (1) each hydrogen; (2) taken together and form a phthalimido group; (3) different and are either hydrogen or an amino-protecting group; or (4) different and are either hydrogen or an acyl group derived from a $C_1$ to $C_{30}$ carboxylic acid;
or a pharmaceutically-acceptable salt thereof.

The protected amino, protected hydroxy and/or protected carboxy compounds represented by Formula I are intermediates to the compounds of Formula I where such groups are in the unprotected form. The unprotected form of the compounds of Formula I possess useful antimicrobial properties. The antimicrobial compounds of the invention can be used to inhibit the growth of microorganisms pathogenic to man and animals.

The compound represented by Formula (I) wherein $R_2$ or $R_1$ is the group —$OR_{11}$ and wherein $R_{11}$ is hydrogen, namely the 3- or 2-hydroxypyrazolidinones, exist predominantly in the tautomeric keto form as shown by the partial formulae below.

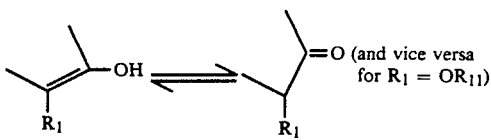

In one of its aspects this invention provides a method for treatment of gram-positive and gram-negative bacterial infections, which comprises administering to an infected host a therapeutically effective amount of a compound of Formula I, wherein:

$R_9$ is hydrogen, an organic or inorganic cation, $C_1$ to $C_6$ alkyl, $C_1$ to $C_6$ substituted alkyl, $C_7$ to $C_{12}$ arylakyl, $C_7$ to $C_{12}$ substituted arylalkyl, phenyl, substituted phenyl, or a non-toxic, metabolically-labile ester-forming group;

$R_{14}$ is hydrogen, an organic or inorganic cation or a non-toxic, metabolically-labile ester-forming group;

and either $R_5$ or $R_6$ is hydrogen and the other of $R_5$ or $R_6$ is an acyl group derived from a $C_1$ to $C_{30}$ carboxylic acid.

Yet another aspect of the invention is a pharmaceutical composition which comprises an antimicrobial compound useful in the above method and a suitable vehicle.

In the above Formula I, the term "$C_1$ to $C_6$ alkyl" denotes such radicals as methyl, ethyl, n-propyl, isopropyl, n-butyl, sec-butyl, tert-butyl, amyl, tert-amyl, hexyl and the like. The preferred "$C_1$ to $C_6$ alkyl" group is methyl.

The term "$C_2$ to $C_7$ alkenyl" denotes such radicals as vinyl, alyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl, as well as dienes and trienes of straight and branched chains. Allyl and 3-butene-1-yl are preferred embodiments.

The term "$C_2$ to $C_7$ alkynyl" denotes such radicals as ethynyl, propynyl, butynyl, pentynyl, hexynyl, heptynyl, as well as di- and tri-ynes.

The term "$C_1$ to $C_6$ substituted alkyl" denotes the above $C_1$ to $C_6$ alkyl groups that are substituted by one or two halogen, hydroxy, protected hydroxy, amino, protected amino, $C_1$ to $C_7$ acyloxy, nitro, carboxy, protected carboxy, carbamoyl, carbamoyloxy, cyano, methylsulfonylamino or $C_1$ to $C_4$ alkoxy groups. The substituted alkyl groups may be substituted once or twice with the same or with different substituents.

Examples of the above substituted alkyl groups include the cyanomethyl, nitromethyl, hydroxymethyl, trityloxymethyl, propionyloxymethyl, aminomethyl, carboxymethyl, allyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, 6-hydroxyhexyl, 2,4-dichloro(n-butyl), 2-amino(iso-propyl), 2-carbamoyloxyethyl chloroethyl, bromoethyl, fluoroethyl, iodoethyl, chloropropyl, bromopropyl, fluoropropyl, iodopropyl and the like. A preferred group of examples within the above "$C_1$ to $C_6$ substituted alkyl" group includes the substituted methyl and substituted ethyl groups, in other words, a methyl or ethyl group substituted by the same substituents as the "$C_1$ to $C_6$ substituted alkyl" group. Examples of the substituted methyl or substituted ethyl groups includes groups such as hydroxymethyl, protected hydroxymethyl, (e.g., tetrahydropyranyloxymethyl), acetoxymethyl, carbamoyloxymethyl, chloromethyl, bromomethyl, iodomethyl, chloroethyl, bromoethyl, fluoroethyl, iodoethyl, chloropropyl, bromopropyl, fluoropropyl and iodopropyl.

The term "$C_1$ to $C_4$ alkoxy" as used herein denotes groups such as methoxy, ethoxy, n-propoxy, isopropoxy, n-butoxy, t-butoxy and like groups. The term "$C_1$ to $C_7$ acyloxy" denotes herein groups such as formyloxy, acetoxy, propionyloxy, butyryloxy, pentanoyloxy, hexanoyloxy, heptanoyloxy, and the like. Similarly, the term "$C_1$ to $C_7$ acyl" encompasses groups such as formyl, acetyl, propionyl, butyryl, pentanoyl, hexanoyl, heptanoyl, benzoyl and the like.

Examples of the term "perfluoro $C_2$ to $C_4$ alkyl" include perfluoroethyl, perfluoro n-propyl, perfluoro iso-propyl, perfluoro n-butyl, perfluoro sec-butyl and the like.

The term "substituted phenyl" specifies a phenyl group substituted with one or two moieties chosen from the group consisting of halogen, hydroxy, protected hydroxy, cyano, nitro, $C_1$ to $C_6$ alkyl, $C_1$ to $C_4$ alkoxy, carboxy, protected carboxy, carboxymethyl, protected carboxymethyl, hydroxymethyl, protected hydroxymethyl, amino, protected amino, aminomethyl, protected aminomethyl, trifluoromethyl or N-(methylsulfonylamino).

Examples of the term "substituted phenyl" include a mono- or di(halo)phenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-propyl)phenyl and the like; a mono- or di(alkoxy)phenyl group, for example, 2,6-dimethoxyphenyl, 4-methoxyphenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such as 4-carboxyphenyl or 2,4-di(protected carboxy)phenyl; a mono- or di(hydroxymethyl)phenyl or (protected hydroxymethyl)phenyl such as 3-(protected hydroxymethyl)phenyl or 3,4-di(hydroxymethyl)phenyl; a mono- or di(aminomethyl)-phenyl or (protected aminomethyl)phenyl such as 2-(aminomethyl)phenyl or 2,4-(protected aminomethyl)-phenyl; or a mono- or di(N-(methylsulfonylamino))phenyl such as 3-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like. Preferred substituted phenyl groups include the 2- and 3-trifluoromethylphenyl, the 4-hydroxyphenyl, the 2-aminomethylphenyl and the 3-(N-(methylsulfonylamino))phenyl groups.

The terms "halo" and "halogen" refer to the fluoro, chloro, bromo or iodo groups.

The term "trihalomethyl" denotes trifluoromethyl, trichloromethyl, tribromomethyl or triiodomethyl.

The term "$C_7$ to $C_{12}$ phenylalkyl" denotes a $C_1$ to $C_6$ alkyl group substituted at any position by a phenyl ring. Examples of such a group include phenyl methyl (benzyl), 2-phenylethyl, 3-phenyl-(n-propyl), 4-phenylhexyl, 3-phenyl-(n-amyl), 3-phenyl-(sec-butyl), and the like. A preferred group is the benzyl group.

The term "$C_7$ to $C_{12}$ substituted phenylalkyl" denotes a $C_7$ to $C_{12}$ arylalkyl group substituted on the $C_1$ to $C_6$ alkyl portion with one or two groups chosen from halogen, hydroxy, protected hydroxy, amino, protected amino, $C_1$ to $C_7$ acyloxy, nitro, carboxy, protected carboxy, carbamoyl, carbamoyloxy, cyano, N-(methylsulfonylamino) or $C_1$ to $C_4$ alkoxy; and/or the phenyl group may be substituted with 1 or 2 groups chosen from halogen, hydroxy, protected hydroxy, nitro, $C_1$ to $C_6$ alkyl, $C_1$ to $C_4$ alkoxy, carboxy, protected carboxy, carboxymethyl, protected carboxymethyl, hydroxymethyl, protected hydroxymethyl, aminomethyl, protected aminomethyl, or a N-(methylsulfonylamino) group. As before, when either the $C_1$ to $C_6$ alkyl portion or the phenyl portion or both are disubstituted, the substituents can be the same or different.

Examples of the term "$C_7$ to $C_{12}$ substituted phenylalkyl" include groups such as 2-phenyl-1-chloroethyl, 2-(4-methoxyphenyl)ethyl, 2,6-dihydroxy-4-phenyl(n-hexyl), 5-cyano-3-methoxy-2-phenyl(n-pentyl), 3-(2,6-dimethylphenyl)n-propyl, 4-chloro-3-aminobenzyl, 6-(4-methoxyphenyl)-3-carboxy(n-hexyl), 5-(4-aminomethyl phenyl)-3-(aminomethyl)(n-pentyl), and the like.

As used above, the terms $C_1$ to $C_6$ alkyl alcohol, $C_1$ to $C_6$ substituted alkyl alcohol, phenyl alcohol (phenol), substituted phenyl alcohol, $C_7$ to $C_{12}$ phenyl alkyl alcohol, and $C_7$ to $C_{12}$ substituted phenylalkyl alcohol, all refer merely to the corresponding terms as defined above, each possessing one free hydroxy moiety.

The term "(monosubstituted)amino" refers to an amino group with one substituent chosen from the group consisting of phenyl, substituted phenyl, $C_1$ to $C_6$ alkyl, and $C_7$ to $C_{12}$ arylalkyl, wherein the latter three substituent terms are as defined above.

The term "(disubstituted)amino" refers to amino groups with two substituents chosen from the group consisting of phenyl, substituted phenyl, $C_1$ to $C_6$ alkyl, and $C_7$ to $C_{12}$ arylalkyl wherein the latter three substituent terms are as described above. The two substituents can be the same or different.

The term "organic or inorganic cation" refers to counter-ions for the carboxylate union of a carboxylate salt. The counter-ions are chosen from the alkali and alkaline earth metals, (such as lithium, sodium, potassium, barium and calcium); ammonium; and the organic cations (such as dibenzylammonium, benzylammonium, 2-hydroxyethylammonium, bis(2-hydroxyethyl)-ammonium, phenylethylbenzylammonium, dibenzylethylenediammonium, and like cations). Other cations encompassed by the above term include the protonated form of procaine, quinine and N-methylglucosamine, and the protonated forms of basic amino acids such as glycine, ornithine, histidine, phenylglycine, lysine and arginine. Furthermore, any zwitterionic form of the instant compounds formed by a carboxylic acid and an amino group is referred to by this term. For example, a cation for a carboxylate anion will exist when $R_2$ or $R_1$ is substituted with a (quaternary ammonium)methyl group. A preferred cation for the carboxylate anion is the sodium cation.

The term "pharmaceutically-acceptable salt" encompasses those salts that form with the carboxylate anions and includes salts formed with the organic and inorganic cations discussed above. Furthermore, the term includes salts that form by standard acid-base reactions with basic groups (such as amino groups) and organic or inorganic acids. Such acids include hydrochloric, sulfuric, phosphoric, acetic, succinic, citric, lactic, maleic, fumaric, palmitic, cholic, pamoic, mucic, D-glutamic, d-camphoric, glutaric, phthalic, tartaric, lauric, stearic, salicyclic, methanesulfonic, benzenesulfonic, sorbic, picric, benzoic, cinnamic, and like acids.

The compounds of Formula I may also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

Furthermore, the compounds of Formula I encompass the requisite negative counter-ion when either $R_1$ or $R_2$ is a (quaternary ammonium)methyl group. Such a counter-ion may be a carboxylate anion at $R_1$ or $R_2$, an anionic group bound at some other place to the bicyclic pyrazolidinone ring, or a separate external counter-ion such as a halo or acyloxy anion.

The term "carboxy-protecting group" as used in the specification refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4''-trimethoxytrityl, 2-phenylprop-2-yl, trimethylsilyl, t-butyldimethylsilyl, phenacyl, 2,2,2-trichloroethyl, $\beta$-(trimethylsilyl)ethyl, $\beta$-(di(n-butyl)methylsilyl)ethyl, p-toluenesulfonylethyl, 4-nitrobenzylsulfonylethyl, allyl, cinnamyl, 1-(trimethylsilylmethyl)-prop-1-en-3-yl, and like moieties. The species of carboxy-protecting group employed is not critical so long as the derivatized carboxylic acid is stable to the condition of subsequent reaction(s) on other positions of the bicyclic pyrazolidinone molecule and can be removed at the appropriate point without disrupting the remainder of the molecule. In particular, it is important not to subject the carboxy-protected bicyclic pyrazolidinone molecule to strong nucleophilic bases or reductive conditions employing highly activated metal catalysts such as Raney nickel. (Such harsh removal conditions are also to be avoided when removing amino-protecting groups and hydroxy-protecting groups, discussed below.) A preferred carboxylic acid protecting group is the allyl group. Similar carboxy-protecting groups used in the cephalosporin, penicillin and peptide arts can also be used to protect a carboxy group substituents of the bicyclic pyrazolidinones. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. A related term is "protected carboxy", which refers to a carboxy group substituted with one of the above carboxy-protecting groups.

The term "hydroxy-protecting group" refers to readily cleavable groups bonded to hydroxyl groups, such as the tetrahydropyranyl, 2-methoxyprop-2-yl, 1-ethoxyeth-1-yl, methoxymethyl, $\beta$-methoxyethoxymethyl, methylthiomethyl, t-butyl, t-amyl, trityl, 4-methoxytrityl, 4,4'-dimethoxytrityl, 4,4',4''-trimethoxytrityl, benzyl, allyl, trimethylsilyl, (t-butyl)dimethylsilyl and 2,2,2-trichloroethoxycarbonyl groups and the like.

The species of hydroxy-protecting groups is not critical so long as the derivatized hydroxyl group is stable to the conditions of subsequent reaction(s) and can be removed at the appropriate point without disrupting the remainder of the bicyclic pyrazolidinone molecule.

Further examples of hydroxy-protecting groups are described by C. B. Reese and E. Haslam, "Protective Groups in Organic Chemistry", J. G. W. McOmie, Ed., Plenum Press, New York, N.Y., 1973, Chapters 3 and 4, respectively, and T. W. Greene, "Protective Groups in Organic Synthesis", John Wiley and Sons, New York, N.Y., 1981, Chapters 2 and 3. Some preferred hydroxy-protecting groups are the trityl group and the tetrahydropyranyl group. The related term "protected hydroxy" denotes a hydroxy group bonded to one of the above hydroxy protecting groups.

The term "amino-protecting group" as used in the specification refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, 9-fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; the benzoylmethylsulfonyl group, the 2-(nitro)phenylsulfenyl group, the diphenylphosphine oxide group and like amino-protecting groups. The species of amino-protecting group employed is not critical so long as the derivatized amino group is stable to the condition of subsequent reaction(s) on other positions of the bicyclic pyrazolidinone molecule and can be removed at the appropriate point without disrupting the remainder of the molecule. Preferred amino-protecting groups are the allyloxycarbonyl, the t-butoxycarbonyl, and the trityl groups. Similar amino-protecting groups used in the cephalosporin, penicillin and peptide art are also embraced by the above terms. Further examples of groups referred to by the above terms are described by J. W. Barton, "Protective Groups In Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7. The related term "protected amino" defines an amino group substituted with an amino-protecting group discussed above.

The term "non-toxic, metabolically-labile ester-forming group" refers to those biologically active ester forms which induce increased blood levels and prolong the efficacy of the corresponding non-esterified forms of the compounds. Such ester groups include the lower alkoxymethyl groups, for example, methoxymethyl, ethoxymethyl, iso-propoxymethyl and the like; the $\alpha$-($C_1$ to $C_4$)alkoxyethyl groups, for example methoxyethyl, ethoxyethyl, propoxyethyl, iso-propoxyethyl, and the like; the 2-oxo-1,3-dioxolen-4-ylmethyl groups, such as 5-methyl-2-oxo-1,3-dioxolen-4-ylmethyl, 5-phenyl2-oxo-1,3-dioxolen-4-ylmethyl, and the like; the $C_1$ to $C_3$ alkylthiomethyl groups, for example methylthiomethyl, ethylthiomethyl, iso-propylthiomethyl, and the like; the acyloxymethyl groups, for example pivaloyloxymethyl, pivaloyloxyethyl, $\alpha$-acetoxymethyl, and the like; the ethoxycarbonyl-1-methyl group; the $\alpha$-acyloxy-$\alpha$-substituted methyl groups, for example $\alpha$-acetoxyethyl; the 3-phthalidyl or 5,6-dimethylphthalidyl groups; the 1-($C_1$ to $C_4$ alkyloxycarbonyloxy)ethyl groups such as the 1-(ethoxycarbonyloxy)ethyl group; and the 1-($C_1$ to $C_4$ alkylaminocarbonyloxy)ethyl groups such as the 1-(methylaminocarbonyloxy)ethyl group.

In the above Formula I, when $R_1$ or $R_2$ is a (quaternary ammonium)methyl group of the formula

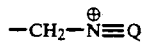

the quaternary ammonium group may be acyclic, cyclic, or a combination of the two, and may contain one or more additional hetero atoms selected from nitrogen, sulfur and oxygen. Examples of acyclic, cyclic and acyclic/cyclic quaternary ammonium groups are found in columns 7, 8, 9, 10 and 36 through 52 of Y. Narita et al., U.S. Pat. No. 4,486,586 ("'586 patent"), issued Dec. 4, 1984, herein incorporated by reference. In part of the incorporated columns (10 and 36 through 52) the quaternary ammonium groups are exemplified as substituents at the 3-position of a prop-1-en-1-yl group, which group is in turn bonded to the 3-position of a cephalosporin ring.

Preferred quaternary ammonium groups are:

(a) a pyridinium ring, which may be substituted once or twice with the following substituents: $C_1$ to $C_6$ alkyl, $C_1$ to $C_6$ substituted alkyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, halo, cyano, hydroxy, protected hydroxy, $C_1$ to $C_4$ alkoxy, $C_1$ to $C_4$ alkythio, $C_1$ to $C_4$ alkylsulfoxide, $C_1$ to $C_4$ alkylsulfonyl, phenyl, substituted phenyl, formyl, $C_2$ to $C_4$ alkanoyl, benzyl, benzoyl, amino, protected amino, $C_1$ to $C_4$ alkylamino, di($C_1$ to $C_4$ alkyl)amino, trifluoromethyl, carboxy, protected carboxy, $C_1$ to $C_4$ alkoxycarbonyl, aminomethyl, protected aminomethyl, carboxymethyl, protected carboxymethyl, carbamoyl, which may be substituted once or twice with a $C_1$ to $C_6$ alkyl group, an aminosulfonyl group (which may be substituted once or twice with a $C_1$ to $C_6$ alkyl group), a sulfonic acid, or a substituted or unsubstituted cycic $C_2$ to $C_{10}$ alkylene or heteroalkylene group;

(b) a quinolinium, isoquinolinium, (1 or 2)-pyradizinium, (1 or 3)-pyrimidinium, (1 or 4)-pyrazinium, thiazolinium, isothiazolinium, oxazolinium, isoxazolinium, (3 or 4)-1,3,4-thiadiazolinium, (2 or 4)-1,2,4-thiadiazolinium, (2 or 5)-1,2,5-thiadiazolinium, (3 or 4)-1,3,4-oxadiazolinium, (2 or 4)-1,2,4-oxadiazolinium, or a (2 or 5)-1,2,5-oxadiazolinium ring, or the mono or di-substituted derivatives thereof, wherein the substituents can be the same or different (and in the case of the quinolinium or isoquinolinium rings, on one or both rings) and are amino, protected amino, $C_1$ to $C_4$ alkylamino, di($C_1$ to $C_4$ alkyl)amino, hydroxy, protected hydroxy, $C_1$ to $C_4$ alkoxy, $C_1$ to $C_4$ alkylthio, $C_1$ to $C_4$ alkylsulfoxide, $C_1$ to $C_4$ alkylsulfonyl, cyano, halo, $C_1$ to $C_6$ alkyl, $C_1$ to $C_6$ substituted alkyl, trifluoromethyl, $C_3$ to $C_7$ cycloalkyl, $C_3$ to $C_7$ substituted cycloalkyl, $C_5$ to $C_7$ alkenyl, sulfonic acid, carboxy, protected carboxy, $C_1$ to $C_4$ alkoxycarbonyl, hydroxy-($C_1$ to $C_3$ alkyl), protected hydroxy-($C_1$ to $C_3$ alkyl), formyl, $C_2$ to $C_4$ alkanoyl, an aminosulfonyl group (which may be substituted once or twice with a $C_1$ to $C_6$ alkyl group), carbamoyl (which may be substituted once or twice with a $C_1$ to $C_6$ alkyl group), aminomethyl, protected aminomethyl, carboxymethyl, (protected carboxy)methyl, phenyl, substituted phenyl, benzoyl or benzyl; or (c) a group of the formula

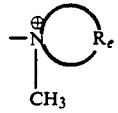

wherein $R_e$ together with the nitrogen atom to which it is attached form a saturated or partially unsaturated 4 to 10 membered heterocyclic ring which may contain one or more further heteroatoms selected from oxygen, nitrogen or sulfur and wherein the substituent may be $C_1$ to $C_6$ alkyl, $C_1$ to $C_6$ substituted alkyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, halo, cyano, hydroxy, protected hydroxy, $C_1$ to $C_4$ alkoxy, $C_1$ to $C_4$ alkylthio, $C_1$ to $C_4$ alkylsulfoxide, $C_1$ to $C_4$ alkylsulfonyl, phenyl, substituted phenyl, formyl, $C_2$ to $C_4$ alkanoyl, benzyl, benzoyl, amino, protected amino, $C_1$ to $C_4$ alkylamino, di($C_1$ to $C_4$ alkyl)amino, trifluoromethyl, carboxy, protected carboxy, $C_1$ to $C_4$ alkoxycarbonyl, aminomethyl, protected aminomethyl, carboxymethyl, protected carboxymethyl, carbamoyl (which may be substituted once or twice with a $C_1$ to $C_6$ alkyl group), aminosulfonyl (which may be substituted once or twice with a $C_1$ to $C_6$ alkyl group), or sulfonic acid, or the benzo-fused analogs of the substituted or unsubstituted, saturated or partially unsaturated ring.

Certain of the terms describing the substituents for the above preferred quaternary ammonium groups have already been defined. Specifically, the terms "$C_1$ to $C_6$ alkyl", "$C_1$ to $C_6$ substituted alkyl", "substituted phenyl", "halo", "$C_1$ to $C_4$ alkoxy", "protected carboxy", "protected hydroxy", and "protected amino" are as defined above for Formula I.

The substituent term "$C_3$ to $C_7$ cycloalkyl" includes the cyclopropyl, cyclobutyl, cyclopentyl, cyclohexyl or cycloheptyl rings. The substituent term "$C_3$ to $C_7$ substituted cycloalkyl" indicates the above cycloalkyl rings substituted by a halogen, hydroxy, protected hydroxy, $C_1$ to $C_6$ alkyl, $C_1$ to $C_4$ alkoxy, carboxy, protected carboxy, amino, or protected amino. The substituent term "$C_5$ to $C_7$ cycloalkenyl" indicates a 1, 2, or 3-cyclopentenyl ring, a 1, 2, 3 or 4-cyclohexenyl ring or a 1, 2, 3, 4 or 5-cycloheptenyl ring, while the term "substituted $C_5$ to $C_7$ cycloalkenyl" denotes the above $C_5$ to $C_7$ cycloalkenyl rings substituted by a $C_1$ to $C_6$ alkyl radical.

The substituent term "$C_1$ to $C_4$ alkylamino" refers to methylamino, ethylamino, n-propylamino, n-butylamino, iso-propylamino and the like. The substituent term "di($C_1$ to $C_4$ alkyl)amino" denotes groups such as dimethylamino, diethylamino, methylethylamino, di(n-butyl)amino, di(n-propyl)amino and the like. Examples of the term "$C_2$ to $C_4$ alkanoyl group" are acetyl, n-propionyl, n-butyryl and the like. The substituent term "$C_1$ to $C_4$ alkoxycarbonyl" refers to groups such as methoxycarbonyl, ethoxycarbonyl, n-propoxycarbonyl, iso-propoxycarbonyl, n-butoxycarbonyl, t-butoxycarbonyl and the like.

The substituent term "$C_1$ to $C_4$ alkylthio" refers to sulfide groups such as methylthio, ethylthio, n-propylthio, iso-propylthio, n-butylthio, t-butylthio and like groups. The substituent term "$C_1$ to $C_4$ alkylsulfoxide" indicates sulfoxide groups such as methylsulfoxide, ethylsulfoxide, n-propylsulfoxide, isopropylsulfoxide, n-butylsulfoxide, sec-butylsulfoxide, and the like.

The term "$C_1$ to $C_4$ alkylsulfonyl" encompasses groups such as methylsulfonyl, ethylsulfonyl, n-propylsulfonyl, iso-propylsulfonyl, n-butylsulfonyl, t-butylsulfonyl, and the like.

The term "hydroxy ($C_1$ to $C_3$ alkyl)" refers to $C_1$ to $C_3$ alkyl groups substituted at any position by a hydroxy group, such as hydroxymethyl, 2-hydroxyethyl, 1-hydroxyethyl, 3-hydroxy(n-propyl), 2-hydroxy(n-propyl), 1-hydroxy(n-propyl), 1-hydroxy(iso-propyl) and the like. Similarly, the term "protected hydroxy-($C_1$ to $C_3$ alkyl)" refers to $C_1$ to $C_3$ alkyl groups substituted at any position by a protected hydroxy group. Examples of such groups are exemplified when, in the above hydroxy ($C_1$ to $C_3$ alkyl groups), the term "hydroxy" is read as "protected hydroxy".

The substituent term "substituted or unsubstituted cyclic $C_2$ to $C_{10}$ alkylene or heteroalkylene group" defines such a cyclic group bonded ("fused") to the b or c face of the pyridinium ring. The cyclic group may be saturated or contain one or two double bonds. Furthermore, the cyclic group may have one or two alkylene groups replaced by one or two oxygen, nitrogen or sulfur atoms.

The cyclic alkylene or heteroalkylene group may be substituted once or twice by substituents selected from the group consisting of the following moieties: hydroxy, protected hydroxy, carboxy, protected carboxy, $C_1$ to $C_4$ alkoxycarbonyl, formyl, $C_2$ to $C_4$ alkanoyl, $C_1$ to $C_6$ alkyl, carbamoyl, $C_1$ to $C_4$ alkoxy, $C_1$ to $C_4$ alkylthio, $C_1$ to $C_4$ alkylsulfoxide, $C_1$ to $C_4$ alkylsulfonyl, halo, amino, protected amino, hydroxymethyl or a protected hydroxymethyl.

The cyclic alkylene or heteroalkylene group fused onto the pyridinium radical can contain two to ten ring members, but it preferably contains three to five members. Examples of such saturated cyclic groups are when the pyridinium group is fused to a cyclopentano, cyclohexano or cycloheptano ring. When the cyclic groups are unsaturated, examples occur when the pyridinium ring is fused to a cyclopenteno, cyclohexeno or cyclohepteno ring. Examples of fused cyclic groups which each contain one oxygen atom and one or two double bonds are when the pyridinium ring is fused to a furo, pyrano, dihydrofuro or dihydropyrano ring, and examples of cyclic groups which each have one sulfur atom and contain one or two double bonds are when the pyridinium ring is fused to a thieno, thiopyrano, dihydrothieno or dihydrothiopyrano ring. Examples of cyclic groups which contain two heteroatoms selected from sulfur and nitrogen and one or two double bonds are when the pyridinium ring is fused to a thiazolo, isothiazolo, dihydrothiazolo or dihydroisothiazolo ring. Examples of cyclic groups which contain two heteroatoms selected from oxygen and nitrogen and one or two double bonds are when the pyridinium ring is fused to an oxazolo, isoxazolo, dihydrooxazolo or dihydroisoxazolo ring. Examples of cyclic groups which contain two nitrogen heteroatoms and one or two double bonds occur when the pyridinium ring is fused to a pyrazolo, imidazolo, dihydropyrazolo or dihydroimidazolo ring.

The b or the c side of the pyridinium group can be fused to a cyclic group with three ring members. In the case of such a cyclic group containing only one heteroatom, the position of the heteroatom can result in a [2,3], [3,2] or [3,4] fusion with the pyridinium group. When the three-membered cyclic group contains two heteroatoms, the position of the heteroatoms can be such that they result in a [4,5], [5,4], [3,4] or [4,3] fusion with the pyridinium group.

Similarly, the b or c side of the pyridinium group can be fused to a cyclic group with four ring members. Such a cyclic group containing only one heteroatom can result in a [3,2], [2,3], [3,4] or [4,3] fusion with the pyridinium group. The four membered cyclic group with two heteroatoms can result in a [4,5], [5,4], [3,4], [4,3], [5,6] or [6,5] fusion to the pyridinium group.

Examples of the bicyclic pyridinium-containing ring systems that can result when the pyridinium ring is substituted with a $C_2$ to $C_{10}$ alkylene or substituted alkylene group includes groups of the formula:

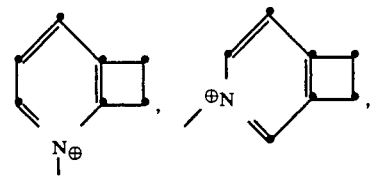

and groups such as: 5H-1-pyrindinium, 7H-1-pyrindinium, 1H-2-pyrindinium, 5H-2-pyrindinium, thieno[3,2-b]pyridinium, thieno[3,2-c]pyridinium, thieno[2,3-c]pyridinium, thieno[2,3-b]pyridinium, thieno[3,4-c]pyridinium, furo[3,2-b]pyridinium, furo[3,2-c]pyridinium, furo-[2,3-b]pyridinium, furo[3,4-c]pyridinium, furo[3,4-b]-pyridinium, oxazolo[4,5-b]pyridinium, oxazolo[5,4-b[-pyridinium, oxazolo4,5-c]pyridinium, oxazolo[5,4-c]-pyridinium, thiazolo[4,5-b]pyridinium, thiazolo[5,4-b]pyridinium, thiazolo[4,5-c]pyridinium, thiazolo-[5,4-c]pyridinium, 5,6,7,8-tetrahydroquinolinium, 5,6-dihydroquinolinium, 7,8-dihydroquinolinium, 5,6,7,8-tetrahydroisoquinolinium, 5,6-dihydroisoquinolinium, 7,8-dihydroisoquinolinium, 1,5- naphthyridinium, 1,6-naphthyridinium, 1,7-naphthyridinium, 1,8-napthyridinium, 2,6-napthyridinium, 2,7-napthyridinium, 2H-pyrano-[3,2-c]pyridinium, 5H-pyrano4,3-b]pyridinium, 1H-pyrano[3,4-b]pyridinium, 2H-pyrano[2,3-b]pyridinium, 1H-pyrano[4,3-c]pyridinium, 1H-pyrano[3,4-c]pyridinium, 5H-thiopyrano[4,3-b]pyridinium, 4H-thiopyrano[2,3-b]-pyridinium, pyrido[3,2-d]pyrimidin-5-yl, pyrido[4,3-d]-pyrimidin-6-yl, pyrido[3,4-d]pyrimidin-7-yl, pyrido[2,3-d]pyrimidin-8-yl, pyrido[2,3-b]pyrazin-5-yl, pyrido[3,4-b]pyrazin-6-yl, pyrido[2,3-d]pyrazin-1-yl, pyrido[3,4-d]pyridazin-6-yl, 4H-pyrido[2,3-d][1,3]-oxazin-8-yl, 2H-pyrido[4,3-b][1,4]oxazin-6-yl, 5H-pyrido[2,3-d][1,2]oxazin-1-yl, 8H-pyrido[3,2-d][1,2]-oxazin-1-yl, 1H-pyrido[2,3-b][1,4]thiazin-5-yl, 3H-pyrido[2,3-b][1,4]thiazin-5 yl, 2H-pyrido[4,3-b][1,4]Thiazin-6-yl, 6,7-dihydro-5H-1-pyrindinium, 6,7-dihydro-5H-2-pyrindinium, 2,3-dihydro-furo[3,2-b]-pyridinium, 2,3-dihydro-furo[2,3-b]-pyridinium, 2,3-dihydro-thieno[2,3-b]pyridinium, 2,3-dihydro-thieno-[3,2-b]pyridinium, 2,3-dihydro-thieno[2,3-c]pyridinium, the substituted derivatives thereof, and the like.

A preferred quaternary ammonium group is a substituted or unsubstituted pyridinium ring.

The substituted pyridinium ring can be substituted once or twice with the above-listed substituents. When the ring is substituted twice, the substituents may be the same or different.

Examples of a group of more particularly preferred substituents on the pyridinium ring are: 3-methyl, 4-methyl, 3-ethyl, 2-ethyl, 4-ethyl, 4-propyl, 3-(iso-propyl), 2-methyl, 2-(pent-3-yl), 4-(t-butyl), 2,4-dimethyl, 3,4-dimethyl, 3,5-dimethyl, 2,5-dimethyl, 3-ethyl-4-methyl, 3-methyl-4-ethyl, 3-ethyl-6-methyl, 2-benzyl, 4-benzyl, 4-phenyl, 3-phenyl, 2-(hydroxymethyl), 3-(hydroxymethyl), 4-(hydroxymethyl), 3-hydroxy, 2-(1-hydroxyeth-1-yl), 3-(1-hydroxyeth-1-yl), 4-(1-hydroxyeth-1-yl), 3-(2-hydroxyprop-2-yl), 4-(2-hydroxy- prop-2-yl), 3-(3-hydroxyprop-1-yl), 3-acetyl, 4-acetyl, 3-benzoyl, 4-benzoyl, 3-methoxy, 4-methoxy, 4-ethoxy, 3-ethoxy, 4-methoxymethyl, 2-methylthio, 4-methylthiomethyl, 3-fluoro, 4-(N-acetamido), 3-ethoxycarbonyl, 4-ethoxycarbonyl, 3-methoxycarbonyl, 3-ethoxycarbonyl, 3-carbamoyl, 4-(N-ethylcarbamoyl), 3-(N,N'-diethylcarbamoyl), 4-cyano, 4-(aminosulfonyl), 4-(potassium eth-1-yl-2-sulfonate), 4-cyclopentyl, 4-(p-chlorobenzyl), 3-alkyl, 5-hydroxy-2-methyl, 3-hydroxy-4-methyl, 4-(1-hydroxypropyl), 3-(1-hydroxypropyl), 3-(2-hydroxy-2-methylpropyl), 2-(hydroxymethyl)-4-methyl, 2-(1,3-di hydroxyprop-2-yl), 4-(2-hydroxypropyl), 4-(3-hydroxypropyl), 3-cyclohexyl, 4-cyclohexyl, 3-cyclopentyl, 4-(cyclohex-1-enyl), 3-(cyclohex-1-enyl), 4-(cyclopent-1-enyl), 3-(cyclopent-1-enyl), 3-(cyclohept-1-enyl), 3-(4-methylcyclohex-1-enyl), 3-(1-hydroxycyclohexyl), 3-(1-hydroxycyclopentyl), 4-(1-hydroxycyclohexyl), 4-(1-hydroxycyclopentyl), 3-(1-hydroxycycloheptyl); 4-methoxy-3-methyl, 3-methoxy-4-methyl, 3-(iso-propoxy), 3-propoxy, 2-(1-methoxyeth-2-yl), 4-(2-ethoxyeth-1-yl), 2-(2-ethoxyeth-1-yl), 4-(acetylmethyl), 4-(3-hydroxypropyl), 3-(3-chloropropyl), 3-trifluoromethyl, 3-bromo-4-methyl, 3-(cyanomethyl), 4-(1-hydroxy-1-(sulfonic acid)methyl), 4-(cyclopent-2-enyl), 4-(cyclopropyl), and the various protected hydroxy analogs thereof; and a pyridinium ring substituted with the above-described $C_2$ to $C_{10}$ alkylene ring, resulting in the following bicyclic ring examples: 5,6-dihydro-5H-1-pyrindinium, 5,6,7,8-tetrahydroquinolinium, 5,6,7,8-tetrahydroisoquinolinium, 3-methyl-5,6,7,8-tetrahydroquinolinium, 6,7-dihydro-5H-2-pyrindinium, 7-hydroxy-5,6-dihydro5H-1-pyrindinium, 5,6,8,9-tetrahydro-7H-cyclohepta[b]-pyridinium, 2,3-dihydro-furo[2,3-b]pyridinium, 3-hydroxy-2,3-dihydro-furo[2,3-b]pyridinium, 3-keto-2,3-dihydro-furo[2,3-b]pyridinium, thieno[3,2-b]-pyridinium, thieno[3,2-c]pyridinium, furo[3,2-c]-pyridinium, 2-methylthiazolo[4,5-c]pyridinium, and 2-methylthiazolo[5,4-c]pyridinium.

A preferred group of substituted pyridinium rings are 4-carbamoylpyridinium, 4-(eth-2-yl-1-sulfonic acid)-pyridinium, 4-(sodium eth-2-yl-1-sulfonate)pyridinium, 5,6-dihydro-5H-1-pyrindinium, thieno[3,2-b]-pyrindinium, thieno[3,2-c]pyridinium, furo[3,2-c]-pyridinium, 2-methylthieno[4,5-c]pyridinium and 2-methylthieno[5,4-c]pyridinium.

A more preferred group of pyridinium rings is pyridinium, 4-carbamoylpyridinium, 4-(sodium eth-1yl-2-sulfonate)pyridinium, 5,6-dihydro-5H-1-pyrindinium, 2-methylthiazolo[4,5-c]pyridinium and 2-methylthiazolo[5,4-c]pyridinium.

Another preferred quaternary ammonium group is the substituted or unsubstituted quinolinium group. The quinolinium group may be substituted on the A or B ring or on both rings with the same or different substituents. Some examples and description of substituted quinolinium groups can be found in W. H. W. Lunn, U.S. Pat. No. 4,396,620, issued Aug. 2, 1983, herein incorporated by reference. Columns 3, 4, 13, 14, 15, 16, 17, 18, 19 and 20 of the '620 patent are particularly helpful in this regard.

A preferred group of quinolinium groups are the quinolinium, 5-aminoquinolinium, 3-aminoquinolinium, 2-aminoquinolinium, 7-aminoquinolinium, 5-hydroxyquinolinium, 6-hydroxyquinolinium and 7-hydroxyquinolinium group.

Another preferred quaternary ammonium group is the substituted or unsubstituted isoquinolinium group. The isoquinolinium ring may be substituted on the A or the B ring or on both rings with the same or different substituents.

Examples and description of substituted isoquinolinium groups can be found in W. H. W. Lunn, U.S. Pat. No. 4,396,619, issued Aug. 2, 1983, herein incorporated by reference. Columns 3, 4, 13, 14, 16, 17, 18, 19, 20, 21 and 22 of the '619 patent are particularly helpful in this regard.

A preferred group of isoquinolinium substituents are isoquinolinium, the hydroxy-substituted isoquinolinium groups such as 5-hydroxyisoquinolinium or 4-hydroxyisoquinolinium, or the amino-substituted isoquinolinium groups such as 4-aminoisoquinolinium, 5-aminoisoquinolinium or 6-aminoisoquinolinium.

A more preferred group of isoquinolinium groups are the isoquinolinium, 5-aminoisoquinolinium and 8-hydroxyisoquinolinium groups.

Another preferred quaternary ammonium group is a 1-pyridazinium or 2-pyridazinium group, or a mono- or di-substituted analog thereof, wherein the substituents can be the same or different.

A preferred group of pyridazinium substituents include: pyridazinium (unsubstituted), 3,6-dichloropyridazinium, 3-methylpyridazinium, 3,6-di(-hydroxy)pyridazinium, 3-chloro-6-methoxypyridazinium, 3,5-di(hydroxy)pyridazinium, 4-methylpyridazinium, 3-methoxypyridazinium, 4-methoxypyridazinium, 3,6-dimethylpyridazinium, 3-(methylthio)pyridazinium, 4-(methylthio)pyridazinium, 3- aminopyridazinium, 4-aminopyridazinium, 3-amino-6-methylpyridazinium, 3,6-di(methoxy)pyridazinium, 6-aminopyridazinium, 6-(methylamino)pyridazinium, 6-chloro-3-methoxypyridazinium, 5-methylpyridazinium, and 5-ethylpyridazinium.

A more preferred pyridazinium group is unsubstituted pyridazinium.

Another preferred quaternary ammonium group is a 1-pyrimidinium or 3-pyrimidinium group, or a mono- or di-substituted analog thereof, wherein the substituents can be the same or different.

A preferred group of pyrimidinium substituents is 4,5-diaminopyrimidinium, 4,6-diaminopyrimidinium, the (protected amino)pyrimidinium analogs thereof, 4-phenylpyrimidinium, 4,6-dichloropyrimidinium, 2,4-dichloropyrimidinium, 4,6-di(methyl)pyrimidinium and the unsubstituted pyrimidinium group. A more preferred pyrimidinium group is unsubstituted pyrimidinium.

Another preferred quaternary ammonium group is the 1-pyrazinium or 4-pyrazinium group, or a mono- or di-substituted analog thereof, wherein the substituents can be the same or different.

A preferred group of pyrazinium substituents include 3-methylpyrazinium, 3,5-di(methyl)pyrazinium, 3-aminopyrazinium, 3-protected aminopyrazinium, 3-ethylpyrazinium, 3-(diethylamino)pyrazinium, 3-(ethylamino)pyrazinium, 3,5-diethylpyrazinium, 3-(dimethylamino)-pyrazinium, 2,6-dimethylpyrazinium, 2-chloropyrazinium, 3-chloropyrazinium, 2-aminopyrazinium, 2-carboxy-3-aminopyrazinium, 2,6-dichloropyrazinium, 2,3-dimethylpyrazinium, 2,5-dimethylpyrazinium, 2-methylpyrazinium, 2-carbamoylpyrazinium, 2-carboxypyrazinium, 2,3-dicarbamoylpyrazinium, 2,3-dicarboxypyrazinium, 2-methylpyrazinium, 2-ethylpyrazinium, 2-ethyl-3-methylpyrazinium, 2-ethyl-5-methylpyrazinium, 2-ethyl-6-methylpyrazinium, 2,5-diethylpyrazinium, 3-(isopropyl)-2-ethoxypyrazinium, 3-(sec-butyl)-2-methoxypyrazinium and 3-(iso-butyl)-2-methoxypyrazinium. A more preferred group of pyrazinium substituents is the unsubstituted pyrazinium and the 2-(dimethylamino)-pyrazinium-1-yl groups.

Another group of preferred quaternary ammonium substituents is the substituted or unsubstituted thiazolinium, isothiazolinium, oxazolinium, isoxazolinium, 1,3,4-thiadiazolinium, 1,2,4-thiadiazolinium, 1,2,5-thiadiazolinium, 1,3,4-oxadiazolinium, 1,2,4-oxadiazolinium or 1,2,5-oxadiazolinium groups, each of which can be substituted once or twice with the same or different substituents. The groups containing two nitrogen atoms in the ring may be quaternized at either ring nitrogen.

A preferred ring system in this group is the substituted or unsubstituted thiazolium group. A preferred thiazolium group is the 4-methyl-5-(1-hydroxyeth-2-yl)-thiazolium ring.

Also, a preferred quaternary ammonium group is a group of quaternary ammonium substituents which have the formula:

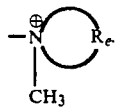

The preferred compounds of the above quaternary ammonium group occur when the variable Re, taken together with the nitrogen atom to which it is bonded, represents a saturated or mono-unsaturated 5-, 6-, 7- or 8-membered heterocyclic ring optionally containing a further nitrogen or oxygen heteroatom. The heterocyclic ring may be mono-substituted and may also be fused with a benzene ring.

A preferred substituent within this quaternary ammonium group is of the formula

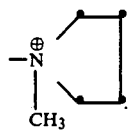

Further examples and description of this type of quaternary ammonium group can be found in P. E. Ayres, U.S. Pat. No. 4,168,309, issued September 18, 1979, herein incorporated by reference.

The term "heterocyclic ring" denotes optionally substituted five-membered or six-membered rings that have 1 to 4 heteroatoms, such as oxygen, sulfur and/or nitrogen, in particular nitrogen, either alone or in conjunction with sulfur or oxygen ring atoms. These five-membered or six-membered rings may be fully unsaturated or partially unsaturated, with fully unsaturated rings being preferred.

Furthermore, the above optionally substituted five-membered or six-membered rings can optionally be fused to a aromatic 5-membered or 6-membered ring to an aromatic 5-membered or 6-membered ring system such as a pyridine or a triazole system, and preferably to a benzene ring.

The following ring systems are examples of the heterocyclic (whether substituted or unsubstituted) radicals denoted by the term "heterocyclic ring": thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo[1,5-b]pyridazinyl and purinyl, as well as benzo-fused derivatives, for example benzoxazolyl, benzthiazolyl, benzimidazolyl and indolyl.

A preferred group of examples of the above heterocyclic rings, when $R_1$ or $R_2$ is either a heterocyclic thiomethyl group or simply a heterocyclic group, are 5-membered ring systems containing a sulfur or oxygen atom and one to three nitrogen atoms. Examples of such preferred groups include thiazolyl, in particular thiazol-2-yl and thiazol-2-yl N-oxide, thiadiazolyl, in particular 1,3,4-thiadiazol-5-yl and 1,2,4-thiadiazol-5-yl, oxazolyl, preferably oxazol-2-yl, and oxadiazolyl, such as 1,3,4-oxadiazol-5-yl, and 1,2,4-oxadiazol-5-yl. A group of further preferred examples of 5-membered ring systems with 2 to 4 nitrogen atoms include imidazolyl, preferably imidazol-2-yl; triazolyl, preferably 1,3,4-triazol-5-yl; 1,2,3-triazol-5-yl, 1,2,4-triazol-5-yl, and tetrazolyl, preferably 1H-tetrazol-5-yl A preferred group of examples of benzo-fused derivatives are, in particular, benzoxazol-2-yl, benzthiazol-2-yl and benzimidazol-2-yl.

Further specific examples of the above heterocyclic ring systems are 6-membered ring systems containing one to three nitrogen atoms. Such examples include pyridyl, such as pyrid-2-yl, pyrid-3-yl and pyrid-4-yl; pyrimidyl, preferably pyrimid-2-yl and pyrimid-4-yl; triazinyl, preferably 1,3,4-triazin-2-yl and 1,3,5-triazin-4-yl; pyridazinyl, in particular pyridazin-3-yl, and pyrazinyl. The pyridine N-oxides and pyridazine N-oxides, and the pyridyl, pyrimid-2-yl, pyrimid-4-yl, pyridazinyl and the 1,3,4-triazin-2-yl radicals, are a preferred group.

The substituents for the optionally substituted heterocyclic ring systems, and further examples of the 5- and 6- membered ring systems discussed above, are found in W. Dürckheimer et al., U.S. Pat. No. 4,278,793, issued July 14, 1981, columns 9 through 21 and columns 33 through 188, herein incorporated by reference. (In columns 33 through 188, examples of term "heterocyclic ring" are included in the heterocyclic thiomethyl groups listed under heading "A".)

A particularly preferred group of examples of the term "heterocyclic ring", when the ring is a 2- or 3-substituent or part of a heterocyclic thiomethyl group is 1,3-thiazol-2-yl, 4-(carboxymethyl)-5-methyl-1,3-thiazol-2-yl, 4-(carboxymethyl)-5-methyl-1,3-thiazol-2-yl sodium salt, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl sodium salt, 2-carboxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-methyl-1,3,4-thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 2-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(N-oxide)-pyridaz-3-yl, 6-hydroxypyridaz-3-yl, 1-methylpyrid-2-yl, 1-methylpyrid-4-yl, 2-hydroxy-pyrimid-4-yl, 1,4,5,6-tetrahydro-5,6-dioxo-4-methyl-astriazin-3-yl, 1,4,5,6-tetrahydro-4-(formylmethyl)-5,6-dioxo-as-triazin-3-yl, 2,5-dihydro-5-oxo-6-hydroxy-astriazin-3-yl, 2,5-dihydro-5-oxo-6-hydroxy-as-triazin-3-yl sodium salt, 2,5-dihydro-S-oxo-6-hydroxy-2-methylas-triazin-3-yl sodium salt, 2,5-dihydro-5-oxo-6-hydroxy-2-methyl-as-triazin-3-yl, 2,5-dihydro-5-oxo-6-methoxy2-methyl-as-triazin-3-yl, 2,5-dihydro-5-oxo-as-triazin3-yl, 2,5-dihydro-S-oxo-2-methyl-as-triazin-3-yl, 2,5-dihydro-5-oxo-2,6-dimethyl-as-triazin-3-yl, tetrazolo[1,5-b]pyridazin-6-yl and 8-aminotetrazolo1,5-b]pyridazin-6-yl.

A most preferred group of examples of the term "heterocyclic ring" is 4-(carboxymethyl)-5-methyl-1,3-thiazol-2-yl, 4-(carboxymethyl)-5-methyl-1,3-thiazol-2-yl sodium salt, 1,3,4-triazol-5-yl, 2-methyl-1,3,4-triazol-5-yl, 1H-tetrazol-5-yl, 1-methyl-1H-tetrazol5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol5-yl sodium salt, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl sodium salt, 2,5-dihydro-5-oxo-6-hydroxy-2-methyl-as- triazin-3-yl, tetrazolo[1,5-b]pyridazin-6-yl, and 8-aminotetrazolo[1,5-b]pyridazin-6-yl.

The term "heterocyclic ring", when used in conjunction with the term "acyl group derived from a $C_1$ to $C_{30}$ carboxylic acid", refers to the rings in W. Dürckheimer et al., U.S. Pat. No. 4,278,793. Particular examples are unsubstituted or substituted rings such as tetrazolyl, oxazolyl, isoxazolyl, thienyl, furyl, thiazolyl, thiadiazolyl, isothiazolyl, pyridyl, 4-pyridonyl, pyrimidyl, benzthienyl, benzfuryl or indolyl. Of course, these examples can be substituted with the substituents discussed in the Dürckheimer et al., '793 patent.

A particular preferred group of heterocyclic rings used in conjunction with the above "acyl group ... " term includes 1-tetrazolyl, 4-pyridonyl, 3,5-dichloro-4-pyridonyl, 2-aminothiazol-4-yl, 5-amino-1,2,4-thiadiazol-3-yl, 3-hydroxy-4-carboxyisothiazol-5-yl, 2-amino-4-phenylthiazol-5-yl, 3-phenyl-5-methylisoxazol4-yl, 3-(2-chlorophenyl)-5-methylisoxazol-4-yl, 3-(2,5-dichlorophenyl)-5-methylisoxazol-4-yl, 3-(2-fluoro-5-chlorophenyl)-5-methylisoxazol-4-yl, 2-thienyl, 2-furyl, 4-pyridinyl, N-methylpyridin-4-yl, 2-amino-pyridin-6-yl, 2-aminopyridin-5-yl, 2-aminopyridin-4-yl, 4-aminopyridin-2-yl, 4-aminopyrimidin-2-yl, 2-amino-pyrimidin-4-yl, 2-benzothienyl, 3-benzothienyl, 2-benzofuranyl, 3-benzofuranyl, 2-indolyl and 3-indolyl.

The term "acyl group derived from a $C_1$ to $C_{30}$ carboxylic acid" represented by either $R_5$ or $R_6$ refers to the acyl moieties which have been bonded to the C-6 amino group of penicillins, the C-7 amino group of cephalosporins, 1-oxadethiacephalosporins or 1-carbacephalosporins and the C-3 amino of monocyclic $\beta$-lactams (such as the azthreonam series). The "acyl group derived from a $C_1$ to $C_{30}$ carboxylic acid" can be optionally interrupted by heteroatoms. Examples of such acyl groups can be found in references such as "Cephalosporins and Penicillins, Chemistry and Biology" edited by Edwin W. Flynn, Academic Press, New York, 1972 and "Chemistry and Biology of $\beta$-lactam Antibiotics" edited by Robert B. Morin and Marvin Gorman, Vols. 1, 2, and 3, Academic Press, New York, 1982.

Examples of acyl groups at $R_5$ or $R_6$ can also be found in M. Yoshioka et al., U.S. Pat. No. 4,478,997, issued Oct. 23, 1984, B. R. Belleau et al., U.S. Pat. No. 4,172,199, issued Oct. 23, 1979, T. Kamiya et al, U.S. Pat. No. 4,472,300, issued Sept. 18, 1984, (especially columns 25 through 36) all of which are herein incorporated by reference. Additional Examples of "acyl groups derived from a $C_1$ to $C_{30}$ carboxylic acid" can be found in Koster et al., U.S. Pat. No. 4,478,749, issued Oct. 23, 1984.

Some specific examples of such acyl groups are when either $R_5$ or $R_6$ is hydrogen and the other of $R_5$ or $R_6$ is an acyl group of the formula $$-COR_{16}$$

wherein $R_{16}$ is:

(A) $C_1$ to $C_6$ alkyl, $C_1$ to $C_6$ substituted alkyl, $C_1$ to $C_4$ alkoxy, $C_1$ to $C_4$ alkylthio, or groups of the formula:

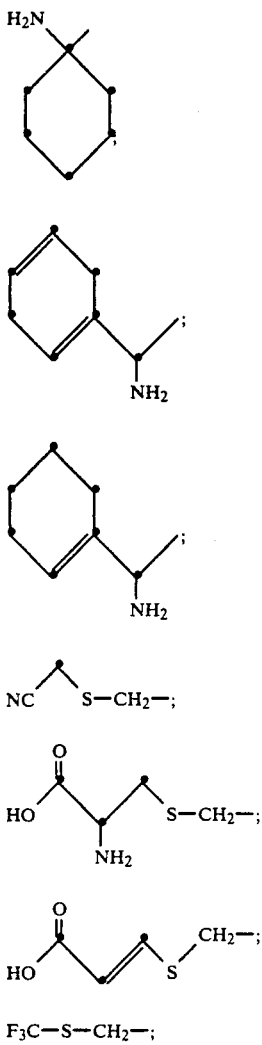

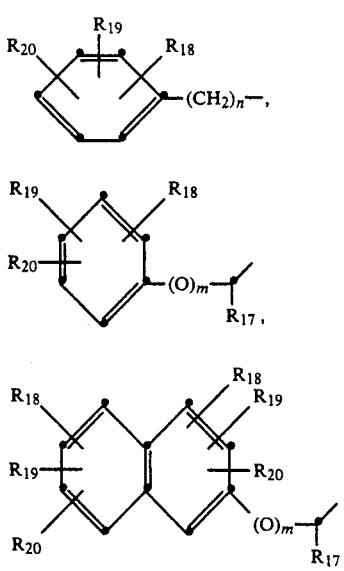

or a protected amino and/or protected carboxy derivative thereof;

(B) a group of the formula

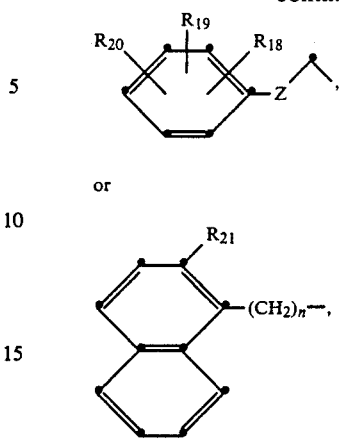

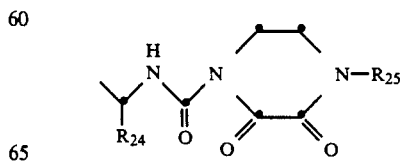

wherein each of $R_{18}$, $R_{19}$ and $R_{20}$ is independently hydrogen, halo, hydroxy, protected hydroxy, nitro, amino, protected amino, an amine salt, cyano, trifluoromethyl, aminomethyl, protected aminomethyl, N-(methyl- or ethylsulfonyl)amino, $C_1$ to $C_6$ alkyl or $C_1$ to $C_4$ alkoxy, $R_{17}$ is hydroxy, protected hydroxy, formyloxy, amino, protected amine, an amine salt, carboxy, a carboxylate salt, protected carboxy, phenyl carboxylate, (5-indanyl)carboxylate, sulfonic acid, a sulfonate salt, azido, halo or $C_1$ to $C_4$ alkyl; $R_{21}$ is $C_1$ to $C_4$ alkoxy; Z is oxygen or sulfur; n is 0, 1, 2 or 3; and m is 0 or 1;

(C) a group of the formula

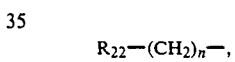

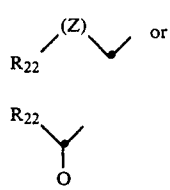

wherein $R_{22}$ is a heterocyclic ring as defined above; $R_{23}$ is hydroxy, protected hydroxy, formyloxy, amino, protected amino, an amine salt, carboxy, a carboxylate salt, protected carboxy, phenyl carboxylate, (5-indanyl)carboxylate, sulfonic acid, a sulfonate salt, azido, halo or $C_1$ to $C_6$ alkyl; n is 0, 1, 2, or 3; and Z is oxygen or sulfur;

(D) a group of the formula wherein $R_{24}$ is:

(a) an aromatic group of the formula

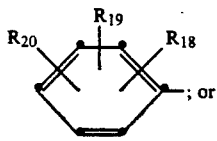

(b) R₂₂; wherein R₁₈, R₁₉, R₂₀ and R₂₂ are as defined above; and R₂₅ is $C_1$ to $C_6$ alkyl or $C_1$ to $C_6$ substituted alkyl;

(E) a group of the formula

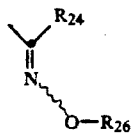

wherein R₂₄ is as defined above and R₂₆ is hydrogen, $C_1$ to $C_6$ alkyl, $C_1$ to $C_6$ substituted alkyl, $C_2$ to $C_7$ alkenyl, $C_2$ to $C_7$ alkynyl, $C_3$ to $C_7$ cycloalkyl, $C_3$ to $C_7$ substituted cycloalkyl, $C_7$ to $C_{12}$ arylalkyl, $C_7$ to $C_{12}$ substituted arylalkyl, phenyl or substituted phenyl;

(F) a group of the formula

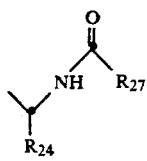

wherein R₂₄ is as defined above and R₂₇ is amino, allylamino, acetylamino, or a group of the formula

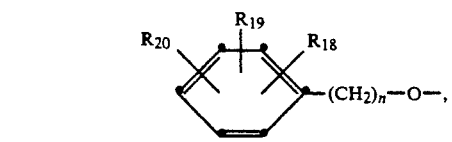

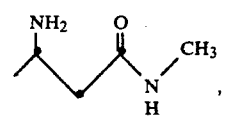

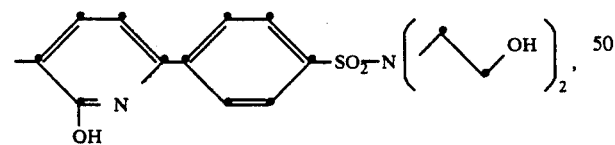

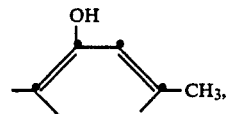

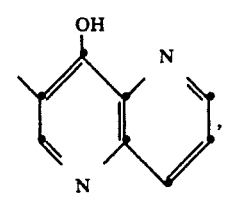

-continued

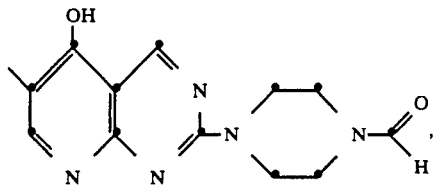

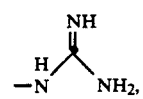

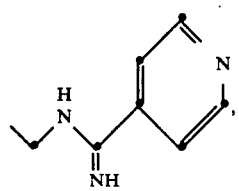

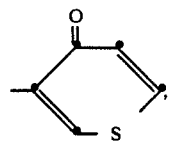

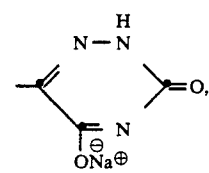

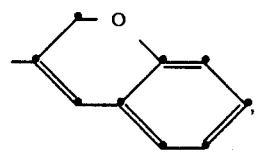

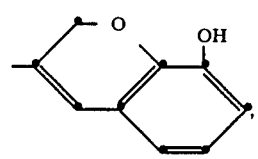

or

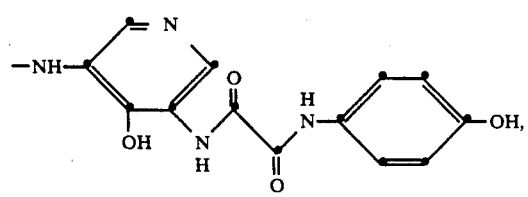

wherein R₁₈, R₁₉ and R₂₀ are as defined above, n is 1, 2 or 3; or a protected hydroxy, protected amino or amine salt derivative thereof;

(G) a group of the formula

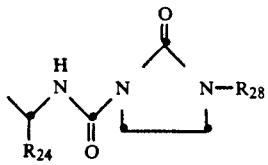

wherein R$_{24}$ is as defined above and R$_{28}$ is hydrogen, C$_1$ to C$_4$ alkylsulfonyl, a group of the formula

(wherein R$_{24}$ is as defined above), a group of the formula

wherein R$_{29}$ is hydrogen, R$_{24}$, C$_1$ to C$_6$ alkyl or C$_1$ to C$_6$ substituted alkyl;

(H) a group of the formula

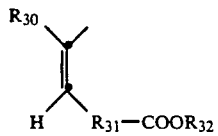

wherein R$_{30}$ is phenyl, furyl, thienyl, oxazolyl, isoxazolyl, (amino)isoxazolyl, (protected amino)isoxazolyl, thiazolyl, aminothiazolyl, (protected amino)thiazolyl, thiadiazolyl, or (protected amino)thiadiazolyl;

R$_{31}$ is C$_1$ to C$_3$ alkyl; and

R$_{32}$ is hydrogen, a carboxy-protecting group, an organic or inorganic cation, or a non-toxic metabolically-labile ester-forming group; or (I) R$_5$ and R$_6$ are taken together to form a group of the formula

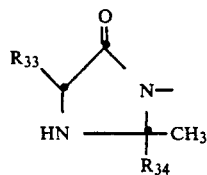

wherein R$_{33}$ is hydrogen, C$_1$ to C$_6$ alkyl, C$_3$ to C$_7$ cycloalkyl, napthyl, benzyl, thien-2-yl, thien-3-yl, phenyl, or p-hydroxyphenyl and R$_{34}$ is C$_1$ to C$_6$ alkyl.

The above set of examples of the term "acyl group derived from a C$_1$ to C$_{30}$ carboxylic acid" contains many terms already defined in the specification. The terms "C$_1$ to C$_4$ alkylthio", "C$_1$ to C$_4$ alkylsulfonyl", "C$_3$ to C$_7$ cycloalkyl" and "C$_3$ to C$_7$ substituted cycloalkyl" have the same definition when used with the "acyl group" term as they do above in conjunction with the "quaternary ammonium group" term. The terms "amine salt", "carboxylic salt" and "sulfonate salt" have been previously referred to by the term "pharmaceutically-acceptable salt". In the latter term the counter-ions for carboxylate anions will also serve as counter-ions for sulfonate anions.

Examples of the acyl groups represented when R$_{16}$ is chosen from the above Group B include: phenylacetyl, phenoxyacetyl, 2-(aminomethyl)phenylacetyl, 2-phenyl-2-hydroxyacetyl, 2-phenyl-2-(sodium sulfonato)acetyl, 2-phenyl-2-carboxyacetyl, 2-(4-hydroxyphenyl)-2-carboxyacetyl, 2-phenyl-2-aminoacetyl, 2-(4-hydroxyphenyl)-2-aminoacetyl, 2-(3-(N-(methylsulfonylamino))phenyl)-2-aminoacetyl, 2-phenyl-2-(5-indanyl carboxylate)acetyl, 2-phenyl-2-(phenyl carboxylate)acetyl, 2-phenyl-2-azidoacetyl, 2-phenoxypropionyl, 2,5-dimethoxybenzoyl, 2-(formyloxy)-2-phenylacetyl, 2-(2-ethoxynaphth-1-yl)acetyl, 2-(naphth-1-yl)-2-aminoacetyl, 2-(napth-2-yl)-2-aminoacetyl, 2-(2,5-dichlorophenylthio)acetyl, 2-(3,4-dichlorophenylthio)acetyl, and the like.

A preferred group of acyl groups when R$_{16}$ is chosen from Group B is represented by the formula

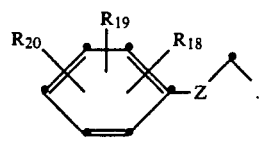

A further preferred group within the above preferred group occurs when R$_{18}$, R$_{19}$ and R$_{20}$ are each halogen and Z is sulfur. A still further preferred group occurs when R$_{16}$ is a 2,5-dichlorophenylthiomethyl group.

Examples of the acyl groups represented when R$_{16}$ is chosen from the above Group C include: 2-(1-tetrazolyl)acetyl, 2-(N-(3,5-dichloropyrid-4-oxyl))acetyl, 2-(2-aminothiazol-4-yl)acetyl, 2-(2-thienyl)acetyl, 2-(4-pyridylthio)acetyl, 2-(N-methyl-4-pyridiniumthio)acetyl, 2-(2-amino-4-phenylthiazol-5-yl)acetyl, 2-(3-hydroxy-4-carboxyisothiazol-5-ylthio)acetyl, 3-phenyl-5-methylisoxazolyl-3-formyl, 3-(2-chlorophenyl)-5-methylisoxazolyl-3-formyl, 3-(2,5-dichlorophenyl)-5-methylisoxazolyl-3-formyl, 3-(2-fluoro-5-chlorophenyl)-5-methylisoxazolyl-3-formyl, 2-(2-thienyl)-2-aminoacetyl, 2-(2-thienyl)-2-(sodium carboxylate)acetyl, 2-(N-(4-pyridonium))acetyl, 2-(2-benzothienyl)acetyl, 2-(3-benzothienyl)acetyl, 2-(2-benzofuryl)acetyl, 2-(3-benzofuryl)acetyl and the like.

A preferred group from the above Group C occurs when R$_{16}$ is a group of the formula

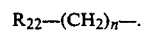

A more preferred group from the above Group C is when R$_{16}$ is (2-thienyl)methyl.

Examples of the acyl groups represented when R$_{16}$ is chosen from the above Group D includes groups of the formula

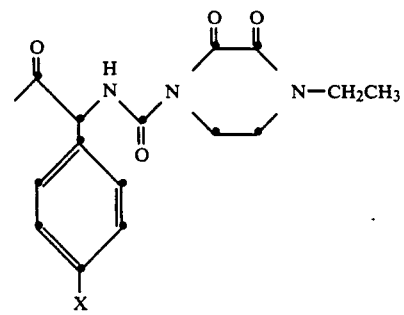

wherein X is hydrogen or hydroxy.

Examples of the acyl groups represented when R$_{16}$ is chosen from the above Group E include:
2-phenyl-2-(Z)-methoxyiminoacetyl, 2-(4-(O-homoserine)phenyl)-2-(Z)-methoxyiminoacetyl,
2-(2-thienyl)-2-(Z)-methoxyiminoacetyl,
2-(2-furyl)-2-(Z)-methoxyiminoacetyl,
2-(2-aminothiazol-4-yl)-2-(Z)-methoxyiminoacetyl,
2-(5-amino-1,2,4-thiadiazol-3-yl)-2-(Z)-methoxyiminoacetyl,
2-(4-aminopyridin-2-yl)-2-(Z)-methoxyiminoacetyl,
2-(2-aminopyridin-6-yl)-2-(Z)-methoxyiminoacetyl,
2-(2-aminopyridin-5-yl)-2-(Z)-methoxyiminoacetyl,
2-(2-aminopyridin-4-yl)-2-(Z)-methoxyiminoacetyl,
2-(2-aminopyrimidin-4-yl)-2-(Z)-methoxyiminoacetyl,
2-(2-aminothiazol-4-yl)-2-(Z)-hydroxyiminoacetyl,
2-(2-aminothiazol-4-yl)-2-(Z)-ethoxyiminoacetyl,
2-(2-aminothiazol-4-yl)-2-(Z)-propoxyiminoacetyl,
2-(2-aminothiazol-4-yl)-2-(Z)-(2-bromoeth-1-yl)-oximinoacetyl,
2-(2-aminothiazol-4-yl)-2-(Z)-(2-chloroeth-1-yl)-oximinoacetyl,
2-(2-aminothiazol-4-yl)-2-(Z)-(2-fluoroeth-1-yl)-oximinoacetyl,
2-(2-aminothiazol-4-yl)-2-(Z)-(2-iodoeth-1-yl)-oximinoacetyl,
2-(2-aminothiazol-4-yl)-2-(Z)-allyloximinoacetyl,
2-(2-aminothiazol-4-yl)-2-(Z)-vinyloximinoacetyl,
2-(2-aminothiazol-4-yl)-2-(Z)-(2-buten-1-yl)-oximinoacetyl,
2-(2-aminothiazol-4-yl)-2-(Z)-(3-butene-1-yl)-oximinoacetyl,
2-(2-aminothiazol-4-yl)-2-(Z)-(2-propyne-1-yl)-oximinoacetyl,
2-(2-aminothiazol-4-yl)-2-(Z)-methylthiomethoximinoacetyl,
2-(2-aminothiazol-4-yl)-2-(Z)-(carboxymethyl)oximinoacetyl,
2-(2-aminothiazol-4-yl)-2-(Z)-benzoxyiminoacetyl,
2-(2-aminothiazol-4-yl)-2-(Z)-(2,5-dichlorobenzyl)oxyiminoacetyl,
2-(2-aminothiazol-4-yl)-2-(Z)-(2-carboxyprop-2-yl)oxyiminoacetyl,
2-(2-aminothiazol-4-yl)-2-(Z)-carboxymethoxyiminoacetyl,
2-(2-aminothiazol-4-yl)-2-(Z)-cyclopropoxyiminoacetyl,
2-(2-aminothiazol-4-yl)-2-(Z)-cyclobutoxyiminoacetyl,
2-(2-aminothiazol-4-yl)-2-(Z)-cyclopentoxyiminoacetyl,
2-(2-aminothiazol-4-yl)-2-(Z)-phenoxyiminoacetyl,
2-(2-aminothiazol-4-yl)-2-(Z)-(4-fluorophenoxy)iminoacetyl,
2-(2-aminothiazol-4-yl)-2-(Z)-(4-chlorophenoxy)iminoacetyl,
2-(2-aminothiazol-4-yl)-2-(Z)-(3-trifluorolphenoxy)iminoaoetyl,
2-(2-aminothiazol-4-yl)-2-(Z)-(3-ethoxycarbonylphenoxy)iminoacetyl,
2-(2-aminothiazol-4-yl)-2-(Z)-(2-methylphenoxy)iminoacetyl,
2-(2-aminothiazol-4-yl)-2-(Z)-(4-methylphenoxy)iminoacetyl,
2-(2-aminothiazol-4-yl)-2-(Z)-(3,4-dichlorophenoxy)iminoacetyl,
2-(2-aminothiazol-4-yl)-2-(Z)-(2,4-dichlorophenoxy)iminoacetyl,
2-(5-amino-1,2,4-thiadiazol-3-yl)-2-(Z)-(2-carboxyprop-2-yloxy)iminoacetyl,
2-(5-amino-1,2,4-thiadiazol-3-yl)-2-(Z)-carboxymethoxyiminoacetyl,
2-(5-amino-1,2,4-thiadiazol-3-yl)-2-(Z)-ethoxyiminoacetyl,
2-(5-amino-1,2,4-thiadiazol-3-yl)-2-(Z)-propoxyiminoacetyl,
2-(5-amino-1,2,4-thiadiazol-3-yl)-2-(Z)-cyclopropoxyiminoacetyl,
2-(5-amino-1,2,4-thiadiazol-3-yl)-2-(Z)-cyclobutoxyiminoacetyl,
2-(5-amino-1,2,4-thiadiazol-3-yl)-2-(Z)-cyclopentoxyiminoacetyl,
2-(5-amino-1,2,4-thiadiazol-3-yl)-2-(Z)-benzyloxyiminoacetyl,
2-(5-amino-1,2,4-thiadiazol-3-yl)-2-(Z)-phenoxyiminoacetyl,
2-(5-amino-1,2,4-thiadiazol-3-yl)-2-(Z)-(4-fluorophenoxy)iminoacetyl,
2-(5-amino-1,2,4-thiadiazol-3-yl)-2-(Z)-(4-chlorophenoxy)iminoacetyl,
2-(5-amino-1,2,4-thiadiazol-3-yl)-2-(Z)-(3-trifluoromethylphenoxy)iminoacetyl,
2-(5-amino-1,2,4-thiadiazol-3-yl)-2-(Z)-(3-(ethoxycarbonyl)phenoxy)iminoacetyl,
2-(5-amino-1,2,4-thiadiazol-3-yl)-2-(Z)-(2-methylphenoxy)iminoacetyl,
2-(5-amino-1,2,4-thiadiazol-3-yl)-2-(Z)-(2-methylphenoxy)iminoacetyl,
2-(5-amino-1,2,4-thiadiazol-3-yl)-2-(Z)-(3,4-dichlorophenoxy)iminoacetyl,
2-(5-amino-1,2,4-thiadiazol-3-yl)-2-(Z)-(2,4-dichlorophenoxy)iminoacetyl, and the protected amino, protected carboxy, amine salt and carboxylate salt derivatives thereof.

A preferred group of acyl groups from among the above examples when $R_{16}$ is chosen from Group E include:
2-(2-aminothiazol-4-yl)-2-(Z)-methoxyiminoacetyl,
2-(2-aminothiazol-4-yl)-2-(Z)-(2-bromoeth-1-yl)oximinoacetyl,
2-(2-aminothiazol-4-yl)-2-(Z)-(2-chloroeth-1-yl)oximinoacetyl,
2-(2-aminothiazol-4-yl)-2-(Z)-(2-fluoroeth-1-yl)oximinoacetyl,
2-(2-aminothiazol-4-yl)-2-(Z)-(2-iodoeth-1-yl)oximinoacetyl,
2-(2-aminothiazol-4-yl)-2-(Z)-allyloximinoacetyl,
2-(2-aminothiazol-4-yl)-2-(Z)-vinyloximinoacetyl,
2-(2-aminothiazol-4-yl)-2-(Z)-(2-buten-1-yl)oximinoacetyl,
2-(2-aminothiazol-4-yl)-2-(Z)-(3-butene-1-yl)oximinoacetyl,
2-(2-aminothiazol-4-yl)-2-(Z)-(2-propyne-1-yl)oximinoacetyl,
2-(2-aminothiazol-4-yl)-2-(Z)-methylthiomethoximinoacetyl,
2-(2-aminothiazol-4-yl)-2-(Z)-(carboxymethyl)-oximinoacetyl,
2-(2-aminothiazol-4-yl)-2-(Z)-carboxymethoxyetyl,
2-(2-aminothiazol-4-yl)-2-(Z)-(2-carboxyprop-2-yloxy)iminoacetyl,
2-(2-aminothiazol-4-yl)-2-(Z)-(2,5-dichlorobenzyl)oxyiminoacetyl,
2-(5-amino-1,2,4-thiadiazol-3-yl)-2-(Z)-carboxymethoxyiminoacetyl,
2-(5-amino-1,2,4-thiadiazol-3-yl)-2-(Z)-(2-carboxyprop-2-yloxy)iminoacetyl,
2-(2-furyl)-2-(Z)-methoxyiminoacetyl,
2-(2-furyl)-2-(Z)-carboxymethoxyiminoacetyl, 2-(2-furyl)-2-(Z)-(2-carboxyprop-2-yloxy)iminoacetyl, and the protected amino, protected carboxy, amine salt and carboxylate salt derivatives thereof.

A further preferred group of acyl groups from among the above preferred groups include:

2-(2-aminothiazol-4-yl)-2-(Z)-methoxyiminoacetyl,
2-(2-(allyloxycarbonylamino)thiazol-4-yl)-2-(Z)-methoxyiminoacetyl,
2-(2-(t-butoxycarbonylamino)thiazol-4-yl)-2-(Z)-methoxyiminoacetyl,
2-(2-aminothiazol-4-yl)-2-(Z)-methoxyiminoacetyl hydrochloride salt,
2-(2-aminothiazol-4-yl)-2-(Z)-(2,5-dichlorobenzyl)oxyiminoacetyl,
2-(2-(allyloxycarbonylamino)thiazol-4-yl)-2-(Z)-(2,5-dichlorobenzyl)oxyiminoacetyl,
2-(2-(t-butoxycarbonylamino)thiazol-4-yl)-2-(Z)-(2,5-dichlorobenzyl)oxyiminoacetyl,
2-(2-(tritylamino)thiazol-4-yl)-2-(Z)-(2,5dichlorobenzyl)oxyiminoacetyl;
2-(2-aminothiazol-4-yl)-2-(Z)-(2-carboxyprop-2-yl)oxyiminoacetyl,
2-(2-(allyloxycarbonylamino)thiazol-4-yl)-2-(Z)-(2-(allyl carboxylate)prop-2-yl)oxyiminoacetyl,
2-(2-(t-butoxycarbonylamino)thiazol-4-yl)-2-(Z)-(2-(t-butyl carboxylate)prop-2-yl)oxyiminoacetyl, and
2-(2-(tritylamino)thiazol-4-yl)-2-(Z)-(2-(t-butyl carboxylate)prop-2-yl)oxyiminoacetyl.

Among the above further preferred acyl groups in the above Group E, the 2-(2-aminothiazol-4-yl)-2-(Z)-methoxyiminoacetyl, 2-(2-(allyloxycarbonylamino)thiazol-4-yl)-2-(Z)-methoxyiminoacetyl, 2-(2-(t-butoxycarbonylamino)thiazol-4-yl)-2-(Z)-methoxyiminoacetyl, 2-(2-(butoxycarbonylamino)thiazol-4-yl)-2-(Z)-(2,5-dichlorobenzyl)oxyiminoacetyl, 2-(2-aminothiazol-4-yl)-2-(Z)-(2,5-dichlorobenzyl)oxyiminoacetyl, 2-(2-(tritylamino)thiazol-4-yl)-2-(Z)-(2-(t-butyl carboxylate)-prop-2-yl)oxyiminoacetyl, 2-(2-aminothiazol-4-yl)-2-(Z)-(3-butene-1-yl)oximinoethyl, and the 2-(2-aminothiazol-4-yl)-2-(Z)-(2-carboxyprop-2-yl)oxyiminoacetyl groups constitute an even more preferred group.

A preferred group of acyl groups from among the above examples when $R_{16}$ is Group F include: (1) when $R_{24}$ is phenyl and $R_{27}$ is a group of the formula

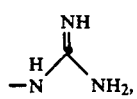

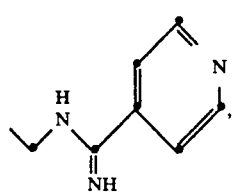

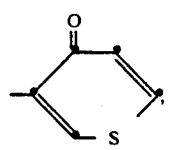

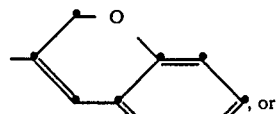

, or

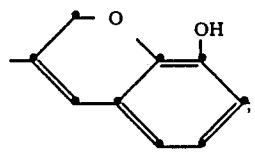

, (2) when $R_{24}$ is 4-hydroxyphenyl and $R_{27}$ is a group of the formula

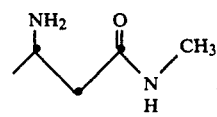

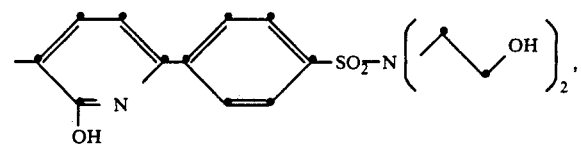

,

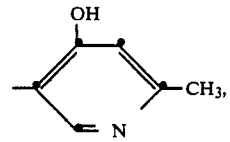

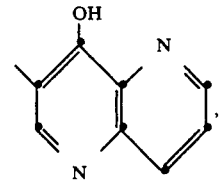

,

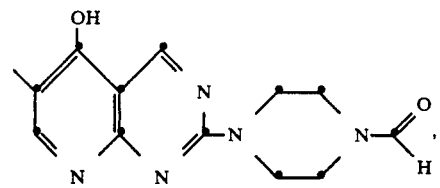

,

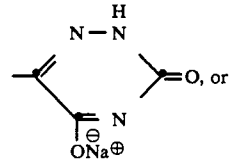

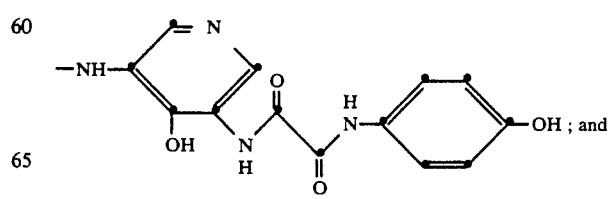

; and (3) when $R_{24}$ is 2-thienyl and $R_{27}$ is an amino group.

Examples of the acyl groups represented when $R_{16}$ is chosen from the above Group G include: (1) when $R_{24}$ is phenyl and $R_{28}$ is hydrogen or methylsulfonyl; and (2) when $R_{24}$ is 4-hydroxyphenyl and $R_{28}$ is a group of the formula

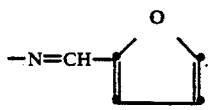

Examples of the acyl groups represented when $R_{16}$ is chosen from the above Group H above include:
2-phenyl-4-(carboxylic acid)but-2-enoyl,
2-phenyl-5-(allyl carboxylate)pent-2-enoyl,
2-phenyl-6-(potassium carboxylate)-(n-hex-2-enoyl),
2-(fur-2-yl)-5-(carboxylic acid)pent-2-enoyl,
2-(fur-3-yl)-6-(acetoxyeth-1-yl carboxylate)-(n-hex-2-enoyl),
2-(fur-2-yl)-4-(sodium carboxylate)but-2-enoyl,
2-(thien-2-yl)-6-(carboxylic acid)-(n-hex-2-enoyl),
2-(thien-3-yl)-4-(benzhydryl carboxylate)-but-2-enoyl,
2-(oxazol-2-yl)-5-(lithium carboxylate)pent-2-enoyl),
2-(isoxazol-3-yl)-6-(carboxylic acid)-(n-hex-2-enoyl),
2-(isoxazol-5-yl)-4-(p-nitrobenzyl carboxylate)but-2-enoyl,
2-(3-aminoisoxazol-5-yl)-4-(carboxylic acid)but-2-enoyl,
2-(3-(N-(t-butylcarbamato))isoxazol-5-yl)-5-(t-butyl carboxylate)-pent-2-enoyl,
2-(thiazol-4-yl)-6-(carboxylic acid)-(n-hex-2-enoyl),
2-(thiazol-2-yl)-4-(pivaloyloxymethyl carboxylate)but-2-enoyl,
2-(2-aminothiazol-4-yl)-4-(carboxylic acid)-but-2-enoyl,
2-(2-(N-(allyloxycarbonylamino))thiazol-4-yl)-5-(allyl carboxylate)pent-2-enoyl,
2-(thiadiazol-3-yl)-6-(carboxylic acid)-(n-hex-2-enoyl),
2-(thiadiazol-5-yl)-4-(sodium carboxylate)-but-2-enoyl,
2-(5-aminothiadiazol-3-yl)-4-(carboxylic acid)-but-2-enoyl,
2-(5-aminothiadiazol-3-yl)-4-(carboxylic acid)-but-2-enoyl hydrochloride,
2-(5-(tritylamino)thiadiazol-3-yl)-5-(p-methoxybenzyl carboxylate)pent-2-enoyl, and the like.

Further examples of such groups can be found Y. Hamashima et al., European Patent Application No. 136,721, published Oct. 4, 1985.

A preferred group of acyl groups of the Group H acyl groups are the 7-(2-((optionally protected amino)-thiazol-4-yl)-4-(optionally protected carboxy)but-2-enoyl ("but-2-enoyl") compounds wherein $R_{30}$ is 2-(protected amino)thiazol-4-yl or 2-aminothiazol-4-yl, $R_{31}$ is a methylene group, and $R_{32}$ is hydrogen or a carboxy-protecting group.

Examples of the acyl group represented when $R_{16}$ is chosen from the above Group I include when $R_{33}$ is phenyl or 4-hydroxyphenyl and $R_{34}$ is methyl.

A more preferred group of the above acyl groups arises when $R_{16}$ is chosen from Groups B, C and E. Among those three groups, Group E is a more preferred group.

In the above Formula I, when $R_1$ or $R_2$ is a group of the formula

wherein $R_7$ is a heterocyclic group, examples of such groups are 1,3-thiazol-2-ylthio, 4-(carboxymethyl)-5-methyl-1,3-thiazol-2-ylthio, 4-(carboxymethyl)-5-methyl-1,3-thiazol-2-ylthio sodium salt, 1,2,4-thiadiazol-5-ylthio, 3-methyl-1,2,4-thiadiazol-5-ylthio, 1,3,4-triazol-5-ylthio, 2-methyl-1,3,4-triazol-5-ylthio, 2-hydroxy-1,3,4-triazol-5-ylthio, 2-(carboxy)-4-methyl-1,3,4-triazol-5-ylthio sodium salt, 2-(carboxy)-4-methyl-1,3,4-triazol-5-ylthio, 1,3-oxazol-2-ylthio, 1,3,4-oxadiazol-5-ylthio, 2-methyl-1,3,4-oxadiazol-5-ylthio, 2-(hydroxymethyl)-1,3,4-oxadiazol-5-ylthio, 1,2,4-oxadiazol-5-ylthio, 1,2,4-oxadiazol-5-ylthio, 1,3,4-thiadiazol-5-ylthio, 2-methyl-1,3,4-thiadiazol-5-ylthio, 2-thiol-1,3,4-thiadiazol-5-ylthio, 2-(methylthio)-1,3,4-thiadiazol-5-ylthio, 2-amino-1,3,4-thiadiazol-5-ylthio, 1H-tetrazol-5-ylthio, 1-methyl-1H-tetrazol-5-ylthio, 1-(1-(dimethylamino)eth-2-ylthio)-1H-tetrazol-5-ylthio, 1-(carboxymethyl)-1H-tetrazol-5-ylthio, 1-(carboxymethyl)-1H-tetrazol-5-ylthio sodium salt, 1-(methylsulfonic acid)-1H-tetrazol-5-ylthio, 1-(methylsulfonic acid)-1H-tetrazol-5-ylthio sodium salt, 2-methyl-1H-tetrazol-5-ylthio, 1,2,3-triazol-5-ylthio, 1-methyl-1,2,3-triazol-5-ylthio, 2-methyl-1,2,3-triazol-5-ylthio, 4-methyl-1,2,3-triazol-5-ylthio, pyrid-2-ylthio N-oxide, 6-methoxy-2-(N-oxide)-pyridaz-3-ylthio, 6-hydroxypyridaz-3-ylthio, 1-methylpyrid-2-ylthio, 1-methylpyrid-4-ylthio, 2-hydroxypyrimid-4-ylthio, 1,4,5,6-tetrahydro-5,6-dioxo-4-methyl-as-triazin-3-ylthio, 1,4,5,6-tetrahydro-4-(2-formylmethyl)-5,6-dioxo-as-triazin-3-ylthio, 2,5-dihydro-5-oxo-6-hydroxy-as-triazin-3-ylthio, 2,5-dihydro-5-oxo-6-hydroxy-as-triazin-3-ylthio sodium salt, 2,5-dihydro-5-oxo-6-hydroxy-2-methyl-as-triazin-3-ylthio sodium salt, 2,5-dihydro-5-oxo-6-hydroxy-2-methyl-as-triazin-3-ylthio, 2,5-dihydro-5-oxo-6-methoxy-2-methyl-as-triazin-3-ylthio, 2,5-dihydro-5-oxo-as-triazin-3-ylthio, 2,5-dihydro-5-oxo-2-methyl-as-triazin-3-ylthio, 2,5-dihydro-5-oxo-2,6-dimethyl-as-triazin-3-ylthio, tetrazolo[1,5-b]pyridazin-6-ylthio and 8-aminotetrazolo-[1,5-b]pyridazin-6-ylthio; the corresponding sulfoxides and sulfones of the above heterocyclic thio groups, and the like.

Examples of the above group when $R_7$ is other than a heterocyclic group include $C_1$ to $C_6$ alkylthio groups such as methylthio, ethylthio, (sec-butyl)thio, (t-amyl)thio and (n-hexyl)thio, $C_7$ to $C_{12}$ phenylalkylthio groups such as 2-phenylpropylthio, benzylthio, 1-phenyl(n-amyl)thio and 4-phenyl(n-butyl)thio; $C_1$ to $C_6$ substituted alkylthio groups such as cyanomethylthio, 2-hydroxyethylthio, 2-nitropropylthio, 2-carbamoyl-(sec-butyl)thio, 5-chloroamylthio, 4-carboxyamylthio, 6-carbamoyloxyhexylthio, 2-methoxyethylthio, isopropoxy(t-butyl)thio, 2-aminoethylthio, 2,5-dihydroxyamylthio, 3,3-dibromo(n-butyl)thio, 3-chloro-2-iodopropylthio and 4-acetoxy-6-fluorohexylthio; $C_7$ to $C_{12}$ substituted phenylalkylthio groups such as 3-(3,4-diiodophenyl)propylthio, 1-(3-chloro-4-fluorophenyl)ethylthio, 6-(4-cyanophenyl)hexylthio, 3-phenyl-1-chloro(-sec-butyl)thio, 2-phenyl-2-hydroxyethylthio, 5-phenyl-2-hydroxyamylthio, 2-(3-nitrophenyl)-3-ethoxypropylthio, 5,6-dihydroxy-2-(4-ethyl-2-hydroxyphenyl)-hexylthio and 5-carbamoyl-3-nitro-2-(2,4-dimethoxyphenyl)amylthio; phenylthio, and (substituted phenyl)thio groups, and the corresponding sulfoxide and sulfone analogs thereof.

Examples of the (substituted phenyl)thio groups represented by $R_7$ include groups such as 4-chlorophenylthio, 2,6-dichlorophenylthio, 2,5-dichlorophenylthio, 3,4-dichlorophenylthio, 3-chlorophenylthio, 3-bromophenylthio, 4-bromophenylthio, 3,4-dibromophenylthio, 3-chloro-4-fluorophenylthio, 2-fluorophenylthio, 4-hydroxyphenylthio, 3-hydroxyphenylthio, 2,4-dihydroxyphenylthio, 3- or 4-nitrophenylthio, 4-cyanophenylthio, 4-methylphenylthio, 2,4-dimethylphenylthio, 2-methylphenylthio, 4-(iso-propyl)phenylthio, 4-ethylphenylthio, 3-(n-propyl)phenylthio, 2,6-dimethoxyphenylthio, 4-methoxyphenylthio, 3-ethoxyphenylthio, 4-(iso-propoxy)phenylthio, 4-(t-butoxy)-phenylthio, 3-ethoxy-4-methoxyphenylthio, a 3- or 4-(trifluoromethyl)phenylthio, 4-carboxyphenylthio, 2,4-di(protected carboxy)phenylthio, 3-(protected hydroxymethyl)phenylthio, 3,4-di(hydroxymethyl)phenylthio, 2-(aminomethyl)phenylthio, 2,4-di(protected aminomethyl)phenylthio, 3-(N-(methylsulfonylamino))phenylthio, 3-methyl-4-hydroxyphenylthio, 3-chloro-4-hydroxyphenylthio, 2-methoxy-4-bromophenylthio, 4-ethyl-2-hydroxyphenylthio, 3-hydroxy-4-nitrophenylthio, 2-hydroxy-4-chlorophenylthio, and the corresponding sulfoxide and sulfone analogs thereof.

A preferred group of examples of the group

include: 4-(carboxymethyl)-5-methyl-1,3-thiazol-2-ylthio, 4-(carboxymethyl)-5-methyl-1,3-thiazol-2-ylthio sodium salt, 1,3,4-triazol-5-ylthio, 2-methyl-1,3,4-triazol-5-ylthio, 1H-tetrazol-5-ylthio, 1-methyl-1H-tetrazol-5-ylthio, 1-(1-(dimethylamino)eth-2-ylthio)-1H-tetrazol-5-ylthio, 1-(carboxymethyl)-1H-tetrazol-5-ylthio, 1-(carboxymethyl)-1H-tetrazol-5-ylthio sodium salt, 1-(methylsulfonic acid)-1H-tetrazol-5-ylthio, 1-(methylsulfonic acid)-1H-tetrazol-5-ylthio sodium salt, 1,2,3-triazol-5-ylthio, 1,4,5,6-tetrahydro-5,6-dioxo-4-methyl-as-triazin-3-ylthio, 1,4,5,6-tetrahydro-4-(formylmethyl)-5,6-dioxo-as-triazin-3-ylthio, 2,5-dihydro-5-oxo-6-hydroxy-2-methyl-as-triazin-3-ylthio sodium salt, 2,5-dihydro-5-oxo-6-hydroxy-2-methyl-as-triazin-3-ylthio, tetrazolo[1,5-b]pyridazin-6-ylthio, 8-aminotetrazolo[1,5-b]pyridazin-6-ylthio, methylthio, phenylthio, phenylsulfonyl, methylsulfonyl, methylsulfoxide, and phenylsulfoxide.

Among the groups above which comprise many of the possibilities for the group

the most preferred is methylsulfonyl.

In the above Formula I, $R_1$ or $R_2$ can be an acyl group of the formula

Examples of such a group include when $R_8$ is: hydrogen (the formyl group); $C_1$ to $C_6$ alkyl, such as acetyl, propionyl, sec-butylcarbonyl, t-amylcarbonyl and the like; $C_1$ to $C_6$ substituted alkyl, such as monofluoroacetyl, (3-cyanopropyl)carbonyl, 4,5-dichloroamylcarbonyl, 2-carboxy-1-nitroethylcarbonyl and the like; phenyl (the benzoyl group); substituted phenyl, for example, 4-methoxybenzoyl, 2,4-dimethylbenzoyl, 3-nitrobenzoyl, 4-trifluoromethylbenzoyl, 2,4-di(alkyloxycarbonyl)benzoyl, 2-(aminomethyl)benzoyl, 3-hydroxy-4-nitrobenzoyl, and the like; $C_7$ to $C_{12}$ arylalkyl, such phenylmethylcarbonyl, 2-phenylethylcarbonyl, phenyl(t-butyl)carbonyl, 3-phenylamylcarbonyl and the like; trihalomethyl, such as trifluoroacetyl, trichloroacetyl, tribromoacetyl or triiodoacetyl; $C_7$ to $C_{12}$ substituted arylalkyl, such as 3-(3,4-diiodophenyl)propylcarbonyl, 1-(3-chloro-4-fluorophenyl)ethylcarbonyl, 6-(4-cyanophenyl)hexylcarbonyl, 3-phenyl-1-chloro(sec-butyl)carbonyl, 2-phenyl-2-hydroxyethylcarbonyl, 5-phenyl-2-hydroxyamylcarbonyl, 2-(3-nitrophenyl)-3-ethoxypropylcarbonyl, 5,6-dihydroxy-2-(4-ethyl-2-hydroxyphenyl)hexylcarbonyl, 5-carbamoyl-3-nitro-2-(2,4-dimethoxyphenyl)amylcarbonyl and the like; perfluoro $C_2$ to $C_4$ alkyl, such as perfluoropropionyl, perfluorobutyryl, perfluoropentanoyl, and the like; amino (the primary amido group); (monosubstituted)amino, such as N-methylamido, N-ethylamido, N-(iso-propyl)amido, N-(n-hexyl)amido, N-phenylamido, N-(4-chlorophenyl)amido, N-(2-hydroxy-4-bromophenyl)amido, N-benzylamido, N-(2-phenyl(n-propyl))amido, and the like; and (disubstituted)amino, such as N,N-dimethylamido, N,N-methylphenylamido, N,N-(phenyl)(phenethyl)amido, N,N-ethyl-4-cyanophenyl)amido, N,N-dibenzylamido, N,N-methylethylamido, N,N-methylbenzylamido, and the like.

A preferred group of examples of the acyl group formed with $R_8$ is the acetyl, monofluoroacetyl, propionyl, benzoyl, N-methylamido, N-phenylamido, trifluoroacetyl, trichloroacety, tribromoacetyl, and triiodoacetyl groups.

When $R_1$ or $R_2$ in the above Formula I is a carboxyl group of the formula

examples include groups when $R_9$ is: $C_1$ to $C_6$ alkyl, such as ethoxycarbonyl, n-propoxycarbonyl, sec-butoxycarbonyl, t-amyloxycarbonyl and the like; $C_1$ to $C_6$ substituted alkyl, such as (3-cyanopropyloxy)carbonyl, 4,5-dichloroamyloxycarbonyl, 2-carboxy-1-nitroethoxycarbonyl, and the like; phenyl (the phenoxycarbonyl group), substituted phenyl, for example, 4-methoxyphenoxycarbonyl, 2,4-dimethylphenoxycarbonyl, 3-nitrophenoxycarbonyl, 4-trifluoromethylphenoxycarbony, 2,4-di(methoxycarbonyl)phenoxycarbonyl, 2-(aminomethyl)phenoxycarbonyl, 3-hydroxy-4-nitrophenoxycarbonyl, and the like; $C_7$ to $C_{12}$ arylalkyl, such benzyloxycarbonyl, 2-phenylethoxycarbonyl, phenyl(t-butoxy)carbonyl, 3-phenylamyloxycarbonyl and the like; trihalomethyl, such as trifluoromethoxycarbonyl, trichloromethoxycarbonyl, tribromomethoxycarbonyl or triiodomethoxycarbonyl; or $C_7$ to $C_{12}$ substituted arylalkyl, such as 3-(3,4-diiodophenyl)propoxycarbonyl, 1-(3-chloro-4-fluorophenyl)ethoxycarbonyl, 6-(4-cyanophenyl)hexyloxycarbonyl, 3-phenyl-1-chloro(sec-butoxy)carbonyl, 2-phenyl-2-hydroxyethoxycarbonyl, 5-phenyl-2-hydroxyamyloxycarbonyl, 2-(3-nitrophenyl)-3-ethoxypropoxycarbonyl, 5,6-dihydroxy-2-(4-ethyl-2-hydroxyphenyl)-hexyloxycarbonyl, and 5-carbamoyl-3-nitro-(2,4-dimethoxyphenyl)amyloxycarbonyl, and the like.

Further examples of the above —COOR$_9$ group are when R$_9$ is: an organic or inorganic cation, such as ammonium Carboxylate, procaine carboxylate, (phenylethylbenzylammonium) carboxylate, phenylglycine carboxylate, lysine carboxylate, lithium carboxylate, potassium carboxylate, sodium carboxylate and the like; a carboxyprotecting group, such as allyl carboxylate, p-methoxybenzyl carboxylate, di-(4-methoxy)benzhydryl carboxylate, benzhydryl carboxylate, 2,2,2-trichloroethyl carboxylate, trimethylsilyl carboxylate, (t-butyl)dimethylsilyl carboxylate, β-(trimethylsilyl)ethyl carboxylate, trityl carboxylate, 4,4',4"-trimethoxytrityl carboxylate, p-toluenesulfonylethyl carboxyate, and the like; a nontoxic, metabolically-labile ester-forming group, such as methoxymethyl carboxylate, 5-methyl-2-oxo-1,3-dioxolen-4-ylmethyl carboxylate, ethylthiomethyl carboxylate, pivaloyloxymethyl carboxylate, 3-phthalidyl carboxylate, 1-(ethoxycarbonyloxy)ethyl carboxylate, 1-(methylaminocarbonyloxy)ethyl carboxylate and the like.

A preferred group of examples of the carboxy group —COOR$_9$ is when R$_9$ is a C$_1$ to C$_6$ alkyl group, a carboxy-protecting group, hydrogen or an organic or inorganic cation. An especially preferred group of examples of the above carboxy group is when R$_9$ is methyl, ethyl, n-propyl, benzyl, hydrogen, allyl, t-butyl, 4-nitrobenzyl, or sodium.

Examples of the group —COOR$_{15}$ are given above in conjunction with the carboxy group —COOR$_9$.

A preferred group of examples of the group —COOR$_{15}$ occurs when R$_{15}$ is a C$_1$ to C$_6$ alkyl group. An especially preferred carboxyl group of the above formula is ethyl carboxylate.

In the above Formula I, R$_1$ and R$_2$ can be a carboxy group of the formula

—COOR$_{14}$.

Examples of this group includes groups wherein R$_{14}$ is: hydrogen (the carboxylic acid); an organic or inorganic cation, such as ammonium carboxylate, procaine carboxylate, phenylethylbenzylammonium carboxylate, phenylglycine carboxylate, lysine carboxylate, lithium carboxylate, potassium carboxylate, sodium carboxylate and the like; a carboxy-protecting group, such as methyl carboxylate, allyl carboxylate, 4-methoxybenzyl carboxylate, di-(4-methoxy)benzhydryl carboxylate, benzhydryl carboxylate, 2,2,2-trichloroethyl carboxylate, trimethylsilyl carboxylate, (t-butyl)dimethylsilyl carboxylate, β-(trimethylsilyl)ethyl carboxylate, trityl carboxylate, 4,4',4"-trimethoxytrityl carboxylate, 4-toluenesulfonylethyl carboxylate, and the like; a nontoxic, metabolically-labile ester-forming group, such as methoxymethyl carboxylate, 5-methyl-2-oxo-1,3-dioxolen-4-ylmethyl carboxylate, ethylthiomethyl carboxylate, pivaloyloxymethyl carboxylate, 3-phthalidyl carboxylate, 1-(ethoxycarbonyloxy)ethyl carboxylate, 1-(methylaminocarbonyloxy)ethyl carboxylate and the like.

A preferred group of examples of the carboxyl group —COOR$_{14}$ occurs when R$_{14}$ hydrogen, allyl, t-butyl, 4-nitrobenzyl or sodium.

Examples of the phosphonato group

—PO$_3$(R$_{10}$)$_2$ includes groups wherein R$_{10}$ is hydrogen (the phosphonic acid moiety); and an organic or inorganic cation, such as disodium phosphonato, dipotassium phosphonato, diammonium phosphonato, and like groups; groups wherein each R$_{10}$ is a C$_1$ to C$_6$ alkyl group, such as dimethylphosphonato, diethylphosphonato, methylethylphosphonato, methyl(iso-propyl)phosphonato, amylhexylphosphonato, dihexylphosphonato and the like; groups wherein each R$_{10}$ is a C$_1$ to C$_6$ substituted alkyl group, such as di(2-nitroethyl)phosphonato, (4-chlorobutyl)(2-carboxyethyl)phosphonato, (3-aminoamyl)(aminomethyl)phosphonato, (2-hydroxyethyl)(2-carbamoylethyl)phosphonato, (3-carbamoyloxypropyl)(2-carbamoyloxypropyl)phosphonato, (3-chlorobutyl)(2-bromobutyl)phosphonato and like groups; groups when R$_{10}$ is phenyl, (the diphenylphosphonato group); groups wherein each R$_{10}$ group is substituted phenyl, for example, di(4-methoxyphenyl)phosphonato, (4-methoxyphenyl)(2-methoxyphenyl)phosphonato, (3-cyanophenyl)(3-nitrophenyl)phosphonato, (3-chlorophenyl)(2,4-dimethylphenyl)phosphonato, (3-aminophenyl)(2,4-diaminophenyl)phosphonato, di(2,4-dimethoxyphenyl)phosphonato, (2,4-methylphenyl)(2,4-methoxyphenyl)phosphonato, (3,5-dinitrophenyl)(2,4-aminophenyl)phosphonato and the like; groups wherein each R$_{10}$ is a C$_7$ to C$_{12}$ arylalkyl radical, such as di(benzyl)phosphonato, di(2-phenylethyl)phosphonato, benzyl(2-phenylethyl)phosphonato, 3-phenylhexyl(phenyl t-butyl)phosphonato and the like; groups wherein each R$_{10}$ is a C$_7$ to C$_{12}$ substituted arylalkyl radical, such as di(4-methoxyphenylmethyl)phosphonato, di(3-phenyl- 2-hydroxypropyl)phosphonato di(3-(4-methylphenyl)-4-aminobutyl)phosphonato, (5-(4-cyanophenyl)amyl)(2-phenyl-2-carbamoylethyl)phosphonato, (2-(3,5-dinitrophenyl)ethyl)(2-(4-hydroxyphenyl)ethyl)phosphonato, (4-phenyl-3-aminobutyl)(4-phenyl-2-iodobutyl)phosphonato and like groups.

Furthermore, each of the R$_{10}$ variables of the above phosphonato group can be chosen from different groups of substituents. For example, one R$_{10}$ can be a C$_1$ to C$_6$ alkyl group while the other R$_{10}$ is hydrogen, an organic or inorganic cation, C$_1$ to C$_6$ substituted alkyl, phenyl, substituted phenyl, C$_7$ to C$_{12}$ arylalkyl or a C$_7$ to C$_{12}$ substituted arylalkyl group. Similarly, when one R$_{10}$ is a C$_1$ to C$_6$ substituted alkyl substituent group, the other R$_{10}$ can be hydrogen, an organic or inorganic cation, C$_1$ to C$_6$ alkyl, phenyl, substituted phenyl, C$_7$ to C$_{12}$ arylalkyl or a C$_7$ to C$_{12}$ substituted arylalkyl group.

A preferred group of phosphonato groups are the phosphonic acid, disodium phosphonato, dipotassium phosphonato, dimethylphosphonato, monomethylphosphonato, diethylphosphonato and diphenylphosphonato groups.

Examples of the group

—OR$_{11}$ include groups wherein R$_{11}$ is C$_1$ to C$_6$ alkyl, such as methoxy, ethoxy, n-propoxy, iso-propoxy, n-butoxy, sec-butoxy, tert-butoxy, amyloxy, tert-amyloxy, hexyloxy and the like; groups wherein R$_{11}$ is C$_1$ to C$_6$ substituted alkyl, such as cyanomethoxy, nitromethoxy, hydroxymethoxy, trityloxymethoxy, propionyloxymethoxy, aminomethyl, carboxymethoxy, allyloxycarbonylmethoxy, allyloxycarbonylaminomethoxy, carbamoyloxymethoxy, methoxymethoxy, ethoxymethoxy, t-butoxymethoxy, acetoxymethoxy, chloromethoxy, bromomethoxy, iodomethoxy, 6-hydroxyhexoxy, 2,4-dichloro(n-butoxy), 2-amino(iso-propoxy), 2-carbamoyloxyethoxy and the like; groups wherein R$_{11}$ is phenyl, (the phenoxy group); groups wherein $R_{11}$ is phenyl, substituted with one or two moieties chosen from the group consisting of halogen, hydroxy, protected hydroxy, cyano, nitro, $C_1$ to $C_6$ alkyl, $C_1$ to $C_4$ alkoxy, carboxy, protected carboxy, carboxymethyl, protected carboxymethyl, hydroxymethyl, protected hydroxymethyl, aminomethyl, protected aminomethyl, trifluoromethyl or N-(methylsulfonylamino); groups wherein $R_{11}$ is $C_7$ to $C_{12}$ arylalkyl, such as benzyloxy, 2-phenylethoxy, 3-phenyl(n-propoxy), 4-phenylhexoxy, 3-phenyl(n-amyloxy), or 3-phenyl(sec-butoxy); groups wherein $R_{11}$ is $C_7$ to $C_{12}$ substituted arylalkyl, (as that term is defined above), such as 2-phenyl-1-chloroethoxy, 2-(4-methoxyphenyl)ethoxy, 2,6-dihydroxy-4-phenyl(n-hexoxy), 5-cyano-3-methoxy-2-phenyl(n-pentoxy), 3-(2,6-dimethylphenyl)n-propoxy, 4-chloro-3-aminobenzoxy, 6-(4-methoxyphenyl)-3-carboxy(n-hexyloxy), 5-(4-aminomethylphenyl)-3-(aminomethyl)(n-pentoxy); or groups wherein $R_{11}$ is $C_1$ to $C_7$ acyl, such as formyloxy, acetoxy, n-propionyloxy, sec-butyryloxy, n-pentanoyloxy, n-hexanoyloxy, benzoyloxy, and the like. When $R_{11}$ is hydrogen, those skilled in the art will recognize that either the 3-hydroxy, or the 3-keto tautomer is represented, in addition to a tautomeric mixture.

Examples of the amino group $$-NR_{12}R_{13}$$

include the primary amino group (wherein $R_{12}$ and $R_{13}$ are hydrogen); the monosubstituted amino groups (wherein $R_{12}$ or $R_{13}$ is hydrogen and the other is: $C_1$ to $C_6$ alkyl (for example, the methylamino, ethylamino, iso-propylamino and n-hexylamino groups); $C_1$ to $C_6$ substituted alkyl (such as the cyanomethylamino, nitromethylamino, hydroxymethylamino, propionyloxymethylamino, carboxymethylamino, carbamoyloxymethylamino, methoxymethylamino, acetoxymethylamino, chloromethylamino, 6-hydroxyhexylamino, 2,4-dichloro(n-butyl)amino, or 2-amino(isopropylamino)); phenyl (the phenylamino group); substituted phenyl (such as 4-bromophenylamino, 3-hydroxyphenylamino, 4-carboxyphenylamino, 4-chloro-3-ethylphenylamino, 2-methylphenylamino, and the like); $C_7$ to $C_{12}$ arylalkyl (such as benzylamino, 2-phenylethylamino, 3-phenyl(n-propylamino), 4-phenylhexylamino, 3-phenyl(n-amylamino), and the like); $C_7$ to $C_{12}$ substituted arylalkyl (such as 2-phenyl-1-chloroethylamino, 2-(4-methoxyphenyl)ethylamino, 2,6-dihydroxy-4-phenyl(n-hexylamino), 5-cyano-3-methoxy-2-phenyl(n-pentylamino), 3-(2,6-dimethylphenyl)n-propylamino, 4-chloro-3-aminobenzylamino, 6-(4-methoxyphenyl)-3-carboxy(n-hexylamino), 5-(4-aminomethylphenyl)-3-(aminomethyl)(n-pentylamino), and the like); $C_1$ to $C_7$ acyl (such as N-(formamido), N-(acetamido), N-(propionylamino), N-(butyrylamino), N-(pentanoylamino), N-(hexanoylamino), N-(benzamido), and the like); or a group of the formula

(such as N-(methylcarbamato), N-(n-butylcarbamato), N-(ethylcarbamato), N-(isopropylcarbamato), N-(phenylcarbamato), N-(benzylcarbamato), N-((3-phenylbutyl)carbamato), N-((5-phenylhexyl)carbamato), and the like).

In addition, examples of the amino group $$-NR_{12}R_{13}$$

include the disubstituted amino groups wherein the substituents can be the same or different $C_1$ to $C_6$ alkyl, $C_1$ to $C_6$ substituted alkyl, phenyl, substituted phenyl, $C_7$ to $C_{12}$ aryalkyl, $C_7$ to $C_{12}$ substituted arylalkyl groups $C_1$ to $C_7$ acyl or a group of the formula

Specific examples of such disubstituted amino groups include dimethylamino, methyl(n-propyl)amino, di(hydroxymethyl)amino, (2-cyanoethyl)(3-chlorobutyl)amino, diphenylamino, (3-fluorophenyl)(2-ethylphenyl)amino, di(4-carboxyphenyl)amino, dibenzylamino, benzyl (3-phenylbutyl)amino, di(2-phenyl-1-chloroethyl)amino, [2-(4-methoxyphenyl)ethyl][4-chloro-3-benzyl]amino, methylphenylamino, (3-fluoropropyl)benzylamino, (2-ethylphenyl)phenylamino, di(formyl)amino, ethyl(acetyl)amino, phenyl(methoxycarbonyl)amino, (propionyl)(ethoxycarbonyl)amino, di(benzyloxycarbonyl)amino, [2-(4-methoxyphenyl)ethyl](propionyl)amino, and the like.

A preferred group of compounds of Formula I, referred to herein as "nucleus intermediate" compounds, occurs when $R_5$ and $R_6$ are (a) each hydrogen;

(b) are taken together and form a phthalimido group; or (c) different and either $R_5$ or $R_6$ is hydrogen and the other is an amino-protecting group; or a pharmaceutically-acceptable salt thereof.

A preferred group of nucleus intermediate compounds occurs when either $R_1$ or $R_2$ is a group of the formula $$-COOR_{14};$$

while the other is a group of the formula:

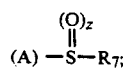

(B) $-PO_3(R_{10})_2$;

(C) hydrogen;

(D) $-COR_8$;

(E) $-CX_3$;

(F) $-COOR_9$;

(G) $C_1$ to $C_6$ substituted alkyl;

(H) phenyl or substituted phenyl;

(I) a heterocyclic ring; or (J) cyano.

A further preferred group of nucleus intermediate compounds has $R_3$ and $R_4$ as hydrogen and are referred to herein as the "4,4-unsubstituted nucleus intermediate" compounds. A preferred group of 4,4-unsubstituted nucleus intermediate compounds has $R_1$ as a group of the formula $$-COOR_{14};$$

and $R_2$ as a group of the formula:

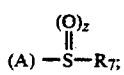

(A) —S—R7;

(B) —PO3(R10)2;
(C) hydrogen;
(D) —COR8;
(E) —CX3;
(F) —COOR9;
(G) substituted methyl;
(I) a heterocyclic ring; or
(J) cyano.

In a further preferred group of 4,4-unsubstituted nucleus intermediate compounds, $R_2$ is a group of the formula:

(A) hydrogen;

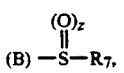

(B) —S—R7, wherein $R_7$ is $C_1$ to $C_6$ alkyl, $C_2$ to $C_7$ alkenyl, or phenyl;

(C) —PO3(R10)2, wherein $R_{10}$ is $C_1$ to $C_6$ alkyl or phenyl;

(D) —CX3 wherein X is fluoro or chloro;

(E) —COR8 wherein $R_8$ is $C_1$ to $C_6$ alkyl, $C_1$ to $C_6$ substituted alkyl, phenyl, substituted phenyl, or (monosubstituted)amino;

(F) —COOR9 wherein $R_9$ is hydrogen, an organic or inorganic cation, a carboxy-protecting group, a non-toxic, metabolically-labile ester-forming group, $C_1$ to $C_6$ alkyl or $C_1$ to $C_6$ substituted alkyl;

(G) substituted methyl, wherein the substituents are hydroxy, protected hydroxy or acetoxy;

(H) thienyl; or (I) cyano.

A more preferred group of 4,4-unsubstituted nucleus intermediate compounds occurs when $R_1$ is carboxy, or sodium, potassium, p-nitrobenzyl, t-butyl or allyl carboxylate, and $R_2$ is methylsulfonyl, phenylsulfonyl, phenylthio, methylthio, dimethylphosphonato, diethylphosphonato, hydrogen, acetyl, propionyl, monofluoroacetyl, N-methylamido, N-phenylamido, benzoyl, trifluoromethyl, methyl carboxylate, ethyl carboxylate, n-propyl carboxylate, benzyl carboxylate, carboxy, sodium, potassium, t-butyl or allyl carboxylate, hydroxymethyl, acetoxymethyl, 2-thienyl or cyano, and $R_5$ and $R_6$ are each hydrogen or the trifluoroacetate or hydrochloride salt of said compound, or either $R_5$ and $R_6$ is hydrogen and the other is trimethylsilyl, t-butoxycarbonyl or allyloxycarbonyl.

Examples of the above more preferred groups of 4,4-unsubstituted nucleus intermediate compounds are given below in Table 1.

TABLE 1

| $R_2$ | $R_{14}$ | $R_6$ |
|---|---|---|
| —COOH | hydrogen | hydrogen |
| —COOCH3 | t-butyl | t-Boc[1] |
| —COOCH3 | allyl | HCl[2] |
| —COOCH3 | allyl | hydrogen |
| —CO-phenyl | allyl | t-Boc |

TABLE 1-continued

| $R_2$ | $R_{14}$ | $R_6$ |
|---|---|---|
| —COCH3 | hydrogen | H[3] |
| —COCH3 | allyl | AOC[4] |
| —COCH3 | hydrogen | TFA[5] |
| —COCH3 | allyl | TMS[6] |
| —COCH3 | allyl | t-Boc |
| —COCH3 | t-butyl | t-Boc |
| —COOCH3 | allyl | HCl |
| —COCH3 | allyl | hydrogen |
| —COEt | allyl | t-Boc |
| —COEt | allyl | HCl |
| —COEt | allyl | hydrogen |
| —PO(OCH3)2 | allyl | t-Boc |
| —PO(OCH3)2 | t-butyl | t-Boc |
| —PO(OCH3)2 | hydrogen | TFA |
| —PO(OET)2 | allyl | t-Boc |
| —(OET)2 | t-butyl | t-Boc |
| —PO(OET)2 | sodium | t-Boc |
| —PO(OET)2 | allyl | AOC |
| hydrogen | t-butyl | t-Boc |
| hydrogen | hydrogen | TFA |
| —COO-allyl | allyl | t-Boc |
| —COO-(t-butyl) | t-butyl | t-Boc |
| —CN | allyl | t-Boc |
| —CN | allyl | HCl |
| —CN | allyl | hydrogen |
| —COOCH3 | H | H |
| —COOCH3 | H | TFA |
| —COOCH3 | allyl | t-Boc |
| —COOCH3 | allyl | AOC |
| —SCH3 | t-butyl | t-Boc |
| —SCH3 | H | H |
| —SCH3 | H | TFA |
| —SO2phenyl | pNB[7] | t-Boc |
| —SO2phenyl | H | TFA |
| —SO2phenyl | H | H |
| —SO2CH3 | H | t-Boc |
| —SO2CH3 | H | TFA |
| —SO2CH3 | pNB[7] | t-Boc |
| —CH2OH | allyl | t-Boc |
| —CH2OH | t-butyl | t-Boc |
| —CH2OH | H | H |
| —CH2OH | H | TFA |
| —CH2OAc | allyl | t-Boc |
| —CH2OAc | t-butyl | t-Boc |
| —CH2OAc | allyl | AOC |
| —CH2OAc | H | H |
| —CH2OAc | sodium | H |
| —CH2OAc | H | TFA |

[1] = t-butoxycarbonyl
[2] = indicates that $R_6$ is hydrogen, and that the compound is the hydrochloride salt thereof
[3] = also indicates the possibility of zwitteronic form with carboxylic acid on molecule
[4] = allyloxycarbonyl
[5] = indicates that $R_6$ is hydrogen, and that the compound is the trifluoroacetate salt thereof
[6] = trimethylsilyl
[7] = 4-nitrobenzyl A preferred group of 4,4-unsubstituted nucleus intermediate compounds discussed above in conjunction with the compounds of Table 1 include compounds wherein $R_{14}$ is hydrogen, sodium, potassium, p-nitrobenzyl, t-butyl or allyl and $R_2$ is acetyl, methyl carboxylate, hydroxymethyl, acetoxymethyl, methylsulfonyl, or cyano.

A second preferred group of nucleus intermediate compounds occurs $R_2$ is a group of the formula

—COOR14 and $R_1$ is a group of the formula:

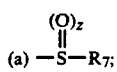

(b) —$COR_8$;
(c) —$COOR_9$, wherein $R_9$ is $C_1$ to $C_6$ alkyl, $C_1$ to $C_6$ substituted alkyl, $C_7$ to $C_{12}$ arylalkyl, $C_7$ to $C_{12}$ substituted arylalkyl, phenyl or substituted phenyl;
(d) phenyl or substituted phenyl;
(e) $C_1$ to $C_6$ substituted alkyl; or

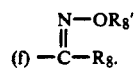

A preferred group of this second group of nucleus intermediate compounds is a group of 4,4-unsubstituted analogs (i.e. $R_3$ and $R_4$ are hydrogen) wherein is a group of the formula:

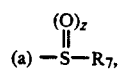

wherein $R_7$ is phenyl or substituted phenyl;
(b) —$COR_8$, wherein $R_8$ is phenyl, substituted phenyl or (monosubstituted)amino;
(c) —$COOR_9$, wherein $R_9$ is $C_1$ to $C_6$ alkyl or $C_1$ to $C_6$ substituted alkyl;
(d) phenyl or substituted phenyl; or
(e) substituted methyl, wherein the substituents are hydroxy, protected hydroxy or $C_1$ to $C_7$ acyloxy; and
$R_2$ is a group of the formula

—$COOR_{14}$ wherein $R_{14}$ is hydrogen, an organic or inorganic cation or a carboxy-protecting group.

A preferred group of the above 4,4-unsubstituted analogs occurs when $R_1$ is phenylthio, benzoyl, methoxycarbonyl, phenyl, N-methylamido, N-phenylamido, acetoxymethyl or hydroxymethyl;
$R_2$ is carboxy or sodium, potassium, t-butyl, methyl, or allyl carboxylate; and
$R_5$ and $R_6$ are: (1) both hydrogen, (or the trifluoroacetate salt or the hydrochloride salt of said compound); or (2) either $R_5$ or $R_6$ is hydrogen and the other is trimethylsilyl, t-butoxycarbonyl, or allyloxycarbonyl.

An especially preferred group of the above 4,4-unsubstituted nucleus intermediate compounds occurs when $R_1$ is methyl carboxylate, acetoxymethyl or hydroxymethyl.

Another preferred group of the above group of intermediate compounds occurs when $R_3$ and $R_4$ are each methyl, which are referred to herein as "4,4-dimethyl nucleus intermediate" compounds. A preferred group of these 4,4-dimethyl compounds occurs when $R_1$ and $R_2$ are the same or different, and either $R_1$ or $R_2$ is a group of the formula

—$COOR_{14}$;

and the other of $R_1$ or $R_2$ is a group of the formula

—$COOR_9$.

A further preferred group of 4,4-dimethyl nucleus intermediate compounds occurs when $R_1$ and $R_2$ are:
(A) the same and are carboxy, or sodium, potassium, t-butyl or allyl carboxylate; or
(B) different, wherein one either $R_1$ or $R_2$ is carboxy or sodium, potassium, t-butyl or allyl carboxylate, and the other of $R_1$ or $R_2$ is methoxycarbonyl.

Within the above group of further preferred 4,4-dimethyl nucleus intermediate compounds are two groups of more preferred compounds. The first group occurs when R is carboxy or sodium, potassium, t-butyl or allyl carboxylate, $R_2$ is carboxy or sodium, potassium, t-butyl, allyl or methyl carboxylate, and (1) $R_5$ and $R_6$ are each hydrogen, (or a trifluoroacetate salt of said compound); or (2) either $R_5$ or $R_6$ is hydrogen and the other is t-butoxycarbonyl, trimethylsilyl or allyloxycarbonyl.

The second group of more preferred 4,4-dimethyl nucleus intermediate compounds occurs when $R_1$ is methyl carboxylate, $R_2$ is carboxy or sodium, potassium, t-butyl or allyl carboxylate, and (1) $R_5$ and $R_6$ are each hydrogen, (or a trifluoroacetate salt of said compound); or (2) either $R_5$ or $R_6$ is hydrogen and the other of $R_5$ or $R_6$ is trimethylsilyl, t-butoxycarbonyl or allyloxycarbonyl.

Another preferred group of the compounds of Formula I is when either $R_5$ or $R_6$ is hydrogen and the other of $R_5$ or $R_6$ is a group of the formula —$COR_{16}$. Such compounds are referred to as the "7-acylamino" compounds. One preferred group of 7-acylamino compounds is the oximino acylamino compounds and occurs when $R_{16}$ is a group of the formula

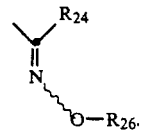

A preferred group of oximino 7-acylamino compounds is the 4,4-unsubstituted oximino 7-acylamino compounds, wherein $R_3$ and $R_4$ are hydrogen. Examples of the 4,4-unsubstituted oximino 7-acylamino compounds includes compounds wherein:
(I) $R_1$ or $R_2$ is a group of the formula

—$COOR_{14}$ and the other is a group of the formula:

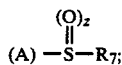

(B) —$PO_3(R_{10})_2$;
(C) hydrogen;
(D) —$COR_8$;
(E) —$CX_3$;
(F) a group of the formula

—$COOR_9$;

(G) $C_1$ to $C_6$ substituted alkyl;
(H) phenyl;
(I) a heterocyclic ring;
(J) cyano; or

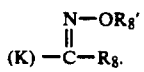

A further specific group of 4,4-unsubstituted oximino 7-acylamino compounds encompasses compounds wherein $R_{24}$ is phenyl, p-(O-(homoserine))phenyl, thien-2-yl, fur-2-yl, 2-aminothiazol-4-yl, 2-(protected amino)thiazol-4-yl, 5-amino-1,2,4-thiadiazol-3-yl, 5-(protected amino)-1,2,4-thiadiazol-3-yl, 4-aminopyridin-2-yl, 4-(protected amino)pyridin-2-yl, 2-aminopyridin-6-yl, 2-(protected amino)pyridin-6-yl, 2-aminopyridin-5-yl, 2-(protected amino)pyridin-5-yl, 2-aminopyridin-4-yl, 2-(protected amino)pyridin-4-yl, 2-aminopyrimidin-4-yl, 2-(protected amino)pyrimidin-4-yl, 4-aminopyrimidin-2-yl, 4-(protected amino)-pyrimidin-2-yl and $R_{26}$ is hydrogen, methyl, ethyl, propyl, 2-carboxyisopropyl, 2-(protected carboxy)isopropyl, carboxymethyl, (protected carboxy)methyl, cyclopropyl, cyclobutyl, cyclopentyl, vinyl, allyl, 2-butene-1-yl, 3-butene-1-yl, benzyl, 2,5-dichlorobenzyl, phenyl, 4-fluorophenyl, 4-chlorophenyl, 3-(trifluoromethyl)phenyl, 3-(ethoxycarbonyl)phenyl, 2-methylphenyl, 4-methylphenyl, 3,4-dichlorophenyl, or 2,4-dichlorophenyl; or a pharmaceutically-acceptable salt thereof.

The above specific group of 4,4-unsubstituted oximino 7-acylamino compounds embraces a preferred group of compounds wherein $R_1$ is a group of the formula

—COOR$_{14}$;

and $R_2$ is a group of the formula:

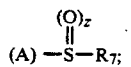

(B) —PO$_3$(R$_{10}$)$_2$;
(C) hydrogen;
(D) —COR$_8$;
(E) —CX$_3$;
(F) —COOR$_9$;

(G) C$_1$ to C$_6$ substituted alkyl;
(H) phenyl;
(I) a heterocyclic ring; or
(J) cyano.

A more preferred group of the above preferred group occurs when $R_2$ is a group of the formula (A) hydrogen,

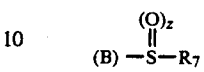

wherein $R_7$ is C$_1$ to C$_6$ alkyl or phenyl;
(C) —PO$_3$(R$_{10}$)$_2$
wherein $R_{10}$ is C$_1$ to C$_6$ alkyl or phenyl;
(D) —CX$_3$
wherein X is fluoro or chloro;
(E) —COR$_8$
wherein $R_8$ is C$_1$ to C$_6$ alkyl, C$_1$ to C$_6$ substituted alkyl, phenyl, substituted phenyl or (monosubstituted amino);
(F) —COOR$_9$
wherein $R_9$ is hydrogen, an organic or inorganic cation, C$_1$ to C$_6$ alkyl, C$_1$ to C$_6$ substituted alkyl, a carboxy-protecting group or a non-toxic, metabolically-labile, ester-forming group;
(G) substituted methyl;
(H) thienyl; or
(I) cyano.

Further preferred compounds with the above group have $R_1$ as carboxyl or sodium, potassium, t-butyl, p-nitrobenzyl or allyl carboxylate and $R_2$ as dimethylphosphonato, diethylphosphonato, methylthio, phenylthio, methylsulfonyl, phenylsulfonyl, hydrogen, acetyl, monofluoroacetyl, propionyl, N-methylamido, N-phenylamido, benzoyl, trifluoromethyl, carboxy or sodium, potassium, methyl, ethyl, n-propyl, benzyl, t-butyl or allyl carboxylate, hydroxymethyl, acetoxymethyl 2-thienyl, or cyano. Examples of this group of further preferred compounds, wherein $R_{24}$ is 2-aminothiazol-4-yl, 2-(protected amino)thiazol-4-yl, 5-amino-1,2,4-thiadiazol-3-yl, 5-(protected amino)-1,2,4-thiadiazol-3-yl or 2-furyl, and $R_{26}$ is methyl, carboxymethyl, 2,5-dichlorobenzyl, (protected carboxy)methyl, 2-carboxyprop-2-yl or 2-(protected carboxy)prop-2-yl, or a pharmaceutically-acceptable salt thereof, are given below in Table 2.

TABLE 2

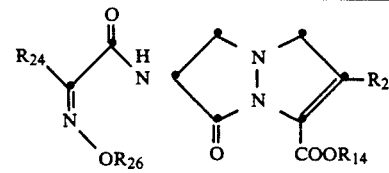

| R$_2$ | R$_{14}$ | R$_{24}$ | R$_{26}$ |
|---|---|---|---|
| —COCH$_3$ | allyl | 2-(AOC$^1$-amino)thiazol-4-yl | methyl |
| —COCH$_3$ | H | 2-aminothiazol-4-yl | methyl |
| —COCH$_3$ | sodium | 2-aminothiazol-4-yl | methyl |
| —COCH$_3$ | t-butyl | 2-(t-Boc$^2$ amino)thiazol-4-yl | methyl |
| —COCH$_3$ | H | 5-amino-1,2,4-thiadiazol-3-yl | methyl |
| —COCH$_3$ | potassium | 5-amino-1,2,4-thiadiazol-3-yl | methyl |
| —COCH$_3$ | t-butyl | 5-(t-Boc amino)-1,2,4-thiadiazol-3yl | methyl |
| —COCH$_3$ | allyl | 2-furyl | methyl |
| —COCH$_3$ | H | 2-furyl | methyl |
| —CH$_2$OAc | sodium | 2-aminothiazol-4-yl | 2-carboxyprop-2-yl, sodium salt |
| —CH$_2$OAc | sodium | 2-furyl | 2-carboxyprop-2-yl, sodium salt |
| —CH$_2$OAc | sodium | 5-amino-1,2,4-thiadiazol-3-yl | 2-carboxyprop-2-yl, sodium salt |
| —SCH$_3$ | potassium | 2-aminothiazol-4-yl | 2-carboxyprop-2-yl, potassium salt |
| —SCH$_3$ | allyl | 2-furyl | carboxymethyl |

TABLE 2-continued

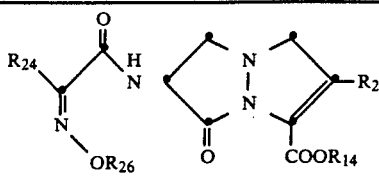

| R$_2$ | R$_{14}$ | R$_{24}$ | R$_{26}$ |
|---|---|---|---|
| —S-phenyl | t-butyl | 5-(AOC-amino)-1,2,4-thiadiazol-3-yl | carboxymethyl |
| —S-phenyl | sodium | 2-aminothiazol-4-yl | methyl |
| phenyl-sulfonyl | allyl | 2-furyl | 2-(allyloxycarbonyl)-prop-2-yl |
| phenyl-sulfonyl | hydrogen | 5-amino-1,2,4-thiadiazol-3-yl | methyl |
| dimethyl-phosphonato | t-butyl | 2-furyl | methyl |
| dimethyl-phosphonato | sodium | 2-aminothiazol-4-yl | carboxymethyl, sodium salt |
| diethyl-phosphonato | allyl | 5-amino-1,2,4-thiadiazol-3-yl | methyl |
| diethyl-phosphonato | sodium | 2-furyl | methyl |
| hydrogen | potassium | 2-aminothiazol-4-yl | carboxymethyl, potassium salt |
| hydrogen | allyl | 2-(AOC-amino)thiazol-4-yl | methyl |
| benzoyl | allyl | 2-(AOC-amino)thiazol-4-yl | 2-(allyloxycarbonyl)-prop-2-yl |
| benzoyl | hydrogen | 5-amino-1,2,4-thiadiazol-3-yl | carboxymethyl |
| trifluoro-methyl | hydrogen | 5-amino-1,2,4-thiadiazol-3-yl | 2-carboxyprop-2-yl |
| trifluoro-methyl | t-butyl | 2-furyl | methyl |
| methyl carboxylate | allyl | 2-(AOC-amino)thiazol-4-yl | methyl |
| methyl carboxylate | sodium | 2-aminothiazol-4-yl | methyl |
| methyl carboxylate | sodium 2-furyl | 2-carboxyprop-2-yl, sodium salt | |
| methyl carboxylate | sodium | 5-amino-1,2,4-thiadiazol-3-yl | carboxymethyl, sodium salt |
| allyl carboxylate | allyl | 2-(AOC-amino)thiazol-4-yl | methyl |
| sodium carboxylate | sodium | 2-aminothiazol-4-yl | methyl |
| CN | sodium | 2-furyl | methyl |
| CN | t-butyl | 2-furyl | methyl |
| CN | sodium | 2-aminothiazol-4-yl | carboxymethyl, sodium salt |
| CN | sodium | 5-amino-1,2,4-thiadiazol-3-yl | carboxymethyl, sodium salt |
| CN | sodium | 2-furyl | carboxymethyl, sodium salt |
| CN | sodium | 2-furyl | 2-carboxyprop-2-yl, sodium salt |
| CN | sodium | 5-amino-1,2,4-thiadiazol-3-yl | 2-carboxyprop-2-yl, sodium salt |
| CN | sodium | 2-aminothiazol-4-yl | 2-carboxyprop-2-yl, sodium salt |
| SO$_2$CH$_3$ | allyl | 2-(AOC-amino)thiazol-4-yl | methyl |
| SO$_2$CH$_3$ | H | 2-aminothiazol-4-yl | methyl |
| SO$_2$CH$_3$ | sodium | 2-aminothiazol-4-yl | methyl |
| SO$_2$CH$_3$ | t-butyl | 2-(t-Boc amino)thiazol-4-yl | methyl |
| SO$_2$CH$_3$ | H | 5-amino-1,2,4-thiadiazol-3-yl | methyl |
| SO$_2$CH$_3$ | potassium | 5-amino-1,2,4-thiadiazol-3-yl | methyl |
| SO$_2$CH$_3$ | t-butyl | 5-(t-Boc amino)-1,2,4-thiadiazol-3-yl | methyl |
| SO$_2$CH$_3$ | H | 2-aminothiazol-4-yl | vinyl |
| SO$_2$CH$_3$ | H | 2-aminothiazol-4-yl | allyl |
| SO$_2$CH$_3$ | H | 2-aminothiazol-4-yl | 2-butene-1-yl |
| SO$_2$CH$_3$ | H | 2-aminothiazol-4-yl | 3-butene-1-yl |
| SO$_2$CH$_3$ | sodium | 2-aminothiazol-4-yl | 3-butene-1-yl |
| SO$_2$CH$_3$ | potassium | 2-aminothiazol-4-yl | 3-butene-1-yl |

[1]AOC = allyloxycarbonyl
[2]t-Boc = t-butoxycarbonyl

A group of compounds of particular note within the above Table of Examples occurs when R$_2$ is either methylsulfonyl, acetyl, methyl carboxylate, propionyl, or cyano, R$_{26}$ is methyl, 2-butene-1-yl, or 3-butene-1-yl, R$_{24}$ is 2-aminothiazol-4-yl, 2-(allyloxycarbonylamino)-thiazol-4-yl, 2-(t-butoxycarbonylamino)thiazol-4-yl, or the hydrochloride salt of 2-aminothiazol-4-yl. Furthermore, additional compounds within this group occur when R$_2$ is acetyl, R$_{24}$ is 2-aminothiazol-4-yl, 2-(allyloxycarbonylamino)thiazol-4-yl, 2-(t-butoxycarbonylamino)thiazol-4-yl, 2-(tritylamino)thiazol-4-yl or 2-aminothiazol-4-yl hydrochloride salt and R$_{26}$ is (a) 2,5-dichlorobenzyl or (b) 2-(t-butyl carboxylate)prop-2-yl or 2-(carboxy)prop-2-yl, or a pharmaceutically-acceptable salt of the latter.

Another preferred group of oximino 7-acylamino compounds are the 4,4-dimethyl oximino 7-acylamino compounds (wherein R$_2$ and R$_4$ are methyl). Examples of the 4,4-dimethyl oximino 7-acylamino compounds include compounds wherein $R_1$ and $R_2$ are:

(A) the same and are carboxy or sodium, potassium, t-butyl or allyl carboxylate; or (B) different, wherein R is carboxy or sodium, potassium, t-butyl or allyl carboxylate and $R_2$ is methyl carboxylate (methoxycarbonyl). A preferred group of 4,4-dimethyl oximino 7-acylamino compounds occurs when $R_{24}$ is 2-aminothiazol-4-yl, 2-(allyloxycarbonylamino)thiazol-4-yl, 2-(t-butoxycarbonylamino)thiazol-4-yl or 2-aminothiazol-4-yl hydrochloride salt and $R_{26}$ is methyl.

Another preferred group of 7-acylamino compounds of Formula I is the aryl 7-acylamino compounds, wherein $R_3$ and $R_4$ are hydrogen and $R_{16}$ is a group of the formula

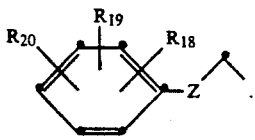

A preferred group of the aryl 7-acylamino compounds is when $R_1$ is carboxy or sodium, allyl or p-nitrobenzyl carboxylate and $R_2$ is phenylsulfonyl, dimethylphosphonato, acetyl, or methyl carboxylate (methoxycarbonyl), and especially when $R_{16}$ is a group of the formula

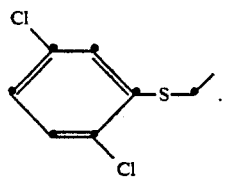

Another preferred group of 7-acylamino compounds of Formula I is the heteroaryl 7-acylamino compounds, wherein $R_{16}$ is a group of the formula

Examples of the above heteroaryl 7-acylamino compounds include the 4,4-unsubstituted compounds when $R_3$ and $R_4$ are hydrogen occurs when $R_1$ is carboxy or sodium or allyl carboxylate and $R_2$ is carboxy or sodium, allyl or methyl carboxylate.

A more preferred group of the 4,4-unsubstituted compounds has $R_{16}$ as a group of the formula

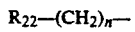

wherein $R_{22}$ is thien-2-yl and n is one.

A second preferred group of 4,4-unsubstituted heteroaryl 7-acylamino compounds occurs when $R_1$ is phenyl, $R_2$ is carboxy, sodium carboxylate or allyl carboxylate, and especially so when $R_{22}$ is 2-thienyl and n is one (i.e., when $R_{16}$ is a 2-thienylmethyl group).

Another group of examples of the above heteroaryl 7-acyl are the 4,4-dimethyl heteroaryl 7-acylamino compounds (i.e., $R_3$ and $R_4$ are each methyl). A preferred group of these 4,4-dimethyl compounds occurs when $R_1$ and $R_2$ are the same and are carboxy, sodium carboxylate or allyl carboxylate. An especially preferred group occurs when $R_{22}$ is 2-thienyl and n is one (i.e., when $R_{16}$ is a 2-thienylmethyl group).

Above all, a preferred class of compounds within those defined by Formula I have the 7-(S) configuration represented by the formula:

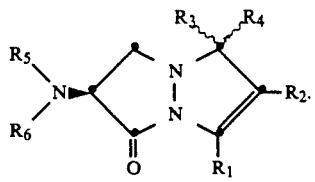

A preferred group of 7-(S) bicyclic pyrazolidinone compounds are the 7-(S) nucleus compounds, and thus have (1) $R_5$ and $R_6$ as hydrogen; or (2) either $R_5$ or $R_6$ as hydrogen and the other as an amino-protecting group; or a pharmaceutically-acceptable salt of the resultant compounds. A more preferred group of 7-(S) nucleus compounds sets $R_1$ as a group of the formula

and $R_2$ as either cyano, a group of the formula

a group of the formula

or a group of the formula

$R_3$ and $R_4$ are hydrogen. This more preferred group of compounds are also referred to as 4,4-unsubstituted 7-(S) nucleus compounds.

A preferred group of 4,4-unsubstituted 7-(S) nucleus compounds occurs where $R_8$ and $R_9$ are each methyl, and especially so when $R_{14}$ is hydrogen, sodium or allyl.

A most preferred group of 4,4-unsubstituted 7-(S) nucleus compounds have $R_2$ as a cyano group ("3-cyano" compounds) or $R_2$ as a methylsulfonyl group. The most interesting 3-cyano-4,4-unsubstituted 7-(S) nucleus compounds have $R_{14}$ as an allyl group, and (a) $R_5$ and $R_6$ are each hydrogen, or the hydrochloride or trifluoroacetate salt thereof; or (b) either $R_5$ or $R_6$ is hydrogen and the other is t-butoxycarbonyl.

A second preferred group of 7-(S) bicyclic pyrazolidinone compounds are the 7-(S) acyl compounds, wherein either $R_5$ or $R_6$ is hydrogen and the other is an acyl group of the formula

A preferred group of 7-(S) acyl compounds are the 7-(S) oximino acyl compounds, wherein $R_{16}$ is a group of the formula

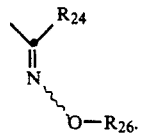

A preferred group of 7-(S) oximino acyl compounds has $R_1$ as a group of the formula $COOR_{14}$, $R_2$ as either cyano, a group of the formula

a group of the formula

—$COR_8$, or as a group of the formula

—$COOR_4$; and $R_3$ and $R_4$ as hydrogen, or a pharmaceutically-acceptable salt thereof. This latter group of compounds is also referred to as the 4,4-unsubstituted 7-(S) oximino acyl compounds, of which group there exists a preferred group wherein:

$R_{24}$ is phenyl, p-(O-(homoserine))phenyl, thien-2-yl, fur-2-yl, 2-aminothiazol-4-yl, 2-(protected amino)-thiazol-4-yl, 5-amino-1,2,4-thiadiazol-3-yl, 5-(protected amino)-1,2,4-thiadiazol-3-yl, 4-aminopyridin-2-yl, 4-(protected amino)pyridin-2-yl, 2-aminopyridin-6-yl, 2-(protected amino)pyridin-6-yl, 2-aminopyridin-5-yl, 2-(protected amino)pyridin-5-yl, 2-aminopyridin-4-yl, 2-(protected amino)pyridin-4-yl, 2-aminopyrimidin-4-yl, 2-(protected amino)pyrimidin-4-yl, 4-aminopyrimidin-2-yl, or 4-(protected amino)pyrimidin-2-yl, and $R_{26}$ is hydrogen, methyl, ethyl, propyl, 2-carboxyisopropyl, 2-(protected carboxy)isopropyl, carboxymethyl, (protected carboxy)methyl, cyclopropyl, cyclobutyl, cyclopentyl, 2,5-dichlorobenzyl, benzyl, phenyl, 4-fluorophenyl, 4-chlorophenyl, 3-(trifluoromethyl)phenyl, 3-(ethoxycarbonyl)phenyl, 2-methylphenyl, 4-methylphenyl, 3,4-dichlorophenyl, or 2,4-dichlorophenyl; or a pharmaceutically-acceptable salt thereof.

A more preferred group of 4,4-unsubstituted 7-(S) oximino acyl compounds has both $R_5$ and $R_6$ as methyl, and especially so when the oximino functionality is the Z isomer of the formula

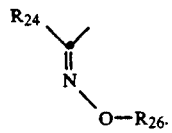

A preferred group of this latter group of 7-(S) (Z)-oximino acyl compounds sets $R_{24}$ as 2-aminothiazol-4-yl or 2-(protected amino)thiazol-4-yl and $R_{26}$ as methyl or 3-butene-1-yl.

Finally, there are three preferred sub-groups of compounds within the above preferred group of 7-(S) (Z)-oximino acyl compounds. These three subgroups occur when $R_2$ is either cyano, acetyl or methyl carboxylate (methoxycarbonyl), respectively. Each one of these subgroups harbors a highly preferred group of compounds, which have $R_{14}$ as hydrogen, sodium or allyl, and $R_{24}$ as 2-aminothiazol-4-yl, 2-(allyloxycarbonylamino)thiazol-4-yl or 2-aminothiazol-4-yl hydrochloride salt.

Further definitions of terms used in the claims, especially regarding those claims concerning pharmaceutical compositions and methods, are found in succeeding parts of the application.

II. SYNTHESIS OF THE COMPOUNDS OF FORMULA I AND THE REQUISITE STARTING MATERIALS

The bicyclic pyrazolidinones of Formula I are prepared by six different routes. Two of these routes are 1,3-dipolar cycloaddition reactions. In the first route, a substituted acetylene moiety is reacted with a 1,3-dipole ("ylide") to give the 2,3-unsaturated bicyclic pyrazolidinone ring system. The second method involves the reaction of a substituted ethylene moiety with an ylide to give the 2,3-saturated pyrazolidinone ring system. The 2,3-saturated system is then reacted with a non-nucleophilic base to give the 2,3-unsaturated system.

The first type of cycloaddition reaction, (i.e., reaction of an ylide with a substituted acetylene) is represented below by Scheme 1:

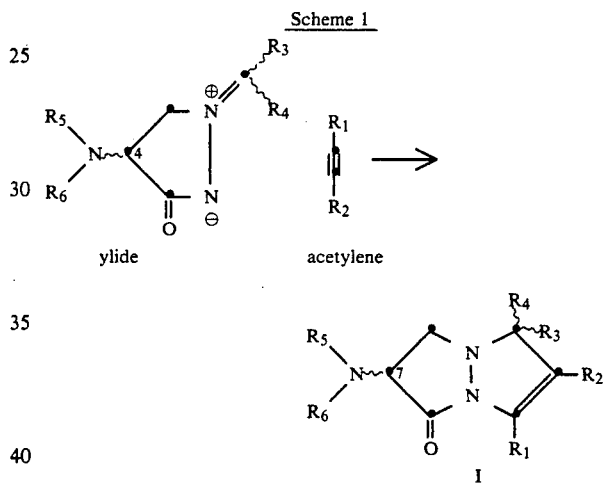

In the above Scheme 1, for brevity's sake, Formula I indicates only one of the two possible 2,3-regioisomer products of the cycloaddition. The reaction represented by Scheme 1 can also produce the opposite 2,3-regioisomer, as well as a mixture of the regioisomers.

In the above Scheme $R_1$, $R_2$, $R_3$ and $R_4$ are as defined above for Formula I, except that neither $R_1$ nor $R_2$ can be halo, a group of the formula

—$OR_{11}$ or a group of the formula

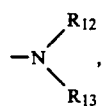

and either $R_5$ or $R_6$ is an amino-protecting group and the other is hydrogen. When carrying out the reaction it is preferable to substitute with protecting groups any of the acidic groups represented by $R_1$, $R_2$, $R_3$ or $R_4$. Examples of such acidic groups are the carboxylic acid group and the hydroxyimino group. It is especially preferred that any carboxylic acid groups be protected.

The cycloaddition should be carried out in aprotic solvents. Examples of such solvents are the chlorinated hydrocarbons, the aromatic hydrocarbons, and alkyl or aromatic cyano solvents. The preferred solvents for the above cycloaddition are dichloromethane, acetonitrile, and 1,2-dichloroethane.

The temperature for the cycloaddition is not critical. It is preferred that the reaction be carried out between about room temperature to about the reflux temperature of the solvent. When $R_3$ and $R_4$ are hydrogen, a more preferred temperature is approximately the reflux temperature of the solvent. For all other combinations of $R_3$ and $R_4$, a more preferred temperature is approximately room temperature.

The reaction usually requires a period of about 1 to about 168 hours. The optimal reaction time can be determined by monitoring the progress of the reaction by conventional means such as chromatographic techniques (such as thin layer chromatography, high performance liquid chromatography or column chromatography) or spectroscopic methods (such as infrared spectroscopy, nuclear magnetic resonance spectrometry and mass spectrometry), or a combination of the two methods.

The usual stoichiometry for the cycloaddition is a 1:1 ratio of ylide to acetylene reagent. Of course, an excess of either reagent is permissible. It is preferred that the acetylene reagent be present in excess, and especially preferred that the acetylene be present in a 2:1 excess. Furthermore, the order of addition of either reagent is not critical.

The regiospecificity of the cycloaddition in Scheme 1 is unpredictable. Usually the reaction yields widely varying mixtures of 2,3-regioisomer products.

The stereospecificity of the cycloaddition of Scheme 1 is determined by the stereochemistry at $C_4$ of the ylide starting material. Thus, a 4-(S) ylide will yield a 7-(S) cycloadduct (Formula 1).

The second synthetic route to bicyclic pyrazolidinone compounds is a two step sequence. In the first step, a 1,3-dipole (ylide) is reacted with a 2-(alkyl or aryl sulfonyl)-1-(substituted or unsubstituted)carboxyethylene moiety. In the second step the elements of (alkyl or aryl)sulfinic acid are eliminated from the 2,3-dihydro ("saturated system") bicyclic pyrazolidinone ring system with a non-nucleophilic base to give the corresponding 2,3-unsaturated system. The second method of cycloaddition reaction is represented by Scheme 2:

Scheme 2
Step 1

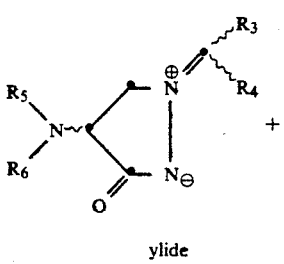

ylide

-continued
Scheme 2

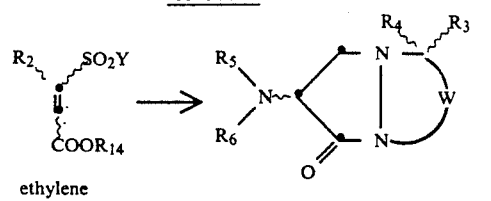

ethylene

Step 2

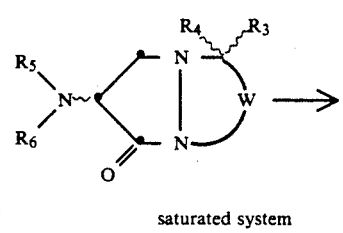

saturated system

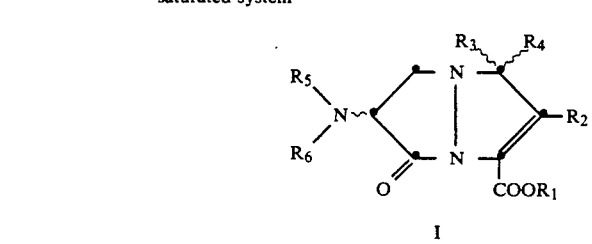

I

In Scheme 2, $R_5$ and $R_6$ are the same as for Scheme 1. $R_3$ and $R_4$ are the same as for Scheme 1, except that either $R_3$ or $R_4$ must be hydrogen. $R_1$ and $R_2$ are the same as for Scheme 1 except that neither one is a phosphonato group, a (quaternary ammonium)methyl group, a group of the formula

—$OR_{11}$;

a group of the formula

—$NR_{12}R_{13}$; or a group of the formula

—$CH_2$—$\overset{\oplus}{N}\equiv Q$.

The variable W is a group of the formula

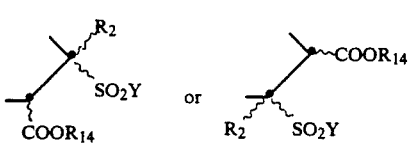

The variable Y in the above partial formulas is $C_1$ to $C_6$ alkyl, $C_1$ to $C_6$ substituted alkyl, phenyl, substituted phenyl, $C_7$ to $C_{12}$ arylalkyl or $C_7$ to $C_{12}$ substituted arylalkyl. When carrying out the reactions of the above Scheme 2, it is preferable to derivatize with protecting groups any acidic groups represented by $R_1$, $R_2$, $R_3$, $R_4$ or Y.

The regiospecificity of the cycloaddition reaction represented by Step 1, Scheme 2 is such that the 3-(alkyl- or arylsulfonyl) regioisomer is the predominant product. (Selected examples of the cycloaddition have shown that the (E)-vinyl sulfone dipolarophile enhances the yield of the 3-(sulfonyl) adduct). Thus, the second method of cycloaddition reaction is especially useful for placing the substituent bonded to the sulfonyl-substituted carbon of the ethylene moiety at the 3-position of the bicyclic pyrazolidinone ring. This regiospecific feature of the cycloaddition makes it an especially useful route to compounds with a substituted methyl group at $R_2$. Examples of such a substituted methyl groups are represented by the formula

—CH$_2$X wherein X can be halo, hydroxy, protected hydroxy, $C_1$ to $C_7$ acyloxy, carbamoyloxy, an -S-heterocyclic ring or a group of the formula

—S—R$_7$ wherein $R_7$ is other than a heterocyclic ring, as defined above.

A bicyclic pyrazolidinone ring substituted at $R_2$ with halomethyl or acyloxymethyl provides an excellent intermediate for the synthesis of the corresponding (quaternary ammonium)methyl or (heterocyclic thio)methyl analogs. The acyloxy or halo substituent on the methyl group of the intermediate is displaced by the amine of the quaternary ammonium group or the thiol of the heterocyclic thio group. The conditions for these displacements are well known and are described in the cephalosporin art for the analogous displacements of halo and acetoxy groups of 3-(halomethyl or acetoxymethyl)cephalosporins.

The cycloaddition reaction (Step 1) in Scheme 2 is carried out in aprotic, preferably polar solvents. Examples of such solvents are the chlorinated hydrocarbons, the aromatic hydrocarbons, and alkyl or aromatic nitrile solvents. A preferred solvent for the above cycloaddition is 1,2-dichloroethane.

The temperature for the cycloaddition is not critical. A preferred temperature is about room temperature to about the reflux temperature of the solvent. A more preferred temperature is approximately the reflux temperature of the solvent.

The cycloaddition usually requires a period of about 1 to about 168 hours. The optimal reaction time can be determined by monitoring the progress of the reaction by conventional chromatographic techniques (such as thin layer chromatography, high performance liquid chromatography, or column chromatography), spectroscopic techniques (such as infrared spectroscopy, nuclear magnetic resonance spectrometry or mass spectrometry), or a combination of the two techniques.

The usual stoichiometry for the cycloaddition in the above Scheme 2 is a 1:1 ratio of ylide to ethylene reactant. Of course, an excess of either reactant is permissible. The order of addition of either reactant is not critical.

The stereospecificity of the reaction at $C_2$ and $C_3$ of the saturated system is unpredictable. The reaction usually produces a mixture of stereoisomers at these positions. The stereospecificity of the cycloaddition at the $C_7$ position of the adduct is determined by the stereochemistry at the $C_4$ position of the ylide. Thus, if a 4-(S)-ylide is the starting material, the cycloadduct has 7-(S) stereochemistry.

For the elimination reaction (labelled "Step 2" in the above Scheme 2) preferred solvents are dichloromethane and 1,2-dichloroethane. Accordingly, it is most expedient to perform both the cycloaddition and elimination in the same reaction vessel and solvent, i.e., using 1,2-dichloroethane. The elimination is conducted from about −78° C. to about room temperature. A non-nucleophilic base, such as 1,8-diazabicyclo[5.4.0]-undec-7-ene ("DBU") 1,5-diazabicyclo[4.3.0]non-5-ene ("DBN"), triethylamine, or N-methylmorpholine is used to eliminate the elements of (alkyl or aryl)sulfinic acid. An excess of the non-nucleophilic base in relation to the "saturated system" is normally used. The preferred base is N-methylmorpholine, as it does not racemize the C-7 position of either the saturated cycloadduct or the unsaturated system of Scheme 2 (Formula I).

The reactions and the 2,3-dihydro bicyclic pyrazolidinone compounds of Scheme 2 are further described in L. N. Jungheim, S. K. Sigmund, C. J. Barnett, and R. E. Holmes, U.S. patent application No. 06/934,054. herein incorporated by reference, which application is a continuation-in-part of L. N. Jungheim and S. K. Sigmund, U.S. patent application No. 728,732, filed Apr. 30, 1985, also herein incorporated by reference.

The third synthetic route to 7-substituted bicyclic pyrazolidinones centers around the cyclization of a 1,2-(disubstituted)diazolidinone via a phosphorane reagent. The third route is diagramed below in Scheme 3:

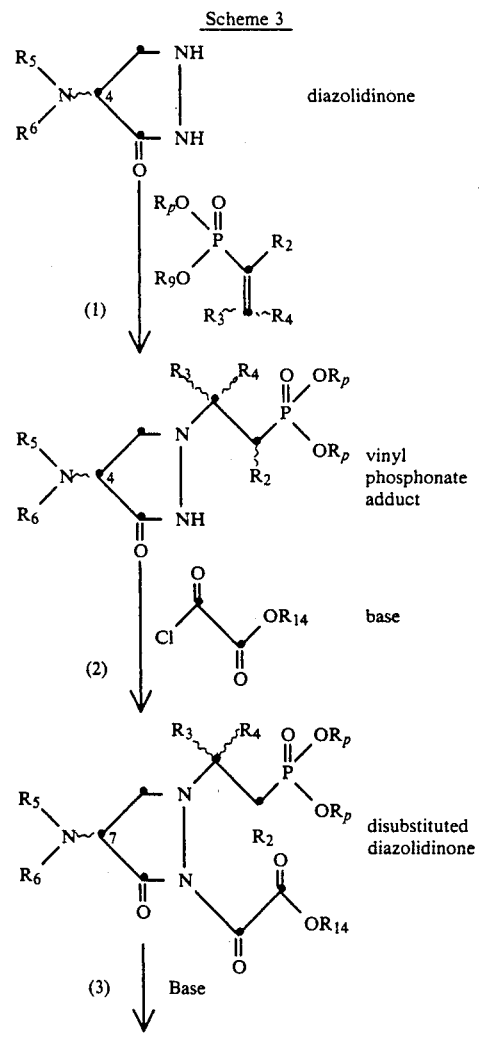

-continued
Scheme 3

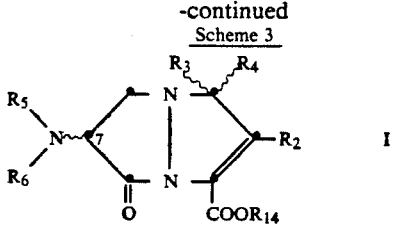

In the above Scheme, $R_p$ is $C_1$ to $C_6$ alkyl or phenyl. The variable $R_2$ is the same as for Formula I, except that $R_2$ in the above Scheme is not a group of the formula

—$COR_8$ wherein $R_8$ is trifluoromethyl, or groups of the formula:

—$OR_{11}$;

—$NR_{12}R_{13}$; and

—$CH_2$—$\overset{\oplus}{N}\equiv Q$.

The variable $R_{14}$ in the above Scheme is a carboxy-protecting group or a non-toxic, metabolically-labile ester-forming group. The variables $R_3$ and $R_4$ are the same as for Formula I. The variables $R_5$ and $R_6$ in the above Scheme are:

(a) taken together to form a phthalimido group; or (b) different and are either hydrogen or an amino-protecting group.

In the above Scheme, it is preferred that any carboxy, amino and hydroxy be in the protected form.

The stereospecificity at $C_7$ of the bicyclic pyrazolidinone product (Formula I) of the above sequence of reactions is determined by the $C_4$ stereochemistry of the diazolidinone starting material. Thus, a 4-(S)-diazolidinone starting material will yield a 7-(S)-bicyclic pyrazolidinone product (Formula I).

The first reaction in the above Scheme 3 (Reaction 1) is the alkylation of the $C_1$-nitrogen of the diazolodinone ring with a vinyl phosphonate reagent. The usual stoichiometry of the alkylation is a 1:1 molar ratio of the two reactants, but an excess of either reactant can be used. The solvent for the alkylation is an alcoholic solvent such as methanol, ethanol or isopropanol. Methanol is the preferred solvent.

The alkylation is usually carried out from between about 0° C. to about room temperature. The reaction is a very rapid one, requiring as little as 1 hour but occasionally up to 48 hours for completion.

The vinyl phosphonate adduct obtained from the alkylation reaction (Reaction 1) is then acylated at the 2-position nitrogen with an oxalate ester acid chloride (after deprotonation of the diazolidinone with di(isopropyl)ethylamine). The acylation reaction yields the corresponding 1,2-disubstituted diazolidinone.

Approximately one molar equivalent of the amine base and one molar equivalent or less of the oxalate reactant per equivalent of the adduct reactant are combined in the acylation reaction. The three reactants can be combined in any order. The usual order is to combine the adduct and the oxalate reactants then add the amine base.

The vinyl phosphonate adduct may be acylated in either chlorinated hydrocarbon or ether solvents. Methylene chloride is the preferred solvent.

The acylation reaction is often complete in as little as one hour. However, the reaction may need to be stirred at the appropriate temperature for as long as approximately 12 hours to reach completion.

At the time when the three reactants are being combined, the temperature of the acylation mixture should be maintained from approximately −78° C. to approximately −50° C. The reaction mixture is often stirred for approximately 1 hour at this temperature then allowed to warm to room temperature with stirring.

The 1,2-disubstituted diazolidinone obtained from Reaction 2 is then cyclized to give the bicyclic pyrazolidinone intermediate of Formula I, as depicted in Reaction 3.

In the cyclization reaction an equimolar or greater amount of the sodium hydride base per equivalent of the diazolidinone reactant is used. Ethers, and in particular tetrahydrofuran, are the preferred solvents. The reactants are usually combined and stirred at approximately 0° C. for approximately 15 minutes to approximately 1 hour. The reaction mixture can be stirred at room temperature for as long as 24 hours.

A preferred reaction sequence for the above Scheme 3 is to acylate the vinyl phosphonate adduct and then cyclize the product without isolating the 1,2-disubstituted diazolidinone. In this preferred combination reaction, the vinyl phosphonate adduct and the acylating reagent are combined in any order and in the stoichiometry discussed for the acylation reaction. The solvent for the combination reaction is the same as for the acylation alone, including the preference for methylene chloride. The combination reaction requires more equivalents of di(isopropyl)ethylamine base per equivalent of adduct starting material (at least 2 versus at least 1) to effect both the acylation and the subsequent cyclization. The combination reaction mixture is stirred for from approximately 15 minutes to approximately 18 hours from about 0° C. to about room temperature.

The progress of Reactions 1, 2, and 3 in Scheme 3 is monitored by conventional chromatographic techniques (such as thin layer chromatography or analytical-scale high pressure liquid chromatography) or spectroscopic techniques (such as infrared spectrometry or nuclear magnetic resonance spectroscopy). Spectroscopic and chromatographic techniques may also be combined to monitor the progress of the reactions. When the monitoring technique(s) demonstrates that the reaction(s) are substantially complete, the products from the above reactions are isolated by conventional methods.

The fourth synthetic route to the compounds of the Formula I is centered around a carbene-insertion ring closure and is diagramed below in Scheme 4.

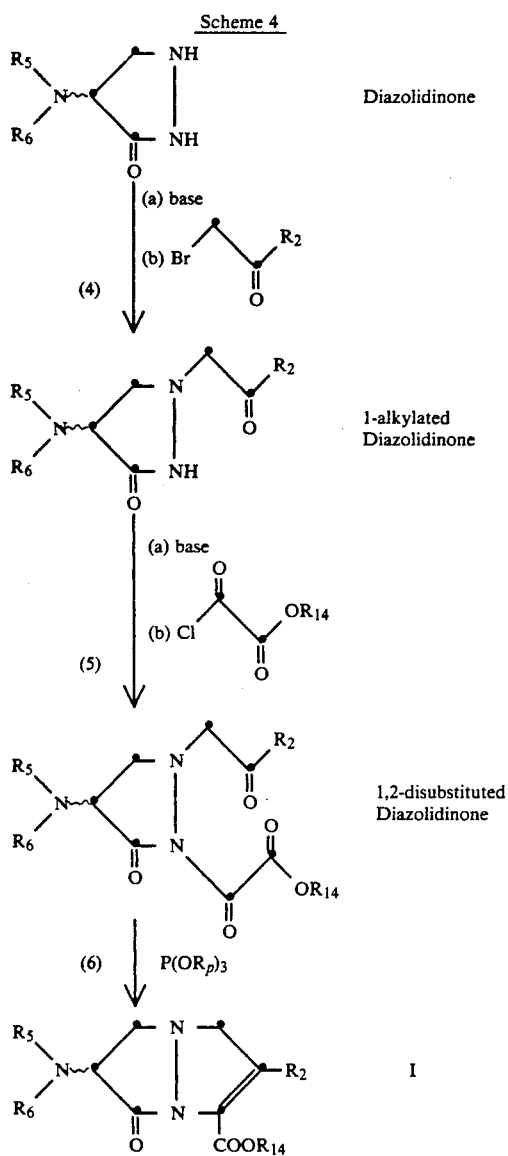

Scheme 4

In the above Scheme 4, $R_2$ is $C_1$ to $C_6$ alkyl, $C_1$ to $C_6$ substituted alkyl, perfluoro $C_2$ to $C_4$ alkyl, $C_7$ to $C_{12}$ arylalkyl, $C_7$ to $C_{12}$ substituted arylalkyl, phenyl, substituted phenyl, a heterocyclic ring, a group of the formula:

$-CX_3$;

or a group of the formula:

wherein Z is 0. $R_{14}$, $R_5$ and $R_6$ are the same as for the above Scheme 3. $R_p$ is $C_1$ to $C_6$ alkyl or phenyl, with ethyl being the preferred group.

The first reaction in Scheme 4 is the alkylation of $C_1$ nitrogen of the diazolidinone with an acetyl fragment that bears the $R_2$ substituent. The first step of the alkylation is the deprotonation of the diazolidinone with a base chosen from sodium hydride, potassium t-butoxide, and the like. The diazolidinone and the base are preferably combined in a 1:1 molar ratio, but an excess of the diazolidinone is permissible.

The deprotonation step, as well as the subsequent alkylation step, is carried out in polar, aprotic solvents such as dimethylformamide, hexamethylphosphoramide, dimethylsulfoxide or dimethylacetamide. Dimethylformamide is the preferred solvent. When sodium hydride is the base, the reaction is stirred for between 1 to about 1.5 hours (to allow dissolution) then the alkylating agent is added. With the other bases, it is preferred to add the alkylating reagent within a few minutes after the addition of base. The deprotonation reaction mixture is stirred from between 0° C. to about room temperature, with 0° C. being the preferred temperature.

The deprotonated diazolidinone and the bromoacetyl alkylating reagent are combined in approximately a 1:1 molar ratio, although an excess of either reagent is permissable. The solvents for the alkylation step are the same as for the deprotonation step, and again dimethylformamide is the preferred solvent. The alkylation is generally complete after about 3 to about 24 hours and is stirred from about 0° C. to about room temperature.

The 1-alkylated diazolidinone obtained from Reaction 4 is acylated to yield the 1,2-disubstituted diazolidinone. The acylation reaction is depicted in the above Scheme as Reaction 5. The first step of Reaction 5 is a deprotonation reaction and the second step is the acylation of the resultant anion. The deprotonation step is preferably carried out with di(isopropyl)ethylamine present in an equimolar amount with the 1-alkylated diazolidinone reactant, although either reactant may be present in excess. The deprotonation reactants are combined in any of the chlorinated hydrocarbon solvents, although dichloromethane is preferred. The mixture is stirred from between about 0° C. to about 25° C., with a range of between about 0° C. to about 10° C. being preferred.

Within a few minutes after the addition of the base, the oxalate ester acid chloride acylating agent is added to the mixture, again usually in an equimolar amount. A slight excess of the oxalate reactant may also be used. The oxalate reactant is generally added in a dropwise fashion over a period of approximately 20 minutes. The solvent for the acylation step is the same as the solvent of the deprotonation step. The temperature for the acylation step is the same as that for the deprotonation step, with approximately 10° C. being preferred. The acylation reaction will be complete after approximately 6 to approximately 48 hours, with the usual time being approximately 24 hours.

In the final reaction in Scheme 4 (Reaction 6) the 1,2-disubstituted diazolidinone is cyclized to a bicyclic pyrazolidinone of Formula I. A 5 to 10 molar equivalent excess of the phosphite reagent is combined with the diazolidinone reactant in either chloroform, 1,2-dichloroethyane, or an aromatic hydrocarbon solvent. Chloroform is the preferred solvent. The cyclization reaction mixture is heated to a range of about 50° C. to about 120° C. for between about 12 to about 72 hours. Twenty-four hours is a typical reaction time.

The progress of Reactions 4, 5, and 6 in Scheme 4 is monitored by conventional chromatographic techniques (such as thin layer chromatography or analytical-scale high pressure liquid chromatography) or spectroscopic techniques (such as infrared spectrometry or nuclear magnetic resonance spectroscopy). Spectroscopic and chromatographic techniques may also be combined to monitor the progress of the reactions. When the monitoring technique(s) demonstrates that the reactions are substantially complete, the products from the above reactions are isolated by conventional methods.

The stereochemistry at $C_7$ of the bicyclic pyrazolidinone product (Formula I) of the reaction sequence in Scheme 4 is determined by the stereochemistry at $C_4$ of the diazolidinone starting material. Thus, a 4-(S) diazolidinone will yield a 7-(S) bicyclic pyrazolidinone product.

A fifth synthetic method is diagramed below in Schemes 5, 6 and 7. The method centers around the 3-chloro-3-(phenylsulfoxide) and 3-hydroxy bicyclic pyrazolidinone intermediates set forth in the following Scheme 5. (In the following Scheme, and also in the remainder of the Specification, reference to the 3-hydroxy unsaturated bicyclic pyrazolidinone implicitly includes the corresponding 3-keto (saturated) tautomer.)

ferred to by Formula I that are compatible with the reaction conditions in Schemes 5, 6, and 7 are also permissible.

Reaction 7 in the above Scheme depicts the addition of thiophenol to the 2,3-double bond of the 3-hydrogen starting material. In the addition reaction, the 3-hydrogen compound, thiophenol, and a nitrogen base are combined in approximately equimolar amounts, with a slight excess of either the thiophenol or the base being permissible. The reactants are combined in aprotic solvents such as benzene. The base employed is preferably a secondary or tertiary amine, such as piperidine. The reaction solution is maintained from about $-20°$ C. to about room temperature for from between about 5 minutes to approximately 24 hours. The addition reaction yields a mixture of stereoisomers at the $C_2$ and $C_3$ positions.

The 3-phenylthio saturated compounds obtained from Reaction 7 are chlorinated or brominated to give the analogous 3-halo-3-phenylthio saturated com-

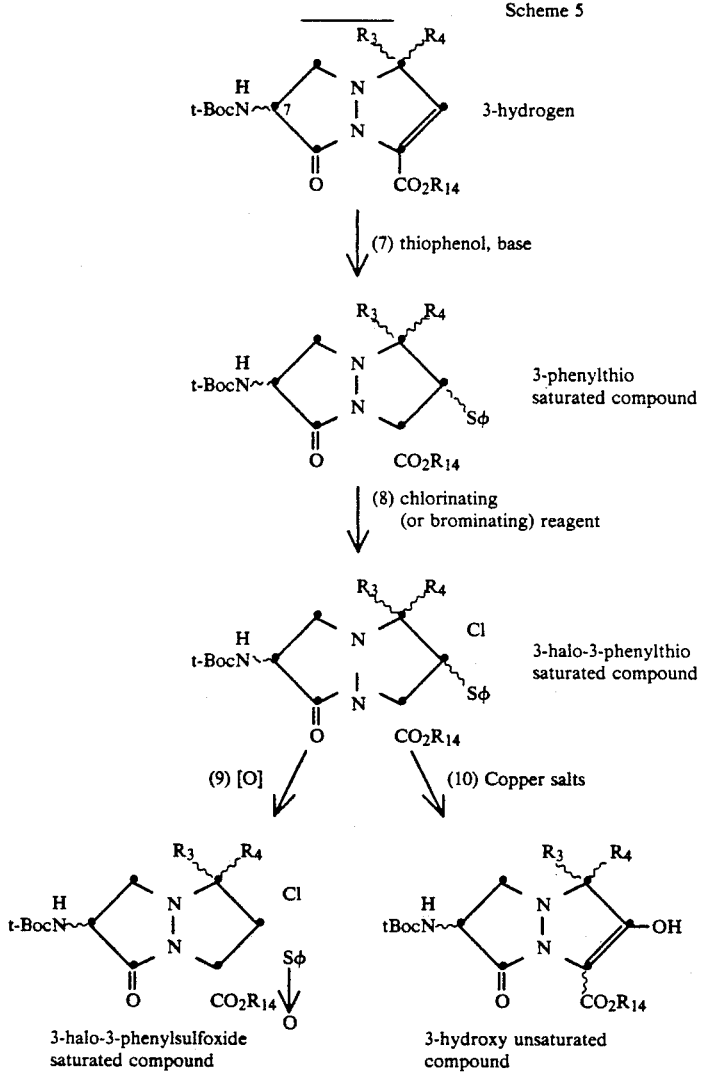

Scheme 5

3-halo-3-phenylsulfoxide saturated compound 3-hydroxy unsaturated compound

In the above Scheme, $R_3$ and $R_4$ are the same as for Formula I. $R_{14}$ is a carboxy-protecting group or a nontoxic, metabolically-labile, ester-forming group. It should be noted that, while Schemes 5, 6 and 7 depicts t-butoxycarbonyl ("t-Boc") as the protecting group for the 7-amino group, other amino-protecting groups repounds. A 3-phenylthio saturated compound is combined in approximately an equimolar amount with the chlorinating or brominating agent in a chlorinated hydrocarbon solvent. Halogenating agents include N- chlorosuccinimide, sulfuryl chloride or N-bromosuccinimide. Examples of the solvent include methylene chloride and carbon tetrachloride, with carbon tetrachloride preferred. The halogenation reaction solution is maintained from approximately room temperature to approximately the reflux temperature of the solvent for about 1 hour to about 24 hours. The halogenation yields a mixture of stereoisomers at the $C_3$-position of the bicyclic pyrazolidinone.

The 3-halo-3-phenylthio saturated compound obtained from Reaction 8 is oxidized to give the corresponding 3-halo-3-phenylsulfoxide compound. The oxidation reaction, set forth above as Reaction 9, entails combining approximately equimolar amounts of the 3-halo-3-phenylthio saturated compound and a peracid (such as meta-chloroperbenzoic acid) in a chlorinated hydrocarbon solvent (such as methylene chloride). The reaction solution is maintained at a very low temperature ($-78°$ C.) for a short period of time (such as from a few minutes to 1 hour).

Alternatively, the 3-halo-3-phenylthio saturated compound may be hydrolyzed to the 3-hydroxy unsaturated compound. This hydrolysis is depicted above as Reaction 10 and entails mixing the 3-halo-3-phenylthio saturated compound with an excess of cupric oxide and cupric chloride dihydrate in acetone containing a small amount of water. The mixture is heated to reflux for a short time (such as approximately 10 to 30 minutes) then cooled rapidly. This oxidation procedure parallels the procedure of P. Bakuzis et al., *J. Org. Chem.*, 42, 2362 (1977).

The 3-hydroxy unsaturated compounds of Scheme 5 above are converted to either the 3-ether, 3-acyloxy, or certain 3-amino compounds of Formula I. These conversions are diagramed below in Scheme 6.

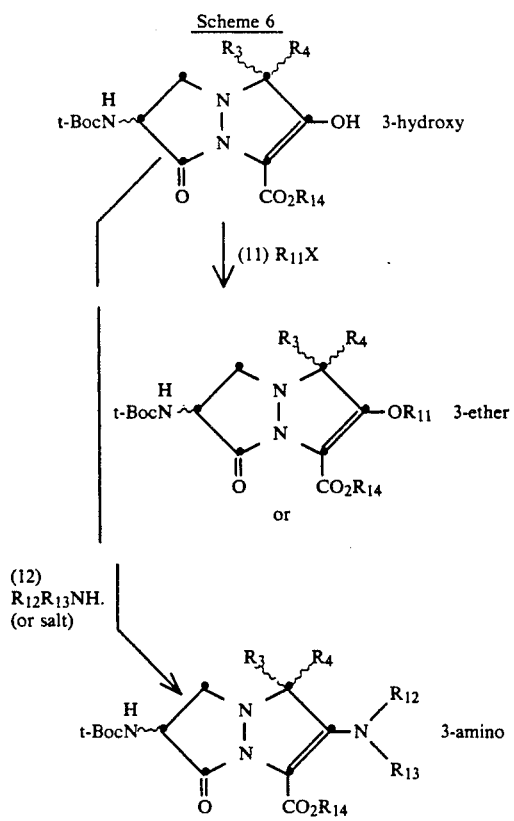

In the above Scheme, $R_3$ and $R_4$ are the same as for Formula I, and $R_{14}$ is the same as in Scheme I. Reaction 11 in the above Scheme represents two different types of reactions. The first type is an etherification reaction ($R_{11}$ is the same for Formula I except that the $C_1$ to $C_7$ acyl groups are excluded). The second type is an acylation reaction, thus yielding compounds wherein $R_{11}$ is only a $C_1$-$C_7$ acyl group. In the etherification reaction, the 3-hydroxy compound and the appropriate alkylating agent are usually combined in equimolar amounts, although use of an excess of the alkylating agent is permissible. The usual ether-forming reagents may be used in Reaction 11, such as the diazoalkanes as well as the alkyl- and arylsulfates, chlorides, bromides, trifluoromethylsulfonates, and fluorosulfates. Suitable conditions for these etherification reactions are described in R. Scartazzini et al., U.S. Pat. No. 4,073,902, issued Feb. 14, 1978, herein incorporated by reference. Also, displacement reactions catalyzed with dialkyl azodicarboxylates and triphenylphosphine can be employed. Examples of conditions for these displacement reactions can be found in O. Mitsunobu, *Synthesis*, Jan., 1981, pp. 1-28.

A more specific example of etherification reaction involves reacting the 3-hydroxy compounds of Scheme 6 with a slight molar excess of diazomethane in an inert, aprotic solvent such as diethyl ether. The mixture is stirred at a low temperature (0° C.) for a short period of time (for example, approximately 10 to approximately 30 minutes) then quenched with acetic acid.

In the acylation reactions represented by the above Reaction 11 (when $R_{11}$ is $C_1$ to $C_7$ acyl), the 3-hydroxy compounds are combined with acylating agents such as those described above for the acylation of the 7-amino compounds with the a $C_1$-$C_{30}$ carboxylic acid side Chain. For example, a 3-hydroxy compound is combined with a molar excess of acetic acid anhydride in the presence of a molar excess of a non-nucleophilic base (such as dimethylaminopyridine) in a polar, aprotic solvent (such as a chlorinated hydrocarbon, and more specifically, methylene chloride). The reaction solution is stirred at a moderate temperature (room temperature) for approximately 1 to 2 hours.

Reaction 12 in the above Scheme 6 yields the majority of 3-amino compounds encompassed by Formula I. The reaction does not yield the 3-(N-($C_1$ to $C_7$ acylamino)) or the 3-(N-(carbamato)) compounds of Formula I.

In Reaction 12, the 3-hydroxy compound is combined with an excess (for example, 4 equivalents) of ammonium chloride in the presence of excess weak base (such as pyridine) in a polar, protic solvent (such as anhydrous ethanol) to yield the 3-(primary amino) compound ($R_{12}$ and $R_{13}$ are both hydrogen). The mixture is heated to approximately the reflux temperature of the solvent for approximately 24 hours.

Reaction 12 yields the 3-(secondary and tertiary) amino compounds when the 3-hydroxy compound is condensed with an equimolar or greater amount of the appropriately substituted primary or secondary amine. The condensation reaction is catalyzed with an excess amount of acid (for example, d-10-camphorsulfonic acid). Molecular sieves are added to the mixture to help drive the reaction to completion. When molecular sieves are used, the condensation reaction occurs under mild conditions (such as room temperature over a period of approximately 24 hours).

The 3-halo-3-phenylsulfoxide saturated compounds of Scheme 5 are precursors to the 3-chloro (and 3-bromo) unsaturated compounds of Formula I. This conversion is set forth below in Scheme 7 as Reaction 13.

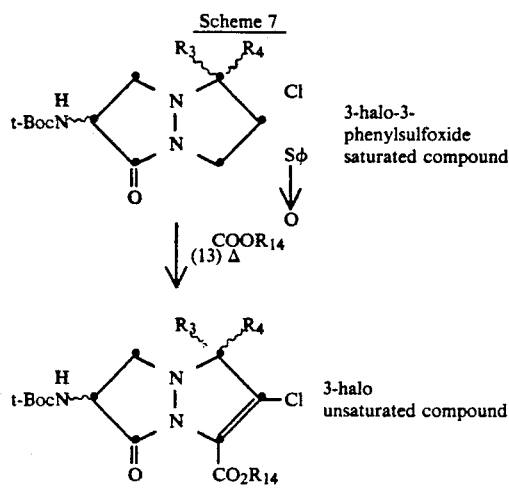

In the above reaction, the 3-halo-3-phenylsulfoxide saturated compound is heated in a suitable aprotic solvent (such as a chlorinated hydrocarbon or an aromatic hydrocarbon) that boils above 75° C.. Carbon tetrachloride is an example of such a solvent. The mixture is heated to above 75° C. for approximately 2 to 8 hours. It is desirable, but not necessary, to heat the saturated compound in the presence of a sulfenic acid trap. Suitable traps include triphenylphosphite or ethyl vinyl ether. The trap is used in an excess amount (for example, approximately 2 molar equivalents) in the reaction.

The synthesis of 3-(N-($C_1$ to $C_7$ acylamino)) compounds parallels the synthesis of 3-($C_1$ to $C_7$ acyloxy) compounds above. In short, a 3-(primary amino) compound is acylated with an acylating agent such as those used to acylate the 7-amino nucleus compounds.

The progress of the Reactions in Schemes 5, 6 and 7 is monitored by conventional chromatographic techniques (such as thin layer chromatography or analyticalscale high pressure liquid chromatography) or spectroscopic techniques (such as infrared spectrometry or nuclear magnetic resonance spectroscopy). Spectroscopic and chromatographic techniques may also be combined to monitor the progress of the reactions. When the monitoring technique(s) demonstrates that the reactions are substantially complete, the products from the above reactions are isolated by conventional methods.

Finally, the synthetic method for the 3-(N-(alkyl- and arylcarbamato)) compounds of Formula I is set forth below in Scheme 8.

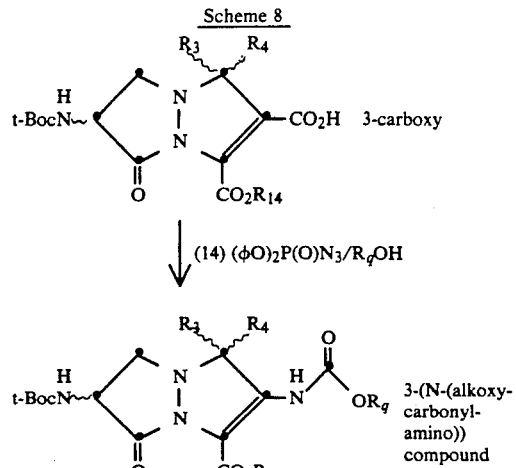

In the above Scheme 8, $R_3$, $R_4$, and $R_{14}$ are as defined for Scheme 5. Also, Reaction 14 will proceed when the 7-amino moiety is substituted with a protecting group other than t-butoxycarbonyl ("t-Boc").

In the above Reaction 14, the 3-carboxy compound is first reacted with approximately equimolar amounts of diphenylphosphoryl azide and triethylamine reagents in an inert, aprotic solvent such as benzene. The mixture must be maintained at a high temperature (approximately the reflux temperature of the solvent) for approximately 0.5 to 2 hours. An excess of the appropriately substituted alcohol (approximately 2 molar equivalents) is added and the solution is again heated to approximately the reflux temperature of the solvent for from approximately 10 minutes to approximately 1 hour. The procedure for Reaction 14 is adapted from M. Fieser and L. F. Fieser, *Reagents for Organic Synthesis*, Wiley-Interscience, New York, 1975, Volume 5, page 280, and the references therein.

The 2,3-unsaturated compounds produced by the reactions in Schemes 1 through 8 above are the 7-(protected amino) compounds of Formula I (i.e., when either $R_5$ or $R_6$ is an amino-protecting group and the other is hydrogen). Replacing the amino-protecting group of the 7-(protected amino) compounds with an acyl group derived from a $C_1$ to $C_{30}$ carboxylic acid converts them to the antimicrobial final products of Formula I. As discussed above, the acyl groups employed are typically those used to achieve the same purpose when bonded to the 6-amino group of a penicillin or a 7-amino group of a cephalosporin.

More specifically, compounds of the present invention wherein $R_2$ keto, amino, and chloro, can also be prepared according to the following scheme:

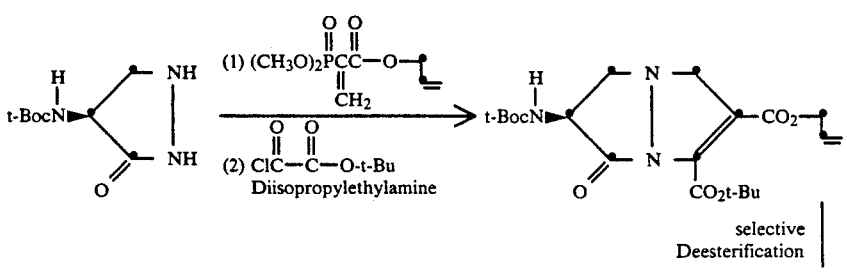

-continued

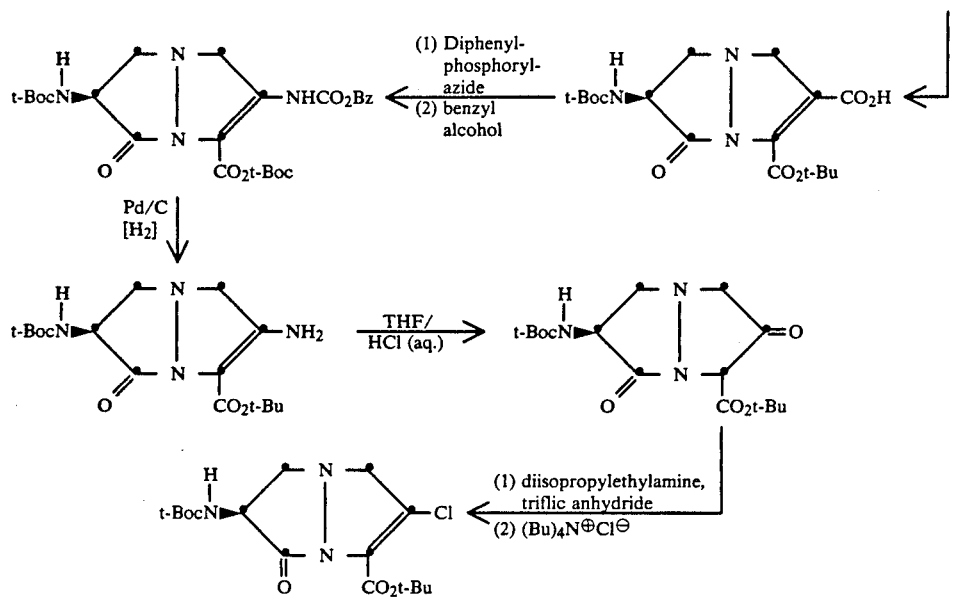

Accordingly, the 3-keto, 3-amino, and 3-carboxy compounds can be used to further derivatize compounds of the present invention. For example, the 3-keto compound can be reacted with triflic anhydride in the presence of a base such as diisopropylethylamine to form a 3-trifluoromethanesulfonyl derivative. This compound can then be reacted with a wide variety of nucleophiles to further derivatize the 3-position. For example, the 3-triflate can be reacted with a nitrogen heterocycle such as tetrazole to provide a compound wherein $R_2$ is "heterocyclic ring", in this case, tetrazole directly substituted at the 1-position nitrogen. Further, the 3-carboxy group or an active derivative thereof can be reacted with a wide variety of compounds, for example, thiols, and amines.

Further, the 3-isocyanate derivative formed in situ by reaction of the 3-carboxy derivative with diphenylphosphoryl azide and N-methylmorpholine can be reacted with sulfur, oxygen, and nitrogen nucleophiles to provide the compounds of the invention wherein ($R_1$ or) $R_2$ is $-NR_{12}R_{13}$ and one of $R_{12}$ or $R_{13}$ is hydrogen and the other is a group of the formula

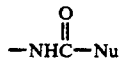

wherein Nu is as defined above. For example, ethanethiol provides the compound of Formula (I) wherein $R_2$ (or $R_1$) is $-NHCSCH_2CH_3$. Further, reaction of the isocyanate with an alcohol provides the 3-carbamate.

In the above scheme, the 4-protected amino diazolidinone is reacted with a vinyl phosphonate and then N-acylated with t-butyl oxalyl chloride in the presence of base, followed by in situ ring closure to form the 3-carboxylic ester. Selection removal of the 3-ester by standard methodology provides the free carboxy group.

The 3-carboxy group can then be readily converted to the carbamate by acylation with diphenylphosphoryl azide in the presence of base and an alcohol followed by rearrangement to provide the carbamate.

The carbamate can then be reduced by catalytic hydrogenation to provide the free 3-amino compounds of the present invention. Of course, protection of the above groups may be desirable for subsequent functionalization of other portions of the bicyclic pyrazolidinone molecule.

The compounds of the present invention wherein $R_2$ is

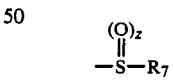

and $R_7$ is (disubstituted)amino can be also prepared by the following scheme):

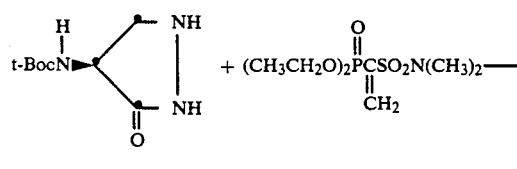

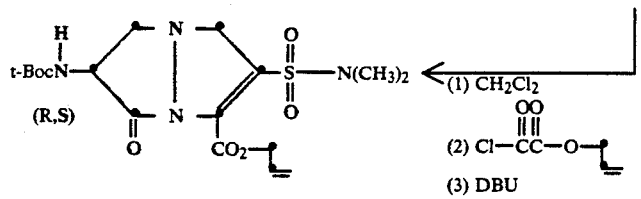

As will be appreciated by the scheme above, other esters of oxalyl chloride can be utilized to provide other esters of the bicyclic pyrazolidinone. Accordingly, other (disubstituted)amino sulfones can be utilized to provide the desired group at the 3-position (i.e., $R_7$).

The first step for the acylation of a 7-(protected amino) bicyclic pyrazolidinone compound ("7-protected amino nucleus") is the removal of the amino-protecting group. For example, the trimethylsilyl protecting group is removed by simple hydrolysis, the t-butoxycarbonyl group is removed by either acidic hydrolysis (with trifluoroacetic acid) or acidolysis (hydrochloric acid in glacial acetic acid), and the allyloxycarbonyl group is removed as a palladium complex. The conditions for the removal of other groups are well known in the cephalosporin and penicillin arts.

Removal of the acid-labile amino-protecting groups usually yields the 7-amino nucleus as a salt. The salt of the nucleus is neutralized by conventional procedures before acylation. For instance, the removal of the t-butoxycarbonyl group with trifluoroacetic acid leaves the trifluoroacetate salt of the resultant 7-amino nucleus. The salt is taken up in tetrahydrofuran and bis(-trimethylsilyl)trifluoroacetamide is added to yield the corresponding (neutralized) 7-amino compound. The neutralized compound can either be isolated then acylated or acylated in situ.

The methods for the acylation of the neutralized 7-amino bicyclic pyrazolidinone with the acyl side chain are similar to the methods for the acylation of 6-aminopenicillanic acid, 7-aminodesacetoxycephalosporanic acid and 7-aminocephalosporanic acid. One method is to simply combine the 7-amino nucleus with an acid chloride or acid bromide in the presence of an acid scavenger. The acid chloride or acid bromide may be formed in situ. Another method is to combine the 7-amino nucleus with the free carboxylic acid form of the side chain (or its acid salt) and a condensing agent. Suitable condensing agents include N,N'-disubstituted carbodiimides such as N,N'-dicyclohexylcarbodiimide, N,N'-diethylcarbodiimide, N,N'-di-(n-propyl)carbodiimide, N,N'-di-(iso-propyl)carbodiimide, N,N'-diallylcarbodiimide, N,N'-bis(p-dimethylaminophenyl)carbodiimide, N-ethyl-N'-(4''-ethylmorpholinyl)carbodiimide, and the like. Other suitable carbodiimides are disclosed by Sheehan in U.S. Pat. No. 2,938,892 and by Hofmann et al. in U.S. Pat. No. 3,065,224. Azolides, such as N,N'-carbonyldiimidazole and N,N'-thionyldiimidazol, may also be used as condensing agents. Dehydrating agents such as phosphorus oxychloride, the alkoxyacetylenes and 2-halogenopyridinium salts (such as 2-chloropyridinium methyl iodide, 2-fluoropyridinium methyl iodide, and the like) may be used to couple the free acid or its acid salt with the 7-amino nucleus.

Another acylation method entails first converting the free carboxylic acid form (or the corresponding salt) of the acyl side chain to the active ester derivative which is in turn used to acylate the nucleus. The active ester derivative is formed by esterifying the free acid form with groups such as p-nitrophenol, 2,4-dinitrophenol, trichlorophenol, pentachlorophenol, 2-chloro-4,6-dimethoxytriazene, N-chlorosuccinimide, N-chloro maleic imide, N-chlorophthalimide, 1-hydroxy-1H-benzotriazole or 1-hydroxy-6-chloro-1H-benzotriazole. The active ester derivatives can also be mixed anhydrides, which are formed with groups such as methoxycarbonyl, ethoxycarbonyl, isobutoxycarbonyl, trichloromethylcarbonyl and iso-but-2ylcarbonyl and the carboxylic acid of the acyl side chain. The mixed anhydrides are synthesized by acylating the carboxylic acid of the acyl side chain.

Alternatively, the 7-amino nucleus can be acylated with the N-ethoxycarbonyl-2-ethoxy-1,2-dihydroquinoline (EEDQ) derivative of the acyl side chain. In general, the free acid form of the acyl side chain and EEDQ are reacted in an inert, polar organic solvent (such as tetrahydrofuran, acetonitrile, and the like). The resultant EEDQ derivative is used in situ to acylate the 7-amino nucleus.

The antimicrobial activity of the bicyclic pyrazolidinones acylated with the appropriate acyl group derived from a $C_1$ to $C_{30}$ carboxylic acid is further enhanced on removal of any remaining amino, hydroxy, and/or carboxy protecting groups on the molecule. As discussed above, such removal methods are generally well known in the cephalosporin, penicillin, and peptide arts. Once the carboxy groups are deprotected, the non-toxic, metabolically-labile, ester-forming ("oral ester") group(s) may be put in place on the desired carboxy groups at $R_1$, $R_2$, $R_3$, and $R_4$. The methods for making the oral ester derivatives are well known in the cephalosporin and penicillin arts.

A $C_4$-racemic mixture of pyrazolidinium ylide starting materials for the reactions in Schemes 1 and 2 and a $C_4$-racemic mixture of starting materials for the reactions in Schemes 3 and 4 are synthesized according to the process depicted below in Scheme 9.

Scheme 9

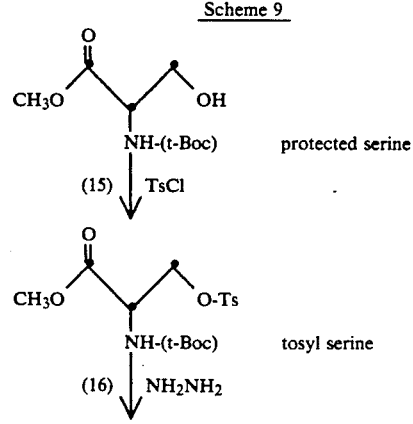

protected serine tosyl serine

-continued
Scheme 9

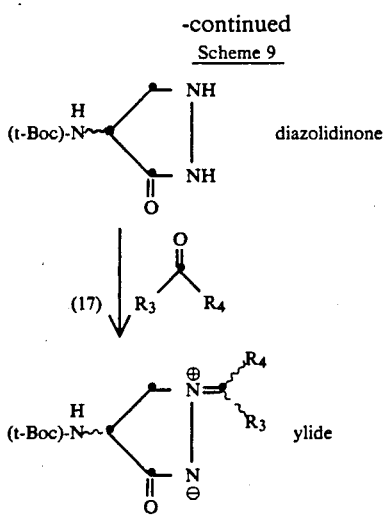

The above Scheme depicts the synthesis of 4-(t-butoxycarbonylamino) starting materials. Starting materials with different amino-protecting groups are obtained by starting with a different protecting group on the protected serine derivative.

The first step in the synthesis of the starting materials, represented by Reaction 15 in the above Scheme, is the tosylation of the hydroxy group of the protected serine derivative. The tosylation is carried out in methylene chloride with p-toluenesulfonyl chloride in the presence of a catalytic amount of 4-dimethylaminopyridine and greater than one equivalent of pyridine. The reaction mixture is stirred at room temperature overnight.

The tosylated serine obtained is cyclized to give the diazolidinone. The cyclization represented by Reaction 16 is carried out by adding the tosyl serine to a solution of 97% hydrazine in methylene chloride under nitrogen. The mixture is then stirred at room temperature for five hours.

The final reaction in the synthesis of a C4-racemic mixture of the pyrazolidinium ylide starting materials comprises the condensation of a ketone or aldehyde with a diazolidinone. As a useful alternative procedure, the ketal of the ketone may be condensed with the diazolidinone in the presence of an acid. For example, the diazolidinone reagent is combined with acetone dimethyl acetal in methanol and then the solution is treated with d-10 camphorsulfonic acid. The mixture is refluxed for 1.5 hours to give the dimethyl ylide (i.e., $R_3$ and $R_4$ are methyl). The unsubstituted ylide (when $R_3$ and $R_4$ are hydrogen) is synthesized by combining the diazolidinone reagent and 37% aqueous formaldehyde in methanol and stirring the mixture for twenty minutes at room temperature. When $R_3$ and $R_4$ are different those skilled in the art will recognize that Reaction 17 will produce a mixture of E and Z isomers.

The stereospecific synthesis of C4-chiral pyrazolidinium ylide and diazolidinone starting materials is diagramed below in Scheme 10.

Scheme 10

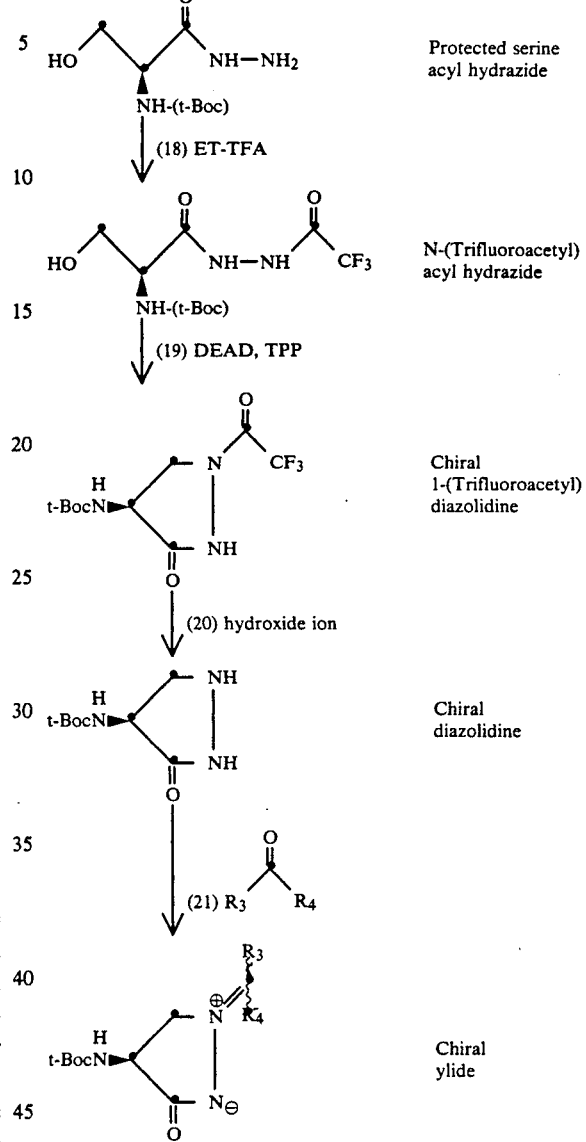

The above Scheme depicts the synthesis of chiral 4-(S)-(t-butoxycarbonylamino) ylide compounds. Ylide compounds with the 4-(R) configuration are synthesized by starting with the protected D-serine acyl hydrazide instead of the L-isomer depicted above. Both 4-(R) or 4-(S) compounds with amino-protecting groups other than t-butoxycarbonyl are synthesized from the corresponding serine enantiomer substituted with an amino-protecting group other than t-butoxycarbonyl.

The protected serine acyl hydrazide precursor of Scheme 10 is synthesized in a procedure analogous to B. Iselin and R. Schwyzer, Helv. Chim. Acta, 44, p. 169 (1961). The precursor is then acylated with the trifluoroacetyl moiety, as set forth in Reaction 18 in the Scheme. The hydrazide precursor is acylated with an excess of ethylthio trifluorothioacetate ("ET-TFA") in ethanol. The reaction mixture is stirred at room temperature for 65 hours.

The N-(trifluoroacetyl) acyl hydrazide obtained from Reaction 18 is cyclized with triphenylphosphine ("TPP") and diethyl azodicarboxylate ("DEAD"), as depicted above in Reaction 19.

The stoichiometry of the cyclization of Reaction 19 has the N-(trifluoroacetyl) acyl hydrazide, phosphine, and diethyl azodicarboxylate reagent present in at least approximately a 1:1:1 molar ratio. The reaction will proceed in the presence of molar excesses above this ratio of any of the reactants.

The cyclization is initiated by first combining (in any order) the solvent, the N-(trifluoroacetyl) hydrazide, and the phosphine, and secondly adding the azodicarboxylate reagent.

The temperature of Reaction 19 is not a critical parameter. The cyclization can be carried out at a temperature from approximately the freezing point to approximately the reflux temperature of the solvent. The preferred temperature is approximately room temperature.

The duration of Reaction 19 can be from approximately five minutes to approximately twenty four hours. The progress of the cyclization can be monitored by standard methods (such as thin layer chromatography, high performance liquid chromatography, etc.) The process is stopped when the monitoring method demonstrates that the reaction is substantially complete.

The solvents for the cyclization are aromatic hydrocarbon solvents such as benzene, toluene or xylenes; ethers such as diethyl ether, tetrahydrofuran, or 1,4-dioxane; chlorinated hydrocarbons such as methylene chloride, chloroform, carbon tetrachloride, dichloroethane, or chlorobenzene; amides such as dimethylformamide and dimethylacetamide; and other solvents such as hexamethylphosphoramide. Tetrahydrofuran is the preferred solvent. It is also desirable, but not essential, to dry and deoxygenate the solvent before use in the process.

While Reaction 19 in the above Scheme depicts the use of diethyl azodicarboxylate, the dimethyl and di(isopropyl)azodicarboxylate analogs can also be used in the reaction.

The chiral 1-(trifluoroacetyl)diazolidine obtained from Reaction 19 is deacylated with dilute sodium hydroxide solution. The deacylation is represented as Reaction 20 in the Scheme. The deacylation entails generally suspending the chiral 1-(trifluoroacetyl)diazolidine in water and adding at least two equivalents of a dilute aqueous solution of either sodium hydroxide or potassium hydroxide. For instance, a two-fold excess of 1M sodium hydroxide solution can be used. It is preferred to have the initial pH of the solution from between about 11 to about 12. The resultant solution can be stirred from about 10 minutes to about 3 hours at a temperature from about 10° C. to about 25° C. When the reaction is substantially complete the reaction solution is neutralized by the addition of dilute acid, such as 1N hydrochloric acid.

The optimal reaction time for the deacylation can be determined by monitoring the progress of the reaction with conventional chromatographic methods (such as thin layer chromatography, high performance liquid chromatography, or column chromatography), or spectroscopic methods, (such as infrared spectroscopy, nuclear magnetic resonance spectrometry, and mass spectrometry) or a combination of both methods. A preferred reaction time is from between about 30 minutes to about 1.5 hours.

The final reaction of Scheme 10, wherein the chiral diazolidines are converted to the chiral pyrazolidinium ylides, is carried out using the conditions described for the analogous reaction (Reaction 17) in Scheme 9.

The synthesis of the above diazolidine and pyrazolidinium ylide starting materials are further described by L. N. Jungheim and R. E. Holmes, U.S. patent application Nos. 06/862,917 and 07/045,011 respectively, herein incorporated by reference. U.S. patent application No. 07/045,011 is a continuation of U.S. patent application No. 06/862,912, which is a continuation-in-part of U.S. patent application No. 06/728,733. U.S. patent application No. 06/862,917 is a continuation-in-part of U.S. patent application No. 06/728,734.

The acetylene, ethylene, vinyl phosphonate, and bromoacetyl starting materials in Schemes 1, 2, 3 and 4, respectively, are made by methods known in the art and/or are commercially available. The synthesis of some of these starting materials are also described in the Experimental Section below.

III. DESCRIPTION OF THE ANTIMICROBIAL PROPERTIES OF THE 7-SUBSTITUTED BICYCLIC PYRAMOLIDINONES

The antimicrobial compounds of Formula I inhibit the growth of certain organisms pathogenic to man and animals. The antimicrobial compounds of Formula I are compounds wherein the various amino, hydroxy and/or carboxy protecting groups have been removed and either $R_5$ and $R_6$ is an acyl group derived from a $C_1$ to $C_{30}$ carboxylic acid and the other is hydrogen. The antimicrobial activity can be demonstrated in vitro using standard tube-dilution techniques. These in vitro tests demonstrate that, in general, the 7-(S) isomers have better antimicrobial activity than either the corresponding 7-(R) isomers or a mixture of the two isomers. Representative pathogens which are sensitive to the antimicrobial compounds of Formula I include *Staphylococcus aureus* X1.1, *Streptococcus pyogenes* C203, *Streptococcus pneumoniae* Park, *Hemophilus influenzae* 76 (ampicillin resistant), *Escherichia coli* N10, *Escherichia coli* EC14, *Escherichia coli* TEM ($\beta$-lactamase producer), *Klebsiella pneumoniae* X26, *Klebsiella pneumoniae* KAE ($\beta$-lactamase producer), *Klebsiella pneumoniae* X68, *Enterobacter aerogenes* C32, *Enterobacter aerogenes* EB17, *Enterobacter cloacae* EB5 (non-$\beta$-lactamase producer), *Salmonella typhi* X514, *Salmonella typhi* B35, *Serratia marcescens* X99, *Serratia marcescens* SE3, *Proteus morganii* PR15, *Proteus inconstans* PR33, *Providencia rettgeri* C24, *Citrobacter freundii* CF17, and the like.

The antimicrobial compounds of this invention are useful for the therapeutic or prophylactic treatment of infections in warm-blooded animals caused by gram-positive, gram-negative and acid-fast bacteria.

The antimicrobial compounds can be administered orally, parenterally (e.g. intravenously, intramuscularly or subcutaneously) or as a topical ointment or solution in treating bacterial infections of warm-blooded animals.

A further aspect of this invention is the pharmaceutical compositions of the antimicrobial compounds of Formula I. In particular, these pharmaceutical compositions are useful for the control of gram positive and gram-negative bacterial infections and comprise a suitable vehicle and a therapeutically effective amount of the antimicrobial compounds of Formula 1.

A preferred pharmaceutical composition is comprised of a therapeutically effective amount of the 7-(S) antimicrobial compounds of the formula

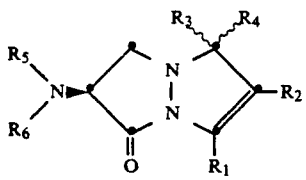

and a suitable vehicle.

With regard to compositions for oral administration (such as tablets and capsules), the term "suitable vehicle" means common excipients such as binding agents, for example, syrup, acacia, gelatin, sorbitol, tragacanth, polyvinylpyrrolidine (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; disintegrators such as croscarmellose sodium, microcrystalline cellulose, corn starch, sodium starch glycolate, alginic acid and mutable wetting agents such as sodium lauryl sulfate; and lubricants such as magnesium stearate and other metallic stearates, stearic acid, silicone fluid, talc, waxes, oils and colloidal silica. Flavoring agents such as peppermint, oil of wintergreen, cherry flavoring or the like can also be used. It may be desirable to add a coloring agent to make the dosage form more aesthetically pleasing in appearance or to help identify the product. The tablets may also be coated by methods well known in the art.

The pharmaceutical compositions of the present invention may also be in the form of oral liquid preparations, which may be either (a) aqueous or oily suspensions, solutions, emulsions or syrups; or (b) a dry powder to be reconstituted with water or another suitable vehicle before use. When used in conjunction with such oral liquid preparations, the term "suitable vehicle" means conventional additives such as suspending agents, for example, sorbitol, syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol or ethyl alcohol; and preservatives such as methyl or propyl p-hydroxybenzoates or sorbic acid.

The pharmaceutical composition can also be for intravenous (IV) use. Specifically, a water soluble form of the antimicrobial compound can be dissolved in one of the commonly used intravenous fluids and administered by infusion. When used in conjunction with compositions for IV use, the term "suitable vehicle" means such fluids as physiological saline, Ringer's solution or 5% dextrose solution.

For intramuscular preparations a sterile formulation of a suitable salt form of the antimicrobial compound (for example, the hydrochloride salt or sodium salt) can be formulated with a "suitable vehicle". Examples of such sterile formulations are a suitable salt form either dissolved in a pharmaceutical diluent (for example, Water-for-Injection, physiological saline, 5% glucose) or suspended in an aqueous base or a pharmaceutically acceptable oil base (for example, an ester of a long chain fatty acid such as ethyl oleate).

Topical compositions can be formulated with "suitable vehicles" such as hydrophobic or hydrophilic bases. Such bases include ointments, creams or lotions.

Veterinary pharmaceutical compositions of the antimicrobial compounds may be administered in the feed or the drinking water of farm animals. Alternatively, the compounds can be formulated as intramammary preparations with "suitable vehicles" such as long- or quick-release bases.

The antimicrobial compounds of Formula I can also be formulated in unit dosage form in sterile vials, sterile plastic pouches containing a port with a septum, or sterile, hermetically sealed ampoules. The antimicrobial compound (or the corresponding pharmaceutically-acceptable salt) may be a dry powder or in crystalline or lyophylized form. The amount of the antimicrobial compound per unit dosage may vary from about 250 milligrams to about 10 grams.

A "therapeutically effective amount" of the antimicrobial compounds of Formula I is from approximately 2.5 mg to about 50 mg of compound per kilogram of body weight. This amount generally totals from about 1 gram to about 12 grams per day for an adult human.

A further aspect of this invention is a method for treating or controlling infectious diseases caused by gram-positive and gram-negative organisms in warm-blooded animals. This method comprises administering to the infected host a therapeutically effective amount of the instant antimicrobial compounds. A typical daily dose for an adult human in this method is from about 0.5 grams to about 12 grams.

A preferred method comprises administering to an infected host a therapeutically effective amount of a 7-(S) antimicrobial compound of the formula

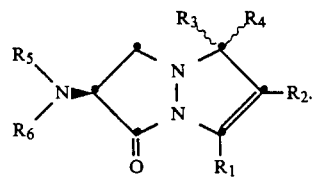

In practicing this method, the antimicrobial compound can be administered in a single daily dose or in multiple doses per day. The treatment regime may require administration over extended periods of time, for example, for several days or for from two to three weeks. The amount administered per dose or the total amount administered will depend on such factors as the nature and severity of the infection, the age and general health of the patient, and the tolerance to the antimicrobial compounds of Formula I of both the patient and the microorganism or microorganisms involved in the infection.

The following Examples are provided to further illustrate the invention. It is not intended that the invention be limited in scope by reason of any of the following Preparations or Examples.

In the following Preparations and Examples, the terms melting point, nuclear magnetic resonance spectra, electron impact mass spectra, field desorption mass spectra, fast atom bombardment mass spectra, infrared spectra, ultraviolet spectra, elemental analysis, specific rotation, high performance liquid chromatography, and thin layer chromatography are abbreviated m.p., n.m.r., m.s., f.d.m.s., f.a.b.m.s., i.r., u.v., anal., o.r., HPLC, and TLC, respectively. In addition, the adsorption maxima listed for the i.r. spectra are only those of interest and not all of the maxima observed.

The abbreviations THF, DMF, TFA, and BSTFA stand for tetrahydrofuran, dimethylformamide, trifluoroacetate and N,O-bis(trimethylsilyl)trifluoroacetamide, respectively.

In conjunction with the n.m.r. spectra, the following abbreviations are used: "s" is singlet, "d" is doublet, "dd" is doublet of doublets, "t" is triplet, "q" is quartet, "m" is multiplet, "dm" is a doublet of multiplets and "br.s", "br.d", "br.t", and "br.m" are broad singlet, doublet, triplet, and multiplet respectively. "J" indicates the coupling constant in Hertz. "DMSO-$d_6$" is dimethyl sulfoxide where all protons have been replaced with deuterium.

The n.m.r. spectra were obtained on a Varian Associates EM-390 90 MHz or T-60 60 MHz instrument, on a Jeol FX-90Q 90 MHz instrument, on a Brüker Corp. 270 MHz instrument or on a General Electric E-300 300 MHz instrument. The chemical shifts are expressed in $\delta$ values (parts per million downfield from tetramethylsilane). The field desorption mass spectra were taken on a Varian-MAT 731 Spectrometer using carbon dendrite emitters. Election Impact Mass Spectra were obtained on a CEC 21-110 instrument from Consolidated Electrodynamics Corporation. Infrared spectra were obtained on a Perkin-Elmer 281 instrument. Ultraviolet Spectra were obtained on a Cary 118 instrument. Specific rotations were obtained on a Perkin-Elmer Q-41 instrument. Thin layer chromatography was carried out on E. Merck silica gel plates. Melting points are uncorrected.

EXPERIMENTAL SECTION

Preparation 1

Methyl 3-(p-Toluenesulfonate)-2-(S)-(t-Butoxycarbonylamino)Propionate

Methyl (3-hydroxy)-2-(S)-(t-butoxycarbonylamino)-propionate (58 g, 196 mmol), dry methylene chloride (150 ml), p-toluenesulfonyl chloride (43.35 g, 227.4 mmol), 4-(dimethylamino)pyridine (2.4 g, 19.6 mmol) and pyridine (30 ml, 371 mmol) were combined and stirred at room temperature overnight. The reaction solution was concentrated in vacuo to a pale yellow oil. The oil was stored in vacuo overnight, then the white solid that formed was isolated to give 75.33 g of crude product. The product was triturated in petroleum ether (approximately 200 ml) to yield methyl 3-(p-toluenesulfonate)-2-(S)-(t-butoxycarbonylamino)propionate: n.m.r.: (CDCl$_1$, 90 MHz): $\delta$7.72, 7.31 (2x dd, 4, aromatic protons), 5.26 (m, 1, nitrogen proton), 4.48 (m, 1, C-2 proton), 4.32 (m, 2, C-3 protons), 3.68 (s, 3, methyl protons of methyl ester), 2.44 (s, 3, methyl protons of toluene moiety), 1.40 (s, 9, protons of t-butyl moiety); i.r. (CHCl$_3$): 3435, 3019, 1753, 1711, 1502, 1369, 1351, 1250, 1215, 1190, 1177 cm$^{-1}$; m.s.: 279, 210, 172, 91, 41;

Anal. Calcd. for C$_{16}$H$_{23}$NO$_7$S: Theory: C, 51.19; H, 6.71; N, 3.73; S, 8.54. Found: C, 51.05; H, 6.50; N, 3.63; S, 8.13.

Preparation 2

4-(R,S)-(t-Butoxycarbonylamino)-3-Oxo-1,2-Diazolidine

Under a nitrogen atmosphere, dry methylene chloride (50 ml) was cooled in an ice bath and anhydrous hydrazine (97%, 11.0 g, 333 mmole) was added. The ice bath was removed and the solution was stirred until it warmed to room temperature. At this time a solution of methyl 3-(p-toluenesulfonate)-2-(S)-(t-butoxycarbonylamino)propionate (20.0 g, 53.6 mmole) in dry methylene chloride (50 ml) was gradually added. The reaction solution was stirred under nitrogen at room temperature for 5 hours. The solution was then concentrated under reduced pressure and the concentrate was taken up in saturated aqueous sodium bicarbonate solution. The aqueous solution was continuously extracted for 14 hours with methylene chloride (700 ml). The methylene chloride solution was dried over sodium sulfate, filtered and concentrated under reduced pressure to yield approximately 5.15 g, 48% of 4-(R,S)-(t-butoxycarbonylamino)-3-oxo-1,2-diazolidine: n.m.r. (CDCl$_3$, 90 MHz): $\delta$7.04 (m, 1), 5.12 (m, 1), 4.28 (m, 1, C-4 proton), 3.94 (m, 1, C-5 proton), 3.20 (m, 1, C-5 proton), 1.45 (s, 9, t-butyl protons); i.r. (CHCl$_3$): 3430, 3250, 3019, 2983, 1702, 1545, 1503, 1370, 1297, 1241, 1215, 1165 cm$^{-1}$; f.d.m.s.: M+=201;

Anal. Calcd. for C$_8$H$_{15}$N$_3$O$_3$: Theory: C, 47.75; H, 7.51; N, 20.88. Found: C, 47.80; H, 7.56; N, 20.61.

Preparation 3

4-(R,S)-(t-Butoxycarbonylamino)-3-Oxo-1,2-Diazolidine p-Toluenesulfonate Salt 4-(R,S)-(t-Butoxycarbonylamino)-3-oxo-1,2-diazolidine (1.7 g, 8.45 mmol) was slurried in methylene chloride (50 ml). p-Toluenesulfonic acid hydrate (1.6 g, 8.45 mmol) was added to the slurry. After 20 minutes the resultant solid material was collected then dried in vacuo for approximately 48 hours to yield 2.95 g of colorless 4-(R,S)-(t-butoxycarbonylamino)-3-oxo-1,2-diazolidine p-toluenesulfonate salt: n.m.r. (90 MHz, DMSO-$d_6$): $\delta$ 7.5 (d, 2, J=8), 7.1 (d, 2, J=8), 4.32 (m, 1), 3.9 (m, 1), 3.4 (m, 1) 2.3 (s, 3), 1.4 (s, 9); i.r. (KBr): 1742, 1704, 1537 cm$^{-1}$.

Preparation 4

1-(p-Toluenesulfonyl)-2-(Allyl Carboxylate)-(E)-Ethylene p-Toluenesulfinic acid sodium salt hydrate (2.03 g, 10.3 mmol) was dissolved in water (15 ml). Glacial acetic acid (0.57 ml, 10 mmol) and sodium acetate (0.82 g, 10 mmol) were added to the solution. A solution of allyl 2,3-dibromopropionate (2.72 g, 10.0 mmol) in dioxane (15 ml) was added to the reaction solution. The resultant emulsion was stirred at room temperature for 48 hours. The emulsion was diluted with methylene chloride and enough water to produce two phases. The organic phase was separated and washed with saturated aqueous sodium bicarbonate solution and brine, dried over sodium sulfate, filtered and concentrated under reduced pressure to yield 2.53 g, 95% of a colorless oil. The oil was stored overnight in vacuo, then dissolved in a minimum amount of ethanol and filtered. The filtrate was concentrated under reduced pressure to give 1-(1-p-toluenesulfonyl)-2-(allyl carboxylate)-(E)-ethylene, which was used without further purification: n.m.r. (90 MHz, CDCl$_3$): $\delta$ 7.76 (d, 2, J=9 aromatic protons), 7.34 (d, 2, J=9, aromatic protons), 7.32 (d, 1, J=16, olefinic proton), 6.78 (d, 1, J=16, olefinic proton), 6.12–5.68 (m, 1, allyl proton), 5.42–5.17 (m, 2, allyl protons), 4.66 (d, 2, J=6, allyl protons), 2.43 (s, 3, methyl protons).

Preparation 5

(Methylthio)(p-Toluenesulfonyl)methane

Dimethylsulfoxide (9.25 g, 118 mmol) and acetic anhydride (15.6 g, 153 mmol) were heated to 80° C. for 24 hours. The reaction solution was cooled to room temperature, then glacial acetic acid (90 ml), sodium acetate (9.7 g, 118 mmol) and sodium p-toluenesulfinate (31.6 g, 178 mmol, dried in vacuo overnight with $P_2O_5$ at 50° C.) were added. The mixture was heated to 100° C. for 24 hours. Brine (150 ml) was added and the solution was extracted with methylene chloride (5X, 100 ml). The organic extracts were washed with brine, dried over magnesium sulfate, filtered and concentrated in vacuo to give a gummy solid. The solid was recrystallized from 95% ethanol (3B) to yield 8.68 g of white crystals of (methylthio)(p-toluenesulfonyl)methane: m.p. 81°–83° C.

Preparation 6 t-Butyl 3-(R,S)-3-(Methylthio)-3-(p-Toluenesulfonyl)Propionate (Methylthio)(p-toluenesulfonyl)methane (3.72 g, 17.2 mmol) was dissolved in THF (70 ml) and the solution was cooled to $-78°$ C. n-Butyl lithium in hexane (11.5 ml. 17.2 mmol) was added and the solution was stirred at $-78°$ C. for 30 minutes. The solution was transferred via cannula to a stirred solution of t-butyl 2-bromoacetate (5.5 ml, 34.4 mmol) in THF (30 ml) at $-78°$ C. The resultant solution was allowed to warm to room temperature, diluted with diethyl ether, washed with 1N hydrochloric acid and brine, dried over magnesium sulfate, filtered and concentrated in vacuo to an oil. The oil was diluted with toluene and concentrated in vacuo. The concentrate was recrystallized from hexanes containing a small amount of ether to yield 3.33 g of colorless powder of t-butyl 3-(R,S)-3-(methylthio)-3-(p-toluenesulfonyl)propionate: n.m.r. (90 MHz, $CDCl_3$): $\delta$ 7.8 (d, 2, J=8), 7.32 (d, 2, J=8), 4.18 (dd, 1, J=4, 11), 3.12 (dd, 1, J=4, 16), 2.46 (dd, 1, J=11, 16), 2.48 (s, 3), 2.26 (s, 3), 1.44 (s, 9); i.r. ($CHCl_3$): 1728 cm$^{-1}$; m.s.: M+=330;

Anal. Calcd. for $C_{15}H_{22}O_4S_2$: Theory: C, 54.52; H, 6.71; S, 19.41. Found: C, 54.78; H, 6.88; S, 19.68.

Preparation 7 t-Butyl 3-(R,S)-3-Chloro-3-Methylthio-3-(p-Toluenesulfonyl)Propionate t-Butyl 3-(R,S)-(3-methylthio)-3-(p-toluenesulfonyl)-propionate (4.36 g, 13.12 mmol), sulfuryl chloride (1.1 ml, 13.5 mmol) and carbon tetrachloride (50 ml) were combined and stirred at room temperature for 16 hours. The reaction mixture was diluted with methylene chloride, then washed with saturated aqueous sodium bicarbonate solution and brine, dried over magnesium sulfate, filtered and concentrated in vacuo to give 4.16 g of yellow oil of t-butyl 3-(R,S)-3-chloro-3-methylthio-3-(p-toluenesulfonyl)propionate: n.m.r. (90 MHz, $CDCl_3$): $\delta$ 7.8 (m, 2), 7.3 (m, 2), 3.14 (s, 3), 2.5 (ABq, 2, J=17), 2.5 (s, 3), 1.48 (s, 9).

Preparation 8 t-Butyl 3-Methylthio-3-(p-Toluenesulfonyl)-Acrylate t-Butyl 3-(R,S)-3-Chloro-3-methylthio-3-(p-toluenesulfonyl)propionate (370 mg, 1 mmol) was dissolved in methylene chloride (5 ml) and the solution was cooled to $-78°$ C. 1,8-Diazabicyclo[5.4.0]undec-7-ene (0.15 ml, 1 mmol) was added and the solution was stirred at $-78°$ C. for 15 minutes. The solution was warmed to room temperature, then diluted with diethyl ether, washed with 1N hydrochloric acid and saturated aqueous sodium chloride solution, dried over magnesium sulfate, filtered and concentrated in vacuo to give 330 mg of yellow oil. The oil was chromatographed on a silica gel preparatory-scale TLC plate with an eluant of 4:1 hexane:ethyl acetate to give 230 mg of yellow oil (70%) of t-butyl 3-methylthio-3-(p-toluenesulfonyl)acrylate: n.m.r. ($CDCl_3$, 90 MHz): $\delta$ 7.8 (d, 2, J=8), 7.3 (d, 2, J=8), 7.18 (s, 1), 2.47 (s, 3), 2.40 (s, 3), 1.50 (s, 9); i.r. ($CHCl_3$): 1716, 1148 cm$^{-1}$; m.s.: M+=328;

Anal. Calcd. for $C_{15}H_{20}O_4S_2$: Theory: C, 54.85; H, 6.14. Found: C, 54.70; H, 6.30.

Preparation 9

4-(R,S)-(t-Butoxycarbonylamino)-3-Oxo-1-(Dimethylmethylene)-1,2-Pyrazolidinium Ylide 4-(R,S)-(t-Butoxycarbonylamino)-3-oxo-1,2-diazolidine (2.01 g, 10 mmol) was dissolved in methanol (20 ml). To this solution was added acetone dimethyl acetal (10 mmol) and d-10-camphorsulfonic acid (approx. 5 mg). The mixture was refluxed for 1.5 hours then concentrated in vacuo. The concentrate was recrystallized from dichloromethane/isopropyl ether to give 2.01 g of 4-(R,S)-(t-butoxycarbonylamino)-3-oxo-1-(dimethylmethylene)-1,2-pyrazolidinium ylide: n.m.r. (270 MHz, DMSO-$d_6$): $\delta$ 7.2 (d, 1, J=6), 4.54 (t, 1, J=10), 4.28 (m, 1), 3.85 (m, 1), 2.25 (s, 3), 2.18 (s, 3), 1.4 (s, 9); i.r. (KBr): 3232, 1692, 1671, 1608 cm$^{-1}$; m.s.: M+=241.

Preparation 10

4-(R,S)-(t-Butoxycarbonylamino)-3-Oxo-1-(Methylene)-1,2-Pyrazolidinium Ylide 4-(R,S)-(t-Butoxycarbonylamino)-3-oxo-1,2-diazolidine (4.02 g, 20 mmol) was dissolved in dry methanol (50 ml). 37% Aqueous formaldehyde (1.62 g, 20 mmol) was added, the mixture was stirred for 20 minutes at room temperature then concentrated in vacuo. The solvent was then azeotropically distilled several times with methanol in vacuo at 40° C. The resultant residue was dried in vacuo at 40° C. overnight to yield 4-(R,S)-(t-butoxycarbonylamino)-3-oxo-1-(methylene)-1,2-pyrazolidinium ylide: n.m.r. (90 MHz, $CDCl_3$): $\delta$ 6.1–5.3 (m, 1), 4.9–4.2 (m, 3), 4.0–3.6 (m, 1), 3.5–3.1 (m, 1), 1.4 (s, 9); i.r. (KBr): 3379, 2980, 2930, 1705, 1524, 1519, 1504, 1455, 1393, 1368, 1297, 1252, 1166 cm$^{-1}$; f.d.m.s.: M$^{\oplus}$=213.

EXAMPLE 1

2,3-di(Allyl Carboxylate)-7-(R,S)-(t-Butoxycarbonylamino)-8-Oxo-1,5-Diazabicyclo[3.3.0]Octa-2-ene 4-(R,S)-(t-Butoxycarbonylamino)-3-oxo-1-(methylene)-1,2-pyrazolidinium ylide from Preparation 10 above was dissolved in dry acetonitrile (50 ml) and diallyl butynedioate (3.88 g, 20 mmol) was added. The mixture was heated to reflux for 3 hours then concentrated in vacuo. The resultant solid was chromatographed by HPLC on silica gel eluted with 2:1 hexane:ethyl acetate, to yield 2.67 g, 32.8% yield of 2,3-di(allyl carboxylate)-7-(R,S)-(t-butoxycarbonylamino)-8-oxo-1,5-diazabicyclo[3.3.0]octa-2-ene: n.m.r. (90 MHz, $CDCl_3$): $\delta$ 6.20–5.70 (m, 2, unsaturated protons on allyl groups), 5.52–5.0 (m, 5, C-7 proton and unsaturated protons on allyl group), 4.82 (dm, 2, J=6, saturated protons on allyl group on C-2 carboxylate), 4.64 (dm, 2, J=6, saturated protons on allyl group on C-3 carboxylate group), 4.38 (d, 1, J=13, C-4 proton), 4.04 (t, 1, J=8, C-6 proton), 3.92 (d, 1, J=13, C-4 proton), 2.88 (dd, 1, J=8, 12, C-6 proton), 1.45 (s, 9, protons of t-butyl group); u.v. (methanol): $\lambda_{max}$=345 ($\epsilon$=8500); i.r. ($CHCl_3$): 3019, 1750, 1736, 1709, 1384, 1370, 1278, 1234, 1215, 1162 cm$^{-1}$;

Anal. Calcd. for $C_{19}H_{25}O_7N_3$: Theory: C, 56.01; H, 6.19; N, 10.31. Found: C, 56.24; H, 6.35; N, 10.10.

EXAMPLE 2

2,3-di(Allyl Carboxylate)-7-(R,S)-[2-(Thien-2-yl)Acetamido]-8-Oxo-1,5-Diazabicyclo[3.3.0]Octa-2-ene

A. Removal of Amino-Protecting Group and Formation of TFA Salt 2,3-di(Allyl carboxylate)-7-(R,S)-(t-butoxycarbonylamino)-8-oxo-1,5-diazabicyclo3.3.0]octa-2-ene (407 mg, 1 mmol) was dissolved in trifluoroacetic acid (2 ml) and the solution was stirred for 5 minutes then concentrated in vacuo.

B. Neutralization of TFA salt

The residue from Step A was taken up in THF (5 ml) and BSTFA (1.5 ml) was added while the mixture was being cooled to 0° C.

C. Acylation of Nucleus

A THF solution (1 ml) of 2-(thien-2-yl)acetyl chloride (176 mg, 1.1 mmol) was added to the solution from Step B and the resultant mixture was stirred at 0° C. for 20 minutes. The reaction mixture was then poured into ethyl acetate and the resulting organic mixture was washed with saturated sodium bicarbonate solution, 0.2N hydrochloric acid, brine, dried over magnesium sulfate and filtered. The filtrate was concentrated in vacuo to give 700 mg of crude oily residue. The residue was chromatographed on a silica gel preparatory-scale TLC plate eluted with 1:1 hexane:ethyl acetate solution to give 270 mg, 62% yield of 2,3-di(allyl carboxylate)-7-(R,S)-[2-(thien-2-yl)acetamido]-8-oxo-1,5-diazabicyclo[3.3.0]octa-2-ene: n.m.r. (90 MHz, CDCl$_3$): $\delta$ 7.22 (m, 1, C-5 proton of thienyl group), 6.96 (m, 2, C-3 and C-4 protons of thienyl group), 6.56 (br. d, 1, J=6, amido proton), 6.20–5.60 (m, 2, C-2 proton of allyl groups), 5.60–5.10 (m, 4, C-3 (unsaturated) protons of allyl groups), 5.0 (m, 1, C-7 proton), 4.80 (dm, 2, J=6, C-1 protons of allyl group on C-2 carboxylate group), 4.64 (dm, 2, J=6, C-1 protons of allyl group on C-3 carboxylate group), 4.36 (d, 1, J=12, C-4 proton), 4.08 (t, 1, J=8, C-6 proton), 3.92 (d, 1, J=12, C-4 proton), 3.80 (s, 2, methylene protons of acetamido group), 2.86 (dd, 1, J=8, 12, C-6 proton); u.v. (methanol): $\lambda_{max}$=340 ($\epsilon$=6850), 230 ($\epsilon$=12,500); m.s.: M$^\oplus$=431; i.r. (CHCl$_3$): 1750, 1705 cm$^{-1}$;

Anal. Calcd. for $C_{20}H_{22}N_3O_6S$: Theory: C, 55.68; H, 4.91; N, 9.74; S, 7.43. Found: C, 55.97; H, 5.21; N, 9.52; S, 7.23.

EXAMPLE 3

2,3-di(Carboxylic Acid)-7-(R,S)-[2-(Thien-2-yl)Acetamido]-8-Oxo-1,5-Diazabicyclo[3.3.0]Octa-2-ene Triphenylphosphine (35 mg, 0.13 mmol) was added to a solution of palladium(II) acetate (6 mg, 0.026 mmol) in acetone (3 ml). The mixture was stirred until a white precipitate formed (10 minutes). An acetone solution (3 ml) of 2,3-di(allyl carboxylate)-7-(S)-[2-(thien-2-yl)acetamido]-8-oxo-1,5-diazabicyclo[3.3.0]octa-2-ene (200 mg, 0.46 mmol) was added to the mixture. After the resultant mixture became homogeneous, it was cooled to 0° C. and tri(n-butyl)tin hydride (0.27 ml, 1 mmol) was added. The solution was stirred at 0° C. for 30 minutes. 1N Hydrochloric acid (1 ml) was added and the solution was stirred for an additional 10 minutes. The solution was filtered, diluted with water (30 ml), then extracted with hexane (4 X, 50 ml). The aqueous phase was separated and freeze-dried to give 170 mg of yellow powder. The powder was triturated with ethyl acetate, sonicated, centrifuged, and the recovered solid was dried in vacuo to give 2,3-di(carboxylic acid)-7-(R,S)-[2-(thien-2-yl)acetamido]-8-oxo-1,5-diazabicyclo[3.3.0]octa-2-ene: n.m.r. (90 MHz, acetone-d$_6$): $\delta$ 7.20 (m, 1, C-5 proton of thienyl group), 6.94 (m, 2, C-3 and C-4 protons of thienyl group), 5.2–4.6 (m, 2, acetamido nitrogen proton and C-7 proton), 4.24 (d, 1, J=13, C-4 proton), 4.0–3.8 (m, 2, side chain methylene protons), 3.80 (s, 2, a C-6 proton and a C-4 proton), 3.0 (dd, 1, J=8, 12, a C-6 proton); u.v. (methanol): $\lambda_{max}$=345 ($\epsilon$=4000), 226 ($\epsilon$=7000); f.d.m.s.: (M+1)$^+$=352; i.r. (KBr): 1730, 1699, 1533, 1438, 1405, 1377, 1338, 1246, 1209, 1188 cm$^{-1}$.

EXAMPLE 4

2,3-di(Allyl Carboxylate)-7-(R,S)-[2-(2-Formamidothiazol-4-yl)-2-(Z)-Methoxyiminoacetamido]-8-Oxo-1,5-Diazabicyclo[3.3.0]Octa-2-ene

A. Removal of Amino-Protecting Group and Formation of TFA Salt 2,3-di(Allyl carboxylate)-7-(R,S)-(t-butoxycarbonylamino)-8-oxo-1,5-diazabicyclo[3.3.0]octa-2-ene (407 mg, 1 mmol) was dissolved in neat trifluoroacetic acid (3 ml) and the solution stirred for 5 minutes then concentrated in vacuo.

B. Neutralization of TFA Salt

The concentrate from Step A was dissolved in THF (10 ml) and BSTFA (1 ml) was added. The resultant mixture was stirred at 0° C. for 30 minutes.

C. Acid Chloride Formation of 7 Side Chain

A solution of ethyl acetate (2 ml) and dimethylformamide (0.123 ml, 1.6 mmol) was cooled to $-5°$ C. Phosphoryl chloride (0.093 ml, 1 mmol) was added and the solution was stirred for 1 hour. 2-(2-Formamidothiazol-4-yl)-2-(Z)-methoxyiminoacetic acid (229 mg, 1 mmol) was added and the solution was stirred for 90 minutes at 0° C.

D. Acylation

The solutions from Paragraphs B and C were combined and stirred at 0° C. for 1.5 hours. The solution was diluted with ethyl acetate, washed with saturated sodium bicarbonate solution and brine, dried over magnesium sulfate, filtered and concentrated in vacuo to give a foam. The foam was chromatographed on a silica gel preparatory-scale TLC plate eluted with 88:10:2 ethyl acetate:methanol:triethylamine. The chromatography yielded 135 mg (26% yield) of a yellow powder of 2,3-di(Allyl carboxylate)-7-(R,S)-[2-(2-formamidothiazol-4-yl)-2-(Z)-methoxyiminoacetamido]-8-oxo-1,5-diazabicyclo[3.3.0]octa-2-ene: n.m.r. (90 MHz, CDCl$_3$): $\delta$ 8.46 (s, 1, formyl proton), 8.04 (m, 1, proton on formamido nitrogen), 7.20 (s, 1, C-5 proton of thiazole group), 6.20–5.60 (m, 2, C-2 protons of allyl groups), 5.56–5.0 (m, 5, C-7 proton and C-3 (unsaturated) protons of allyl groups), 4.80 (d, 2, J=6, C-1 protons of allyl group on C-2 carboxylate group), 4.62 (d, 2, J=6, C-1 protons on allyl group of C-3 carboxylate group), 4.36 (d, 1, J=12, one of the C-4 protons), 4.2–3.6 (m, 2, one of the C-4 protons and one of the C-6 protons), 3.86 (s, 3, methoxime methyl protons), 3.16 (dd, 1, J=8, 12, one of the C-6 protons).

EXAMPLE 5

2,3-di(Allyl Carboxylate)-7-(R,S)-[2-(2-Aminothiazol-4-yl)-2-(Z)-Methoximinoacetamido]-8-Oxo-1,5-Diazabicyclo[3.3.0]Octa-2-ene 2,3-di(Allyl carboxylate)-7-(R,S)-[2-(2-formamidothiazol-4-yl)-2-(Z)-methoxyiminoacetamido]-8-oxo-1,5-diazabicyclo[3.3.0]octa-2-ene was produced as in Example 4 above except that the 600 mg of foam was not subjected to preparatory-scale thin layer chromatography. Instead, the foam was dissolved in methanol then concentrated hydrochloric acid (0.2 ml) was added. The solution was stirred for 1 hour and concentrated in vacuo. The concentrate was dissolved in chloroform and the solution was washed with saturated aqueous sodium bicarbonate solution, brine, dried over magnesium sulfate, filtered and concentrated in vacuo to give 400 mg of yellow foam of 2,3-di(allyl carboxylate)-7-(R,S)-[2-(2-aminothiazol-4-yl)-2-(Z)-methoxyiminoacetamido]-8-oxo-1,5-diazabicyclo[3.3.0]octa-2-ene:

n.m.r. (90 MHz, CDCl$_3$): $\delta$ 6.9 (s, 1) 6.2–5.1 (m, 7), 4.8 (d, 2, J=6), 4.62 (d, 2, J=6), 4.36 (d, 1, J=12), 4.2–3.6 (m, 2) with 3.9 (s, 3) superimposed, 3.2 (m, 1).

EXAMPLE 6

2,3-di(Sodium Carboxylate)-7-(R,S)-[2-(2-Aminothiazol-4-yl)-2-(Z)-Methoximinoacetamido]-8-Oxo-1,5-Diazabicyclo[3.3.0]Octa-2-ene Tetrakis[triphenylphosphine]palladium(0) (35 mg, 0.03 mmol) and triphenylphosphine (8 mg, 0.03 mmol) were dissolved in ethyl acetate (5 ml). An ethyl acetate solution (5 ml) of sodium 2-ethylhexanoate (332 mg, 2 mmol) was then added. To this mixture was added a solution of 2,3-di(allyl carboxylate)-7-(R,S)-[2-(2-aminothiazol-4-yl)-(Z)-methoxyiminoacetamido]8-oxo-1,5-diazabicyclo[3.3.0]octa-2-ene (1 mmol) in ethyl acetate (10 ml). The resultant mixture was stirred under a nitrogen atmosphere at room temperature for 2 hours. The precipitate from the reaction mixture was collected by centrifugation, triturated with ethyl acetate and diethyl ether, then dried in vacuo. The powder obtained (380 mg) was dissolved in water, washed with ethyl acetate, methylene chloride and diethyl ether then freeze-dried to give 270 mg of 2,3-di(sodium carboxylate)-7-(R,S)-[2-(2-aminothiazol-4-yl)-2-(Z)-methoxyiminoacetamido]-8-oxo-1,5-diazabicyclo[3.3.0]octa-2-ene: n.m.r. (90 MHz, D$_2$O): $\delta$ 7.0 (s, 1), 5.12 (m, 1), 4.08 (d, 1, J=12), 3.88 (s, 3), 3.9–3.0 (m, 3).

EXAMPLE 7

2,3-di(Carboxylic Acid)-7-(R,S)-[2-(2-Aminothiazol-4-yl)-2-(Z)-Methoxyiminoacetamido]-8-Oxo-1,5-Diazabicyclo[3.3.0]Octa-2-ene 2,3-di(Sodium carboxylate)-7-(R,S)-[2-(2-aminothiazol-4-yl)-2-(Z)-methoxyiminoacetamido]-8-oxo-1,5-diazabicyclo[3.3.0]octa-2-ene (approx. 270 mg) was dissolved in water (30 ml) and the pH of the solution was taken to 2 by the addition of 0.1N hydrochloric acid. The aqueous solution was extracted with diethyl ether the aqueous layer was freeze-dried to give 240 mg of yellow powder of 2,3-di-(carboxylic acid)-7-(R,S)-[2-(2-aminothiazol-4-yl)-2-(Z)-methoxyiminoacetamido-8-oxo-1,5-diazabicyclo[3.3.0]octa-2-ene: n.m.r. (270 MHz, D$_2$O): $\delta$ 7.24 (s, 1), 5.25 (m, 1), 4.32 (d, 1, J=13), 4.20 (m, 1), 4.0 (m, 1), with superimposed peak at 4.08 (s, 3), 3.30 (m, 1); m.s.: 303 (100%), 156 (20%); i.r. (KBr): 1721, 1687, 1681, 1634 cm$^{-1}$.

EXAMPLE 8

2,3-di(Allyl Carboxylate)-4,4-Dimethyl-7-(R,S)-(t-Butoxycarbonylamino)-8-Oxo-1,5-Diazabicyclo[3.3.0]Octa-2-ene 4-(R,S)-(t-Butoxycarbonylamino)-3-oxo-1-(dimethylmethylene)-1,2-pyrazolidinium ylide (1.68 g, approx. 7 mmol) was dissolved in methylene chloride (25 ml) and diallyl butynedioate (1.35 g, 7 mmol) was added to the solution. The mixture was stirred at room temperature for 3 days then concentrated in vacuo. The solid was chromatographed by HPLC using a silica gel column and a 2:1 hexane:ethyl acetate gradient elution. The chromatography yielded 2.06 g, 67% yield of 2,3di(allyl carboxylate)-4,4-dimethyl-7-(R,S)-(t-butoxycarbonylamino)-8-oxo-1,5-diazabicyclo[3.3.0]octa-2-ene: n.m.r. (270 MHz, CDCl$_3$) $\delta$ 5.90 (m, 2), 5.50–5.20 (m, 4), 5.10 (m, 1), 4.90–4.50 (m, 5), 3.74 (m, 1), 3.05 (m, 1), 1.52 (s, 3), 1.46 (s, 9), 1.32 (s, 3); m.s.: M$^+$=435; u.v. (methanol): $\lambda_{max}$=350 ($\epsilon$=7700); i.r. CHCl$_3$): 1749, 1707, 1436, 1385, 1370, 1274, 1231, 1215, 1161 cm$^{-1}$.

EXAMPLE 9

2,3-di(Allyl Carboxylate)-4,4-Dimethyl-7-(R,S)-[2-(Thien-2-yl)Acetamido]-8-Oxo-1,5-Diazabicyclo[3.3.0]Octa-2-ene

A. Removal of Amino Protecting Group and Formation of TFA Salt 2,3-di(Allyl carboxylate)-4,4-dimethyl-7-(R,S)-(t-butoxycarbonylamino)-8-oxo-1,5-diazabicyclo[3.3.0]octa-2-ene (435 mg, 1 mmol) was dissolved in neat trifluoroacetic acid (2 ml). The solution was allowed to stand for 5 minutes then concentrated in vacuo to a semi-solid. The semi-solid was dissolved in a 1:1 acetone:water solvent (6 ml) and the pH of the resultant solution was adjusted to 7 by the addition of sodium bicarbonate solution.

B. Acylation of Nucleus

The solution from Step A was cooled to 0° C. and 2-(thien-2-yl)acetyl chloride (240 mg, 1.5 mmol) was added dropwise while maintaining the pH of the solution between 6.5 to 7.5 by the addition of sodium bicarbonate solution. The reaction mixture was stirred for 30 minutes, diluted with chloroform, the layers separated the organic layer was washed with 1N sodium carbonate and brine, dried over magnesium sulfate, filtered and concentrated in vacuo. The resulting concentrate was chromatographed on a silica gel preparatory-scale TLC plate eluted with 2:1 hexane:ethyl acetate. The chromatography yielded 290 mg, 63% yield of yellow 2,3-di(allyl carboxylate)-4,4-dimethyl-7-(R,S)-[2-(thien-2-yl)acetamido]-8-oxo-1,5-diazabicyclo[3.3.0]-octa-2-ene: n.m.r. (90 MHz, CDCl$_3$): $\delta$ 7.16 (m, 1, C-5 proton of thienyl group), 6.90 (m, 2, C-3 and C-4 protons of thienyl group), 6.57 (d, 1, J=6, proton on nitrogen of acetamido group), 6.20–5.60 (m, 2, C-2 proton of allyl groups), 5.50–5.00 (m, 4, C-3 (unsaturated) protons of allyl groups), 85 (m, 1, C-7 proton), 4.72 (d, 2, J=6, C-1 protons of allyl group on C-2 carboxylate group), 4.58 (d, 2, J=6, C-1 protons of allyl group on C-3 carboxylate), 3.76 (s, 2, methylene protons of acetamido group), 3.68 (m, 1, one of the C-6 protons), 2.98 (dd, 1, J=9, 12, one of the C-6 protons), 1.49 (s, 3, protons on one of the C-4 methyl groups), 1.32 (s, 3, protons on one of the C-4 methyl groups); m.s.: M⊕=459; u.v. (methanol): $\lambda_{max}$=350 (ε=7900); i.r. (CHCl$_3$): 1750, 1729, 1706, 1438, 1386, 1375, 1334 cm$^{-1}$.

EXAMPLE 10

2,3-di(Sodium Carboxylate)-4,4-Dimethyl-7-(R,S)-[2-(Thien-2-yl)Acetamido]-8-Oxo-1,5-Diazabicyclo[3.3.0]Octa-2-ene Palladium(11) acetate (5 mg, 0.022 mmol) was dissolved in acetone (2 ml) and triphenylphosphine (29 mg, 0.11 mmol) was added. After approximately 5 minutes, a colorless precipitate of tetrakis(triphenylphosphine)palladium(0) was formed. To this solution was added a solution of sodium 2-ethylhexanoate (180 mg, 1.08 mmol) in acetone (1 ml) followed by the addition of a solution of 2,3-di(allyl carboxylate)-4,4-dimethyl-7-(R,S)-[2-(thien-2-yl)acetamido]-8-oxo-1,5-diazabicyclo[3.3.0]octa-2-ene (250 mg, 0.54 mmol) in acetone (3 ml). The mixture was stirred first until it was homogeneous and then for an additional 4 hours at room temperature. The reaction solution was concentrated in vacuo to yield 1.2 g of non-volatile oil. The oil was triturated with diethyl ether, centrifuged, and the resultant solid was dried in vacuo. A portion of the solid material (125 mg of the resultant 185 mg) was taken up in water (40 ml). The solution was washed with methylene chloride and diethyl ether then freeze-dried to yield 110 mg of yellowish-tinted solid of 2,3-di(sodium carboxylate)-4,4-dimethyl-7-(R,S)-[2-(thien-2-yl)-acetamido]-8-oxo-1,5-diazabicyclo-[3.3.0]octa-2-ene: n.m.r. (90 MHz, D$_2$O): 7.18 (m, 1, C-2 of thienyl group), 6.84 (m, 2, C-3 and C-4 protons of thienyl group), 4.82 (dd, 1, J=9, 12, C-7 proton); 3.73 (s, 2, protons on methylene protons of acetamido group), 3.60-2.95 (m, 2, C-6 protons), 1.24 (s, 3, protons on one of C-4 methyl groups), 1.20 (s, 3, protons on one of C-4 methyl groups); i.r. (KBr): 1685, 1610, 1580, 1374 cm$^{-1}$.

EXAMPLE 11

2,3-di(Allyl Carboxylate)-4,4-Dimethyl-(R,S)-[2-(2-Formamidothiazol-4-yl)-2-(Z)-Methoxyiminoacetamido]-8-Oxo-1,5-Diazabicyclo3.3.0]Octa-2-ene

A. Formation of the Side Chain Acid Chloride

Ethyl acetate (2 ml) and dimethylformamide (0.123 ml, 1.6 mmol) were combined and cooled to −5° C. then phosphoryl chloride (0.093 ml, 1 mmol) was added. The solution was stirred for 75 minutes at 0° C. then 2-(2-formamidothiazol-4-yl)-2-(Z)-methoxyiminoacetic acid (229 mg, 1 mmol) was added. The mixture was stirred at 0° C. for 80 minutes.

B. Removal of the Amino-Protecting Group 2,3-di(Allyl carboxylate)-4,4-dimethyl-7-(R,S)-(t-butoxycarbonylamino)-8-oxo-1,5-diazabicyclo[3.3.0]-octa-2-ene (435 mg, 1 mmol) was dissolved in neat trifluoroacetic acid (3 ml). The solution was stirred for 5 minutes at room temperature then concentrated and dried in vacuo. The residue is dissolved in 50% aqueous acetone (12 ml) and the pH of the resultant solution was adjusted to 7 by the addition of saturated sodium bicarbonate solution.

C. Acylation

The mixture of Paragraph A and the solution from Paragraph B were combined. The temperature of the resultant solution was maintained at 0° C. and the pH was maintained at 7 by the addition of sodium bicarbonate solution. The reaction solution was stirred for 30 minutes. The solution was poured into chloroform, the phases were separated, and the aqueous phase was back-extracted with chloroform. The chloroform extracts were combined, washed with brine, dried over magnesium sulfate, filtered and concentrated in vacuo to yield 540 mg of 2,3-di(allyl carboxylate)-4,4-dimethyl-7-(R,S)-[2-(2-formamidothiazol-4-yl)-2-(Z)-methoxyiminoacetamido]-8-oxo-1,5-diazabicyclo[3.3.0]octa-2-ene: n.m.r. (90 MHz, CDCl$_3$): δ 8.45 (s, 1, formyl group proton), 8.19 (m, 1, formamido nitrogen proton), 7.25 (s, 1, C-5 proton of thiazolyl group), 6.20-5.60 (m, 2, C-2 protons of allyl groups), 5.58-4.90 (m, 5, C-7 proton and C-3 protons (unsaturated) of allyl groups), 4.76 (br. d, 2, J=6, C-1 (saturated) protons of allyl group on C-2 carboxylate group), 4.60 (br. d, 2, J=6, C-1 (saturated) protons of allyl group on C-3 carboxylate group), 3.88 (s, 3, protons on methyl group of methoxime function), 3.68 (t, 1, J=8, one of C-6 protons), 3.30 (m, 1, one of C-6 protons), 1.55 (s, 3, protons on one of C-4 methyl group protons), 1.41 (s, 3, protons on one of C-4 methyl groups).

EXAMPLE 12

2,3-di(Allyl Carboxylate)-4,4-Dimethyl-7-(R,S)-[2-(2-Aminothiazol-4-yl)-2-(Z)-Methoxyiminoacetamido]-8-Oxo-1,5-Diazabicyclo[3.3.0]Octa-2-ene 2,3-di(Allyl carboxylate)-4,4-dimethyl-7-(R,S)-[2-(2-formamido-thiazol-4-yl)-2-(Z)-methoxyiminoacetamido]-8-oxo-1,5-diazabicyclo-[3.3.0]octa-2-ene (540 mg) was dissolved in methanol (10 ml) and concentrated hydrochloric acid (0.2 ml) was added. The solution was stirred for 1 hour then concentrated in vacuo. The concentrate was diluted with chloroform and the resultant solution was washed with saturated aqueous sodium bicarbonate solution and brine, dried over magnesium sulfate, filtered and concentrated in vacuo to give 500 mg of yellow foam of 2,3-di(allyl carboxylate)-4,4-dimethyl-7-(R,S)-[2-(2-aminothiazol-4-yl)-2-(Z)-methoxyiminoacetamido]-8-oxo-1,5-diazabicyclo-[3.3.0]-octa-2-ene; n.m.r. (90 MHz, CDCl$_3$): δ 8.4 (br. d, 1, J=7), 6.78 (s, 1), 6.1-5.0 (m, 7), 4.65 (d, 2, J=6), 4.58 (d, 2, J=6), 3.88 (s, 3), 4.1-3.0 (m, 3), 1.52 (s, 3), 1.38 (s, 3).

EXAMPLE 13

2,3-di(Sodium Carboxylate)-4,4-Dimethyl-7-(R,S)-[2-(2-Aminothiazol-4-yl)-2-(Z)-Methoxyiminoacetamido]-8-Oxo-1,5-Diazabicyclo[3.3.0]Octa-2-ene Palladium(II) acetate (7 mg, 0.031 mmol) was dissolved in acetone (4 ml) and triphenylphosphine (0.156 mmol, 35 mg) was added. After approximately 5 minutes, sodium 2-ethylhexanoate (332 mg, 2 mmol), dissolved in acetone (2 ml), was added to the mixture. To this mixture was added an acetone solution (5 ml) of 2,3-di(allyl carboxylate)-4,4-dimethyl-7-(R,S)-[2-(2-aminothiazol-4-yl)-2-(Z)-methoxyiminoacetamido]-8-oxo-1,5-diazabicyclo3.3.0]octa-2-ene (500 mg). The reaction mixture was stirred at room temperature for 3 hours. The mixture was centrifuged and the solvent was decanted. Acetone (20 ml) was added, the mixture was sonicated, centrifuged, and the acetone was decanted and the combination sonication/centrifugation procedure repeated again. The solid was triturated 3 more times with diethyl ether (20 ml) using the same procedure as with the acetone sonication/centrifugations. The trituration procedure was then carried out twice with ethyl acetate (20 ml). The resultant solid was dried in vacuo to yield 335 mg of 2,3-di(sodium carboxylate)-4,4-dimethyl-7-(R,S)-[2-(2-aminothiazol-4-yl)-2-(Z)-methoxyiminoacetamido]-8-oxo-1,5-diazabicyclo3.3.0]-octa-2-ene: n.m.r. (90 MHz, D$_2$O): δ 6.96 (s, 1, C-5 proton of thiazolyl group), 5.10 (dd, 1, J=8, 12, C-7 proton), 3.90 (s, 3, protons of methyl group of methoxime functionality), 3.80–2.96 (m, 2, C-6 protons), 1.38 (s, 3, protons on one of C-4 methyl groups), 1.36 (s, 3, protons on one of C-4 methyl groups); u.v. (methanol): $\lambda_{max}$=350 (ε=4200), 295 (ε=6600), 230 (ε=14,200); i.r. (KBr): 1685, 1662, 1616, 1576, 1536, 1370 cm$^{-1}$.

EXAMPLE 14

2,3-di(Carboxylic Acid)-4,4-Dimethyl-7-(R,S)-[2-(2-Aminothiazol-4-yl)-2-(Z)-Methoxyiminoacetamido]-8-Oxo-1,5-Diazabicyclo[3.3.0]Octa-2-ene 2,3-di(Sodium carboxylate)-4,4-dimethyl-7-(R,S)[2-(2-aminothiazol-4-yl)-2-(Z)-methoxyiminoacetamido]-8-oxo-1,5-diazabicyclo-[3.3.0]octa-2-ene (335 mg) was chromatographed by HPLC on a C$_{18}$ mu bond pack reverse phase cartridge and with a combination of water, 1% acetic acid and a 0 to 5% acetonitrile gradient. The fraction containing the desired product was freeze-dried to give 140 mg of a yellow powder of 2,3-di(carboxylic acid)-4,4-dimethyl-7-(R,S)-[2-(2-aminothiazol-4-yl)-2-(Z)-methoxyiminoacetamido]-8-oxo-1,5-diazabicyclo [3.3.0]octa-2-ene: n.m.r. (90 MHz, D$_2$O): δ 7.08 (s, 1, C-5 proton of thiazolyl group), 5.10 (dd, 1, J=8, 12, C-7 proton), 3.99 (s, 3, protons of methyl group of methoxime functionality), 3.68 (t, 1, J=8, one of C-6 protons), 3.38 (t, 1, J=12, one of the C-6 protons), 1.49 (s, 3, protons of one of the C-4 methyl groups), 1.36 (s, 3, protons of one of C-4 methyl groups); u.v. (methanol : $\lambda_{max}$=348 (ε=5000), 296 (ε=7100), 230 (ε=16,000); i.r. (KBr): 1685, 1670, 1582, 1577, 1542, 1437, 1410, 1369, 1311, 1050 cm$^{-1}$.

EXAMPLE 15

2-(Allyl Carboxylate)-3-(Methyl Carboxylate)-4,4-(Dimethyl)-7-(R,S)-(t-Butoxycarbonylamino)-8-Oxo-1,5-Diazabicyclo[3.3.0]Octa-2-ene and the Corresponding 2,3-Regioisomer 4-(R,S)-(t-Butoxycarbonylamino)-3-oxo-1-(dimethylmethylene)-1,2-pyrazolidinium ylide (0.72 g, 3.00 mmol), methyl allyl butynedioate (0.504 g, 3.00 mmol) and dry methylene chloride (10 ml) were combined under an argon atmosphere. The mixture was stirred at room temperature for one week, then adsorbed onto a silica gel column. The column was eluted with a solvent gradient of 0 to 50% ethyl acetate in hexane. The product-containing factions were combined to give a mixture of 2-(allyl carboxyate)-3-(methyl carboxylate)-4,4-(dimethyl)-7-(R,S)-(t-butoxycarbonylamino)-8-oxo1,5-diazobicyclo[3.3.0]octa-2-ene and the corresponding 2,3-regioisomer: n.m.r. (90 MHz, CDCl$_3$): (both regioisomers) δ 6.15–5.62 (m, 1), 5.52–4.92 (m, 3), 4.88–4.52 (m, 3), 3.86 and 3.69 (2x s, 3) 3.80–3.50 (m, 1), 3.14–2.85 (m, 1), 1.49 (s, 3), 1.43 (s, 9), 1.34 (s, 3).

EXAMPLE 16

2-(Allyl Carboxylate)-3-(Methyl Carboxylate)-4,4-(Dimethyl)-7-(R,S)-[2-(2-Allyloxycarbonylamino)-thiazol-4-yl)-2-(Z)-Methoxyiminoacetamido]-8-Oxo-1,5-Diazabicyclo-[3.3.0]Octa-2-ene and the Corresponding 2,3-Regioisomer

A. Formation of Side Chain Acid Chloride

Under an argon atmosphere, ethyl acetate (2 ml) and phosphoryl chloride (0.079 ml, 0.85 mmol) were combined and the solution was stirred and cooled to approximately 0° C. DMF (0.096 ml, 1.24 mmol) was added and the solution was stirred at ice bath temperature for 1 hour and 15 minutes. 2-(2-(Allyloxycarbonylamino)-thiazol-4-yl)-2-(Z)-methoxyiminoacetic acid (0.242 g, 0.85 mmol) was added and the solution was stirred at 0° C. for 2 hours.

B. Removal of Amino-Protecting Group and Formation of the TFA Salt 2-(Allyl carboxylate)-3-(methyl carboxylate)-4,4-(dimethyl)-7-(R,S)-(t-butoxycarbonylamino)-8-oxo-1,5-diazabicyclo[3.3.0]octa-2-ene and the corresponding 2,3-regioisomer (0.32 g, 0.78 mmol) were dissolved in trifluoroacetic acid (4 ml) and stirred for approximately 10 minutes. The solution was concentrated in vacuo and the concentrate was taken up in dry methylene chloride and concentrated 3 times. The resulting foam was dried in vacuo at room temperature for 0.5 hour.

C. Neutralization of the TFA Salt

The foam from Step B was dissolved in THF (10 ml) and BSTFA (0.80 ml, 3.0 mmol) was added. The reaction solution was stirred at room temperature under argon for 0.5 hour.

D. Acylation of Nucleus

The solution from Step C was cooled to approximately 0° C. and combined with the acid chloride solution from Step A. The resultant reaction mixture was stirred under argon for 0.5 hour at 0° C. Ethyl acetate (10 ml) was added and the solution was washed with 1N hydrochloric acid (45 ml), saturated aqueous sodium bicarbonate solution and brine, dried over magnesium sulfate, filtered and concentrated in vacuo. The concentrate was dried in vacuo for 48 hours to give 0.43 g, 96% yield of crude product. The product was recrystallized from methylene chloride/isopropyl ether and dried in vacuo at room temperature overnight to give 0.278 g, 62% yield of 2-(allyl carboxylate)-3-(methyl carboxylate)-4,4-(dimethyl)-7-(R,S)-[2-(2-(allyloxycarbonylamino)thiazol-4-yl)-2-(Z)-methoxyiminoacetamido]-8-oxo-1,5-diazabicyclo[3.3.0]octa-2-ene and the corresponding 2,3-regioisomer: n.m.r. (90 MHz, CDCl$_3$): δ 8.11 (d, 1,), 7.12 (s, 1,), 7.0–6.4 (br. m, 1), 6.20–5.64 (m, 2), 5.60–5.12 (m, 4), 4.88–4.52 (m, 4), 4.10–3.60 (m, 2), 3.93 (s, 3), 3.84 and 3.72 (2x s, 3), 3.40–3.08 (m, 1,), 1.54 (s, 3), 1.39 (s, 3); i.r. (CHCl$_3$): 1753, 1726, 1702, 1562, 1555, 1449, 1430, 1275, 1235, 1215 cm$^{-1}$; u.v. (ethanol): $\lambda_{max}$=352 (ε=8633), $\lambda_{max}$=263 (ε=12,764), $\lambda_{max}$=220 (ε=21,768); f.d.m.s.: M$^+$= 577 (0.21), M$^+$=576 (1.0); m.p. 193°–195° C.

Anal. Calcd. for C$_{24}$H$_{28}$N$_6$O$_9$S: Theory: C, 50.00; H, 4.90; N, 14.58; S, 5.56. Found: C, 50.23; H, 4.83; N, 14.57; S, 5.33.

EXAMPLE 17

2-(Carboxylic Acid)-3-(Methyl Carboxylate)-4,4-(Dimethyl)-7-(R,S)-2-(2-Aminothiazol-4-yl)-2-(Z)-Methoxyiminoacetamido]-8-Oxo-1,5-Diazabicyclo[3.3.0]Octa-2-ene and the Corresponding 2,3-Regioisomer Tetrakis[triphenylphosphine]palladium(0) (30 mg, 0.026 mmol) was added to a solution of triphenylphosphine (6.8 mg, 0.026 mmol) in acetone (3 ml). An acetone solution (12 ml) of 2-(allyl carboxylate)-3-(methyl carboxylate)-4,4-dimethyl-7-(R,S)-[2-(2-(allyloxycarbonylamino)thiazol-4-yl)-2-(Z)-methoxyiminoacetamido]-8-oxo-1,5-diazabicyclo3.3.0]octa-2-ene and the corresponding 2,3-regioisomer (250 mg, 0.43 mmol) was added. The solution was cooled to 0° C. and tri(n-butyl)tin hydride (0.23 ml, 0.86 mmol) was added dropwise. The resultant solution was stirred at 0° C. for 30 minutes then 1M hydrochloric acid (0.86 ml) was added and the solution was stirred for 10 minutes. Water (20 ml) was added and the resultant solution was extracted with hexane (3x, 40 ml). The layers were separated and the aqueous phase was concentrated in vacuo by azeotropically distilling the phase with acetonitrile. The distillation yielded 240 mg of residue. The residue was taken up in methanol (4 ml) and diethyl ether was added with sonication. The resultant precipitate was collected by centrifugation and dried in vacuo to give 150 mg of a yellow solid of the title product. The yellow solid was chromatographed by HPLC on a C-18 reverse phase column (11×300 mm column). The column was eluted with a mixture of 10% acetonitrile:2% acetic acid in water (500 ml) then with 15% acetonitrile:2% acetic acid in water. The chromatography yielded approximately 80 mg of yellow powder of the 2-(carboxylic acid)-3-(methyl carboxylate)regioisomer and approximately 30 mg of the 2-(methyl carboxylate)-3-(carboxylic acid)regioisomer: 2-(carboxylic acid)-3-(methyl carboxylate) regioisomer: n.m.r. (90 MHz, $D_2O$): δ 7.04 (s, 1), 5.05 (dd, 1, J=8,11), 3.96 (br. s, 3), 3.63 (s, 3), 4.8–4.2 (m, 2), 1.42 and 1.30 (2 x s, 6); i.r. (KBr): 1698, 1634, 1534 cm$^{31}$ $^1$; m.s.: $(M^+—CO_2)=408$; u.v. (ethanol): $\lambda_{max}=335$ ($\epsilon=10,500$); 2-(methyl carboxylate)-3-(carboxylic acid) regioisomer: n.m.r. (90 MHz, $D_2O$): δ 6 5.10 (m, 1), 4.2–3.1 (m, 2), 3.8 (s, 6), 1.36 (s, 6); i.r. (KBr): 1738, 1700, 1675, 1625, 1592 cm$^{-1}$; m.s.: $M^+=452$; u.v.: (ethanol) $\lambda_{max}=302$ ($\epsilon=9700$).

EXAMPLE 18

2-(Allyl Carboxylate)-3-(Methyl Carboxylate)-7-(R,S)-(t-Butoxycarbonylamino)-8-Oxo-1,5-Diazaicyclo-[3.3.0]Octa-2-ene and the Corresponding 2,3-Regioisomer 4-(R,S)-(t-Butoxycarbonylamino)-3-oxo-1-(methylene)-1,2-pyrazolidinium ylide, (32.6 g, 153 mmol), 1,2-dichloroethane (150 ml) and allyl methyl butynedioate (23.46 g, 139.5 mmol) were combined and refluxed under argon for 4 hours. The reaction solution was adsorbed onto a silica gel column which was eluted with a gradient of hexane to 1:1 hexane:ethyl acetate. The chromatography gave 3.69 g of the 2-(methyl carboxylate)-3-(allyl carboxylate) regioisomer. Further purification on preparatory scale HPLC of the unseparated column chromatography products yielded 3.41 g of the 2-(allyl carboxylate)-3-(methyl carboxylate)regioisomer. 2-(Allyl carboxylate)-3-(methyl carboxylate) regioisomer: n.m.r. (90 MHz, CDCl$_3$): 6.2–5.6 (m, 1), 5.50–5.04 (m, 3), 4.78 (dm, 2, J=5, C-1 protons (saturated) of allyl group), 4.60 (br. m, 1), 4.40–3.70 (m, 3, C-4 protons and one of C-6 protons), 3.66 (s, 3, protons of methyl group of methyl ester), 2.83 (dd, 1, J=8, 12, one of C-6 protons), 1.36 (s, 9, methyl protons of t-butoxy group); m.s.: $M^+=381$; u.v. (methanol): $\lambda_{max}=345$ ($\epsilon=7300$); i.r. (CHCl$_3$) 1750, 1737, 1710, 1417, 1370, 1285, 1234 cm$^{31}$ $^1$;

Anal. Calcd. for $C_{17}H_{23}O_7N_3$: Theory: C, 53.54; H, 6.08; N, 11.02. Found: C, 53.69; H, 6.05; N, 10.73.

2-(Methyl carboxylate)-3-(allyl carboxylate) regioisomer:

n.m.r. (90 MHz, CDCl$_3$) δ 6.10–5.60 (m, 1), 5.50–5.04 (m, 3), 4.70 (br. m, 1), 4.56 (dm, 2, J=5, C-1 (saturated) protons of allyl group), 4.40–3.56 (m, 3, the C-4 protons and one of C-6 protons), 3.84 (s, 3, methyl protons of methyl ester), 2.84 (dd, 1, J=9, 12, one of C-6 protons), 1.36 (s, 9, methyl protons of t-butoxy group); m.s.: $M^+=381$; u.v. (methanol): $\lambda_{max}=345$ ($\epsilon=7950$); i.r. (CHCl$_3$): 1753, 1709, 1438, 1377, 1371, 1280, 1234, 1215, 1163 cm$^{31}$ $^1$;

Anal. Calcd. for $C_{17}H_{23}O_7N_3$: Theory: C, 53.54; H, 6.08; N, 11.02. Found: C, 53.73; H, 6.08; N, 10.87.

EXAMPLE 19

2-(Allyl Carboxylate)-3-(Methyl Carboxylate)-7-(R,S)-[2-(2,5-Dichlorophenylthio)Acetamido]-8-Oxo-1,5-Diazabicyclo[3.3.0]Octa-2-ene

A. Removal of the Amino-Protecting Group and the Formation of the TFA Salt 2-(Allyl carboxylate)-3-(methyl carboxylate)-7-(R,S)-(t-butoxycarbonylamino)-8-oxo-1,5-diazabicyclo[3.3.0]octa-2-ene (195 mg, 0.5 mmol) was dissolved in trifluoroacetic acid (2 ml) and the solution was allowed to stand for 5 minutes. The solution was concentrated in vacuo and methylene chloride was added to the concentrate. The solution was concentrated in vacuo then dried in vacuo.

B. Neutralization of TFA Salt

The solid from Step B was dissolved in THF (3 ml) and the solution was cooled to 0° C. BSTFA (0.5 ml) was added and the solution was stirred at 0° C. for 20 minutes.

C. Formation of the Side Chain Acid Chloride 2-(2,5-Dichlorophenylthio)acetic acid (142 mg, 0.6 mmol) was dissolved in THF (20 ml) and the solution was cooled to 0° C. To the solution was added triethylamine (84 μl, 0.6 mmol) then oxalyl chloride (53 μl, 0.6 mmol). The reaction solution was stirred for 20 minutes.

D. Acylation

The solution of Step C was added through a filter to the solution of Step B. The resultant solution was stirred for 45 minutes. The solution was diluted with ethyl acetate, washed with 0.5N hydrochloric acid, saturated aqueous sodium bicarbonate solution and brine, dried over magnesium sulfate and concentrated in vacuo. The concentrate was chromatographed on a preparatory-scale TLC plate eluted with 1:1 hexane:ethyl acetate. Two elutions gave a yellow band ($R_f=0.15$) containing 60 mg, 24% yield of 2-(allyl carboxylate)-3-(methyl carboxylate)-7-(R,S)-[2-(2,5-dichlorophenylthio)acetamido]-8-oxo-1,5-diazabicyclo[3.3.0]octa-2-ene: n.m.r. (90 MHz, CDCl$_3$): 7.6–7.2 (m, 3), 6.4–5.9 (m, 1), 5.7–5.38 (m, 2), 5.18 (m, 1), 5.0 (dm, 2, J=7), 4.5 (d, 1, J=13), 4.20 (t, 1, J=7), 4.08 (d, 1, J=13), 3.88 (s, 3), 3.85 (s, 2), 3.02 (dd, 1, J=7, 13).

EXAMPLE 20

2-(Sodium Carboxylate)-3-(Methyl Carboxylate)-7-(R,S)-[2-(2,5-Dichlorophenylthio)Acetamido]-8-Oxo-1,5-Diazabicyclo[3.3.0]Octa-2-ene Tetrakis(triphenylphosphine)palladium(0) (10 mg, 0.008 mmol) and triphenylphosphine (2 mg, 0.007 mmol) were dissolved in tetrahydrofuran (2 ml). To the solution was added sodium 2-ethylhexanoate (20 mg, 0.12 mmol) followed by a solution of 2-(allyl carboxylate)-3-(methyl carboxylate)-7-(R,S)-[2-(2,5-dichlorophenylthio)acetamido]-8-oxo-1,5-diazabicyclo[3.3.0]octa-2-ene (60 mg, 0.12 mmol) in THF (3 ml). The reaction mixture was stirred at room temperature for 30 minutes then allowed to stand overnight. A small amount (approximately 2 ml) of THF was evaporated and diethyl ether (5 ml) was added, causing a precipitate. The precipitate was collected by centrifugation, triturated several times with diethyl ether then dried in vacuo to give 40 mg of 2-(sodium carboxylate)-3-(methyl carboxylate)-7-(R,S)-[2-(2,5-dichlorophenylthio)acetamido]-8-oxo-1,5-diazabicyclo[3.3.0]octa-2-ene: n.m.r. (90 MHz, $D_2O$): $\delta$ 7.3 (m, 3, aromatic protons), 4.90 (dd, 1, J=8, 12, C-7 proton), 4.16 (d, 1, J=12, one of the C-4 protons), 3.8–3.3 (m, 2, one of the C-4 protons and one of the C-6 protons), 3.66 (s, 3, methyl protons of methyl ester group), 3.72 (s, 2, methylene protons of acetamido group), 2.94 (dd, 1, J=9, 12, one of the C-6 protons).

EXAMPLE 21

2-(Allyl Carboxylate)-3-(Methyl Carboxylate)-7-(R,S)-[2-(Thien-2-yl)Acetamido]-8-Oxo-1,5-Diazabicyclo-[3.3.0]Octa-2-ene

A. Removal of the Amino-Protecting Group and Formation of the TFA Salt 2-(Allyl carboxylate)-3-(methyl carboxylate)-7-(S)-(t-butoxycarbonylamino)-8-oxo-1,5-diazabicyclo[3.3.0octa-2-ene (110 mg, 0.28 mmol) was dissolved in neat trifluoroacetic acid (2 ml), the solution was allowed to stand for 5 minutes and concentrated in vacuo.

B. Neutralization of the TFA Salt

The concentrate from Step A was taken up in THF (3 ml) and BSTFA (0.4 ml) was added. The solution was stirred for 15 minutes at 0° C.

C. Acylation 2-(Thien-2-yl)acetyl chloride (56 mg, 0.35 mmol) was added to the solution from Step B. The resultant solution was stirred at 0° C. for 45 minutes. The solution was poured into ethyl acetate, washed with saturated aqueous sodium bicarbonate solution, 0.2N hydrochloric acid and brine, dried over magnesium sulfate, filtered and concentrated in vacuo. The concentrate was chromatographed on a silica gel preparatory-scale TLC plate eluted with 1:1 hexane:ethyl acetate. Two elutions of this chromatography system gave 30 mg of 2-(allyl carboxylate)-3-(methyl carboxylate)-7-(R,S)-[2-(thien-2-yl)acetamido]-8-oxo-1,5-diazabicyclo[3.3.0]octa-2-ene: n.m.r. (90 MHz, $CDCl_3$): $\delta$ 7.17 (m, 1, C-5 proton of thienyl group), 6.90 (m, 2, C-3 and C-4 protons of thienyl group), 6.52 (br. m, 1, proton on nitrogen of amido group), 6.20–5.68 (m, 1, C-2 proton of allyl group), 5.50–5.10 (m, 2, $sp^2$ methylene protons of allyl group), 4.92 (m, 1), 4.76 (d, 2, J=6, C-1 protons of allyl group), 4.30 (d, 1, J=12, one of C-4 protons), 4.23 (t, 1, J=8, one of the C-6 protons), 3.98 (d, 1, J=12, one of the C-4 protons), 3.74 (s, 2, methylene protons of acetamido group), 3.67 (s, 3, protons of methyl group of methyl ester), 2.80 (dd, 1, J=8, 12, one of the C-6 protons).

EXAMPLE 22

2-(Sodium Carboxylate)-3-(Methyl Carboxylate)-7-(R,S)-[2-(Thien-2-yl)Acetamido]-8-Oxo-1,5-Diazabicyclo[3.3.0]Octa-2-ene Tetrakis[triphenylphosphine]palladium(0) (10 mg, 0.008 mmol) was slurried in ethyl acetate (2 ml). Triphenylphosphine (2 mg, 0.008 mmol) and sodium 2-ethylhexanoate (11 mg, 0.066 mmol) were added to the slurry. 2-(Allyl carboxylate)-3-(methyl carboxylate)-7-(R,S)-[2-(thien-2-yl)acetamido]-8-oxo-1,5-diazabicyclo[3.3.0]octa-2-ene (25 mg, 0.06 mmol) added to the slurry which was stirred for 5 minutes to effect solution. The slurry was stirred for an additional 2 hours at room temperature. The resultant precipitate was collected by centrifugation. The precipitate was triturated with ethyl acetate and diethyl ether then dried in vacuo to give 2-(sodium carboxylate)-3-(methyl carboxylate)-7-(R,S)-2-(thien-2-yl)acetamido]-8-oxo-1,5-diazabicyclo[3.3.-0]octa-2-ene: n.m.r. (90 MHz, $D_2O$): $\delta$ 7.28 (m, 1, C-5 proton of thienyl group), 6.94 (m, 2, C-3 and C-4 protons of thienyl group), 4.96 (dd, 1, J=8, 11, C-7 proton), 4.19 (d, 1, J=11, one of the C-4 protons) 4.00–3.60 (m, 3), 3.80 (s, 2, methylene protons of acetamido group) 3.66 (s, 3, protons of methyl group of methyl ester), 3.06 (dd, 1, J=8, 11, one of the C-6 protons); i.r. (KBr): 1726, 1689, 1635, 1416, 1271, $cm^{-1}$.

EXAMPLE 23

2-(Allyl Carboxylate)-3-(Methyl Carboxylate)-7-(R,S)-[2-(2-Formamidothiazol-4-yl]-2-(Z)-Methoxyiminoacetamido)-8-Oxo-1,5-Diazabicyclo[3.3.0]Octa-2-ene

A. Removal of the Amino-Protecting Group and Formation of the TFA Salt 2-(Allyl carboxylate)-3-(methyl carboxylate)-7-(R,S)-(t-butoxycarbonylamino)-8-oxo-1,5-diazabicyclo[3.3.-0]octa-2-ene (350 mg, 0.92 mmol) was dissolved in trifluoroacetic acid (3 ml). The solution was stirred for 5 minutes then concentrated in vacuo. Methylene chloride (200 ml) was added to the concentrate and the solution was concentrated and taken to dryness in vacuo.

B. Neutralization of the TFA Salt

The residue from Step A was taken up in THF (3 ml) and the solution was cooled to 0° C. BSTFA (1 ml) was added and the solution was stirred for 30 minutes at 0° C.

C. Formation of the Side Chain Acid Chloride

DMF (0.123 ml, 1.6 mmol) was dissolved in ethyl acetate (2 ml) and the solution was cooled to 0° C. Phosphoryl chloride (0.093 ml, 1 mmol) was added and the solution was stirred for one hour. 2-(2-Formylamido-thiazol-4-yl)-2-(Z)-methoxyiminoacetic acid (229 mg, 1 mmmol) was added and the solution was stirred at 0° C. for an additional 90 minutes.

D. Acylation

The solutions from the Steps B and C are combined and the solution was stirred at 0° C. for 30 minutes. The solution was diluted with ethyl acetate, washed several times with saturated aqueous sodium bicarbonate solution and brine, dried over magnesium sulfate, filtered then concentrated in vacuo. The concentrate was chromatographed on silica gel eluted with a gradient of hexane to ethyl acetate to yield 170 mg of 2-(allyl carboxylate)-3-(methyl carboxylate)-7-(R,S)-[2-(2-formamidothioazol-4-yl]-2-(Z)-methoxyiminoacetamido)-8-oxo-1,5-diazabicyclo[3.3.0]octa-2-ene: n.m.r. (90 MHz, CDCl$_3$): δ 8.52 (s, 1, formyl proton), 8.02 (m, 1, proton of formamido nitrogen), 7.28 (s, 1, C-5 proton of thiazolyl group), 6.28–5.76 (m, 1, C-2 proton of allyl group), 5.60–5.10 (m, 3, C-7 proton and C-3 (unsaturated) methylene protons of allyl group), 4.84 (dm, 2, J=6, C-1 protons of allyl group), 4.52–3.60 (m, 3, C-4 protons and one of the C-6 protons), 3.92 (s, 3, methyl protons on methoxime group), 3.74 (s, 3, methyl protons of methyl ester), 3.14 (dd, 1, J=7.5, 11, one of the C-6 protons): m.s.: M+ =492; u.v. (methanol): $\lambda_{max}$=345 (ε=6400), 272 (ε=8500): i.r. (KBr): 1751, 1697, 1674, 1559, 1425, 1380, 1280, 1254, 1208 cm$^{-1}$.

EXAMPLE 24

2-(Sodium Carboxylate)-3-(Methyl Carboxylate)-7-(R,S)-[2-(2-Formamidothiazol-4-yl)-2-(Z)-Methoxyiminoacetamido]-8-Oxo-1,5-Diazabicyclo[3.3.0]Octa-2-ene Tetrakis[triphenylphosphine]palladium(0) (10 mg), triphenylphosphine (2 mg) and sodium 2-ethylhexanoate (58 mg, 0.34 mmol) were dissolved in ethyl acetate (5 ml). To this solution was added a slurry of 2-(allyl carboxylate)-3-(methyl carboxylate)-7-(R,S)-[2-( 2-formamidothiazol-4-yl)-2-(Z)-methoxyiminoacetamido]-8-oxo-1,5-diazabicyclo[3.3.0]octa-2-ene (170 mg, 0.34 mmol) in ethyl acetate (15 ml). The reaction solution was stirred overnight at room temperature. The resultant precipitate was collected by centrifugation. The precipitate was triturated with ethyl acetate (20 ml), then centrifuged and the solvent was decanted. The trituration/centrifugation procedure was repeated with ethyl acetate and diethyl ether. The solid was dried in vacuo to give 137 mg, 85% yield of 2-(sodium carboxylate)-3-(methyl carboxylate)-7-(R,S)-2-(2-formamidothiazol-4-yl)-2-(Z)-methoxyiminoacetamido]-8-oxo-1,5-diazabicyclo[3.3.0]octa-2-ene: n.m.r. (90 MHz, D$_2$O): δ 8.52 (br. d, 1, formyl proton), 7.50 (br. d, 1, C-5 proton of thiazoyl group), 5.16 (m, 2), 4.40–3.80 (m, 3, C-4 protons and one of C-6 protons), 3.92 (s, 3,), 3.67 (s, 3), 3.20 (t, 1, J=10, one of the C-6 protons); i.r. (KBr): 1725, 1684, 1636, 1632, 1554, 1417, 1413, cm$^{-1}$.

EXAMPLE 25

2-(Carboxylic Acid)-3-(Methyl Carboxylate)-7-(R,S)-[2-(2-Aminothiazol-4-yl)-2-(Z)-Methoxyiminoacetamido]-8-Oxo-1,5-Diazabicyclo[3.3.0]Octa-2-ene 2-(Sodium Carboxylate)-3-(methyl carboxylate)-7(R,S)-(2-(2-formamidothiazol-4-yl)-2-(Z)-methoxyiminoacetamido)-8-oxo-1,5-diazobioyclo[3.3.0]octa-2-ene (414 mg) was dissolved in methanol (10 ml). Concentrated hydrochloric acid (0.25 ml) was added and the solution was stirred at room temperature for 30 minutes. The solution was concentrated in vacuo and the residue was dissolved in water. The solution extracted with methylene chloride, ethyl acetate, and diethyl ether. The aqueous phase was freeze-dried to give 330 mg of yellow powder. The powder was chromatographed using a 50 ml-volume column of HP-20 resin and a series of eluants that began with water (100 ml) then 1%, 2%, 3%, 4%, 5% and 6% acetonitrile/water (100 ml each). The chromatography yielded 120 mg of 2-(carboxylic acid)-3-(methyl carboxylate)-7-(R,S)-2-(2-aminothiazol-4-yl)-2-(Z)-methoxyiminoacetamido]-8-oxo-1,5-diazobicyclo[3.3.0]octa-2-ene: n.m.r. (270 MHz, D$_2$O): δ 7.08 (s, 1, C-5 proton of thiazolyl group), 5.25 (m, 1, C-7 proton), 4.30 (d, 1, J=11, one of the C-4 protons), 4.20–3.60 (m, 2, one of the C-4 protons and one of the C-6 protons), 4.02 (s, 3, methyl protons of methoxy functionality), 3.78 (s, 3, methyl protons of methyl ester), 3.28 (t, 1, J=8, one of the C-6 protons); m.s.: M+ =424; i.r. (KBr): 1731, 1693, 1686, 1680, 1675, 1634, 1630 cm$^{-1}$.

EXAMPLE 26

2-(Allyl Carboxyl)-3-(Methyl Carboxylate)-7-(R,S)-[2-(2-allyloxycarbonylamino)thiazol-4-yl)-2-(Z)-Methoxyiminoacetamido]-8-Oxo-1,5-Diazabicyclo[3.3.0]Octa-2-ene

A. Formation of Side Chain Acid Chloride

Under an argon atmosphere, ethyl acetate (20 ml) and phosphoryl chloride (0.91 ml, 9.86 mmol) were combined and the solution was cooled in an icebath. DMF (1.11 ml, 14.3 mmol) was added and the mixture was stirred at 0° C. under argon for 50 minutes. 2-[2-(allyloxycarbonylamino)thiazol-4-yl-2-(Z)-methoxyiminoacetic acid (2.78 g, 9.74 mmol) was added to the mixture, which changed approximately 5 minutes later to a clear yellow solution. The solution was stirred for an additional 90 minutes.

B. Removal of Amino-Protecting Group and Formation of the TFA Salt 2-(Allyl carboxylate)-3-(methyl carboxylate)-7-(R,S)-(t-butoxycarbonylamino)-8-oxo-1,5-diazabicyclo[3.3.0]octa-2-ene (3.41 g, 8.93 mmol) was dissolved in trifluoroacetic acid (20 ml) and the solution was stirred for approximately 5 minutes. The solution was concentrated under reduced pressure, taken up in methylene chloride then concentrated in vacuo several times. The foam was again taken up in a mixture of methylene chloride and ether and the solution was concentrated. The residual foam/syrup was stored in vacuo.

C. Neutralization of TFA Salt

The foam/syrup of Step B above was dissolved in dry THF (120 ml) then treated with BSTFA (8 ml). The solution was stirred under argon at room temperature for 30 minutes then cooled to 0° C.

D. Acylation

To the solution of neutralized compound from Step C was added the acid chloride solution of Step A. The mixture was stirred for 20 minutes at 0° C. The mixture was added to ethyl acetate (150 ml) and the solution was washed with 1M hydrochloric acid (2x, 125 ml), saturated aqueous sodium bicarbonate (125 ml) and brine (100 ml), dried over magnesium sulfate, filtered and concentrated under reduced pressure. The dried residue was crystallized from methylene chloride/isopropyl ether to yield 1.6 g, 33% of 2-(allyl carboxylate)-3-(methyl carboxylate)-7-(R,S)-2-(allyloxycarbonylamino)thiazol-4-yl)-2-(Z)-methoxyiminoacetamido]-8-oxo-1,5-diazabicyclo[3.3.0]octa-2-ene: n.m.r. (90 MHz, CDCl$_3$): δ 8.16 (br. d, 1, J=7), 7.10, (s. 1), 6.20–5.70 (m, 2), 5.48–5.18 (m, 4), 4.90–4.65 (m, 4), 4.38 (d, 1, J=11), 4.2–3.9 (m, 3), 3.92 (s, 3), 3.73 (s, 3), 3.10 (dd, 1, J=8, 11); i.r. (KBr): 1753, 1733, 1704, 1676, 1563, 1422, 1287, 1282, 1252, 1232 cm$^{31}$ $^1$; u.v. (ethanol): $\lambda_{max}$=343 (ε=7500), 262 (ε=13,000), 225

(shoulder, ε=20,000); f.d.m.s.: 549 (0.76), 548 (1.0), 547 (0.20);

Anal. Calcd. for $C_{22}H_{24}O_9N_6S$: Theory: C, 48.17; H, 4.41; N, 15.32; S, 5.85. Found: C, 47.95; H, 4.22; N, 15.11; S, 5.83.

EXAMPLE 27

2-(Carboxylic Acid)-3-(Methyl Carboxylate)-7-(R,S)-[2-(2-Aminothiazol-4-yl)-2-(Z)-Methoxyiminoacetamido]-8-Oxo-1,5-Diazabicyclo[3.3.0]Octa-2-ene Under an argon atmosphere, palladium(II) acetate (0.114 g, 0.508 mmol) and acetone (30 ml) were combined. Triphenylphosphine (0.472 g, 1.80 mmol) was added to the stirred solution and rinsed in with an additional amount of acetone (10 ml). The mixture was stirred at room temperature under argon for 20 minutes. 2-(Allyl carboxylate)-3-(methyl carboxylate)-7-(R,S)-[2-(2-(allyloxycarbonylamino)thiazol-4-yl)-2-(Z)-methoxyiminoacetamide-]-8-oxo-1,5-diazabicyclo[3.3.-0]octa-2-ene (3.48 g, 6.34 mmol), dissolved in acetone (300 ml), was added. The mixture was stirred at room temperature for 35 minutes then cooled to 0° C. and tri(n-butyl)tin hydride (3.41 ml, 12.7 mmol) was added dropwise. The resultant solution was stirred at 0° C. for 25 minutes, then the cooling bath was removed and the solution was stirred for an additional 45 minutes at room temperature. The cooling bath was replaced and 1M hydrochloric acid (12.7 ml) was added. The resultant solution was stirred at ice-bath temperature for approximately 10 minutes and at room temperature for approximately 5 minutes. The solution was filtered and water was added (400 ml) to the filtrate resulting in a precipitate. The precipitate was collected by filtration and the cloudy filtrate was washed with hexane (4x, 25 ml). The aqueous mixture was then filtered through Celite and the filtrate concentrated in vacuo to yield a orange gum precipitate. The precipitate was removed by filtration. The yellow aqueous filtrate was washed once with ether (150 ml), the dissolved ether was removed in vacuo, and the solution was filtered then lyophilized over night. The lyophilization yielded 2.50 g, 93% of the 2-(carboxylic acid)-3-(methyl carboxylate)-7-(R,S)-[2-(2-aminothiazol-4-yl)-2-(Z)-methoxyiminoacetamido]-8-oxo-1,5-diazabicyclo3.3.0]octa-2-ene.

EXAMPLE 28

2-(Methyl Carboxylate)-3-(Allyl Carboxylate)-7-(R,S)-[2-(2-Thien-2-yl)Acetamido]-8-Oxo-1,5-Diazabicyclo[3.3.0]octa-2-ene

A. Removal of the Amino-Protecting Group and Formation of the TFA Salt 2-(Methyl carboxylate)-3-(allyl carboxylate)-7-(R,S)-(t-butoxycarbonylamino)-8-oxo-1,5-diazobicyclo-[3.3.0]octa-2-ene (and the corresponding 2,3-regioisomer) (120 mg, 0.31 mmol) was dissolved in neat trifluoroacetic acid (2 ml). The solution was allowed to stand for 5 minutes then concentrated in vacuo.

B. Neutralization of the TFA Salt

The concentrate from Step A was taken up in THF (3 ml) and BSTFA (0.4 ml) was added. The solution was stirred at 0° C. for 15 minutes.

C. Acylation 2-(Thien-2-yl)acetyl chloride (64 mg, 0.4 mmol) was added to the solution from Step B. The reaction solution was stirred at 0° C. for 45 minutes then poured into ethyl acetate, washed with saturated sodium bicarbonate solution, 0.2N hydrochloric acid solution and brine, dried over magnesium sulfate, filtered and concentrated in vacuo. The resultant concentrate was chromatographed on a preparatory-scale TLC plate eluted with 1:1 hexane:ethyl acetate. The chromatography yielded 50 mg of a 3:2 mixture of 2,3-regioisomers: 2-(Methyl carboxylate)-3-(allyl carboxylate)-7-(R,S)(2-(2-thien-2-yl)acetamido)-8-oxo-1,5-diazabicyclo-[3.3.0]octa-2-ene: n.m.r. (90 MHz, CDCl$_3$): δ 7.17 (m, 1, C-5 proton of thienyl group) 6.90 (m, 1, C-3 and C-4 protons of thienyl group), 6.60 (br. m, 1, proton on nitrogen of amido group), 6.20–5.60 (m, 1, C-2 proton of the allyl group), 5.50–5.10 (m, 2, C-3 (unsaturated) protons of allyl group), 4.95 (m, 1, C-7 proton), 4.56 (dm, 2, J=6, C-1 protons of the allyl group), 4.28 (d, 1, J=13, one of the C-4 protons), 4.16–3.6 (m, 2), 3.82 (s, 3, protons on methyl group of methyl ester), 3.72 (s, 2, methylene protons of acetamido group), 2.81 (dd, 1, J=8, 12).

EXAMPLE 29

2-(Methyl Carboxylate)-3-(Sodium Carboxylate)-7-(R,S)-[2-(Thien-2-yl)Acetamido]-8-Oxo-1,5-Diazabicyclo[3.3.0]Octa-2-ene Tetrakis[triphenylphosphine]palladium(0) (10 mg, 0.008 mmol) was dissolved in ethyl acetate. Triphenylphosphine (2 mg, 0.008 mmol) then sodium 2-ethylhexanoate (20 mg, 0.12 mmol) was added to the solution followed by the addition of an ethyl acetate solution (2 ml) of the product of Example 28: 2-(methyl carboxylate)-3-(allyl carboxylate)-7-(R,S)-(2-(thien-2-yl)acetamido)-8-oxo-1,5-diazabicyclo[3.3.0]octa-2-ene (and the corresponding 2,3-regioisomer) (50 mg). The reaction solution was stirred for three hours at room temperature. The solution was centrifuged, the solid product was collected, triturated with ethyl acetate and diethyl ether and dried in vacuo to give a yellowish powder that was a 4:1 mixture of 2,3-regioisomers. (The 2-(methyl carboxylate)-3-(sodium carboxylate) regioisomer was the predominant component of the mixture.) 2-(Methyl carboxylate)-3-(sodium carboxylate)-7-(R,S)-[2-(thien-2-yl)acetamido]-8-oxo-1,5-diazabicyclo[3.3.0]octa-2-ene: n.m.r. (90 MHz, D$_2$O): δ 7.26 (m, 1), 6.96 (m, 2), 4.96 (dd, 1, J=8, 12), 4.20 (d, 1, J=11), 4.04–3.60 (m, 3), 3.80 (s, 5, superimposed on 3.60 absorbance), 3.08 (m, 1).

EXAMPLE 30

2-(Methyl Carboxylate)-3-(Allyl Carboxylate)-7-(R,S)-[2-(2-Formamidothiazol-4-yl)-2-(Z)-(Methoxyiminoacetamido]-8-Oxo-1,5-Diazabicyclo[3.3.0]Octa-2-ene

A. Formation of Side Chain Acid Chloride

Ethyl acetate (2 ml) and DMF (0.123 ml, 1.6 mmol) were combined and cooled to 0° C. Phosphoryl chloride (93 μl, 1 mmol) was added and the resultant solution was stirred for 45 minutes. To this solution was added 2-(2-formamidothiazol-4-yl)-2-(Z)-methoxyiminoacetic acid (229 mg, 1 mmol) and the solution was then stirred for 80 minutes at 0° C.

B. Removal of the Amino-Protecting Group and Formation of the TFA Salt 2-(Methyl carboxylate)-3-(allyl carboxylate)-7-(R,S)-(t-butoxycarbonylamino)-8-oxo-1,5-diazabicyclo[3.3.0]octa-2-ene (360 mg, 0.94 mmol) was dissolved in neat trifluoroacetic acid (3 ml). The solution was allowed to stand for 5 minutes then concentrated in vacuo.

C. Neutralization of TFA Salt

The concentrate from Step B was taken up in THF (5 ml) and the solution was cooled to 0° C. BSTFA (1 ml) was added and the solution was stirred at 0° C. for 30 minutes.

D. Acylation

The solutions from the Steps A and C were combined and the reaction solution was stirred at 0° C. for 1.5 hours. The solution was washed with ethyl acetate and saturated aqueous sodium bicarbonate solution, dried over magnesium sulfate, filtered and concentrated in vacuo to give 400 mg of a yellow waxy solid. The solid was chromatographed on silica gel (4 g) eluting with a 100% hexane to 100% ethyl acetate gradient. The chromatography yielded 190 mg, 41% yield of yellow powder of 2-(methyl carboxylate)-3-(allyl carboxylate)-7-(R,S)-2-(2-formamidothiazol-4-yl)-2-(Z)-methoxyiminoacetamido]-8-oxo-1,5-diazabicyclo[3.3.0]octa-2-ene: n.m.r. (90 MHz, CDCl$_3$): $\delta$ 8.52 (s, 1, proton of formamido group), 7.96 (m, 1, proton on nitrogen of formamido group), 7.24 (s, 1, C-5 proton of thiazolyl group), 6.10–5.60 (m, 1, C-2 proton of allyl group), 5.52–5.12 (m, 3, sp$^2$ methylene protons of allyl group and C-7 proton), 4.65 (dm, 2, J=6, C-1 (saturated) protons of allyl group), 4.52–3.60 (m, 3, C-4 protons and one of C-6 protons), 3.97 (s, 3), 3.92 (s, 3), 3.10 (dd, 1, J=7.5, 11, one of the C-6 protons); u.v. (methanol): $\lambda_{max}$=350 ($\epsilon$=5600), 270 ($\epsilon$= 10,200); i.r. (CHCl$_3$): 1738, 1702, 1558, 1438, 1429, 1374 cm$^{-1}$.

EXAMPLE 31

2-(Methyl Carboxylate)-3-(Sodium Carboxylate)-7-(R,S)-[2-(Formamidothiazol-4-yl)-2-(Z)-Methyoxyiminoacetamido]-8-Oxo-1,5-Diazabicyclo[3.3.0]octa-2-ene Tetrakis[triphenylphosphine]pallidium(0) (10 mg), triphenylphosphine (2 mg) and sodium 2-ethylhexanoate (64 mg, 0.38 mmol) were dissolved in ethyl acetate (5 ml). To the solution was added a THF suspension (10 ml) of 2-(methyl carboxylate)-3-(allyl carboxylate)-7-(R,S)-[2-(2-formamidothiazol-4-yl)-2-(Z)methoxyiminoacetamido]-8-oxo-1,5-diazabicyclo[3.3.0]octa-2-ene (190 mg, 0.38 mmol). The reaction mixture was stirred at room temperature overnight. The mixture was centrifuged and the solvent decanted. Ethyl acetate (20 ml) was added, the suspension was sonicated, centrifuged and the solvent was again decanted. This procedure was repeated with ethyl acetate and diethyl ether and the solid collected was dried in vacuo to give 160 mg, 88% yield of 2-(methyl carboxylate)-3-(sodium carboxylate)-7-(R,S)-[2-(formamidothiazol-4-yl)-2-(Z)-methoxyiminoacetamido]-8-oxo-1,5-diazabicyclo[3.3.0]octa-2-ene: n.m.r. (90 MHz, D$_2$O): $\delta$ 8.52 (d, 1, J=5, proton of formamido group), 7.50 (d, 1, J=4, C-5 proton of thiazolyl group), 5.20 (m, 1, C-7 proton), 4.2–3.50 (m, 3, C-4 protons and one C-6 protons), 3.92 (s, 3), 3.82 (s, 3), 3.22 (t, 1, J=9, one of the C-6 protons); m.s.: M$^+$=474; i.r. (KBr): 1679, 1598, 1559, 1441, 1371, 1331 cm$^{31}$ $^1$;

Anal. Calcd. for C$_{16}$H$_{15}$O$_8$N$_6$S: Theory: C, 40.51; H, 3.19; N, 17.46. Found: C, 40.26; H, 3.33; N, 17.46.

EXAMPLE 32

2-(Methyl Carboxylate)-3-(Carboxylic Acid)-7-(R,S)-[2-(2-Aminothiazol-4-yl)-(Z)-Methoxyiminoacetamido]-8-Oxo-1,5-Diazabicyclo[3.3.0]Octa-2-ene 2-(methyl carboxylate)-3-(sodium carboxylate)-7-(R,S)-[2-(2-formamidothiazol-4-yl)-2-(Z)-methoxyiminoacetamido]-8-oxo-1,5-diazabicyclo[3.3.0]octa-2-ene (43 mg, 0.09 mmol) was dissolved in methanol (1 ml) and treated with 2 drops of concentrated hydrochloric acid. The solution was stirred for 30 minutes and then concentrated in vacuo. The concentrate was partitioned between water and chloroform, and the aqueous phase was freeze-dried to obtain approximately 35 mg of 2-(methyl carboxylate)-3-(carboxylic acid)-7-(R,S)-[2-(2-aminothiazol-4-yl)-2-(Z)-methoxyiminoacetamido]-8-oxo-1,5-diazabicyclo[3.3.0]octa-2-ene: n.m.r. (90 MHz, D$_2$O): $\delta$ 7.06 (s, 1, C-5 proton of thiazolyl group), 5.1 (m, 1, C-7 proton), 4.50–3.50 (m, 3, C-4 protons and one of the C-6 protons), 3.94 (s, 3, protons of methyl group of methoxime functionality), 3.86 (s, 3, protons of methyl group of methyl ester), 3.28 (dd, 1, J=5, 6, one of the C-6 protons): m.s.: (M$^+$+1)=425, (M$^+$−1)=423; i.r. (KBr): 1735, 1706, 1670, 1653, 1631 cm$^{-1}$.

EXAMPLE 33

2-Phenyl-3-(Allyl Carboxylate)-7-(R,S)-(t-Butoxycarbonylamino)-8-Oxo-1,5-Diazabicylo[3.3.0]Octa-2-ene 4-(R,S)-(t-Butoxycarbonylamino)-3-oxo-1-(methylene)-1,2-pyrazolidinium ylide (810 mg, 3.8 mmol), allyl 3-phenylpropynoate (710 mg, 3.8 mmol) and acetonitrile (10 ml) were combined and the solution was refluxed for approximately 8 hours then stirred for approximately 48 hours at room temperature. The solution was concentrated in vacuo to give an orangetinted oil. The oil was chromatographed on a silica gel preparatory-scale TLC plate eluted with 1:1 hexane:ethyl acetate. The chromatography yielded 160 mg, 10% yield of 2-phenyl-3-(allyl carboxylate)-7-(R,S)-(t-butoxycarbonylamino)-8-oxo-1,5-diazabicyclo[3.3.0]octa-2-ene: n.m.r. (90 MHz, CDCl$_3$): $\delta$ 7.40 (m, 5), 5.96–4.94 (m, 3), 4.62 (m, 1), 4.50 (d, 2, J=6), 4.40 (d, 1, J=12) 4.04 (t, 1, J=8), 3.92 (d, 1, J=12), 2.81 (dd, 1, J=8, 12), 1.40 (s, 9); m.s.: M$^+$=399; u.v. (methanol): $\lambda_{max}$=350 ($\epsilon$=6800), 245 ($\epsilon$=7600); i.r. (CHCl$_3$): 1708, 1369, 1362, 1277, 1230 cm$^{31}$ $^1$;

Anal. Calcd. for C$_{21}$H$_{25}$N$_3$O$_5$:
Theory: C, 63.15; H, 6.31; N, 10.52. Found: C, 62.88; H, 6.40; N, 10.35.

EXAMPLE 34

2-Phenyl-3-(Allyl Carboxylate)-7-(R,S)-[2-(Thien-2-yl)Acetamido-8-Oxo-1,5-Diazabicyclo[3.3.0]-Octa-2-ene

A. Removal of Amino-Protecting Group and Formation of TFA Salt

2-Phenyl-3-(allyl carboxylate)-7-(R,S)-(t-butoxycarbonylamino)-8-oxo-1,5-diazabicyclo[3.3.0]octa-2-ene (160 mg, 0.4 mmol) was dissolved in neat trifluoroacetic acid (3 ml). The solution stirred for 5 minutes then concentrated in vacuo.

B. Neutralization of the TFA Salt

The concentrate from Step A was taken up in THF (2 ml), cooled to 0° C. and treated with BSTFA (0.7 ml). The solution was stirred for 15 minutes.

C. Acylation 2-(Thien-2-yl)acetyl chloride (80 mg, 0.5 mmol) was added to the solution from Step B. The solution was stirred for 30 minutes at 0° C. The solution was poured into ethyl acetate, washed with saturated aqueous sodium bicarbonate solution, 0.2N hydrochloric acid and brine, dried over magnesium sulfate, filtered and concentrated in vacuo. The solid obtained was chromatographed on a preparatory-scale TLC plate eluted with 1:1 hexane:ethyl acetate. Two elutions on this system gave 70 mg, 41% yield of 2-phenyl-3-(allyl carboxylate)-7-(R,S)-[2-(thien-2-yl)acetamido]-8-oxo-1,5-diazabicyclo3.3.0]-octa-2-ene: n.m.r. (90 MHz, CDCl$_3$): $\delta$7.3 (m, 5), 7.05 (m, 1), 6.9 (m, 2), 6.4 (br. d, 1), 5.9–5.45 (m, 1), 5.2–4.5 (m, 3), 4.5 (dm, 2, J=5), 4.3 (d, 1, J=12), 3.96 (t, 1, J=7), 3.7 (d, 1, J=12), 3.58 (s, 3), 2.55 (m, 1).

EXAMPLE 35

2-Phenyl-3-(Sodium Carboxylate)-7-(R,S)-[2-(Thien-2-yl)Acetamido]-8-Oxo-1,5-Diazabicyclo[3.3.0]Octa2-ene Tetrakis[triphenylphosphine]palladium(0) (10 mg, 0.008 mmol) was slurried in ethyl acetate (3 ml). Triphenylphosphine (2 mg, 0.008 mmol) then sodium 2-ethylhexanoate (28 mg, 0.16 mmol) was added. An ethyl acetate solution (3 ml) of 2-phenyl-3-(allyl carboxylate)-7-(R,S)-[2-(thien-2-yl)acetamido]-8-oxo-1,5-diazabicyclo[3.3.0]octa-2-ene (70 mg, 0.16 mmol) was added to the slurry. The resultant solution was stirred for approximately 2 hours at room temperature then centrifuged to collect the solid. The solid was triturated with ethyl acetate and diethyl ether then dried in vacuo to give 58 mg (89% yield) of 2-phenyl-3-(sodium carboxylate)-7-(R,S)-[2-(thien-2-yl)acetamido]-8-oxo-1,5-diazabicyclo[3.3.0]octa-2-ene: n.m.r. (90 MHz, D$_2$O ): $\delta$7.36 (s, 5), 7.28 (m, 1), 6.90 (m, 2), 4.96 (m, 1) 4.40–3.60 (m, 3), 3.78 (s, 2), 3.04 (br. t, 1, J=10); u.v. (methanol); $\lambda_{max}$=320 ($\epsilon$=6700), 233 ($\epsilon$=15,700); i.r. (KBr): 1698, 1694, 1668, 1627, 1581, 1570, 1370, 1324 cm$^{-1}$.

EXAMPLE 36

2-(Allyl Carboxylate)-3-(Dimethylphosphonato)-7-(R,S)-(t-Butoxycarbonylamino)-8-Oxo-1,5-Diazabicyclo-[3.3.0]Octa-2-ene 4-(R,S)-(t-Butoxycarbonylamino)-3-oxo-1,2-diazolidine (1.60 g, 8 mmol) was dissolved in methanol (30 ml) and 37% aqueous formaldehyde (0.7 g, 8 mmol) was added. The reaction solution was stirred at room temperature for 30 minutes then concentrated in vacuo. Isopropanol was added to the concentrate which in turn was concentrated in vacuo. This concentration procedure was repeated several times. The concentrate was dried in vacuo overnight then was dissolved in 1,2-dichloroethane (50 ml) and the solution was refluxed for approximately 30 minutes using an apparatus with a Dean-Stark trap. Allyl 3-(dimethylphosphonato)-propynoate (1.74 g, 7.98 mmol) was added and the resultant solution was refluxed for 2.5 hours. The solution was cooled and concentrated in vacuo to give a yellow gum. The gum was chromatographed by HPLC on a Waters Prep 500 silica gel column and a gradient of 40% hexane/60% ethyl acetate to 100% ethyl acetate as the eluant to give 1.6 g, 46% yield of 2-(allyl carboxylate)-3-(dimethylphosphonato)-7-(R,S)-(t-butoxycarbonylamino)-8-oxo-1,5-diazabicyclo-[3.3.0]octa-2-ene: n.m.r. (90 MHz, CDCl$_3$): $\delta$6.2–5.8 (m, 1), 5.6–5.0 (m, 3), 4.84 (dm, 2, J=6), 4.7 (m, 1), 4.4 (dd, 1, J=3, 12), 4.05 (m, 1), 3.85 (dd, 1, J=3, 12), 3.84 (s, 3), 3.72 (s, 3), 2.90 (dd, 1, J=9, 12), 1.5 (s, 9); m.s.: M$^+$=431; u.v. (95% ethanol): $\lambda_{max}$=321 ($\epsilon$=5090); i.r. (CHCl$_3$) 1714, 1502, 1055, 1038 cm$^{-1}$;

Anal. Calcd. for C$_{17}$H$_{25}$O$_8$N$_3$P: Theory: C, 47.33; H, 6.08; N, 9.74; P, 7.18. Found: C, 47.29; H, 6.08; N, 9.58; P, 6.90.

EXAMPLE 37

2-(Allyl Carboxylate)-3-(Dimethylphosphonato)-7-(R,S)-[2-(2,5-Dichlorophenylthio)Acetamido-8-Oxo-1,5-Diazabicyclo[3.3.0]Octa-2-ene

A. Removal of Amino-Protecting Group and Formation of TFA Salt 2-(Allyl carboxylate)-3-(dimethylphosphonato)-7-(R,S)-(t-butoxycarbonylamino)-8-oxo-1,5-diazabicyclo-[3.3.0]octa-2-ene (160 mg, 0.37 mmol) was dissolved in trifluoroacetic acid (2 ml). The solution was allowed to stand for 5 minutes and then concentrated in vacuo.

Methylene chloride (10 ml) was added to the concentrate and the solution was concentrated in vacuo. This procedure with methylene chloride was repeated and then the residue was dried in vacuo for 30 minutes.

B. Neutralization of TFA Salt

The residue from Step A was taken up in THF (3 ml), the solution was cooled to 0° C. then BSTFA (0.5 ml) was added. The solution was stirred for 30 minutes at 0° C.

C. Acylation 2-(2,5-Dichlorophenylthio)acetyl chloride (115 mg, 0.45 mm) was added to the solution from Step B. The reaction solution was stirred for 2 hours at 0° C. The solution was diluted with ethyl acetate, washed with 0.5N hydrochloric acid, saturated sodium bicarbonate solution and brine, dried over magnesium sulfate, filtered and concentrated in vacuo. The concentrate was chromatographed on a preparatory-scale TLC plate eluted with 1% methanol in ethyl acetate to give 120 mg, 67% yield of 2-(allyl carboxylate)-3-(dimethylphosphonato)-7-(R,S)-[2-(2,5-dichlorophenylthio)acetamido]-8-oxo-1,5-diazabicyclo-[3.3.0]octa-2-ene: n.m.r. (90 MHz, CDCl$_3$): $\delta$7.42 (br. d, 1), 7.3–6.96 (m, 3), 6.15–5.7 (m, 1), 5.5–5.1 (m, 2), 4.96 (m, 1), 4.75 (dm, 2, J=7), 4.24 (dd, 1, J=3, 12), 4.05–3.6 (m, 2), 3.76 (d, 3, J=2), 3.65 (s, 2), 3.64 (d, 3, J=2), 2.92 (dd, J=9, 12),; u.v. (95% ethanol): $\lambda_{max}$=324 ($\epsilon$=5500), 255 ($\epsilon$=9000); i.r. (CHCl$_3$): 1745, 1680 cm$^{-1}$.

EXAMPLE 38

2-(Sodium Carboxylate)-3-(Dimethylphosphonato)-7-(R,S)-[2-(2,5-Dichlorophenylthio)Acetamido]-8-Oxo-1,5-Diazabicyclo[3.3.0]Octa-2-ene Tetrakis[triphenylphosphine]palladium(0) (10 mg, 0.008 mmol) and triphenylphosphine (2 mg, 0.007 mmol) were dissolved in ethyl acetate (3 ml). To this solution was added sodium 2-ethylhexanoate (31 mg, 0.19 mmol) then an ethyl acetate solution (3 ml) of 2-(allyl carboxylate)-3-(dimethylphosphonato)-7-(R,S)-[2-

(2,5-dichlorophenylthio)acetamido]-8-oxo-1,5-diazabicyclo-[3.3.0]octa-2-ene (90 mg, 0.185 mmol). The reaction solution was stirred overnight at room temperature. Ethyl acetate (approximately 3 ml) was removed under a stream of nitrogen then diethyl ether (3 ml) was added. The precipitate that formed was collected by centrifugation then triturated with 1:1 ethyl acetate:diethyl ether and dried in vacuo to give 66 mg of 2-(sodium carboxylate)-3-(dimethylphosphonato)-7-(R,S)-[2-(2,5-dichlorophenylthio)acetamido]-8-oxo-1,5-diazabicyclo[3.3.0]octa-2-ene: n.m.r. (90 MHz, D$_2$O): $\delta$7.25 (m, 3, aromatic protons), 4.90 (dd, 1, J=8, 12, C-7 proton), 4.5–3.2 (m, 3, the C-4 protons and one of C-6 protons), 3.74 (s, 3, protons on one of the methyl groups of dimethylphosphonato), 3.7 (s, 2, methylene protons of acetamido group), 3.62 (d, 3, protons of one of the methyl groups on dimethylphosphonato group), 2.94 (m, 1, one of the C-6 protons).

EXAMPLE 39

2-(Allyl Carboxylate)-3-(Dimethylphosphonato)-7-(R,S)-[2-(2-allyloxycarbonylamino)Thiazol-3-yl-2-(Z)-Methoximinoacetamido]-8-Oxo-1,5-Diazabicyclo[3.3.0]-Octa-2-ene

A. Formation of Side Chain Acid Chloride

Phosphoryl Chloride (51 microliters, 0.55 mmol) was dissolved in an ethyl acetate solution (2 ml) of DMF (68 microliters, 0.8 mmol). The solution was stirred for 1 hour at 0° C. 2-(2-(Allyloxycarbonylamino)thiazol-4-yl)-2-(Z)-methoximinoacetic acid (143 mg, 0.5 mmol) was added and the solution stirred at 0° C. for an additional 90 minutes.

B. Removal of the Amino-Protecting Group and Formation of TFA Salt 2-(Allyl carboxylate)-2-(dimethylphosphonato)-7-(R,S)-(t-butoxycarbonylamino)-8-oxo-1,5-diazabicyclo-[3.3.0]octa-2-ene (194 mg, 0.45 mmol) was dissolved in neat trifluoroacetic acid. The solution was allowed to stand for 5 minutes at room temperature then concentrated in vacuo. The concentrate was dissolved in methylene chloride, the methylene chloride was removed in vacuo and the concentration procedure was repeated. The residue was dried under vacuum for 15 minutes. Diethyl ether was added to the residue and the solution was sonicated. The diethyl ether was decanted and the sonication/decant procedure with diethyl ether was repeated. The solid residue was dried in vacuo.

C. Neutralization of the TFA Salt

The solid residue from Step B above was dissolved in dry THF (2 ml) and BSTFA (0.5 ml) was added. The mixture was stirred for 5 minutes.

D. Acylation

The product solutions from Step A and Step C were combined and the resultant solution was stirred at 0° C. for 1.5 hours. The reaction solution was then diluted with ethyl acetate, washed with 1N hydrochloric acid, saturated aqueous sodium bicarbonate solution and brine, dried over magnesium sulfate, filtered and concentrated in vacuo to give approximately 260 mg of a yellow gum. The yellow gum was applied to a silica gel preparatory-scale TLC plate and eluted with ethyl acetate. The product-containing bands were extracted from the TLC plate using a mixture of 20% methanol in ethyl acetate to give 35 mg, 12.6% of a yellow gum of the 2-(allyl carboxylate)-3-(dimethylphosphonato)-7-(R,S)-[2-(allyloxycarbonylamino)thiazol-3-yl-2-(Z)-methoximinoacetamido]- 8-oxo-1,5-diazabicyclo[3.3.0]octa-2-ene; n.m.r. (90 MHz, CDCl$_3$) $\delta$8.44 (d, 1, J=7), 7.08 (s, 1), 6.1–5.6 (m, 2), 5.6–5.1 (m, 5), 4.72 (m, 4), 4.5–3.6 (m, 3), 3.92, 3.80, 3.68 (3x s, 3 each), 3.05 (m, 1); i.r. (CHCl$_3$): 1727, 1713, 1679, 1562 cm$^{-1}$; u.v. (95% ethanol): $\lambda_{max}$=320 ($\epsilon$=6,000 shoulder), 266 ($\epsilon$=13,400);

Anal. Calcd. for C$_{21}$H$_{27}$O$_{10}$N$_6$PS: Calcd.: C, 44.15; H, 4.55; N, 14.04. Found: C, 44.23; H, 4.63; N, 13.94.

EXAMPLE 40

2-(Carboxylic Acid)-3-(Dimethylphosphonato)-7-(R,S)-[2-(2-Aminothiazol-4-yl)-2-(Z)-Methoxyiminoacetamido]-8-Oxo-1,5-Diazabicyclo-[3.3.0]Octa-2-ene Triphenylphosphine (2 mg, 0.008 mmol) and tetrakis[triphenylphosphine]palladium(0) (0.008 mmol) were slurried in acetone (2 ml). An acetone solution (2 ml) of the product from Example 39, Step D was added. The resultant solution was cooled to 0° C. and tri(n-butyl)tin hydride (20.6 $\mu$l, 0.077 mmol) was added. The resultant mixture was stirred at 0° C. for 20 minutes then at room temperature for 1.5 hour. The solution was cooled to 0° C. and 1N hydrochloric acid (77 $\mu$l) was added. The solution was stirred for 10 minutes then centrifuged to remove a small amount of precipitate. Water was added to the solution and the resultant mixture was extracted several times with hexane. The aqueous phase was freeze-dried to yield a yellowish-tinted powder, some of which was partitioned between acetonitrile and pentane. The layers were separated and the acetonitrile layer was concentrated in vacuo to give 7 mg of 2-(carboxylic acid)-3-(dimethylphosphonato)-7-(R,S)-[2-(2-aminothiazol-4-yl)-2-(Z)-methoxyiminoacetamido]-8-oxo-1,5-diazabicyclo-[3.3.0]octa-2-ene; n.m.r.: (D$_2$O, 270 MHz): $\delta$7.08 (s, 1), 5.28 (dd, 1), 4.25 (dd, 1), 4.1–3.5 (m, 3), 3.99, 3.86, 3.78 (3 x s, superimposed on multiplet at 4.1–3.5, 3 each).

EXAMPLE 41

2-(Allyl Carboxylate)-3-(Diethylphosphonato)-7-(R,S)-(t-Butoxycarbonylamino)-8-Oxo-1,5-Diazabicylo-[3.3.0]Octa-2-ene 4-(R,S)-(t-Butoxycarbonylamino)-3-oxo-1-(methylene)-1,2-pyrazolidinium ylide (1.61 g, 7.5 mmol), allyl 3-(diethylphosphonato)propynoate (1.85 g, 7.5 mmol) and 1,2-dichloroethane (50 ml) were combined, refluxed for 4 hours, cooled and concentrated in vacuo. The concentrate was chromatographed over silica gel (100 g silica) eluting sequentially with 1:1 ethyl acetate:-hexane (1.5 L), 7:3 ethyl acetate:hexane (1 L) and 100% ethyl:acetate (1 L). The chromatography yielded 1.25 g of yellow foam of the 2-(allyl carboxylate)-3-(diethylphosphonato)-7-(R,S)-(t-butoxycarbonylamino)-8-oxo-1,5-diazabicylo-[3.3.0]octa-2-ene; n.m.r. (90 MHz, CDCl$_3$): $\delta$5.9 (m, 1), 5.3 (m, 2), 4.78 (dm, 2, J=6), 4.62 (m, 1), 4.50 (dd, 1, J=3, 12), 4.1 (m, 4), 3.98 (m, 1), 3.78 (dd, 1, J=3, 12), 2.84 (dd, 1, J=9, 11), 1.42 (s, 9), 1.36 (t, 6, J=7); i.r. (CHCl$_3$): 1713, 1501, 1393, 1369, 1272, 1253 cm$^{-1}$; m.s.: M$^+$=459; u.v. (ethanol): $\lambda_{max}$=320 ($\epsilon$=4303);

EXAMPLE 42

2-(Carboxylic Acid)-3-(Diethylphosphonato)-7-(R,S)-(Amino)-8-Oxo-1,5-Diazabicylo[3.3.0]Octa-2-ene Zwitterion

A. Removal of Carboxy-Protecting Group

Tetrakis[triphenylphosphine]palladium(0) (58 mg, 0.05 mmol)/ triphenylphosphine (13 mg, 0.05 mmol) and sodium 2-ethylhexanoate (166 mg, 1 mmol) were suspended in THF (3 ml). The solution was added to a THF solution (7 ml) of 2-(allyl carboxylate)-3-(diethylphosphonato)-7-(R,S)-(t-butoxycarbonylamino)-8-oxo-1,5-diazabicylo[3.3.0]octa-2-ene (440 mg, 0.95 mmol). The resultant solution was stirred at room temperature overnight then concentrated in vacuo to give approximately 600 mg of a gum.

B. Removal of Amino-Protecting Group and Formation of the TFA Salt

The gum from Step A was taken up in neat trifluoroacetic acid (5 ml). The solution was allowed to stand for 5 minutes then concentrated in vacuo. Diethylether was added to the concentrate and the resultant suspension was sonicated and the diethyl ether was decanted. Chloroform was added to the wet residue, the suspension was sonicated, and the insoluble material was collected by centrifugation to yield 230 mg of yellow solid. The solid was dissolved in warm methanol (10 ml) then ethyl acetate (ʃʋ ɯɯj and the resultant solution was cooled. The solid formed was collected by centrifugation and dried in vacuo to give 75 mg of 2-(carboxylic acid)-3-(diethylphosphonato)-7-(R,S)-(amino)-8-oxo-1,5-diazabicylo[3.3.0]octa-2-ene; n.m.r. (90 MHz, D$_2$O): $\delta$4.58 (t, 1, J=9), 4.3–3.7 (m, 7), 3.2 (t, 1, J=10), 1.24 (t, 6, J=7); i.r. (KBr): 1731, 1639, 1606, 1426, 1396, 1303, 1246 cm$^{-1}$; m.s.: M+1=320; u.v. (ethanol): $\lambda_{max}$=308 ($\epsilon$=7600).

EXAMPLE 43

2-(Carboxylic Acid)-3-(Diethylphosphonato)-7-(R,S)-[2-(2-Aminothiazol-4-yl)-2-(Z)-Methoxyiminoacetamido]-8-Oxo-1,5-Diazabicyclo3.3.0]Octa-2-ene 2-(Carboxylic acid)-3-(diethylphosphonato)-(R,S)-(amino)-8-oxo-1,5-diazabicyclo[3.3.0]octa-2-ene (32 mg, 0.1 mmol) was dissolved in 50% aqueous acetone (2 ml). The pH of the solution was adjusted to 7 by the addition of saturated aqueous sodium bicarbonate solution. Benzotriazole 2-(2-aminothiazol-4-yl)-2-(Z)-methoxyiminoacetate (40 mg) was added and the solution was stirred at room temperature for 3 hours while maintaining the pH of the solution at 7. The solution was diluted with water (25 ml) and extracted with 3:1 chloroform:isopropanol (2x, 10 ml). The layers were separated and the aqueous phase was acidified to a pH of 2.5 with 0.1N hydrochloric acid. The aqueous phase was extracted with a 3:1 chloroform:isopropanol mixture (2x, 10 ml) and concentrated in vacuo using acetonitrile to azeotropically remove the water. The residue was dissolved in methanol, filtered and the filtrate was then diluted with ethyl acetate to precipitate 50 mg of yellow powder of 2-(carboxylic acid)-3-(diethylphosphonato)-7-(R,S)-[2-(2-aminothiazol-4-yl)-2-(Z)-methoxyiminoacetamido]-8-oxo-1,5-diazabicyclo-3.3.0]- octa-2-ene; n.m.r. (90 MHz, D$_2$O): $\delta$7.10 (s, 1), 5.16 (dd, 1, J=8, 11), 4.2–3.6 (m, 7), 3.97 (s, 3, which absorbance is superimposed on the absorbance at 4.2–3.6), 3.20 (m, 1), 1.28 (t, 6, J=7); i.r. (KBr): 1733, 1674, 1631, 1238 cm$^{-1}$; m.s. M+=459; u.v. (ethanol): $\lambda_{max}$=295 ($\epsilon$=8,000), 232 ($\epsilon$=9650).

EXAMPLE 44

2-(Thiophenoxy)-3-(Allyl Carboxylate)-7-(R,S)-(t-Butoxycarbonylamino)-8-Oxo-1,5-Diazabicyclo[3.3.0]-Octa-2-ene 4-(R,S)-(t-butoxycarbonylamino)-3-oxo-1-(methylene)-1,2-pyrazolidinium ylide (2.13 g, 10 mmol) was dissolved in 1,2-dichloroethane (20 ml) and allyl 3-(thiophenoxy)-propynoate (2.18 g, 10 mmol) was added to the solution. The reaction solution was refluxed for 18 hours, cooled and concentrated in vacuo. The concentrate was chromatographed by HPLC on a Waters Prep 500 silica gel column eluted with a gradient of hexane to 40% ethyl acetate in hexane to give 1.04 g, 24% yield of 2-(thiophenoxy)-3-(allyl carboxylate)-7-(R,S)-(t-butoxycarbonylamino)-8-oxo-1,5-diazabicyclo[3.3.0]-octa-2-ene: n.m.r. (270 MHz, CDCl$_3$) $\delta$ 7.45 (m, 2), 7.30 (m, 3), 5.96 (m, 1), 5.32 (m, 2), 5.08 (br. s, 1), 4.75 (d, 2), 4.28 (d, 1), 4.08 (t, 1), 3.75 (d, 1), 2.74 (dd, 1), 1.44 (s, 9); u.v. (methanol): $\lambda_{max}$=342 ($\epsilon$=10,800); i.r. (CHCl$_3$): 1712, 1500, 1369, 1331 cm$^{-1}$;

Anal. Calcd. for C$_{21}$H$_{25}$O$_5$N$_3$S: Theory: C, 58.45; H, 5.84; N, 9.74; S, 7.43. Found: C, 58.70; H, 5.66; N, 9.45; S, 7.46.

EXAMPLE 45

2-((p-Nitrobenzyl)Carboxylate)-3-(Phenyl-sulfonyl)-7-(R,S)-(t-Butoxycarbonylamino)-8-Oxo-1,5-Diazabicyclo[3.3.0]Octa-2-ene 4-(R,S)-(t-Butoxycarbonylamino)-3-oxo-1-(methylene)-1,2-pyrazolidinium ylide (2.10 g, 9.85 mmol), p-nitrobenzyl 3-(phenylsulfonyl)propynoate (3.41 g, 9.87 mmol) and 1,2-dichloroethane (40 ml) were combined under nitrogen. The resultant solution was refluxed for 4 hours then cooled to room temperature and concentrated under reduced pressure. The concentrate was adsorbed onto silica gel for chromatography. The silica gel column was eluted with a solvent gradient of 0 to 50% ethyl acetate in hexane to yield approximately 1 gm of material. The material was chromatographed by HPLC on a silica gel column eluted with the same gradient of solvents as above. The HPLC chromatography yielded 1.08 g of material that was taken up in hot toluene, filtered, then concentrated to a volume of approximately 40 ml. Crystallization of the concentrated solution was induced and the crystals were dried in vacuo to yield 0.49 g of material which was stored in vacuo at 40° C. overnight to give 2-((p-nitrobenzyl)-carboxylate)-3-(phenylsulfonyl)-7-(R,S)-(t-butoxycarbonylamino)-8-oxo-1,5-diazabicyclo[3.3.0]octa-2-ene:

n.m.r. (90 MHz, CDCl$_3$): $\delta$8.28–8.08 (m, 2), 7.90–7.74 (m, 2), 7.74–7.36 (m, 5), 5.46 (s, 2), 5.12–5.00 (m, 1), 4.84–4.44 (m, 1), 4.25 (d, 1, J=11), 3.9 (t, 1, J=8), 3.76 (d, 1, J=11), 2.88 (dd, 1, J=8, 12), 1.40 (s, 9); i.r. (CHCl$_3$): 1751, 1718, 1610, 1526, 1500, 1445, 1408, 1395, 1350, 1328, 1270, 1215, 1183, 1154 cm$^{-1}$: u.v. (95% ethanol): $\lambda_{max}$=334 ($\epsilon$=6090), 261 ($\epsilon$=11,720), 235 (s=13,740); f.d.m.s.: M+=558;

Anal. Calcd. for C$_{25}$H$_{26}$O$_9$N$_4$S: Theory: C, 53.76; H, 4.69; N, 10.03; S, 5.74. Found: C, 54.0; H, 4.57; N, 9.90; S, 5.55.

EXAMPLE 46

2-((p-Nitrobenzyl)Carboxylate)-3-(Phenylsulfonyl)-7-(R,S)-[2-(2,5-Dichlorophenylthio)Acetamido]-8-Oxo-1,5-Diazabicyclo[3.3.0]Octa-2-ene

A. Removal of Amino-Protecting Group and Formation of TFA Sat 2-((p-Nitrobenzyl)carboxylate)-3-(phenylsulfonyl)-7-(R,S)-(t-butoxycarbonylamino)-8-oxo-1,5-diazabicyclo[3.3.0]octa-2-ene (0.455 g, 0.815 mmol) and trifluoroacetic acid (approximately 5 ml) were combined and the solution was stirred at room temperature for 5 minutes. The solution was concentrated under reduced pressure and the concentrate was taken up in dry methylene chloride and concentrated twice. The concentrate was dried in vacuo at room temperature for approximately 0.5 hour.

B. Neutralization of the TFA Salt

The dried concentrate from Step A was dissolved in dry THF (10 ml) and the solution was cooled to 0° C. BSTFA (1.0 ml) was added and the solution was stirred for 15 minutes at 0° C.

C. Acylation

To the cooled solution from Step B a 0.5M solution of 2-(2,5-dichlorophenylthio)acetyl chloride (2 ml) was added. The reaction solution was stirred at 0° C. for 1 hour and 15 minutes. The solution was diluted with ethyl acetate, washed with 0.2N hydrochloric acid (2x, 25 ml), saturated aqueous sodium bicarbonate solution (25 ml) and brine, dried over magnesium sulfate, filtered and concentrated under reduced pressure. The concentrate was chromatographed on silica gel eluting with a gradient of 0 to 50% ethyl acetate in hexane. The chromatography yielded 50 mg of 2-((p-nitrobenzyl)-carboxylate)-3-(phenylsulfonyl)-7-(R,S)-[2-(2,5-dichlorophenylthio)acetamido]-8-oxo-1,5-diazabicyclo[3.3.0]octa-2-ene: n.m.r. (90 MHz, CDCl$_3$): $\delta$8.20–6.96 (m, 12), 5.48–5.30 (m, 2), 5.0–4.72 (m, 1), 4.70 (m, 1), 4.32–4.07 (m, 1), 3.92–3.76 (m, 1), 3.74–3.48 (m, 2), 2.92–2.65 (m, 1).

EXAMPLE 47

2-((t-Butyl)Carboxylate)-3-(Trifluoromethyl)-7-(R,S)-(t-Butoxycarbonylamino)-8-Oxo-1,5-Diazabicyclo[3.3.0]Octa-2-ene t-Butyl 4,4,4-trifluoro-3-keto-2-(triphenylphosphorane)butanoate (14.16 g, 30 mmol) was slurried in 50 ml of silicone oil containing 2,6-(di(t-butyl))-4-methylphenol (30 mg). Nitrogen was bubbled through the stirred slurry for 10 minutes then with continued nitrogen flushing the mixture was heated to 260° C. and the volatiles from this mixture were collected in a flask cooled to −78° C. via a short-path still head. A crude distillate of approximately 1.55 g of yellow oil and some solid was collected. The distillate was immediately dissolved in 1,2-dichloroethane (15 ml) and 4-(R,S)-(t-butoxycarbonylamino)-3-oxo-1-(methylene)-1,2-pyrazolidinium ylide (1.5 g, 7 mmol) was added. The resultant solution was refluxed for 21 hours, cooled, filtered and concentrated in vacuo. The concentrate was chromatographed on silica gel (30 g) eluted with 40% ethyl acetate in hexane to give 250 mg, 9% yield of a yellow foam of 2-((t-butyl)carboxylate)-3-(trifluoromethyl)-7-(R,S)-(t-butoxycarbonylamino)-8-oxo-1,5-diazabicyclo[3.3.0]octa-2-ene: n.m.r. (90 MHz, CDCl$_3$): $\delta$5.36 (d, 1, J=7), 4.7 (m, 1), 4.24 (dm, 1, J=12), 3.96 (t, 1, J=8), 3.8 (dm, 1, J=12), 3.85 (m, 1), 1.45 (s, 9), 1.36 (s, 9); i.r. (CHCl$_3$) 1738, 1715, 1379, 1310 cm$^{-1}$; u.v. (95% ethanol): $\lambda_{max}$=310 ($\epsilon$=4450); m.s.: (M+1)$^+$=408;

Anal. Calcd. for C$_{14}$H$_{24}$O$_5$N$_3$F$_3$: Theory: C, 50.12; H, 5.94; N, 10.31; F, 13.99. Found: C, 49.87; H, 5.88; N, 10.16; F, 13.84.

EXAMPLE 48

2-(Carboxylic Acid)-3-Trifluoromethyl-7-(R,S)-[2-(2-Aminothiazol-4-yl)-2-(Z)-Methoximinoacetamido]-8-Oxo-1,5-Diazabicyclo[3.3.0]Octa-2-ene

A. Deprotection of the Amino and Carboxy Groups 2-(t-Butyl carboxylate)-3-(trifluoromethyl)-7-(R,S)-(t-butoxycarbonylamino)-8-oxo-1,5-diazabicyclo-[3.3.0]octa-2-ene (240 mg, 0.59 mmol) was dissolved in trifluoroacetic acid (3 ml) and the solution was allowed to stand for 30 minutes. The solution was concentrated in vacuo. Methylene chloride was added to the concentrate and the resultant solution was reconcentrated in vacuo to a yellow powder. The yellow powder was dried in vacuo for 15 minutes at room temperature.

B. Acylation

The powder from Step A was taken up in 1:1 acetone:water (10 ml) and the pH of the solution was adjusted to 7.5 by the addition of saturated aqueous sodium bicarbonate solution. Benzotriazole 2-(2-aminothiazol-4-yl)-2-(Z)-methoximinoacetate (250 mg, 0.7 mmol) was added to the solution and the resultant solution was stirred at room temperature for 3 hours, maintaining the pH between 7 to 8. After 3 hours the acetone was removed in vacuo. Water was added (30 ml) and the aqueous solution was extracted with 3:1 chloroform:isopropanol (2x, 25 ml). The pH of the aqueous phase was adjusted to 2 then reextracted with 3:1 chloroform:isopropanol. The aqueous phase was concentrated in vacuo by azeotropically distilling the solution with acetonitrile. The concentrate was taken up in methanol, filtered, and isopropyl ether was added. The resultant precipitate was collected by centrifugation to give 200 mg of a yellow solid of 2-(carboxylic acid)-3-trifluoromethyl-7-(R,S)-[2-(2-aminothiazol-4-yl)-2-(Z)-methoximinoacetamido]-8-oxo-1,5-diazabicyclo[3.3.-0]octa- 2-ene: n.m.r. (90 MHz, D$_2$O) $\delta$6.98 (s, 1), 5.16 (dd, 1, J=7, 11), 4.2 (dm, 1, J=11), 4.1–3.8 (m, 3), 3.88 (s, 3, superimposed on the absorbance at 4.1–3.8), 3.20 (m, 1); i.r. (KBr): 3405, 1711, 1658, 1534 cm$^{-1}$; u.v. (ethanol): $\lambda_{max}$=294 ($\epsilon$=9800); m.s.: (M+1)$^+$=435.

EXAMPLE 49

2-(Allyl Carboxylate)-7-(R,S)-(t-Butoxycarbonylamino)-8-Oxo-1,5-Diazabicyclo[3.3.0]Octa-2-ene

PROCEDURE A 4-(R,S)-(t-butoxycarbonylamino)-3-oxo-1-methylene-1,2-pyrazolidinium ylide (426 mg, 2 mmol), allyl propynoate (220 mg, 2 mmol) and 1,2-dichloroethane (10 ml) were combined and refluxed for 16 hours. The reaction mixture was cooled and concentrated in vacuo to give a yellow foam. The foam was chromatographed on a preparatory-scale TLC. plate eluted with 3:2 ethyl acetate:hexane as the eluant. Two elutions of the TLC plate gave 150 mg, 23% yield of a yellow gum of 2-(allyl carboxylate)-7-(R,S)-(t-butoxycarbonylamino)-8-oxo-1,5-diazabicyclo[3.3.0]-octa-2-ene: n.m.r. (90 MHz, CDCl$_3$): $\delta$6.26 (t, 1, J=2.5), 6.1–5.6 (m, 1), 5.5–5.1 (m, 3), 4.9 (br. d, 2, J=6), 4.58 (br. t, 1), 4.18 (dd, 1, J=2.5, 14), 4.05 (t, 1, J=7), 3.64 (dd, 1, J=14, 2.5), 2.86 (dd, 1, J=7, 12), 1.4 (s, 9); i.r. (CHCl$_3$): 1710 cm$^{-1}$; u.v. (95% ethanol): $\lambda_{max}$=311 ($\epsilon$=2150); m.s.: M$^+$=323.

PROCEDURE B

Step 1: The Cycloaddition Reaction 4-(R,S)-(t-Butoxycarbonylamino)-3-oxo-1-methylene-1,2-pyrazolidinium ylide (1.92 g, 9.0 mmol), allyl 3-(p-toluenesulfonyl)acrylate (2.4 g, 9.0 mmol) and 1,2-dichloroethane (25 ml) were combined under nitrogen and refluxed for 48 hours. The reaction solution was concentrated under reduced pressure and chromatographed on a silica gel column eluted with a solvent gradient of 0 to 50% ethyl acetate in hexane. The chromatography yielded a mixture of 2R,3S and 2S,3R stereoisomers of 2-(allyl carboxylate)-3-(p-toluenesulfonyl)-7-(R,S)-(t-butoxycarbonylamino)-8-oxo-1,5-diazabicyclo-[3.3.0]octane: n.m.r. (270 MHz, DMSOd$_6$) δ7.90–7.80 (m, 2), 7.58–7.46 (m, 2), 5.82–5.56 (m, 1), 5.28–5.12 (m, 2), 4.87–4.68 (m, 2), 4.66–4.28 (m, 3), 3.85–3.74 (m, 1), 3.66–3.46 (m, 1), 3.40–3.26 (m, 1), 3.20–3.08 (m, 0.5), 3.05–2.96 (m, 0.5), 2.88–2.72 (m, 1), 2.55 (s, 3), 1.39 (s, 9): i.r. (CHCl$_3$) 3018, 1711, 1502, 1369, 1326, 1306, 1291, 1284, 1215, and 1153 cm$^{-1}$; f.d.m.s.: (M+2)$^+$=482, (M+1)$^+$=481, M$^+$=480, (M−1)$^+$=479.

Step 2: The Elimination Reaction

A mixture of 2R,3S and 2S,3R stereoisomers of 2-(allyl carboxylate)-3-(p-toluenesulfonyl)-7-(R,S)-(t-butoxycarbonylamino)-8-oxo-1,5-diazabicyclo3.3.0]-octane (0.100 g, 0.209 mmol) was dissolved in dry methylene chloride (5 ml) and the solution was cooled to −78° C. DBU (0.040 g, 0.263 mmol) was dissolved in dry methylene chloride (5 ml) and added to the cooled solution of bicyclic pyrazolidinone. The resultant reaction solution was stirred at −78° C. for 1 hour, then warmed slowly to room temperature. Methylene chloride (15 ml) was added and the solution was washed with aqueous 0.1N hydrochloric acid (10 ml), saturated aqueous sodium bicarbonate solution (10 ml) and brine (10 ml), dried over magnesium sulfate, filtered and concentrated under reduced pressure to yield 0.080 g of 2-(allyl carboxylate)-7-(R,S)-(t-butoxycarbonylamino)-8-oxo-1,5-diazabicyclo3.3.0]octa-2-ene.

EXAMPLE 50

2-(Allyl Carboxylate)-7-(R,S)-[2-(2-(Allyl-oxycarbonylamino)Thiazol-4-yl)-2-(Z)-Methoximinoacetamido]-8-Oxo-1,5-Diazabicyclo[3.3.0]Octa-2-ene

A. Formation of the Side Chain Acid Chloride

DMF (0.136 ml, 1.6 mmol) was dissolved in ethyl acetate (4 ml) and the solution was cooled to 0° C. Phosphoryl chloride (0.102 ml, 1.1 mmol) was added and the solution was stirred at 0° C. for 1 hour. 2-(2-(allyloxycarbonylamino)thiazol-4-yl)-2-(Z)-methoxyiminoacetic acid (314 mg, 1.1 mmol) was added and the solution was stirred for 1.5 hours at 0° C.

B. Removal of Amino-Protecting Group and Formation of TF Salt 2-(Allyl carboxylate)-7-(R,S)-(t-butoxycarbonylamino)-8-oxo-1,5-diazabicyclo3.3.0]octa-2-ene (323 mg, 1 mmol) was dissolved in trifluoroacetic acid (3 ml). The solution was allowed to stand for 5 minutes then concentrated in vacuo. Methylene chloride (10 ml) was added to the concentrate and the resultant solution was concentrated in vacuo. Diethyl ether (15 ml) was added to the concentrate. The solution was sonicated and the diethyl ether was decanted to leave a yellow powder.

C. Neutralization of TFA Salt

The yellow powder from Step B was taken up in dry THF (5 ml) and BSTFA (1 ml) was added. The solution was stirred at 0° C. for 30 minutes.

D. Acylation

The solutions from Steps A and C above were combined and stirred at 0° C. for 2 hours. The solution was diluted with ethyl acetate, washed with 0.1M hydrochloric acid, saturated aqueous sodium bicarbonate solution and brine, dried over magnesium sulfate, filtered and concentrated in vacuo to give 350 mg of a brown solid. The solid was chromatographed on a preparatory-scale TLC plate eluted with 10% methanol in ethyl acetate. The chromatography yielded 102 mg of 2-(allyl carboxylate)-7-(R,S)-[2-(2-(allyloxycarbonylamino)thiazol-4-yl)-2-(Z)-methoximinoacetamido)]-8-oxo-1,5-diazabicyclo[3.3.0]octa-2-ene: n.m.r. (90 MHz, CDCl$_3$) δ8.4 (d, 1, J=8), 7.1 (s, 1), 6.32 (br. s, 1), 6.2–5.6 (m, 2), 5.6–5.1 (m, 5), 4.7 (br. d, 5), 4.4–3.6 (m, 3), 3.88 (s, 3, superimposed on the absorption at 4.4–3.6), 3.02 (dd, 1, J=8, 11); i.r. (CHCl$_3$) 1728, 1705, 1677, 1562 cm$^{-1}$; u.v. (95% ethanol): λ$_{max}$=310 (shoulder), 265 (ε=13,400), 228 (ε=18,200); m.s.: M$^+$=490.

EXAMPLE 51

2-(Carboxylic Acid)-7-(R,S)-[2-(2-Aminothiazol-4-yl)-2-(Z)-Methoximinoacetamido]-8-Oxo-1,5-Diazabicyclo[3.3.0]Octa-2-ene Triphenylphosphine (3 mg, 0.011 mmol) was dissolved in acetone (1 ml) then tetrakis[triphenylphosphine]palladium(0) (15 mg, 0.013 mmol) was added. 2-(Allyl carboxylate)-7-(R,S)-[2-(2-(N-allylurethan)-thiazol-4-yl)-2-(Z)-methoximinoacetamido]-8-oxo-1,5-diazabicyclo[3.3.0]octa-2-ene (90 mg, 0.18 mmol) dissolved in acetone (3 ml) was added. The resultant solution was cooled to 0° C. and tri(n-butyl)tin hydride (0.103 ml, 0.38 mmol) was added. The solution was stirred at room temperature for 1 hour then cooled again to 0° C. 1N Hydrochloric acid (0.38 ml) was added and the solution was stirred for 10 minutes. Water (10 ml), followed by a small amount of acetonitrile, was added and the solution was washed with hexane (3X, 40 ml). The aqueous phase was freeze-dried after the acetone and acetonitrile were removed in vacuo. The freeze-drying procedure yielded 80 mg of crude yellow powder. The powder was taken up in water, filtered, and the filtrate was freeze-dried to yield 72 mg of 2-(carboxylic acid)-7-(R,S)-2-(2-aminothiazol-4-yl)-2-(Z)-methoximinoacetamido]-8-oxo-1,5-diazabicyclo[3.3.0]octa-2-ene:

n.m.r. (90 MHz, D$_2$O): δ7.5 (m, 2), 7.0 (s, 1), 6.1 (m, 1), 5.2–4.8 (m, 2), 4.1–3.5 (m, 3), 3.84 (s, 3, superimposed on the absorbance at 4.1–3.5), 3.04 (dd, 1, J=9, 12).

EXAMPLE 52

2-(Allyl Carboxylate)-3-(Acetyl)-7-(R,S)-(t-Butoxycarbonylamino)-8-Oxo-1,5-Diazabicyclo[3.3.0]-Octa-2-ene and the Corresponding 2,3-Regioisomer

PROCEDURE A

Allyl 4-oxopentynoate (0.256 g, 1.68 mmol), 4-(R,S)-(t-butoxycarbonylamino)-3-oxo-1-methylene-1,2- pyridazolinium ylide (0.358 g, 1.68 mmol) and 1,2-dichloroethane (4 ml) were refluxed under argon for 4 hours. The reaction solution was adsorbed onto silica gel and chromatographed with a gradient elution of 0 to 50% ethyl acetate and hexane. The product-containing fractions were combined and concentrated to give 0.07 g of the 2-(acetyl)-3-(allyl caroboxylate) regioisomer plus 0.14 g of a mixture of the regioisomers. 2-(acetyl)-3-(allyl carboxylate)regioisomer: n.m.r. (90 MHz, CDCl$_3$): δ 6.08–5.64 (m, 1), 5.42–5.04 (m, 3), 4.92–4.5 (m, 1), 4.60 (d, 2, J=6), 4.3 (d, 1, J=12), 4.0 (t, 1, J=7), 3.83 (d, 1, J=12), 3.06–2.76 (dd, 1, J=7, 12), 2.52 (s, 3), 1.43 (s, 9).

PROCEDURE B

Different amounts of the same components 8.87 g, 58.3 mmol of the acetylene, 12.43 g, 58.3 mmol of the ylide, and 100 ml of 1,2-dichloroethane from Procedure A were refluxed under argon for 4 hours. The solution was absorbed onto silica gel and chromatographed with a gradient elution of 0 to 50% ethyl acetate in hexane. The product-containing fractions were combined, concentrated and chromatographed by preparatory-scale HPLC, on a silica gel column with the same gradient elution system as the above column chromatography procedure. The HPLC procedure yielded 5.51 g of a mixture of the 2,3-regioisomers. A small portion of this mixture was chromatographed on a silica gel preparatory-scale TLC plate eluted with 40% ethyl acetate in hexane. The TLC plate was eluted three times and the product-containing band was again eluted on an analytical-scale TLC strip (0.25 mm silica gel thickness) with 1:1 hexane:ethyl acetate. The chromatography yielded the 2-(allyl carboxylate)-3-(acetyl)regioisomer: n.m.r. (90 MHz, CDCl$_3$) δ 6.22–5.76 (m, 1), 5.54–5.00 (m, 3), 4.84 (d, 2, J=6), 4.92–4.50 (m, 1), 4.38 (d, 1, J=12), 4.0 (t, 1, J=7), 3.83 (d, 1, J=12), 2.96–2.68 (dd, 1, J=7, 12), 2.25 (s, 3), 1.43 (s, 9).

EXAMPLE 53

2-(Allyl Carboxylate)-3-(Acetyl)-7-(R,S)-[2-(2-(Allyloxycarbonylamino)Thiazol-4-yl)-2-(Z)-Methoximinoacetamido]-8-Oxo-1,5-Diazabicyclo[3.3.0]Octa-2-ene and the Corresponding 2,3-Regioisomer

A. Formation of the Side Chain Acid Chloride

Under an argon atmosphere, ethyl acetate (18 ml) was cooled to 0° C and dimethylformamide (0.74 ml, 9.6 mmol) was added. Phosphoryl chloride (0.62 ml, 6.6 mmol) was added and the solution was stirred at 0° C. for 1 hour. 2-(2-(Allyloxycarbonylamino)thiazol-4-yl)-2-(Z)-methoxyiminoacetic acid (1.882 g, 6.66 mmol) was added to the solution and the solution was stirred for 2 hours at 0° C.

B. Removal of the Amino-Protecting Group and Formation of the TFA Salt 2-(Allyl carboxylate)-3-(acetyl)-7-(R,S)-(t-butoxycarbonylamino)-8-oxo-1,5-diazabicyclo[3.3.0]-octa-2-ene admixed with the corresponding 2,3-regioisomer (2.25 g, 6.16 mmol) was dissolved in trifluoroacetic acid (30 ml). The solution was stirred at room temperature for 5 minutes then concentrated under reduced pressure. The concentrate was taken up in methylene chloride, concentrated and then reconcentrated from methylene chloride. The concentrate was then dried in vacuo at room temperature for 20 minutes.

C. Neutralization of TFA Salt

The concentrate from Step B was dissolved in dry THF (70 ml), the solution was cooled to 0° C. and BSTFA (6.0 ml) was added. The solution was stirred at. 0° C. for 25 minutes.

D. Acylation

The acid chloride solution of Step A was combined with the solution from Step C and the solution was stirred at 0° C. for 40 minutes. Ethyl acetate (100 ml) was added and the solution was washed with 1N hydrochloric acid (40 ml), saturated aqueous sodium bicarbonate solution (60 ml) and brine (50 ml), dried over magnesium sulfate, filtered and concentrated under reduced pressure. The concentrate was adsorbed onto silica gel and chromatographed with a gradient elution of 100% hexane to 100% ethyl acetate to give 0.73 g of a mixture of the 2,3-regioisomers. The mixture was recrystallized from methylene chloride/diisopropyl ether to yield 0.348 g of a mixture of 2-(allyl carboxylate)-3-(acetyl)-7-(R,S)-[2-(2-(allyloxycarbonylamino)-thiazol-4-yl)-2-(Z)-methoximinoacetamido]-8-oxo-1,5-diazabicyclo[3.3.0]octa-2-ene and the corresponding 2,3-regioisomer: n.m.r. (90 MHz, CDCl$_3$): δ 8.35 (d, 1), 7.06 (s, 1), 6.20–5.60 (m, 2), 5.60–5.12 (m, 4), 4.82–4.50 (m, 4), 4.48–3.80 (m, 4), 3.89 (s, 3), 2.40–2.00 (m, 1), 2.50 and 2.25 (2x s, 3); i.r. (CHCl$_3$) 1728, 1698, 1555, 1422, 1370, 1275, 1229, 1207, and 1045 cm$^{-1}$; u.v. (95% ethanol): $\lambda_{max}$=344 (ϵ=7102), 263 (ϵ=14,575), 207 (ϵ=22,602); f.d.m.s.: M+ =533;

Anal. Calcd. for C$_{22}$H$_{24}$N$_6$O$_8$S: Theory: C, 49.62; H, 4.54; N, 15.78; S, 6.02. Found: C, 49.53; H, 4.74; N, 15.60; S, 6.00.

EXAMPLE 54

2-(Carboxylic Acid)-3-(Acetyl)-7-(R,S)-[2-(2-Aminothiazol-4-yl-2-(Z)-Methoxyiminoacetamido]-8-Oxo-1,5-Diazabicyclo[3.3.0]Octa-2-ene and the Corresponding 2,3-Regioisomer Under an argon atmosphere, palladium(II) acetate (0.011 g, 0.049 mmol) was suspended in acetone (3 ml) and triphenylphosphine (0.044 g, 0.17 mmol) was rinsed into the mixture with additional acetone (1 ml). The mixture was stirred at room temperature for approximately 5 minutes, when a precipitate formed. 2-(Allyl carboxylate)-3-(acetyl)-7-(R,S)-[2-(2-(allyloxycarbonylamino)thiazol-4-yl)-2-(Z)-methoximinoacetamido]-8-oxo-1,5-diazabicyclo[3.3.0]octa-2-ene in a mixture with the corresponding 2,3-regioisomer (0.300 g, 0.563 mmol) was added as an acetone solution (10 ml). The solution was stirred for 35 minutes then cooled to 0° C. Tri(n-butyl)tin hydride (0.30 ml, 1.12 mmol) was added and the solution was stirred at 0° C. for 15 minutes then at room temperature for 25 minutes. The solution was cooled to 0° C., 1N hydrochloric acid (1.12 ml) was added and the solution was stirred for an additional 5 minutes at 0° C. and for a few additional minutes without a cooling bath. The solution was filtered and water (50 ml) was added to the filtrate. The filtrate washed with hexane (2×, 50 ml) then filtered through celite. The aqueous solution was washed with ether (2×, 50 ml) and hexane (2×, 50 ml), concentrated in vacuo, filtered through celite and the filtrate lyophilized. The lyophilization yielded 0.21 g of crude product. A portion of the crude product (approximately 130 mg) was dissolved in water and chromatographed by HPLC on a reverse phase C-18 column (silica) eluted with a mixture of 2% acetic acid and 5% acetonitrile in water. The fractions containing the (2-carboxylic acid)-3-(acetyl) regioisomer of the title product were combined and concentrated to give a total of 0.027 g of this regioisomer product: n.m.r. (90 MHz, D$_2$O): δ 7.08 (s, 1), 5.32 (dd, 1, J=7, 11), 4.54–3.80 (m, 2) with 4.30 (d, 1, J=11) superimposed, 3.92 (s, 3), 3.20 (dd, 1, J=8, 11), 2.26 (s, 3); i.r. (KBr): 1716, 1634, 1534, 1382, 1327 and 1285 cm$^{-1}$; u.v. (ethanol): λ$_{max}$=352 (ε=9165); 299 (ε=6728), 230 (ε=15,607); m.s.: (M+1)$^+$=409.

EXAMPLE 55

3-(Benzoyl)-2-(Allyl Carboxylate)-7-(R,S)-(t-Butoxycarbonylamino)-8-oxo-1,5-Diazabicyclo[3.3.0]-Octa-2-ene and the Corresponding 2,3-Regioisomer.

PROCEDURE A 4-(R,S)-(t-Butoxycarbonylamino)-3-oxo-1-methylene-1,2-pyrazolidinium ylide (18.4 g, 86.2 mmol), allyl 4-oxo-4-phenylbutynoate (18.49 g, 86.3 mmol) and 1,2-dichloroethane (100 ml) were combined and brought to reflux under argon. The reaction solution was refluxed for 6 hours then stirred overnight at room temperature. The reaction mixture was concentrated in vacuo then adsorbed onto silica gel for column chromatography. The silica gel column was eluted with a solvent gradient of 0 to 50% ethyl acetate in hexane. The product-containing fractions were combined, reduced in vacuo, and the residue was recrystallized from a mixture of ethyl acetate/hexane to give 1.721 g of the 3-(allyl ester)-2-(benzoyl) isomer. A further amount of impure 3-(allyl ester)-2-(benzoyl) regioisomer was obtained from the chromatography procedure. This oil was chromatographed on a silica gel column eluted with a gradient elution of 0–40% ethyl acetate in hexane to give a foam (0.710 g) of 3-(allyl carboxylate)-2-(benzoyl)-7-(R,S)-(t-butoxycarbonylamino)-8-oxo-1,5-diazabicyclo[3.3.0]octa-2-ene: n.m.r. (90 MHz, CDCl$_3$) δ8.00–7.79 (m, 2), 7.72–7.31 (m, 3), 5.80–5.35 (m, 1), 5.28–4.90 (m, 3), 4.94–4.31 (m, 4), 4.14–3.89 (m, 2), 2.98 (dd, 1, J=8, 11) 1.40 (s, 9); i.r. (CHCl$_3$) 3430, 3025, 2980, 1707, 1502, 1370, 1275, 1234, 1223, 1212, 1211, 1175, 1162 cm$^{-1}$; u.v. (ethanol): λ$_{max}$=344 nm (ε=7173), 257 nm (ε=12,783); f.d.m.s.: (M+1)$^+$=428, M$^+$=427;

Anal. Calcd. for C$_{22}$H$_{25}$N$_3$O$_6$: Theory: C, 61.82; H, 5.90; N, 9.83. Found: C, 61.97; H, 5.84; N, 9.69.

PROCEDURE B 4-(R,S)-(t-Butoxycarbonylamino)-3-oxo-1-(methylene)-1,2-pyrazolidinium ylide (4.43 g, 20.8 mmol), allyl 4-oxo-4-phenylbutynoate (4.45 g, 20.8 mmol) and 1,2-dichloroethane (50 ml) were combined under argon. The reaction solution was refluxed for 6 hours then stirred overnight at room temperature for 18 hours. The crude reaction mixture was adsorbed onto silica gel. The silica gel column was eluted with a solvent gradient of 0–40% ethyl acetate in hexane to yield 0.47 g of the higher R$_f$(2-allyl carboxylate)-3-benzoyl) isomer, 0.51 g of a mixture of regioisomers, and 1.60 g of the lower R$_f$(2-benzoyl-3-(allyl carboxylate) regioisomer. 3-(Benzoyl)-2-(allyl carboxylate)-7-(R,S)-(t-butoxycarbonylamino)-8-oxo-1,5-diazabicyclo[3.3.0]octa-2-ene: n.m.r. (90 MHz, CDCl$_3$): δ7.76–7.28 (m, 5), 5.77–5.32 (m, 1), 5.26–5.00 (m, 2), 4.93–4.58 (m, 1), 4.56'3.95 (m, 5), 2.86 (dd, 1, J=8, 11), 1.43 (s, 9); i.r. (CHCl$_3$): 3430, 3020, 1744, 1715, 1500, 1413, 1370, 1347, 1285, 1232, 1209, 1160 cm$^{-1}$; u.v. (ethanol): λ$_{max}$=375 (ε=6774), 245 (ε=9285); m.s.: (M-57)$^+$=370;

Anal. Calcd. for C$_{22}$H$_{25}$N$_3$O$_6$: Theory: C, 61.82; H, 5.90; N, 9.83. Found: C, 62.03; H, 6.20; N, 9.54.

EXAMPLE 56

2-(Allyl Carboxylate)-3-(Benzoyl)-7-(R,S)-[2-(2-(Allyloxycarbonylamino)Thiazol-4-yl)-2-(Z)-Methoxyiminoacetamido]-8-Oxo-1,5-Diazabicyclo[3.3.0]-Octa-2-ene

A. Formation of Side Chain Acid Chloride

Ethyl acetate (6.0 ml) and dry DMF (0.180 ml, 2.33 mmol) were combined under argon and cooled to 0° C. To the solution was added phosphoryl chloride (0.164 ml, 1.76 mmol) and the reaction solution was stirred at 0° C. for 1 hour. 2-[2-(Allyloxycarbonylamino)thiazol-4-yl]-2-(Z)-methoxyiminoacetic acid (0.496 g, 1.73 mmol) was added and the solution was stirred at 0° C. under argon for 3.5 hours.

B. Removal of the Amino-Protecting Group and Formation of the TFA Salt 2-(Allyl carboxylate)-3-(benzoyl)-7-(R,S)-(t-butoxycarbonylamino)-8-oxo-1,5-diazabicyclo3.3.0]octa-2-ene (0.34 g, 0.80 mmol) was added to trifluoroacetic acid (4 ml). The reaction solution was stirred at room temperature for 10 minutes then concentrated in vacuo.

C. Neutralization of the TFA Salt

The concentrate from Step B was taken up in methylene chloride and concentrated in vacuo. This procedure was repeated 2 more times and the resultant residue was stored in vacuo at room temperature for 30 minutes. The dried residue was dissolved in dry THF (9 ml) and BSTFA (0.8 ml, 3.0 mmol) was added. The reaction solution was stirred at room temperature for 30 minutes.

D. Acylation

The solution from Step C was cooled to 0° C. and the acid chloride solution from Step A (4 ml, 1.15 mmol) was added. The reaction solution was stirred for 45 minutes at 0° C. and was diluted with ethyl acetate (25 ml), then washed with 1N hydrochloric acid (15 ml), saturated aqueous sodium bicarbonate solution (15 ml) and brine (10 ml), dried over magnesium sulfate, filtered and concentrated in vacuo to yield 0.60 g of crude material. The crude material was adsorbed onto silica gel and the silica gel column was eluted with a solvent gradient of 0–75% ethyl acetate in hexane. The product-containing fractions were combined and concentrated under reduced pressure to yield 0.185 g, 39% of crude product. The crude product was crystallized from methylene chloride/isopropyl ether to yield 0.043 g of 2-(allyl carboxylate)-3-(benzoyl)-7-(R,S)-[2-(2-(allyloxycarbonylamino)thiazol-4-yl)-2-(Z)-methoxyiminoacetamido] -8-oxo-1,5-diazabicyclo[3.3.0]octa-2-ene:

n.m.r. (90 MHz, CDCl$_3$): δ 7.83–7.24 (m, 6), 7.23 (s, 1), 6.17–5.69 (m, 2), 5.60–5.00 (m, 6), 4.81–4.09 (m, 5), 4.40 (d, 1, J=11) 4.00 (s, 3), 3.10 (dd, 1, J=8, 12); i.r. (KBr); 3320 (broad), 1731, 1711, 1676, 1564, 1373, 1347, 1288, 1251, 1229, 1038 cm$^{-1}$ u.v. (ethanol): λ$_{max}$=369 (ε=7333), 255 (ε=20.559), 230 (ε=23.558); m.s.: M$^+$=595;

Anal. Calcd. for C$_{27}$H$_{26}$N$_6$O$_8$S: Theory: C, 54.54; H, 4.41; N, 14.13; S, 5.39. Found: C, 54.40; H, 4.13; N, 13.96; S, 5.12.

EXAMPLE 57

2-(Carboxylic Acid)-3-(Benzoyl)-7-(R,S)-[2-(2-Aminothiazol-4-yl)-2-(Z)-Methoxyiminoacetamido]-8-Oxo-1,5-Diazabicyclo[3.3.0]Octa-2-ene Palladium(II) acetate (0.0019 g, 0.0085 mmol), triphenylphosphine (0.0076 g, 0.029 mmol) and reagent-grade acetone (0.5 ml) were combined under argon and stirred at room temperature for approximately 5 minutes. 2-(Allyl carboxylate)-3-(benzoyl)-7-(R,S)-[2-(2-(allyloxycarbonylamino)thiazol-4-yl)-2-(Z)-methoxyiminoacetamido]-8-oxo-1,5-diazabicyclo[3.3.0]octa-2-ene (0.050 g, 0.084 mmol) was dissolved in acetone (1.0 ml) and added to the stirring suspension of palladium compound. The resultant solution was stirred at room temperature for 1 hour, then cooled to approximately 0° C. with an ice bath. Tri(n-butyl)tin hydride (0.046 ml, 0.171 mmol) was added and the cooled solution was stirred at 0° C. for 30 minutes, then at room temperature for 30 minutes. The solution was then cooled again to 0° C. and 1N hydrochloric acid (0.168 ml, 0.168 mmol) was added. The resultant solution was stirred at 0° C. for approximately 15 minutes, then allowed to warm to room temperature. Water (10 ml) was added and the solution was filtered through a thin pad of celite. The filtrate was washed with hexane (4×, 10 ml) and ether (10 ml), then lyophilized to yield 0.017 g, 43% of a bright yellow solid. This material was combined with 21.7 mg of material made from an identical procedure and chromatographed by HPLC on a C-18 reverse phase silica gel column, with a step gradient elution of 2% acetic acid and 10% acetonitrile in water to 3% acetic acid and 20% acetonitrile in water. The product-containing fractions were lyophilized overnight to give 5 mg of 2-(carboxylic acid)-3-(benzoyl)-7-(R,S)-[2-(2-aminothiazol-4-yl)-2-(Z)-methoxyiminoacetamido]-8-oxo-1,5-diazabicyclo[3.3.0]-octa-2-ene: n.m.r. (270 MHz, D$_2$O): $\delta$7.74–7.64 (m, 3), 7.56–7.48 (m, 2), 7.10 (s, 1) 5.38–5.27 (m, 1), 4.49 (d, 1, J=11), 4.24 (d, 1, J=11), 4.18–4.08 (m, 1), 4.01 (s, 3), 3.39–3.25 (m, 1).

EXAMPLE 58

2-(Benzoyl)-3-(Allyl Carboxylate)-7-(R,S)-2-(2-(Allyloxycarbonylamino)Thiazol-4-yl)-2-(Z)-Methoximinoacetamido]-8-Oxo-1,5-Diazabicyclo[3.3.0]Octa-2-ene

A. Formation of the Side Chain Acid Chloride

Ethyl acetate (5 ml) was cooled to 0° C. and DMF (0.18 ml, 2.3 mmol) was added. Phosphoryl chloride (0.15 ml, 1.6 mmol) was added and the resultant solution was stirred at 0° C. under argon for 1 hour. 2-[2-(Allyloxycarbonylamino)thiazol-4-yl]-2-(Z)-methoximinoacetic acid (0.456 g, 1.60 mmol) was added and the solution was stirred at 0° C. for 4 hours.

B. Removal of the Amino-Protecting Group and Formation of the TFA Salt 2-(Benzoyl)-3-(allyl carboxylate)-7-(R,S)-(t-butoxycarbonylamino)-8-oxo-1,5-diazabicyclo[3.3.0]octa-2-ene (0.630 g, 1.47 mmol) was added to TFA (10 ml). The solution was stirred for 5 minutes and concentrated under reduced pressure. The concentrate was taken up in methylene chloride and concentrated twice. The residue was dried in vacuo at room temperature for 1 hour.

C. Neutralization of the TFA Salt

The residue from Step B was dissolved in THF (20 ml) and the solution was cooled to 0° C. BSTFA (15 ml) was added and the solution was stirred at 0° C. under argon for 40 minutes.

D. Acylation

The solutions from Step A and Step C were combined and stirred at 0° C. for 40 minutes. The reaction mixture was warmed to room temperature then ethyl acetate (25 ml) was added. The solution was washed with 1N hydrochloric acid (15 ml), saturated aqueous sodium bicarbonate solution (15 ml) and brine (15 ml), then dried over magnesium sulfate, filtered and concentrated under reduced pressure. The concentrate was adsorbed onto silica gel, loaded onto a silica gel column, and the column eluted with a gradient of 100% hexane to 100% ethyl acetate to obtain 0.056 g of product. The product was recrystallized from methylene chloride/isopropyl ether to give 0.016 g of 2-(benzoyl)-3-(allyl carboxylate)-7-(R,S)-[2-(2-(allyloxycarbonylamino)-thiazol-4-yl)-2-(Z)-methoximinoacetamido]-8-oxo-1,5-diazabioyclo[3.3.0]octa-2-ene: n.m.r. (90 MHz, CDCl$_3$) $\delta$ 8.20–8.05 (br. d, 1, J=7), 7.94–7.78 (m, 2), 7.64–7.24 (m, 3), 7.00 (s, 1), 6.30 (br. s, 1), 6.04–5.44 (m, 2), 5.44–5.08 (m, 4), 4.96 (m, 1), 4.58 (dm, 2, J=6), 4.52–4.36 (m, 2), 4.20–3.88 (m, 3), 3.93 (s, 3), 3.24 (dd, 1, J=8, 11); u.v. (ethanol): $\lambda_{max}$=329 ($\epsilon$=4446), 233 ($\epsilon$=24,111); m.s.: (M-31)$^+$ =563;

Anal. Calcd. for C$_{27}$H$_{26}$N$_6$O$_8$S: Theory: C, 54.54; H, 4.41; N, 14.13; S, 5.39; Found: C, 54.74; H, 4.50; N, 13.92; S, 5.56.

EXAMPLE 59

2-(Benzoyl)-3-(Carboxylic Acid)-7-(R,S)-2-(2-Aminothiazol-4-yl)-2-(Z)-Methoxyiminoacetamido]-8-Oxo-1,5-Diazabicyclo[3.3.0]Octa-2-ene Palladium(II) acetate (0.022 g, 0.098 mmol) was suspended in reagent-grade acetone (6 ml) then triphenylphosphine (0.088 g, 0.336 mmol) was added. The mixture was stirred at room temperature for approximately 5 minutes, then a reagent-grade acetone solution (20 ml) of 2-(benzoyl)-3-(allyl carboxylate)-7-(R,S)-[2-(2-(allyloxycarbonylamino)thiazol-4-yl)-2-(Z)-methoximinoacetamido]-8-oxo-1,5-diazabicyclo[3.3.0]-octa-2-ene (0.670 g, 1.126 mmol) was added. The mixture was stirred at room temperature under argon for 40 minutes and cooled to 0° C. Tri(n-butyl)tin hydride (0.61 ml, 2.27 mmol) was added and the reaction solution was stirred at 0° C. for 15 minutes. The ice bath was removed and the solution was stirred for an additional 35 minutes, then the ice bath was replaced and 1N hydrochloric acid (2.27 ml) was added. The resultant solution was stirred at 0° C. for 5 minutes, then allowed to warm to room temperature. The reaction solution was filtered, water (100 ml) was added to the filtrate and the filtrate was filtered again. The filtrate was washed with hexane (2×, 50 ml), ether (2×, 50 ml) and hexane (2×, 50 ml) then concentrated in vacuo to remove the organic solvents. The concentrate was filtered and lyophilized. The resultant crude product (0.240 g) was chromatographed by HPLC on C-18 reverse phase silica gel with a step-gradient elution of 2% acetic acid and 10% acetonitrile in water to 2.5% acetic acid and 50% acetonitrile in water. The chromatography yielded 0.190 g of 2-(benzoyl)-3-(carboxylic acid)-7-(R,S)-[2-(2-aminothiazol-4-yl)-2-(Z)-methoxyiminoacetamido]-8-oxo-1,5- diazabicyclo-[3.3.0]octa-2-ene: n.m.r. (90 MHz, D$_2$O): $\delta$8.00–7.43 (m, 5), 6.87 (s, 1), 5.12–3.88 (m, 5), 3.90 (s, 3), 3.54–3.31 (m, 1); i.r. (KBr): 3335, 3329, 1676, 1630, 1597, 1580, 1533, 1366, 1270, 1044 cm$^{-1}$; u.v. (ethanol): $\lambda_{max}$=291 nm ($\epsilon$=13,628), 248 nm ($\epsilon$=20,935); f.d.m.s.: (M+1)$^+$=471.

EXAMPLE 60

2-(t-Butyl Carboxylate)-3-(Methylthio)-7-(R,S)-(t-Butoxycarbonylamino)-8-Oxo-1,5-Diazabicyclo-[3.3.0]Octa-2-ene

Step A. The Cycloaddition Reaction t-Butyl 3-methylthio-3-(p-toluenesulfonyl)acrylate (1.7 g, 5.18 mmol), 4-(R,S)-(t-butoxycarbonylamino)-3-oxo-1-methylene-1,2-pyrazolidinium ylide (1.065 g, 5 mmol) and 1,2-dichloroethane (10 ml) were combined and refluxed for 24 hours. Additional pyrazolidinium ylide (570 mg, 2.67 mmol) was added and the solution was refluxed for an additional 24 hours. The solution was concentrated in vacuo and was chromatographed by HPLC on a Waters Prep 500 silica gel column, with a gradient elution of 0–10% ethyl acetate in hexane to give 650 mg of 2-(R,S)-3-(R,S)-2-(t-butyl carboxylate)-3-methylthio-3-(p-toluenesulfonyl)-7-(t-butoxycarbonylamino)-8-oxo-1,5-diazabicyclo[3.3.0]octane: n.m.r. (90 MHz, CDCl$_3$): $\delta$7.72 (m, 2), 7.24 (m, 2), 5.2–2.8 (m, 7), 2.54 (s, 3), 2.43 (br. s, 3), 1.46 and 1.43 (2 X s, 9), 1.35 (s, 9).

Step B. The Elimination Reaction 2-(R,S)-3-(R,S)-2-(t-Butyl carboxylate)-3-methylthio-3-(p-toluenesulfonyl)-7-(R,S)-(t-butoxycarbonylamino)-8-oxo-5-diazabicyclo3.3.0]octane (650 mg, 1.2 mmol) was dissolved in dichloromethane (2 ml) and the solution was cooled to −78° C. 1,8-Diazabicyclo[5.4.0]undec-7-ene (DBU) (195 microliters, 1.3 mmol) was added and the resultant solution was stirred at −78° C. for 30 minutes then warmed to room temperature. The solution was diluted with ethyl acetate and washed with 1N hydrochloric acid, saturated aqueous sodium bicarbonate solution and brine, dried over magnesium sulfate, filtered and concentrated in vacuo to give 600 mg of residue. The residue was chromatographed on a preparatory-scale silica gel TLC plate eluted with a 1:1 mixture of hexane to ethyl acetate. The chromatography yielded 80 mg of 2-(t-butyl carboxylate)-3-(methylthio)-7-(R,S)-(t-butoxycarbonylamino)-8-oxo-1,5-diazabicyclo[3.3.0-octa-2-ene: n.m.r. (90 MHz, CDCl$_3$): $\delta$5.32 (br. d, 1), 4.6 (m, 1), 4.34 (d, 1, J=13), 4.04 (t, 1, J=8), 3.72 (d, 1, J=13), 2.68 (dd, 1, J=8, 12), 2.31 (s, 3), 1.50 (s, 9), 1.40 (s, 9); u.v. (ethanol): $\lambda_{max}$=332 ($\epsilon$=3900); m.s.: M$^+$=385; i.r. (CHCl$_3$): 1710 cm$^{-1}$.

EXAMPLE 61

2-(Allyl Carboxylate)-3-(Hydroxymethyl)-7-(R,S)-(t-Butoxycarbonylamino)-8-Oxo-1,5-Diazabicyclo-[3.3.0]Octa-2-ene and the Opposite 2,3-Regioisomer 4-(R,S)-(t-Butoxycarbonylamino)-3-oxo-1,2-diazolidine (8.95 g, 44.5 mmol) was suspended in 1,2-dichloroethane (50 ml). Gaseous formaldehyde was passed through the suspension with a nitrogen gas carrier until all the diazolidine had gone into solution. (The gaseous formaldehyde was generated by heating paraformaldehyde in a separate flask). Allyl 4-hydroxybutynoate (6.23 g, 44.5 mmol) was added and the solution was refluxed under argon for approximately 18 hours. The reaction solution was then adsorbed onto silica gel and the silica gel was chromatographed with a gradient elution of 100% hexane to 100% ethyl acetate. The 2-(hydroxymethyl)-3-(allyl carboxylate) regioisomer of the title product eluted from the column first to give 2.36 g, 15% yield of this regioisomer. After elution with the gradient was completed, an additional elution with neat ethyl acetate (1 liter) flushed the 2-(allyl carboxylate)-3-(hydroxymethyl) regioisomer of the title product from the column in 2.11 g, 13% yield. 2-(Allyl carboxylate)-3-(hydroxymethyl) regioisomer: n.m.r. (90 MHz, CDCl$_3$) $\delta$6.19–5.71 (m, 1), 5.51–5.10 (m, 3), 5.03–4.41 (m, 4), 4.47 (s, 1), 4.39–3.63 (m, 3), 2.75 (dd, 1, J=9, 12) 1.43 (s, 9); i.r. (KBr): 3375 (br), 2985, 2970, 1715, 1522, 1392, 1368, 1276, 1250, 1165, 1115, 1044, 1026 cm$^{-1}$; u.v. (ethanol): $\lambda_{max}$=434 nm ($\epsilon$=75), 283 nm ($\epsilon$=2078); f.d.m.s. (M+1) =354, M$^+$=353; 2-(hydroxymethyl)-3-(allyl carboxylate) regioisomer: n.m.r. (90 MHz, CDCl$_3$): $\delta$6.12–5.67 (m, 1), 5.58–5.12 (m, 3), 4.82 (s, 1), 4.86–4.52 (m, 3), 4.24 (d, 1, J=11), 3.97 (t, 1, J=8), 3.76 (d, 1, J=11), 2.92 (dd, 1, J=8, 12), 1.40 (s, 9); i.r. (KBr): 3345 (br), 2985, 2940, 2850, 1711, 1691, 1535, 1434, 1367, 1286, 1268, 1239, 1163, 1139 cm$^{-1}$; u.v. (ethanol): $\lambda_{max}$=335 nm ($\epsilon$=9553), 265 nm ($\epsilon$=886); f.d.m.s.: (M+2)$^+$=355, (M+1)$^+$=354, M$^+$=353 (100%).

EXAMPLE 62

2-(Allyl Carboxylate)-3-(Acetoxymethyl)-7-(R,S)-(t-Butoxycarbonylamino)-8-Oxo-1,5-Diazabicyclo-[3.3.0Octa-2-ene 2-(Allyl carboxylate)-3-(hydroxymethyl)-7-(R,S)-(t-butoxycarbonylamino)-8-oxo-1,5-diazabicyclo-[3.3.0]octa-2-ene (0.108 g, 0.306 mmol) was dissolved in dry methylene chloride (1.0 ml). Dimethylaminopyridine (0.005 g, 0.04 mmol) and acetic acid anhydride (0.030 ml, 0.32 mmol) were added and the reaction solution was stirred for 1.5 hours at room temperature. The solution was diluted with additional methylene chloride then washed with 1N hydrochloric acid, saturated aqueous sodium bicarbonate solution and brine, dried over magnesium sulfate, filtered and concentrated in vacuo. The residue (approximately 93 mg) was applied to three preparatory-scale silica gel TLC plates (0.25 mm thickness, 20 cm×20 cm) and the plates were eluted with 1:1 ethyl acetate:hexane. The major band on the plates was then extracted overnight with ethyl acetate. The ethyl acetate extract was concentrated to yield 0.036 g, 30% of yellow oil of 2-(allyl carboxylate)-3-(acetoxymethyl)-7-(R,S)-(t-butoxycarbonylamino)-8-oxo-1,5-diazobicyclo[3.3.0]octa-2-ene: n.m.r. (90 MHz, CDCl$_3$): $\delta$6.16–5.70 (m, 1), 5.48–5.06 (m, 3), 4.95–4.45 (m, 4), 4.2 (dm, 1, J=14), 4.10 (t, 1, J=8), 3.68 (dm, 1, J=14) 2.72 (dd, 1, J=8, 12) 2.07 (s, 3), 1.44 (s, 9); i.r. (CHCl$_3$): 3017, 2980, 2930, 1717, 1500, 1393, 1369, 1273, 1234, 1216, 1162, 1027 cm$^{-1}$; u.v. (ethanol): $\lambda_{max}$=308 nm ($\epsilon$=2150); f.d.m.s.: (M+1)$^+$=396 (30%), M=395 (100%).

EXAMPLE 63

2-(Allyl Carboxylate)-3-(Acetyl)-7-(R,S)-(2-(2,5-Dichlorophenylthio)acetamido)-8-Oxo-1,5-Diazabicyclo-[3.3.0]Octa-2-ene

Step A

Removal of Amino-Protecting Group 2-(Allyl carboxylate)-3-(acetyl)-7-(R,S)-(t-butoxycarbonylamino)-8-oxo-1,5-diazabicyclo[3.3.0]octa-2-ene (365 mg, 1 mmol) was dissolved in a mixture of 3N hydrochloric acid in glacial acetic acid (10 ml). The solution was stirred at room temperature for five minutes and concentrated in vacuo. Acetonitrile was added to the residue then removed in vacuo twice, and the resultant residue was dried in vacuo at room temperature for 30 minutes.

Step B

Synthesis of Active Ester 2-(2,5-dichlorophenylthio)acetic acid was dissolved in methylene chloride (5 ml) and the resultant solution was cooled to 0° C. N-Methylmorpholine (0.11 ml, 1 mmol) then 2-chloro-4,6-dimethoxy-1,3,5-triazine (176 mg, 1 mmol) were added and the solution was stirred for 45 minutes at 0° C. Additional N-methylmorpholine (0.11 ml, 1 mmol) and then a methylene chloride slurry (5 ml) of the compound from Step A above were added to the solution. The solution was stirred at 0° C. for one hour, at room temperature for three hours, then diluted with methylene chloride, washed sequentially with 1N hydrochloric acid, saturated aqueous sodium bicarbonate solution, brine solution, dried over magnesium sulfate, filtered and concentrated in vacuo. The residue was flash chromatographed on silica gel, eluted with 1:1 hexane/ethyl acetate to give 155 mg, 32% yield of the 2-(allyl carboxylate)-3-(acetyl)-7-(R,S)-(2-(2,5-dichlorophenylthio)acetamido-8-oxo-1,5-diazabicyclo-[3.3.0]octa-2-ene: n.m.r. (90 MHz, CDCl$_3$): δ7.32–6.92 (m, 4), 6.16–5.76 (m, 1), 5.52–5.2 (m, 2), 4.88 (m, 1), 4.82 (d of m, 2, J=6), 4.32 (d, 1, J=13), 4.02 (t, 1, J=8), 3.83 (d, 1, J=13), 3.61 (s, 2), 2.70 (dd, 1, J=8 and 12), 2.20 (s, 3); i.r. (CHCl$_3$): 1743, 1681, 1661 cm$^{-1}$, u.v. (ethanol): $\lambda_{max}$=363 ($\epsilon_{max}$=6899); f.d.m.s. (m/e): M$^+$=483, 485, 486 and 488.

Anal. Calcd for C$_{20}$H$_{19}$Cl$_2$N$_3$O$_5$S: Theory: C, 49.60; H, 3.95; N, 8.68. Found: C, 49,87; H, 4.03; N, 8.44

EXAMPLE 64

2-(Carboxylic Acid)-3-Acetyl-7-(R,S)-(2-(2,5-Dichlorophenylthio)Acetamido-8-Oxo-1,5-Diazabicyclo-[3.3.0]Octa-2-Ene Tetrakis(triphenylphosphine)palladium(0) (11.7 mg, 0.01 mmol) and an ethyl acetate solution of triphenylphosphine (3 mg, 0.011 mmol) were combined and then sodium 2-ethylhexanote (35 mg, 0.21 mmol) was added. To the solution was added 2-(allyl carboxylate)-3-acetyl-7-(R,S)-(2-(2,5-dichlorophenylthio)acetamido)-8-oxo-1,5-diazabicyclo3.3.0]octa-2-ene (100 mg, 0.206 mmol). The mixture was stirred at room temperature for three hours then centrifuged. The solid collected was triturated with ethyl acetate (2×) and dried in vacuo to yield 90 mg of a yellow powder. The powder was chromatographed by medium pressure liquid chromatography on a C18 reverse phase silica column eluted with 15% acetonitrile/0.5% acetic acid in water to give 25 mg of the 2-(carboxylic acid)-3-acetyl-7-(R,S)-(2-(2,5-dichlorophenylthio) acetamido-8-oxo-1,5-diazabicyclo-3.3.0]octa-2-ene: n.m.r. (300 MHz, DMSO-d$_6$): δ 8.94 (br. d, 1), 7.46 (m, 2), 7.26 (m, 1), 4.85 (m, 1), 4.0–3.9 (m, 3), 3.65 (t, 1, J=8), 2.56 (d, 1, J=13), 2.75 (t, 1, J=8), 2.23 (s, 3); i.r. (KBr): 1715, 1638, 1570 cm$^{-1}$; u.v. (ethanol): $\lambda_{max}$=353 ($\epsilon_{max}$=9750), 254 (11,040); f.a.b.m.s. (m/e): M$^+$=443.

EXAMPLE 65

2-(Allyl Carboxylate)-3-Acetyl-7-(R,S)-[2-(2-Tritylamino)Thiazol-4-yl)-2-(Z)-(2,5-Dichlorobenzyloxyimino)Acetamido]-8-Oxo-1,5-Diazabicyclo[3.3.0]Octa-2-Ene

STEP A

Synthesis of Acylating Agent 2-(2-(Tritylamino)thiazol)-4-yl)-2-(Z)-(2,5-diohlorobenzyloxyimino)acetic acid (294 mg, 0.5 mmol) was dissolved in methylene chloride (5 ml) and the solution was cooled to 0° C. N-methylmorpholine (0.055 ml, 0.5 mmol) then 2-chloro-4,6-dimethoxy-1,3,5-triazine (88 mg, 0.5 mmol) were added and the resultant solution was stirred for one hour at 0° C.

STEP B

Removal of Amino-Protecting Group 2-(Allyl carboxylate)-3-(acetyl)-7-(R,S)-(t-butoxycarbonylamino)-8-oxo-1,5-diazabicyclo[3.3.0]octa-2-ene (186 mg, 0.5 mmol) was added to a mixture of 3N hydrochloric acid in glacial acetic acid (5 ml). The resultant mixture was stirred for 5 minutes at room temperature then concentrated in vacuo. To the residue was added methylene chloride (1 ml) and carbon tetrachloride (10 ml) and the solution was concentrated in vacuo then redissolved and reconcentrated. The residue was dried in vacuo for 15 minutes at room temperature.

STEP C

Acylation

The residue from Step B was slurried in methylene chloride (5 ml); an additional amount of N-methylmorpholine (0.055 ml, 0.5 mmol) and then the slurry containing the product of Step B were added to the solution of Step A. The resultant solution was stirred for 4 hours at 0° C., diluted with ethyl acetate, washed with 0.2N hydrochloric acid, saturated aqueous sodium bicarbonate solution, brine, dried over magnesium sulfate, and concentrated in vacuo. The solid was flash chromatographed on silica gel eluted with a 3:2 hexane:ethyl acetate mixture to give 83 mg, 20% yield of the 2-(allyl carboxylate)-3-acetyl-7-(R,S)-[2-(2-tritylamino)thiazol-4-yl)-2-(Z)-(2,5-dichlorobenzyloxyimino)acetamido]-8-oxo-1,5-diazabicyl[3.3.0]octa-2-ene: n.m.r. (90 MHz, CDCl$_3$); δ 7.2 (m, 18), 7.02 (br.s, 1), 6.70 (s, 1), 6.1–5.7 (m, 1), 5.5–5.1 (m, 2), 5.26 (s, 2), 4,98 (m, 1), 4.76 (br. d, 2, J=6), 4.3 (d, 1, J=13), 4.08 (t, 1, J=8), 3.8 (d, 1, J=13), 2.88 (dd, 1, J=8 and 12), 2.20 (s, 3); i.r. (CHCl$_3$) 1743, 1684, 1660 cm$^{-1}$; u.v. (ethanol): $\lambda_{max}$=363 ($\lambda_{max}$=7362), 299 (7672).

EXAMPLE 66

2-(Allyl Carboxylate)-3-(Acetyl)-7(R,S)-[2-(2-Tritylamino)thiazol-4-yl)-2-(Z)-(2-(t-Butyl Carboxylate)-prop-2-yloxyimino)acetamido]-8-Oxo-1,5-Diazabicyclo[3.3.0]-Octa-2-En

STEP A

Removal of Amino-Protecting Group 2-(Allyl carboxylate)-3-(acetyl)-7-(R,S)-(t-butoxycarbonylamino)-8-oxo-1,5-diazabicyclo3.3.0]octa-2-ene (0.185 g, 0.506 mmol) was dissolved in a mixture of 3N hydrochloric acid in glacial acetic acid (5 ml). This mixture was stirred for five minutes at room temperature then concentrated in vacuo. The resultant dark yellow oil was taken up in carbon tetrachloride and the solution was concentrated in vacuo to give a yellow foam. The foam was dried in vacuo at room temperature for about one hour.

STEP B

Acylation

Under an argon atmosphere, 2-(2-tritylaminothiazol-4-yl)-2-(Z)-(2-(t-butyl carboxylate)prop-2-yloxyimino)acetic acid (0.286 g, 0.50 mmol) was suspended in dry methylene chloride (5 ml) then the suspension was cooled to 0° C. 2-Chloro-4,6-dimethoxy-1,3,5-triazine (0.088 g, 0.50 mmol) and N-methyl morpholine (0.055 ml, 0.50 mmol) were added and the solution was stirred at 0° C. for 35 minutes. Additional N-methylmorpholine (0.055 ml, 0.50 mmol) then a methylene chloride solution (5 ml) of 2-(allyl carboxylate)-3-acetyl-7-(R,S)-amino-8-oxo-1,5-diazabicyclo[3.3.0]octa-2-ene hydrochloride (from Step A above) were added. The resultant solution was stirred at room temperature for 4 hours, and concentrated in vacuo. The resultant yellow oil was chromatographed on Kieselgel 60 (25×2.5 cm column, 230–400 mesh) eluted with 40% ethyl acetate/hexane to give 0.26 g of a yellow powder of 2-(allyl carboxylate)-3-(acetyl)-7-(R,S)-[2-(2-tritylamino)thiazol-4-yl)-2-(Z)-(2-(t-butyl carboxylate)-prop-2-yloxyimino)acetamido]-8-oxo-1, 5-diazabicyclo[3.3.0]octa-2-ene: n.m.r. (90 MHz, CDCl₃); δ 1.365 (s, 9), 1.50 (m, 6), 2.20 (s, 3), 2.78–3.00 (m, 1), 3.78–4.05 (m, 2), 2.30 (m, 1), 4.80 (m, 2), 4.90–5.40 (m, 3), 5.65–6.05 (m, 1), 7.22 (s, 15), 7.9 (m, 1); i.r. (CHCl₃): 3018, 1737, 1680, 1525, 1370, 1278, 1228, 1211, 1210, 1144 cm⁻¹; u.v. (ethanol): $\lambda_{max}$=362 ($\epsilon_{max}$=7767.2); f.d.m.s. (m/e): (M)⁺=819 (100%).

EXAMPLE 67

2-(Carboxylic Acid)-3-Acetyl-7-(R,S)-[2-(2-(Tritylamino)-thiazol-4-yl)-2-(Z)-(2-(t-Butyl Carboxylate)-Prop-2-yloxyimino)acetamido]-8-Oxo-1,5-Diazabicyclo[3.3.0]Octa-2-ene Under an argon atmosphere, palladium(II) acetate (0.0030 g, 0.013 mmol) and triphenylphosphine (0.016 g, 0.061 mmol) were suspended in acetonitrile (2.0 ml). An acetonitrile solution (7.0 ml) of 2-(allyl carboxylate)-3-acetyl-7-(R,S)-[2-(2-tritylaminothiazol-4-yl)-2-(Z)-(2-(t-butyl carboxylate)prop-2-yloxyimino)acetamido]-8-oxo-1,5-diazabicyclo[3.3.0]octa-2-ene (0.100 g, 0.122 mmol) was added and the resultant solution was cooled to 0° C. Tri(n-butyl)tin hydride (0.033 ml, 0.12 mmol) was added and the solution was stirred for 25 minutes at 0° C., 30 minutes at room temperature, then cooled to 0° C. 1N Hydrochloric acid (0.13 ml) was added, and the solution was stirred at room temperature for 15 minutes, diethyl ether was added and the resultant precipitate was collected by filtration. Additional ether was added to the filtrate and the resultant precipitate was also collected by filtration. The two lots of precipitate thus collected were combined to give approximately 50 mg of the 2-(carboxcylic acid)-3-acetyl-7-(R,S)-[2-(2-tritylaminothiazol-4-yl)-2-(Z)-(2-(t-butyl carboxylate)-prop-2-yloxyimino)acetamido]-8-oxo-1,5-diazabicyclo[3.3.0]octa-2-ene: n.m.r. (90 MHz, CDCl₃): 1.40 (s, 9), 1.50 (s, 6), 2.25 (s, 3), 2.70–3.00 (m, 1), 3.60–4.30 (m, 3), 4.75–5.05 (m, 1), 6.68 (s, 1), 7.22 (s, 15), 7.50–7.70 (m, 1), 7.95–8.05 (m, 1).

EXAMPLE 68

2-(Allyl Carboxylate)-3-(Acetoxymethyl)-7-(R,S)-[2-(2-Aminothiazol-4-yl)-2-(Z)-Methoxyiminoacetamido]-8-Oxo-1,5-Diazabicyclo[3.3.0]Octa-2-ene

Step A

Removal of Amino-Protecting Group

Under an argon atmosphere, 2-(allyl carboxylate)-3-(acetoxymethyl)-7-(R,S)-(t-butoxycarbonylamino)-8-oxo-1,5-diazabicyclo[3.3.0]octa-2-ene (0.300 g, 0.76 mmol) was dissolved and stirred in trifluoroacetic acid (5.0 ml, 63 mmol) at 0° C. for 50 minutes. Saturated aqueous sodium bicarbonate solution (20 ml) was added to the solution and the aqueous mixture was added to additional saturated aqueous sodium bicarbonate solution (40 ml). The mixture was extracted with chloroform (6X, 25 ml) and the extracts were combined and washed with brine, dried over magnesium sulfate, filtered, and concentrated in vacuo to yield 0.120 g of the free amine.

STEP B

Acylation

The free amine of Step A above was dissolved in acetonitrile (15 ml) then (1-hydroxy N-benzotriazolyl) 2-(2-aminothiazol-4-yl)-2-(Z)-methoximinoacetate (0.130 g, 0.43 mmol) and di(iso-propyl)ethylamine (0.075 ml) were added to the solution. The solution was stirred at room temperature under argon overnight then concentrated in vacuo. The residue was chromatographed on Kieselgel 60 (230–400 mesh) eluted with 1% di(iso-propyl)ethylamine:10% methanol in ethyl acetate to give the 2-(allyl carboxylate)-3-(acetoxymethyl)-7-(R,S)-[2-(2-aminothiazol-4-yl)-2-(Z)-methoxyiminoacetamido]-8-oxo-1,5diazabicyclo[3.3.0]octa-2-ene: n.m.r. (90 MHz, CDCl₃); δ 2.07 (s, 3), 2.90–3.10 (m, 1), 3.66–4.26 (m, 3), 3.94 (s, 3), 4.75–4.81 (m, 2), 4.86–5.50 (m, 4), 5.65–6.05 (m, 2).

EXAMPLE 69

2-(Carboxylic Acid)-3-(Acetoxymethyl)-7-(R,S)-[2-(2-Aminothiazol-4-yl)-2-(Z)-Methoxyiminoacetamido]-8-Oxo-1,5-Diazabicyclo3.3.0]Octa-2-ene Under an argon atmosphere, tetrakis(triphenylphosphine)palladium(0) (0.080 g, 0.69 mmol) and triphenylphosphine (0.018 g, 0.069 mmol) were suspended in acetone (1.0 ml). An acetone solution (3.0 ml) of 2-(allyl carboxylate)-3-(acetoxymethyl)-7-(R,S)-[2-(2-aminothiazol-4-yl)-2-(Z)-methoxyiminoacetamido]-8-oxo-1,5-diazabicyclo[3.3.0]octa-2-ene (0.32 g, 0.67 mmol) was added and the resultant solution was stirred first at room temperature for 15 minutes then cooled to 0° C. tri(n-Butyl)tin hydride (0.18 ml, 0.65 mmol) was added, the solution was stirred at 0° C. for 25 minutes then 1N hydrochloric acid (0.65 ml) was added. The solution was warmed to room temperature, and acetonitrile (10 ml) was added. The resultant precipitate was removed by suction filtration. The filtrate was diluted slowly with diethyl ether (20 ml) and the precipitate was collected by suction filtration and dried in vacuo at room temperature for 2 hours to yield 0.125 g of material. The material was chromatographed by medium pressure liquid chromatography on C s reverse phase silica eluted with 1% ammonium acetate/7% acetonitrile/water. The product-containing fractions were combined and lyophilized repeatedly to give 4.1 mg of 2-

(carboxylic acid)-3-(acetoxymethyl)-7-(R,S)-[2-(2-aminothiazol-4-yl)-2-(Z)-methoxyiminoacetamido]-8-oxo-1,5-diazabicyclo[3.3.0]octa-2-ene: n.m.r. (90 MHz, D₂O): δ 1.96 (s, 3), 2.94–3.20 (m, 1), 3.60–4.10 (m, 3), 3.82 (s, 3), 4.80–5.20 (m, 3), 6.95 (s, 1).

EXAMPLE 70

2-(Acetoxymethyl)-3-(Allyl Carboxylate)-7-(R,S)-(t-Butoxycarbonylamino)-8-Oxo-1,5-Diazabicyclo[3.3.0]Octa-2-ene Under an argon atmosphere, 2-(hydroxymethyl)-3-(allyl carboxylate)-7-(R,S)-(t-butoxycarbonylamino)-8-oxo-1,5-diazabicyclo[3.3.0]octa-2-ene (1.06 g, 3.00 mmol) was dissolved in pyridine (16 ml) and the solution was cooled to 0° C. N,N-Dimethylaminopyridine (0.040 g, 0.33 mmol) was added and the solution was stirred at room temperature for 4 hours. The solution was cooled to 0° C., acetic anhydride (0.287 ml, 3.03 mmol) was added and the solution was stirred at room temperature overnight. The solution was diluted with diethyl ether (25 ml), washed with 1N hydrochloric acid (2X, 25 ml), brine, dried over magnesium sulfate, filtered, and concentrated in vacuo. The residue was taken up in toluene and concentrated in vacuo twice then chromatographed on silica gel (Kieselgel 60, 230–400 mesh) eluted with 40% ethyl acetate/hexane to yield 0.62 g, 52% of the 2-(acetoxymethyl)-3-(allyl carboxylate)-7-(R,S)-(t-butoxycarbonylamino)-8-oxo-1,5-diazabicyclo[3.3.0]octa-2-ene: n,m,r, (90 MHz, CDCl₃): δ 6.1–5.65 (m,1), 5.50–5.1 (m, s), 4.67–4.61 (m, 2), 4.32 (d, 1, J=12), 3.97 (t, 1, J=7), 3.78 (d, 1, J=12), 2.85 (dd, 1, J=12, 8), 2.03 (s, 3), 1.41 (s, 9). i.r. (CHCl³): 1702, 1420, 1369 cm⁻¹. u.v. (EtOH): λmax=339 (ε$_{max}$=9272), F.D.M.S. M+=395; m.p. 105°–106° C.

EXAMPLE 71

2-(Acetoxymethyl)-3-(Allyl Carboxylate)-7-(R,S)-[2-(2-Aminothiazol-4-yl)-2-(Z)-Methoxyiminoacetamido]-8-Oxo-1,5-Diazabicyclo[3.3.0]Octa-2-ene

STEP A

Removal of Amino-Protecting Group

Under an argon atmosphere, 2-(acetoxymethyl)-3-(allyl carboxylate)-7-(R,S)-(t-butoxycarbonylamino)-8-oxo-1,5-diazabicyclo[3.3.0]octa-2-ene (0.210 g, 0.531 mmol) and trifluoroacetic acid (3.5 ml, 44.1 mmol) were combined and the solution was stirred for one hour at 0° C. Saturated aqueous sodium bicarbonate solution (25 ml also at 0° C.) was added, the layers were separated, the aqueous phase was extracted with chloroform (4X, 25 ml) and the chloroform extracts were combined and washed with brine, dried over magnesium sulfate, and concentrated in vacuo to give 0.130 g of the free amine.

STEP B

Acylation

The free amine from Step A was dissolved in acetonitrile (15 ml) then di(iso-propyl)ethylamine (0.080 ml, 0.46 mmol) and (1-hydroxy N-benzotriazolyl) 2-(2'-aminothiazol-4'-yl)-2-(Z)-methoximinoacetate (0.140 g, 0.463 mmol) were added. The reaction mixture was stirred at room temperature overnight and then concentrated under reduced pressure. The residue was chromatographed on silica gel (Kieselgel 60, 230–400 mesh) eluted with 10% methanol:1% di(iso-propyl)ethylamine in ethyl acetate. The collected product was triturated with diethyl ether to give a bright yellow powder (0.094 g, 45% yield) of the 2-(acetoxymethyl)-3-(allyl carboxylate)-7-(R,S)-[2-(2-aminothiazol-4-yl)-2-(Z)-methoxyiminoacetamido]-8-oxo-1,5-diazabicyclo[3.3.0]octa-2-ene: n.m.r. (90 MHz, CDCl₃): δ 2.07 (s, 3), 2.90–3.20 (m, 1), 3.76–4.10 (m, 2), 3.95 (s, 3), 4.26–4.46 (m, 1) 4.65–4.71 (m, 2), 5.22–5.44 (m, 4), 5.56 (m, 1), 5.60–6.10 (m, 1), 6.86 (s, 1); i.r. (CHCl₃): 3018, 1742, 1695, 1432, 1371, 1238, 1224, 1206, 1049, 1034 cm⁻¹; u.v. (ethanol): λ$_{max}$=333 (ε$_{max}$=9586), 223 (18,987); f.d.m.s. (m/e): M+=479.

EXAMPLE 72

2-(Acetoxymethyl)-3-(Carboxylic Acid)-7-(R,S)-[2-(2-Aminothiazol-4-yl)-2-(Z)-Methoxyiminoacetamido-8-Oxo-1,5-Diazabicyclo[3.3.0]Octa-2-ene Under an argon atmosphere, tetrakis(triphenylphosphine)palladium (0) (0.017 g, 0.015 mmol) and triphenylphosphine (0.004 g, 0.015 mmol) were suspended in acetone (0.5 ml) and the resultant suspension was stirred at room temperature. An acetone solution (1.0 ml) of 2-(acetoxymethyl)-3-(allyl carboxylate)-7-(R,S)-[2-(2-aminothiazol-4-yl)-2-(Z)-methoxyiminoacetamido]-8-oxo-1,5-diazabicyclo[3.3.0]octa-2-ene (0.070 g, 0.146 mmol) was added and the solution was stirred at room temperature for 10 minutes. The solution was cooled to 0° C., tri(n-butyl)tin hydride (0.040 ml, 0.144 mmol) was added, and the solution was stirred for 45 minutes. 1N Hydrochloric acid (0.140 ml) was added and the resultant precipitate was removed by suction filtration. The filtrate was diluted with 1:1 water:acetone (50 ml) then washed with hexane (5X, 25 ml) and ether (1X, 50 ml), concentrated in vacuo, and lyophilized to yield 0.061 g, 95% of 2-(acetoxymethyl)-3-(carboxylic acid)-7-(R,S)-[2-(2-aminothiazol-4-yl)-2-(Z)-methoxyiminoacetamido]-8-oxo-1,5-diazabicyclo[3.3.0]octa-2-ene: u.v. (ethanol): λ$_{max}$=302 (ε$_{max}$=1206).

EXAMPLE 73

2-(t-Butyl Carboxylate)-3-(N-Methylamido)-7-(R,S)-(t-Butoxycarbonylamino)-8-Oxo-1,5-Diazabicyclo[3.3.0]Octa-2-ene and the Corresponding Regioisomer

STEP A

Formation of Ylide 4-(R,S)-(t-Butoxycarbonylamino)-3-oxo-1,2-diazolidine (1.05 g, 5 mmol) was slurried in 1,2-dichloroethane (20 ml). Aqueous formaldehyde (37%, 0.41 g, 5 mmol) was added and the slurry was stirred at room temperature for 90 minutes.

STEP B

Cycloaddition

The solution from Step A was combined with 1-(t-butoxycarbonyl)-2-(N-methylamido)acetylene (915 mg, 5 mmol) and the solution was stirred at reflux temperature for 5 hours then cooled and concentrated in vacuo. The resultant residue was flash chromatographed on silica gel eluted with a gradient of 3:2 ethyl acetate:hexane to 3:1 ethyl acetate: hexane to give 280 mg of the 2-(t-butyl carboxylate)-3-(N-methylamido)-7-(R,S)-(t-butoxycarbonylamino)-8-oxo-1, 5-diazabicyclo[3.3.0]octa-2-ene (more polar isomer) and 290 mg of the opposite 2,3-regioisomer (less polar isomer) in addition to 140 mg of the regioisomeric mixture. Physical data for the more polar isomer: n.m.r. (90 MHz, CDCl₃): δ 8.3 (br. s, 1), 5.1 (br. s, 1), 4.7 (m, 1), 4.59 (d, 1, J=14), 4.06 (t, 1, J=8), 3.8 (d, 1, J=14), 2.90 and 2.84 (2x, s, 3), 2.72 (dd, 1, J=8 and 11), 1.54 (s, 9), 1.43 (s, 9); i.r. (CHCl$_3$): 1709, 1651 cm$^{-1}$; u.v. (ethanol): $\lambda_{max}$=331 ($\delta_{max}$=7305); f.d.m.s. (m/e): M$^+$=396.

Anal. Calcd for C$_{18}$H$_{28}$N$_4$O$_6$: Theory: C, 54.53; H, 7.12; N, 14.13. Found: C, 54.28; H, 6.93; N, 13.86.

EXAMPLE 74

2-(Carboxcylic Acid)-3-(N-Methylamido)-7-(R,S)-[2-(2-Aminothiazol-4-yl)-2-(Z)-Methoxyiminoacetamido]-8-Oxo-1,5-Diazabicyclo[3.3.0]Octa-2-ene

Step A

Removal of Amino-Protecting Group 2-(t-Butyl carboxylate)-3-(N-methylamido)-7-(R,S)-(t-butoxycarbonylamino)-8-oxo-1,5-diazabicyclo[3.3.0]octa-2-ene (40 mg, 0.1 mmol) was dissolved in trifluoroacetic acid (3. ml) and the solution was stirred at room temperature for 30 minutes and concentrated in vacuo. Acetonitrile was added to the residue and the solution was reconcentrated twice to give a yellow solid.

STEP B

Acylation

The yellow solid of Step A was taken up in water (1 ml) and the pH of the solution was adjusted to 8 by the addition of saturated aqueous sodium bicarbonate solution. Acetonitrile (1 ml) then (1-hydroxy N-benzotriazolyl) 2-(2-aminothiazol-4-yl)-2-(Z)-methoxyiminoacetate (40 mg, 0.11 mmol, 85%) were added and the solution was stirred at room temperature for 3 hours. The solution was diluted with water, extracted with 3:1 chloroform:iso-propanol, the pH of the aqueous layer was adjusted to 2 with 1N hydrochloric acid then extracted again with 3:1 chloroform:isopropanol. The aqueous layer was separated and the water was removed by azeotropic distillation with acetonitrile in vacuo. The resultant solid was chromatographed by medium pressure liquid chromatography on a C$_{18}$ reverse phase column eluted with 3% acetonitrile/water with 1% ammonium acetate to yield 9 mg of the 2-(carboxylic acid)-3-(N-methylamido)-7-(R,S)-[2-(2-aminothiazol-4-yl)-2-(Z)-methoxyiminoacetamido]-8-oxo-1,5-diazabicyclo[3.3.0]-octa-2-ene: n.m.r. (90 MHz, D$_2$O): $\delta$ 6.92 (s, 1), 5.10 (dd, 1, J=8 and 12), 4.2 (d, 1, J=13), 4.0–3.78 (m, 2), 3.82 (s, 3), 3.10 (dd, 1, J=8 and 12), 2.66 (s, 3); i.r. (KBr): 1701, 1640, 1570 cm$^{-1}$; u.v. (ethanol): $\lambda_{max}$=298 ($\epsilon_{max}$=8827).

EXAMPLE 75

2-(N-Methylamido)-3-(Carboxylic Acid)-7-(R,S)-[2-(2-Aminothiazol-4-yl)-2-(Z)-Methoxyiminoacetamido]-8-Oxo-1,5-Diazabicyclo[3.3.0]Octa-2-ene

STEP A

Removal of Amino-Protecting Group 2-(N-Methylamido)-3-(t-butyl carboxylate)-7-(R,S)-(t-butoxycarbonylamino)-8-oxo-1,5-diazabicyclo[3.3.0]octa-2-ene (40 mg, 0.1 mmol) was slurried in trifluroacetic acid (3 ml) and the slurry was stirred for 30 minutes at room temperature then concentrated in vacuo. The residue was subjected to repeated acetonitrile additions followed by concentrations in vacuo to give a yellow foam.

STEP B

Acylation

Water (2 ml) was added to the yellow foam of Step A and the pH of the resultant solution was adjusted to 7.5–8 with saturated aqueous sodium bicarbonate solution. Acetonitrile (2 ml) and (1-hydroxy N-benzotriazolyl) 2-(2-aminothiazol-4-yl)-2-(Z)-methoxyiminoacetate (85%, 40 mg, 0.11 mmol) were added, the solution was stirred for three hours at pH 7.5-8 at room temperature then concentrated in vacuo. The concentrate was diluted with water, extracted with chloroform, the layers were separated. The pH of the aqueous layer was adjusted to 2 by the addition of 1N hydrochloric acid, extracted with 3:1 chloroform:iso-propanol and the aqueous phase was freeze dried to give approximately 90 mg of a yellow powder. The powder was chromatographed by medium pressure liquid chromatography on a C$_{18}$ reverse-phase column eluted with 3% acetonitrile/water with 1% ammonium acetate to give 11.5 mg of the 2-(N-methylamido)-3-(carboxylic acid)-7-(R,S)-[2-(2-aminothiazol-4-yl)-2-(Z)-methoxyiminoacetamido]-8-oxo-1,5-diazabicyclo[3.3.0]octa-2-ene: n.m.r. (90 MHz, D$_2$O): $\delta$ 6.96 (s, 1), 5.02 (dd, 1, J=8 and 12), 4.12 (d, 1, J=13), 4.0–3.64 (m, 2), 3.76 (s, 3), 3.10 (br. t, 1, J=9), 2.68 (s, 3); i.r. (KBr): 1664, 1635, 1583 cm$^{-1}$; u.v. (ethanol): $\lambda_{max}$=298 ($\epsilon_{max}$=8728).

PREPARATION 11

1-(t-Butyl Carboxylate)-2-(N-Phenylamido)acetylene t-Butyl propiolate (3.78 g, 30 mmol) was dissolved in THF and cooled to −78° C. A hexane solution of N-butyl lithium (1.5 m, 20 ml, 30 mmol) was added and the solution was stirred at −78° C. for 30 minutes.

Phenyl isocyanate (3.25 ml, 30 mmol) was added and the solution was stirred for ten minutes at −78° C. The cooling bath was removed and reaction was quenched with saturated aqueous ammonium chloride solution. The solution was warmed to room temperature, diluted with ethyl acetate, washed with saturated ammonium chloride solution, water, and brine, dried over magnesium sulfate, filtered and concentrated in vacuo to give an oil. The oil was flash chromatographed on silica gel eluted with a gradient of 10% ethyl acetate/hexane to 15% ethyl acetate/hexane to give 5.0 g, 68% yield of the 1-(t-butyl carboxylate)-2-(N-phenylamido)acetylene: n.m.r. (90 MHz, CDCl$_3$): $\delta$ 8.10 (br. s, 1), 7.7–7.1 (m, 5), 1.60 (s, 9); i.r. (CHCl$_3$): 1710, 1675 cm$^{-1}$; m.s. (m/e): M$^+$245.

EXAMPLE 76

2-(t-Butyl Carboxylate)-3-(N-Phenylamido)-7-(R,S)-(t-Butoxycarbonylamino)-8-Oxo-1,5-Diazabicyclo[3.3.0]Octa-2-Ene

STEP A

Synthesis of Ylide 4-(R,S)-(t-Butoxycarbonylamino)-3-oxo-1,2-diazolidine (2.01 g, 10 mmol) was slurried in 1,2-dichloroethane (40 ml). To the slurry was added aqueous formaldehyde (37%, 0.81 g, 10 mmol) and the solution was stirred at room temperature for 2 hours.

STEP B

Cycloaddition

To the solution of Step A above was added a 1,2-dichloroethane solution (10 ml) of 1-(t-butyl carboxylate)-2-(N-phenylamido)acetylene (2.45 g, 10 mmol) and the solution was heated to reflux for 6 hours then cooled and concentrated in vacuo. The concentrate was flash chromatographed over silica gel eluted with 7:3 hexane:ethyl acetate to give 600 mg of the 2-(t-butyl carboxylate) isomer and 550 mg of the corresponding 2,3-regioisomer (2-(N-phenylamido)). Spectra for the 2-(t-butyl carboxylate) regioisomer: n.m.r. (90 MHz, CDCl$_3$): δ 7.6–6.92 (m, 5), 5.18 (br. d, 1), 4.72 (m, 1), 4.64 (d, 1, J=14), 4.04 (t, 1, J=8), 3.84 (d, 1, J=14), 2.76 (dd, 1, J=8 and 12), 1.56 (s, 9), 1.42 (s, 9); i.r. (CHCl$_3$): 1711, 1704 and 1658 cm$^{-1}$; u.v. (ethanol): $\lambda_{max}$=337 ($\epsilon_{max}$=6490), 229 (11,120); f.d.m.s. (m/e): M$^+$=458. Spectra for 2-(N-phenylamido) regioisomer: n.m.r. (90 MHz, CDCl$_3$); δ 9.4 (br. s, 1), 7.7–6.96 (m, 5), 5.36 (br. d, 1, J=6), 4.70 (m, 1), 4.31 (d, 1, J=13), 3.97 (t, 1, J=8), 3.82 (d, 1, J=13), 2.90 (dd, 1, J=8 and 12), 1.44 (s, 18), i.r. (CHCl$_3$): 1692 cm$^{-1}$; u.v. (ethanol): $\lambda_{max}$=337 ($\epsilon_{max}$=8461), 239 (13505); f.d.m.s. (m/e): M$^+$=458.

EXAMPLE 77

2-(Carboxylic Acid)-3-(N-Phenylamido)-7-(R,S)-[2-(2-Aminothiazol-4-yl)-2-(Z)-Methoxyiminoacetamido]-8-Oxo-1,5-Diazabicyclo[3.3.0]Octa-2-ene

STEP A

Removal of Amino-Protecting Group 2-(t-Butyl carboxylate)-3-(N-phenylamido)-7-(R,S)(t-butoxycarbonylamino)-8-oxo-1,5-diazabicyclo[3.3.0]octa-2-ene (115 mg, 0.25 mmol) was added to trifluoroacetic acid (5 ml) the mixture was stirred at room temperature for 30 minutes then concentrated in vacuo. The resultant residue was dissolved in acetonitrile, concentrated in vacuo then dried in vacuo at room temperature for 15 minutes.

STEP B

Acylation

The residue from Step A above was slurried in 1:1 acetonitrile:water (4 ml) and the pH of the solution was adjusted to 7–7.5 by the addition of saturated aqueous sodium bicarbonate solution. (1-hydroxy N-benzotriazolyl)-2-(2-aminothiazol-4-yl)-2-(Z)-methoxyiminoacetate (85%, 100 mg, 0.275 mmol) was added and the solution was stirred at room temperature overnight. The solution was diluted with water, extracted with 3:1 chloroform:iso-propanol, the layers were separated. The pH of the aqueous phase was adjusted to 2 by the addition of 0.2N hydrochloric acid and the acidified solution was freeze dried. The resultant residue was chromatographed by medium pressure liquid chromatography on a C$_{18}$ reverse phase column eluted with 20% methanol:1% acetic acid in water. The product-containing fractions were concentrated in vacuo and again chromatographed under the same conditions. The column was eluted with a gradient of 10% methanol:1% acetic acid in water to 40% methanol:1% acetic acid in water to give the 2-(carboxylic acid)-3-(N-phenylamido)-7-(R,S)-[2-(2-aminothiazol-4-yl)-2-(Z)-methoxyiminoacetamido]-8-oxo-1,5-diazabicyclo[3.3.-0]octa-2-ene: n.m.r. (300 MHz, DMSO-d$_6$): 10.2 (bs, 1), 9.18 (br. d, 1), 7.6–7.0 (m, 5), 6.99 (s, 1), 5.04 (m, 1). 4.38 (d, 1. J=12), 4.08 (d, 1, J=12), 3.84 (s, 3), 3.8 (m, 1), 3.10 (m, 1); i.r. (KBr): 1688, 1655, 1628, 1594, 1563, 1530 cm$^{-1}$; u.v. (EtOH): $\lambda_{max}$=355 ($\epsilon_{max}$=9,337), 287 (10,635), 231 (24, 836); m.s. (FD): M$^+$=486.

EXAMPLE 78

2-Phenyl-3-(Methyl Carboxylate)-7-[R,S)-(t-Butoxycarbonylamino)-8-Oxo-1,5-Diazabicyclo[3.3.0]Octa-2-ene

STEP A

Synthesis of Ylide 4-(R,S)-(t-butoxycarbonylamino)-3-oxo-1,2-diazolidine (4.02 g, 20 mmol) was slurried in acetonitrile (50 ml). Aqueous formaldehyde (37%, 1.62 g, 20 mmol) was added to the slurry and the resultant solution was stirred overnight at room temperature.

STEP B

Cycloaddition

1-Phenyl-2-(methyl carboxylate)acetylene (3.2 g, 20 mmol) was added to the solution from Step A above and the resultant mixture was heated to reflux for eight hours, cooled and concentrated in vacuo. The concentrate was flash chromatographed on silica gel eluted with 40% ethyl acetate/toluene to give 1.11 g, 14.8% of the 2-phenyl-3-(methyl carboxylate)-7-(R,S)-(t-butoxycarbonylamino)-8-oxo-1,5-diazabicyclo[3.3.0]octa-2-ene: n.m.r. (90 MHz, CDCl$_3$): δ 7.52–7.2 (m, 5), 5.0 (br.s, 1), 4.70 (m, 1), 4.42 (d, 1, J=11), 4.06 (t, 1, J=8), 3.90 (d, 1, J=11), 3.56 (s, 3), 2.78 (dd, 1, J=8 and 12), 1.40 (s, 9); i.r. (CHCl$_3$): 1710 cm$^{-1}$; u.v. (ethanol): $\lambda_{max}$=345 ($\delta_{max}$=7746), 247 (6360); f.d.m.s. (m/e): M$^+$=373.

EXAMPLE 79

2-Phenyl-3-(Methyl Carboxylate)-7-(R,S)-[2-(2-Aminothiazol-4-yl)-2-(Z)-Methoxyiminoacetamido]-8-Oxo-1,5-Diazabicyclo[3.3.0]Octa-2-ene

STEP A

Removal of Amino-Protecting Group

2-Phenyl-3-(methyl carboxylate)-7-(R,S)-(t-butoxycarbonylamino)-8-oxo-1,5-diazabicyclo[3.3.0]octa-2-ene (373 mg, 1 mmol) was added to neat trifluoroacetic acid (30 ml). After dissolution the mixture was concentrated in vacuo. The residue was partitioned between ethyl acetate and saturated aqueous sodium bicarbonate solution, the layers were separated and the aqueous phase was back-extracted with ethyl acetate severl times. The combined ethyl acetate extracts were dried over potassium carbonate, filtered, then concentrated in vacuo to give 230 mg of a yellow foam.

STEP B

Acetylation

The foam from Step A was taken up in aceto- nitrile (20 ml) and di(iso-propyl)ethylamine (175 μl, 1 mmol) then (1-hydroxy N-benzotriazolyl) 2-(2-aminothiazol-4yl)-2-(Z)-methoximinoacetate (355 mg, 1 mmol) were added and the solution was stirred at room temperature overnight. The resultant slurry was concentrated in vacuo. Ethyl acetate (50 ml) was added to the concentrate and the solution was sonicated and filtered. The collected solid was taken up in chloroform and the solution washed with saturated aqueous sodium bicarbonate solution, dried over magnesium sulfate, filtered and concentrated in vacuo to give a yellow solid. The solid was recrystallized from ethyl acetate to give 76 mg of the 2-phenyl-3-(methyl carboxylate)-7-(R,S)-2-(2-aminothiazol-4-yl)-2-(Z)-methoxyiminoacetamido]-8-oxo-1,5-diazabicyclo[3.3.0]octa-2-ene: n.m.r. (90 MHz, DMSO-$d_6$): $\delta$ 9.02 (d, 1, J=7), 7.6–7.2 (m, 5), 7.16 (br. s, 2), 5.0 (m, 1), 4.28 (d, 1, J=11), 4.1–3.7 (m, 2), 3.77 (s, 3), 3.54 (s, 3), 3.06 (dd, 1, J=8 and 12); i.r. (KBr): 1726, 1688, 1622, 1536 cm$^{-1}$; u.v. (ethanol): $\lambda_{max}$=343 ($\epsilon_{max}$=9269), 285 (10,454), 233 (19,000); f.d.m.s. (m/e): M$^+$=456.

PREPARATION 12 n-Propyl 2-Bromoacetate

Under a nitrogen atmosphere, n-propanol (30 ml, 0.4 mol) was dissolved in diethyl ether (200 ml). The solution was cooled to 0° C. then pyridine (15.82 g, 16.2 ml) was syringed into the solution. Bromoacetyl bromide (17.4 ml, 0.2 mol) was added in a rapid dropwise fashion. The resultant thick white suspension was stirred and allowed to come to room temperature over a 2.5 hour period. The solid component of the suspension was removed by filtration and washed with diethyl ether. The filtrate was evaporated in vacuo to an oil. The oil was distilled in vacuo and the fraction boiling at 56° C. collected to give 28.7 g, 79% yield of the n-propyl 2-bromoacetate: n.m.r. (90 MHz, CDCl$_3$): $\delta$ 0.95 (t, 7.2, 3), 1.51–1.91 (m, 2); 3.79 (s, 2), 4.08 (t, J=7.2, 2).

PREPARATION 13 n-Propyl 2-(Dimethylphosphonato)acetate n-Propyl-2-bromoacetate (27.15 g, 0.15 mol) was dissolved in toluene (25 ml) and trimethylphosphite (17.7 ml, 18.6 g) was added. The resultant solution was heated to reflux for 5 hours then evaporated to dryness in vacuo to give 32 g of n-propyl 2-(dimethylphosphonato)acetate: n.m.r. (300 MHz, CDCl$_3$): $\delta$ 0.97 (t, J=7.5, 3), 1.63–1.75 (m, 2), 2.99 (d, J=21, 2), 3.83 (d, J=12, 6), 4.22 (t, J=7.5, 2); i.r. (CHCl$_3$): 3007, 2856, 1732, 1275, 1117, 1060, 1040 cm$^{-1}$; f.d.m.s. (m/e): M+1$^+$=211.

PREPARATION 14 n-Propyl 2-(Dimethylphosphonato)Prop-2-enoate

Paraformaldehyde (6 g, 0.2 mol) and pyrrolidine (1.67 ml, 0.02 mol) were suspended in methanol (150 ml). The suspension was heated to reflux to dissolve all the solids then the solution was cooled to 0° C. n-Propyl 2-(dimethylphosphonato)acetate (32 g, 0.15 mol) was added and the resultant solution was heated to reflux under nitrogen for 7 hours, 15 minutes, and stirred at room temperature overnight. Toluene was added and the reaction mixture was distilled under vacuum. The fraction boiling at 131° C.–133° C. was collected to give 11.25 g, 34% of a clear thick oil of n-propyl 2-(dimethylphosphonato)prop-2-enoate: n.m.r. (90 MHz, CDCl$_3$): $\delta$ 0.86 (t, J=7.2, 3), 1.42–1.82 (m, 2), 3.72 (d, J=11.7, 6), 4.09 (t, J=7.2, 2), 6.65 (dd, J=20.7 and 1.8, 1), 6.94 (dd, J=41.4 and 1.8, 1); i.r. (CHCl$_3$): 3004, 2950, 1732, 1257, 1056, 1041 cm$^{-1}$.

PREPARATION 15

4-(R,S)-(t-Butoxycarbonylamino)-3-Oxo-1-[1'-(n-Propyl Carboxylate)-1'-(Dimethylphosphonato)eth-2'-yl]-1,2-Diazolidine Under a nitrogen atmosphere, 4-(R,S)-(t-butoxycarbonylamino)-3-oxo-1,2-diazolidine (8.14 g, 40.5 mmol) was dissolved in methanol. The solution was cooled to 0° C. then n-propyl 2-(dimethylphosphonato)-prop-2-enoate (8.14 g, 40.5 mmol) was added and the solution was stirred for 2 hours and was allowed to warm to room temperature. Additional n-propyl 2-(dimethylphosphonato)prop-2-enoate (2 g) was added and the solution was stirred for an additional 30 minutes then the methanol was evaporated in vacuo. The residue was chromatographed on silica gel eluted with 1% methanol/ethyl acetate to yield 10.9 g, 64% of 4-(R,S)-(t-butoxycarbonylamino)-3-oxo-1-[1'-(n-propyl carboxylate)-1'-(dimethylphosphonato)eth-2'-yl-1,2-diazolidine: n.m.r. (300 MHz, CDCl$_3$): $\delta$ 6 0.96 (t, J=7.5, 3), 1.45 (s, 9), 1.62–1.75 (m, 2), 3.83 (d, J=12, 6), 4.12 (t, J=7.5, 2), 3.08–5.10 (m, 8); i.r. (CHCl$_3$): 3019, 3000, 2970, 1729, 1709, 1270, 1257, 1165, 1057, 1041 cm$^{-1}$.

EXAMPLE 80

2-(Allyl Carboxylate)-3-(n-Propyl Carboxylate)-7-(R,S)-(t-Butoxycarbonylamino)-8-Oxo-1,5-Diazabicyclo[3.3.0]Octa-2-ene Under a nitrogen atmosphere, 4-(R,S)-(t-butoxycarbonylamino)-3-oxo-1-[1'-(n-propyl carboxylate)-1'-(dimethylphosphonato)eth-2'-yl]-1,2-diazolidine (10.6 g, 25 mmol) was dissolved in methylene chloride (50 ml) and the solution was cooled to -78° C. Allyl oxalate acid chloride (3.7 g, 25 mmol) then bis(iso-propyl)ethylamine (8.7 ml, 50 mmol) was added and the solution was stirred at −78° C. for 15 minutes then at room temperature for 45 minutes. The solution was washed with water, dried over magnesium sulfate, filtered and evaporated in vacuo to an oil. The oil was chromatographed on silica gel eluted first with 50% ethyl acetate:hexane then with ethyl acetate to give 4.66 g, 46% yield of a thick yellow oil which crystallized on standing overnight. The solid was recrystallized from diethyl ether to give 2-(allyl carboxylate)-3-(n-propyl carboxylate-7-(R,S)-(t-butoxycarbonylamino)-8-oxo-1,5-diazabicyclo[3.3.0]octa-2-ene: n.m.r. (300 MHz, CDCl$_3$): $\delta$ 6 0.94 (t, J=7.5, 3), 1.46 (s, 9), 1.60–1.73 (m, 2), 2.80–2.93 (m, 1), 3.93, 4.37 (ABq, J=12, 2), 4.04–4.16 (m, 3), 4.66–4.92 (m, 3), 5.02–5.15 (m, 1), 5.33 (dd, 1, J=12 and 1.5), 5.44 (dd, J=16.5 and 1.5, 1), 5.92–6.07 (m, 1); i.r. (CHCl$_3$): 3018, 2970, 1750, 1707, 1393, 1283, 1162 cm$^{-1}$; u.v. (EtOH): $\lambda_{max}$=344 ($\epsilon$=8915); f.d.m.s. (m/e): M$^+$=409; m.p. 99°–101° C.

Anal. Calcd for C$_{19}$H$_{27}$N$_3$O$_7$: Theory: C, 55.74; H, 6.65; N, 10.26; Found: C, 55.70; H, 6.58; N, 10.11.

EXAMPLE 81

2-(Allyl Carboxylate)-3-(n-Propyl Carboxylate)-7-(R,S)-Amino-8-Oxo-1,5-Diazabicyclo[3.3.0]Octa-2-ene Hydrochloride Under a nitrogen atmosphere, 2-allyl carboxylate)-3-(n-propyl carboxylate)-7-(R,S)-(t-butoxycarbonylamino)-8-oxo-1,5-diazabicyclo[3.3.0]octa-2-ene (246 mg, 0.6 mmol) was dissolved in a solution of glacial acetic acid that contained a 3N concentration of anhydrous hydrogen chloride (10 ml) and the solution was stirred at room temperature for 10 minutes then evaporated to dryness in vacuo. The remaining solvent on the resultant yellow solid was removed by azeotropic distillation with methylene chloride (3x) then carbon tetrachloride (2x) to yield 2-(allyl carboxylate)-3-(n-propyl carboxylate)-7-(R,S)-amino-8-oxo-1,5-diazabicyclo[3.3.0]octa-2-ene hydrochloride.

EXAMPLE 82

2-(Allyl Carboxylate)-3-(n-Propyl Carboxylate)-7-(R,S)-[2-(2-(Allyloxycarbonylamino)thiazol-4-yl)-2-(Z)-Methoxyiminoacetamido]-8-Oxo-1,5-Diazabicyclo[3.3.0]Octa-2-ene Under a nitrogen atmosphere, 2-[2-(allyloxycarbonylamino)thiazol-4-yl]-2-(Z)-methoxyiminoacetic acid (171 mg, 0.6 mmol) was suspended in methylene chloride (4 ml) and the suspension was cooled to 0° C. 2-Chloro-4,6-dimethoxy-1,3,5-triazine (105.4 mg, 0.6 mmol) followed by N-methylmorpholine (60.7 mg, 0.6 mmol) was added and the solution was stirred at 0° C. A methylene chloride solution (5 ml) of 2-(allyl carboxylate)-3-(n-propyl carboxylate)-7-(R,S)-(amino)-8-oxo-1,5-diazabicyclo[3.3.0]octa-2-ene hydrochloride (0.6 mmol) then additional methylene chloride (3 ml) and additional N-methylmorpholine (60.7 mg, 0.6 mmol) were added. The resultant solution was stirred at 0° C. then allowed to warm gradually to room temperature over 2.5 hours. The reaction mixture was washed with water (1 x), dried over magnesium sulfate, filtered and evaporated in vacuo to dryness. The residue was dissolved in methylene chloride then hexane was added to the solution to cause precipitation. The precipitate was collected by filtration to give 247 mg, 71% of 2-(allyl carboxylate)-3-(n-propyl carboxylate)-7-(R,S)-[2-(2-(allyloxycarbonylamino)thiazol-4-yl)-2-(Z)-methoxyiminoacetamido]-8-oxo-1,5-diazabicyclo[3.3.0]octa-2-ene: n.m.r. (300 MHz, CDCl$_3$): $\delta$ 0.94 (t, J=7.5, 3), 1.54–1.68 (m, 2), 3.08 (dd, J=12 and 15, 1), 3.99 (s, 3), 3.97, 4.21 (ABq, J=12, 2), 3.70–4.17 (m, 5), 4.75 (d, J=6, 2), 4.82 (t, J=6, 2), 5.31 (d, J=9, 2), 5.40 (d, J=18, 2), 5.90–6.06 (m, 2), 7.18 (s, 1), 8.04 (br. s, 1); i.r. (KBr): 3230, 2970, 2940, 1753, 1730, 1699, 1674, 1564, 1392, 1327, 1270, 1232 cm$^{-1}$; u.v. (EtOH): $\lambda_{max}$=267 ($\epsilon$=11657), 329 ($\epsilon$=8005); f.d.m.s. (m/e): M$^+$=576; m.p. 175°–178° C.

Anal. Calcd for C$_{24}$H$_{28}$N$_6$O$_9$S$_1$: Theory: C, 50.00; H, 4.90; N, 14.58; Found: C, 50.23; H, 4.95; N, 14.82.

EXAMPLE 83

2-(Carboxylic Acid)-3-(n-Propyl Carboxylate)-7-(R,S)-[2-(2-Aminothiazol-4-yl)-2-(Z)-Methoxyiminoacetamido]-8-Oxo-1,5-Diazabicyclo[3.3.0]Octa-2-ene Under a nitrogen atmosphere, tetrakis(triphenylphosphine)palladium(O) (46.2 mg, 0.04 mmol) and triphenylphosphine (10.5 mg, 0.04 mmol) was suspended in acetone (10.5 ml). The suspension was stirred for 5 minutes then an acetone solution (8 ml) of 2-(allyl carboxylate)-3-(n-propyl carboxylate)-7-(R,S)-[2-( 2-allyloxycarbonylamino)thiazol-4-yl)-2-(Z)-methoxyimminoacetamido]-8-oxo-1,5-diazabicyclo[3.3.0]octa-2-ene (230.4 mg, 0.4 mmol) was added and the solution was stirred at room temperature for 10 minutes then cooled to 0° C. Tri(n-butyl)tin hydride (0.22 ml, 0.8 mmol) was added and the resultant solution was stirred for one hour at 0° C. Additional tri(n-butyl)tin hydride (0.22 ml, 0.8 mmol) was added and the solution was stirred for 45 minutes at 0° C. 1N Hydrochloric acid (0.8 ml) was added, the solution was filtered and the filtrate was concentrated in vacuo. The concentrate was chromatographed on an HP-20 column that was first flushed with water (500 ml) then by acetonitrile. The product-containing fractions (acetonitrile) were evaporated to dryness in vacuo; the residue was chromatographed by medium pressure liquid chromatography on a C$_{18}$ column eluted with 10% methanol:1% ammonium acetate in water. The product-containing fractions were lyophilized to give 12.3 mg of the title product. n.m.r. (300 MHz, DMSO): $\delta$ 0.89 (t, J=7.5, 3), 1.49–1.61 (m, 2), 3.83 (s, 3), 2.85–4.05 (m, 5), 3.94 (t, J=7.5, 2), 4.87–4.99 (m, 1), 7.10 (s, 1), 7.23 (br. s, 2), 9.13 (br. d, 1, J=6); i.r. (KBr): 3191 (br), 1722, 1676, 1620, 1534, 1431, 1391, 1329, 1266 cm$^{-1}$; u.v. (EtOH): $\lambda_{max}$=232 ($\epsilon$=13722), 309 ($\epsilon$=8622); m.p. d>150° C., f.a.b.m.s. (m/e) M+1=453.

PREPARATION 16

Benzyl 2-(Dimethylphosphonato)acetate

Under a nitrogen atmosphere, benzyl 2-bromoacetate (50 g, 0.218 mol) was dissolved in toluene (50 ml). Trimethylphosphite (25.8 ml, 0.218 mol) was added and the solution was heated to reflux for 4 hours then evaporated in vacuo to an oil. The oil was distilled under house vacuum and two fractions were collected, one with a boiling point of 55°–60° C. and the other with a boiling point of 130°–135° C. The undistilled material from this distillation constituted 39.77 g of benzyl 2-(dimethylphosphonato)acetate: n.m.r. (300 MHz, CDCl$_3$): $\delta$ 3.04 (d, J=21, 2), 3.77 (d, J=10.5, 6), 5.19 (s, 2), 7.38 (s, 5); i.r. (CHCl$_3$) 3030, 3009, 2958, 1737, 1456, 1272, 1114, 1060, 1040 cm$^{-1}$; f.d.m.s. (m/e): M$^+$=258;

Anal. Calcd for C$_{11}$H$_{15}$O$_5$: Theory: C, 51.17; H, 5.86. Found: C, 51.37; H, 5.63.

PREPARATION 17

Benzyl 2-(Dimethylphosphonato)prop-2-enoate

Under a nitrogen atmosphere, paraformaldehyde (0.8 g, 27 mmol) was suspended in benzene (40 ml). Acetic acid (20 ml) and pyrrolidine (0.22 ml, 2.6 mmol) were added and the mixture was heated to reflux for 30 minutes then cooled to 0° C. Benzyl 2-(dimethylphosphonato)acetate (5.15 g, 20 mmol) was added and the solution was heated to reflux for 1.5 hours in an apparatus fitted with a Dean-Stark trap. Additional paraformaldehyde (0.8 g, 27 mmol) was added and the solution was heated to reflux first for 30 minutes without the Dean-Stark trap then for one hour with the trap. Another portion of paraformaldehyde (0.8 g, 27 mmol) was added and the reflux procedure repeated. The reaction solution was concentrated in vacuo then chromatographed on silica gel eluted with 5% methanol:ethyl acetate to give 2.58 g, 48% yield of benzyl 2-(dimethylphosphonato)prop-2-enoate: n.m.r. (90 MHz, CDCl$_3$): $\delta$ 3.70 (d, J=10.8, 6), 5.18 (s, 2), 6.70 (dd, J=25.2 and 1.8, 1), 7.00 (dd, J=42.3 and 1.8, 1), 7.26 (s, 5); f.d.m.s. (m/e): M$^+$=270.

PREPARATION 18

4-(R,S)-(t-Butoxycarbonylamino)-3-Oxo-1-[1'-(Benzyl carboxylate)-1'-(Dimethylphosphonato)Eth-2'-yl]-1,2-Diazolidine Under a nitrogen atmosphere, 4-(R,S)-(t-butoxycarbonylamino)-3-oxo-1,2-diazolidine (1.12 g, 5.6 mmol) was dissolved in methanol (25 ml) and the solution was cooled to 0° C. Benzyl 2-(dimethylphosphonato)prop-2-enoate (1.6 g, 5.9 mmol) was added, the solution was stirred at 0° C., allowed to warm to room temperature over a period of 2 hours then evaporated in vacuo to an oil. The oil was flash chromatographed on silica gel eluted with 1% methanol:ethyl acetate (500 ml) then 4% methanol:ethyl acetate to yield 1.8 g, 64% of 4-(R,S)-(t-butoxycarbonylamino)-3-oxo-1'-[1-(benzyl carboxylate)- 1'-(dimethylphosphonato)eth-2'-yl]-1,2-diazolidine: n.m.r. (90 MHz, CDCl$_3$): δ 1.40 (s, 9), 2.60–3.88 (m, 6), 3.62 (d, J=10.8, 6); 4.10–4.70 (m, 1), 5.13 (s, 2), 4.96–5.44 (m, 1), 7.26 (s, 5); i.r. (CHCl$_3$): 3020, 1708, 1499, 1369, 1258, 1162, 1057, 1040 cm$^{-1}$; f.d.m.s. (m/e): M$^+$=471.

EXAMPLE 84

2-(Allyl Carboxylate)-3-(Benzyl Carboxylate)-7-(R,S)-(t-Butoxycarbonylamino)-8-Oxo-1,5-Diazabicyclo[3.3.0]Octa-2-ene Under a nitrogen atmosphere, 4-(R,S)-(t-butoxycarbonylamino)-3-oxo-1-[1'-(benzyl carboxylate)-1'-(dimethylphosphonato)eth-2'-yl]-1,2-diazolidine (1.79 g, 3.8 mmol) was dissolved in methylene chloride and the solution was cooled to 0° C. Allyl oxalate acid chloride (564 mg, 3.8 mmol) then bis(iso-propyl)ethylamine (1.3 ml, 7.6 mmol) were added in a dropwise fashion. The solution was allowed to warm to room temperature gradually over a period of 1.5 hours. Additional allyl oxalate acid chloride (30 mg) was added and the solution was stirred at room temperature for 1.5 hours. The solution was washed with water, dried over magnesium sulfate, filtered and evaporated in vacuo to give a residue. The residue was flash chromatographed on silica gel eluted with 50% ethyl acetate:hexane to give 1.09 g, 63% yield of a yellow oil of 2-(allyl carboxylate)-3-(benzyl carboxylate)-7-(R,S)-(t-butoxycarbonylamino)-8-oxo-1,5-diazabicyclo[3.3.0]octa-2-ene: n.m.r. (300 MHz, CDCl$_3$): δ 1.45 (s, 9), 2.74–2.94 (m, 1), 3.92, 4.39 (ABq, J=12, 2), 4.54–4.80 (m, 3), 5.07 (brs, 1), 5.12–5.38 (m, 5), 5.76–5.92 (m, 1), 7.28–7.43 (m, 5); i.r. (CHCl$_3$): 3020, 1750, 1724, 1500, 1385, 1370, 1280, 1167 cm$^{-1}$; f.d.m.s. (m/e): M$^+$=457; u.v. (EtOH) λ$_{max}$=345 (ε=5600);

Anal. Calcd for C$_{23}$H$_{27}$N$_3$O$_7$: Theory: C, 60.39; H, 5.95; N, 9.19; Found: C, 60.68; H, 6.10; N, 8.93.

EXAMPLE 85

2-(Allyl Carboxylate)-3-(Benzyl Carboxylate)-7-(R,S)-Amino-8-Oxo-1,5-Diazabicyclo3.3.00cta-2-ene Hydrochloride Under a nitrogen atmosphere, 2-(allyl carboxylate)-3-(benzyl carboxylate)-7-(R,S)-(t-butoxycarbonylamino)-8-oxo-1,5-diazabicyclo[3.3.0]octa-2-ene hydrochloride (370 mg, 0.81 mmol) was combined with a glacial acetic acid solution that contained a 3N concentration of anhydrous hydrogen chloride (15 ml) and the solution was stirred at room temperature for 25 minutes. The acid was removed in vacuo and the remaining volatiles on the resultant residue were removed by azeotropic distillation with methylene chloride (2 x) to give 2-(allyl carboxylate)-3-(benzyl carboxylate)-7-(R,S)-(amino)-8-oxo-1,5-diazabicyclo[3.3.0]octa-2-ene hydrochloride.

EXAMPLE 86

2-(Allyl Carboxylate)-3-(Benzyl Carboxylate)-7-(R,S)-[2-(2-(Allyloxycarbonylamino)thiazol-4-yl)-2-(Z)-Methoxyiminoacetamido]-8-Oxo-1,5-Diazabicyclo[3.3.0]-Octa-2-ene Under a nitrogen atmosphere, 2-[2-(allyloxycarbonylamino)thiazol-4-yl]-2-(Z)-methoxyiminoacetic acid (231 mg, 0.81 mmol) was suspended in methylene chloride (5 ml) and the suspension was cooled to 0° C. 2-Chloro-4,6-dimethoxy-1,3,5-triazine (142 mg, 0.81 mmol) followed by N-methylmorpholine (0.09 ml, 0.81 mmol) were added and the solution was stirred at 0° C. for 30 minutes. A methylene chloride solution (10 ml) of 2-(allyl carboxylate)-3-(benzyl carboxylate)-7-(R,S)-amino-8-oxo-1,5-diazabicyclo[3.3.0]octa-2-ene hydrochloride (0.81 mmol) followed by additional N-methylmorpholine (0.09 ml, 0.81 mmol) were added and the solution was stirred and allowed to warm gradually to room temperature over 1.5 hours. The methylene chloride was removed in vacuo and the resultant residue was flash chromatographed on silica gel eluted with 10% hexane:ethyl acetate to give 340 mg, 67% yield of 2-(allyl carboxylate)-3-(benzyl carboxylate)-7-(R,S)-[2-(2-(allyloxycarbonylamino)thiazol-4-yl)-2-(Z)-methoxyiminoacetamido]-8-oxo-1,5-diazabicyclo3.3.0]-octa-2-ene: n.m.r. (90 MHz, CDCl$_3$): δ 3.08 (dd, J=10.8 and 10.8, 1), 3.96 (s, 3), 3.99, 4.43 (ABq, J=12.6, 2), 3.88–4.28 (m, 2), 4.56–4.92 (m, 4), 5.16 (s, 2), 5.23 (d, J=9, 2), 5.42 (d, J=10.8, 2), 5.50–6.16 (m, 2), 7.10 (s, 1), 7.28 (br. s, 5), 8.09 (br. d, 1), 9.38 (br. s, 1); i.r. (CDCl$_3$): 3025, 1731, 1704, 1557, 1386, 1369, 1277 cm$^{-1}$; f.d.m.s. (m/e): M$^+$+1=625; u.v. (EtOH): λ$_{max}$=264 (ε=10926), 338 (ε=6493);

Anal. Calcd for C$_{28}$H$_{28}$N$_6$O$_9$S$_1$: Theory: C, 53.84; H, 4.52; N, 13.45; Found: C, 53.68; H, 4.59; N, 13.21.

EXAMPLE 87

2-(Carboxylic Acid)-3-(Benzyl Carboxylate)-7-(R,S)-[2-(2-Aminothiazol-4-yl)-2-(Z)-Methoxyiminoacetamido]-8-Oxo-1,5-Diazabicyclo[3.3.0]Octa-2-ene Under a nitrogen atmosphere, 2-(allyl carboxylate)-3-(benzyl carboxylate)-7-(R,S)-[2-(2-(allyloxycarbonylamino)thiazol-4-yl)-2-(Z)-methoxyiminoacetamido]-8-oxo-1,5-diazabicyclo[3.3.0]octa-2-ene (340 mg, 0.54 mmol) was suspended in a mixture of acetonitrile (10 ml) and diethyl ether (5 ml) then palladium(II) acetate (6.1 mg, 0.027 mmol,) and triphenylphosphine (56.7 mg, 0.216 mmol,) were added. Acetone (20 ml) was added and the resultant solution was stirred for 30 minutes at room temperature then cooled to 0° C. Tri(n-butyl)tin hydride (0.3 ml, 1.1 mmol) was added and the solution was stirred for 1.5 hours at room temperature. 12N hydrochloric acid (0.09 ml, 1.1 mmol) was added and the solution was concentrated in vacuo. The resultant residue was dissolved in methylene chloride, diethyl ether was added to effect precipitation and the precipitate was collected by filtration to give 2-(carboxylic acid)-3-(benzyl carboxylate)-7-(R,S)-[2-(2-aminothiazol-4-yl)-2-(Z)-methoxyiminoacetamido]-8-oxo-1,5-diazabicyclo[3.3.0]octa-2-ene: n.m.r. (90 MHz, DMSO-d$_6$): δ 2.60–4.14 (m, 5), 3.76 (s, 3), 4.64–5.20 (m, 2), 5.04 (s, 2), 7.12 (br. s, 2), 7.24 (br. s, 5), 9.01 (br. d, 1, J=7); i.r. (KBr): 3417, 1696, 1662, 1617, 1521, 1442, 1396, 1380, 1331, 1272 cm$^{-1}$; u.v. (EtOH); λ$_{max}$=231 (ε=15547), 329 (ε=11296); m.p. d>160° C., f.a.b.m.s. (m/e) M+1=501.

PREPARATION 19

4-(Dimethylphosphonato)butan-3-one

Under a nitrogen atmosphere, O,O-(dimethyl) methyl phosphonate (32.5 ml, 300 mmol) was dissolved in THF (450 ml) and then triphenylmethane (20–30 mg) was added. The solution was cooled to −78° C. and n-butyl lithium (1.54 M in hexane, 195 ml, 300 mmol) was added in a dropwise fashion. Additional n-butyl lithium (50 ml) was added followed by the addition of methyl propionate (26.4 g, 28.9 ml, 300 mmol) over a 15 minute period. The resultant solution was stirred at −78° C. for 75 minutes then the solution was allowed to warm to 0° C. over 75 minutes. The solution was quenched with water (250 ml), extracted with diethyl ether (2x) and the layers were separated. The aqueous layer was acidified to pH 3.0 by the addition of concentrated hydrochloric acid and extracted with diethyl ether (2x) and methylene chloride (2x). The organic extracts were combined, dried over magnesium sulfate and evaporated dryness. The residue was distilled in vacuo and the fraction boiling at 125° C. constituted 20.3 g, 41% yield of 4-(dimethylphosphonato)butan-3-one n.m.r. (300 MHz, CDCl$_3$): δ 1.08 (t, J=7.5, 3), 2.64 (q, J=7.5, 2), 3.10 (d, J=21 and 2), 3.80 (d, J=12 and 6); i.r. (CHCl$_3$): 3007, 2950, 1717, 1262, 1251, 1186, 1061, 1038, 880, 815 cm$^{-1}$; f.d.m.s. (m/e): M$^+$=180;

Anal. Calcd for C$_6$H$_{13}$O$_4$P: Theory: C, 40.01, H, 7.27; Found: C, 39.68; H, 7.14.

PREPARATION 20

4-(Dimethylphosphonato)pent-4-en-3-one

Under a nitrogen atmosphere, paraformaldehyde (2.43 g, 81 mmol) was suspended in benzene. Acetic acid (50 ml) and pyrrolidine (0.58 g, 0.68 ml, 8.1 mmol) were added to the suspension and the mixture was heated to reflux for 10 minutes then cooled to 0° C. 4-(Dimethylphosphonato)butan-3-one (10 g, 61 mmol) was added and the mixture was first heated to reflux for 5 minutes then refluxed in an apparatus fitted with a Dean-Stark trap for 20 minutes. The reaction solution was concentrated in vacuo and the remaining volatiles were removed by azeotropic distillation with toluene (5x). The distillation yielded 13 g of 4-(dimethylphosphonato)pent- 4-en-3-one. n.m.r. (90 MHz, CDCl$_3$): δ 1.08 (t, J=7.2, 3), 2.74 (q, J=7.2, 2), 3.76 (d, J=10.8, 6), 6.46–7.18 (m, 2).

PREPARATION 21

4-(R,S)-(t-Butoxycarbonylamino)-3-Oxo-1-[4'-(Dimethylphosphonato)-3'-Oxopentan-5'-yl]-1,2-Diazolidine Under a nitrogen atmosphere, 4-(R,S)-(t-butoxycarbonylamino)-3-oxo-1,2-diazolidine (12.3 g, 61 mmol) was dissolved in methanol (250 ml) and the solution was cooled to 0° C. 4-(Dimethylphosphonato)pent-4-en-3-one (61 mmol) was added and the solution was stirred at room temperature overnight. The methanol was evaporated in vacuo and the resultant oil was flash chromatographed on silica gel eluted with 50% ethyl acetate:hexane to give 8.3 g of 4-(R,S)-(t-butoxycarbonylamino)-3-oxo-1-[4'-(dimethylphosphonato)-3'-oxopentan-5'-yl]-1,2-diazolidine: n.m.r. (90 MHz, CDCl$_3$): δ 1.07 (t, J=7.2, 3), 1.44 (s, 9), 2.50–4.82 (m, 8), 3.74 (d, J=11.7, 6), 5.30 (br. s, 1).

EXAMPLE 88

2-(Allyl carboxylate)-3-(Propionyl)-7-(R,S)-(t-Butoxycarbonylamino)-8-Oxo-1,5-Diazabicyclo3.3.0]-Octa-2-ene Under a nitrogen atmosphere, 4-(R,S)-(t-butoxycarbonylamino)-3-oxo-1-[4'-(dimethylphosphonato)-3'-oxo-pentan-5'-yl]-1,2-diazolidine (8 g, 20 mmol) was dissolved in methylene chloride (50 ml). The solution was cooled to 0° C. then allyl oxalate acid chloride (2.97 g) and bis(iso-propyl)ethylamine (5.17 g, 7 ml, 40 mmol) were added to the solution in a dropwise fashion. The solution was allowed to warm to room temperature gradually over 1.5 hours. The solution was washed with water (2x), dried over magnesium sulfate, filtered and evaporated to give a yellow oil. The oil was flash chromatographed on silica gel eluted with 50% ethyl acetate:hexane to give 1.4 g of a solid. The solid was recrystallized from a diethyl ether/hexane mixture to give 2-(allyl carboxylate)-3-(propionyl)-7-(R,S)-(t-butoxycarbonylamino)-8-oxo-1,5-diazabicyclo[3.3.0]octa-2-ene: n.m.r. (90 MHz, CDCl$_3$): δ 1.06 (t, J=7.2, 3), 1.42 (s, 9), 2.40–2.68 (m, 2), 2.83 (dd, J=9 and 10.8, 1), 3.90, 4.38 (ABq, J=10.8, 2), 3.94–4.16 (m, 1), 4.54–5.24 (m, 4), 5.26–5.62 (m, 2), 6.16–7.26 (m, 1); i.r. (CHCl$_3$): 3021, 1716, 1503, 1418, 1380, 1354, 1272, 1161; f.d.m.s. (m/e): M$^+$=379; u.v.: (EtOH) λ$_{max}$=224 (ε=7600), 364 (ε=8100); m.p. 129°–130° C.

Anal. Calcd for C$_{18}$H$_{25}$N$_3$O$_6$: Theory: C, 56.98; H, 6.64; N, 11.08; Found: C, 56.73; H, 6.89, N, 11.01.

EXAMPLE 89

2-(Allyl carboxylate)-3-(Propionyl)-7-(R,S)-Amino-8-Oxo-1,5-Diazabicyclo[3.3.0]octa-2-ene Hydrochloride Under a nitrogen atmosphere, 2-(allyl carboxylate)-3-(propionyl)-7-(R,S)-(t-butoxycarbonylamino)-8-oxo-1,5-diazabicyclo[3.3.0]octa-2-ene (330 mg, 0.87 mmol) was combined with a glacial acetic acid solution that had a 3N concentration of anhydrous hydrogen chloride (15 ml). The solution was stirred for 25 minutes at room temperature then concentrated in vacuo. The remaining volatiles on the concentrate were removed by azeotropic distillation with methylene chloride (2 x) to yield 2-(allyl carboxylate)-3-(propionyl)-7-(R,S)-amino-8-oxo-1,5-diazabicyclo[3.3.0]octa-2-ene hydrochloride.

EXAMPLE 90

2-(Allyl Carboxylate)-3-(Propionyl)-7-(R,S)[2-(2-(Allyloxycarbonylamino)thiazol-4-yl)-2-(Z)-Methoxyiminoacetamido]-8-oxo-1,5-diazabicyclo[3.3.0]octa-2-ene Under a nitrogen atmosphere, 2-[2-(allyloxycarbonylamino)thiazol-4'-yl]-2-(Z)-methoxyiminoacetic acid (248 mg, 0.87 mmol) was suspended in methylene chloride (5 ml) and the suspension was cooled to 0° C. 2-Chloro-4,6-dimethoxy-1,3,5-triazine (153 mg, 0.87 mmol) then N-methylmorpholine (0.095 ml, 0.87 mmol) were added and the resultant solution was stirred at 0° C. for 30 minutes. A methylene chloride solution (10 ml) of 2-(allyl carboxylate)-3-(propionyl)-7-(R,S)-amino-8-oxo-1,5-diazabicyclo[3.3.0]octa-2-ene hydrochloride (0.87 mmol) was added followed by the addition of N-methylmorpholine (0.095 ml, 0.87 mmol). The solution was allowed to warm gradually to room temperature over 1.5 hours and then the methylene chloride was removed in vacuo. The resultant residue was flash chromatographed on silica gel eluted with 10% hexane:ethyl acetate to give 270 mg, 57% yield of 2-(allyl carboxylate)-3-(propionyl)-7-(R,S)-[2-(2-(allyloxycarbonylamino)thiazol-4-yl)-2-(Z)-methoxyiminoacetamido]-8-oxo-1,5-diazabicyclo[3.3.0]octa-2-ene: n.m.r. (90 MHz, CDCl$_3$): δ 1.11 (t, 3, J=7.2), 2.39–2.79 (m, 2), 3.09 (dd, 1, J=9 and 11.7), 3.95 (s, 3), 3.80–4.24 (m, 3), 4.42 (½ABq, 1, J=12.5), 4.60–4.96 (m, 4), 5.16–5.68 (m, 4), 5.72–6.22 (m, 2), 7.09 (s, 1), 8.28 (br.d, 1, J=7.2), 9.55 (br.s, 1); i.r. (CHCl$_3$): 3230, 1733, 1679, 1554, 1423, 1377, 1353, 1044 cm$^{-1}$; u.v. (EtOH):

λ$_{max}$=208 (ε=21522), 228 (ε=22084), 261 (ε=13612), 365 (ε=8122); f.d.m.s. (m/e): M$^+$+1=547; m.p. 183°–186° C.

Anal. Calcd for $C_{23}H_{26}N_6O_8S$: Theory: C, 50.54; H, 4.80; N, 15.38; Found: C, 50.28; H, 4.82; N, 15.43.

EXAMPLE 91

2-(Carboxylic acid)-3-(Propionyl)-7-(R,S)-[2-(2-Aminothiazol-4-yl)-2'-(Z)-Methoxyiminoacetamido]-8-Oxo-1,5-Diazabicyclo[3.3.0]Octa-2-ene Under a nitrogen atmosphere, 2-(allyl carboxylate)-3-(propionyl)-7-(R,S)-[2-(2-(allyloxycarbonylamino)-thiazol-4-yl)-2-(Z)-methoxyiminoacetamido]-8-oxo-1,5-diazabicyclo[3.3.0]octa-2-ene (270 mg, 0.49 mmol) was suspended in a mixture of acetonitrile (10 ml)/diethyl ether (5 ml). Palladium(11) acetate (5.5 mg, 0.0245 mmol) and triphenylphosphine (51.4 mg, 0.196 mmol) were added to the suspension then acetone (45 ml) was added to effect solution and the resultant solution was stirred for 30 minutes at room temperature then cooled to 0° C. Tri(n-butyl)tin hydride (291.05 mg, 0.27 ml, 1 mmol) was added and the resultant solution was stirred at room temperature for 3 hours. Concentrated hydrochloric acid (12 M, 0.08 ml, 1 mmol) was added and the solution was concentrated in vacuo. The concentrate was dissolved in methylene chloride, precipitation was effected by the addition of diethyl ether and the precipitate was collected by filtration. The precipitate was chromatographed by medium pressure liquid chromatography on a $C_{18}$ column eluted with 10% acetonitrile/1% acetic acid in water. The product-containing fractions were lyophilized to give 43 mg (21%) of 2-(carboxylic acid)-3-(propionyl)-7-(R,S)-[2-(2-aminothiazol-4-yl)-2-(Z)-methoxyiminoacetamido]-8-oxo-1,5-diazabicyclo[3.3.0]octa-2-ene: n.m.r. (300 MHz, DMSO-d$_6$): δ 0.92 (t, 3, J=6), 2.97 (dd, 1, J=6, 12), 2.46–2.48 (m, 2), 3.83 (s, 3), 3.00–4.20 (m, 3), 4.92–5.06 (m, 1), 7.03 (s, 1), 7.24 (br. s, 2), 9.15 (d, 1, J=9); i.r. (KBr) 3310 (br), 1716, 1636, 1534, 1414, 1380, 1257, 1050 cm$^{-1}$; u.v. (EtOH) λ$_{max}$=233 (ε=15992), 300 (ε=6987), 350 (ε=9801); m.p.>260° C.; f.a.b.m.s. (m/e) M$^+$+1=423.

PREPARATION 22

1-Fluoro-3-(Dimethylphosphonate)propan-2-one

Under a nitrogen atmosphere, O,O-(dimethyl) methylphosphonate (37.2 g, 32.5 ml, 300 mmol) was combined with THF (450 ml) and the resultant solution was cooled −78° C. n-Butyl lithium (1.54 M in hexane, 220 ml, 340 mmol) was added in a dropwise fashion and the resultant suspension was cooled to −78° C. Ethyl mono-fluoroacetate (31.8 g, 29 ml, 300 mmol) was added over 20 minutes and the solution was stirred at −78° C. for one hour then quenched with water (50 ml). The solution was stirred at room temperature for 1.5 hours then additional water (100 ml) was added and the reaction solution was extracted with diethyl ether (2x). The layers were separated and the aqueous layer was acidified to pH 3.0 by the addition of concentrated hydrochloric acid then extracted with methylene chloride (2x). The methylene chloride extracts were combined, dried over magnesium sulfate, and concentrated in vacuo. The concentrate was distilled under vacuum and the fraction with a boiling point of 125°–130° C. constituted 28.4 g, 52% yield of 1-fluoro-3-(dimethyl-phosphonato)propan-2-one: n.m.r. (300 MHz, CDCl$_3$): δ 3.26 (dd, 2, J=24 and 3), 3.83 (d, 6, J=12), 4.92 (d, 4, J=48); i.r. (CHCl$_3$): 3030, 3009, 2958, 1740, 1263, 1186, 1038, 831 cm$^{-1}$; f.d.m.s. (m/e): M$^+$=184;

Anal. Calcd for $C_5H_{10}O_4FP$: Theory: C, 32.62; H, 5.48; Found: C, 32.37; H, 5.27.

PREPARATION 23

1-Fluoro-3-(Dimethylphosphonato)but-4-en-2-one

Under a nitrogen atmosphere, paraformaldehyde (480 mg, 16 mmol) was suspended in benzene (20 ml) then trifluoroacetic acid (4 ml, 48 mmol) and pyrrolidine (0.134 ml, 1.6 mmol) were added. The mixture was heated to reflux to effect solution then cooled to room temperature. 1-Fluoro-3-(dimethylphosphonato)propan-2-one (2.2g, 12 mmol) was added and the solution was heated to reflux for 20 minutes then concentrated in vacuo. Additional paraformaldehyde (480 mg, 16 mmol) was suspended in benzene (20 ml) under nitrogen. To the suspension was added acetic acid (5 ml) and pyrrolidine (0.134 ml, 1.6 mmol) and the mixture was heated to reflux for 10 minutes. The resultant solution was cooled to room temperature and added to the mixture containing the phosphonate compound. The resultant reaction mixture was heated to reflux for 25 minutes in an apparatus fitted with a Dean-Stark trap. The reaction solution was concentrated to an oil to yield 1-fluoro-3-(dimethylphosphonato)but-4-en-2-one: n.m.r. (90 MHz, CDCl$_3$): δ 3.80 (d, 6, J=11), 5.22 (d, 2, J=47), 6.46–7.22 (m, 2).

PREPARATION 24

4-(R,S)-(t-Butoxycarbonylamino)-3-Oxo-1-[1'-(Fluoro)-3'-(Dimethylphosphonato)butan-2'-oxo-4'-yl]-1,2-Diazolidine Under a nitrogen atmosphere, 4-(R,S)-(t-butoxycarbonylamino)-3-oxo-1,2-diazolidine (2.4 g, 12 mmol) was dissolved with heating in methanol (50 ml) then cooled to 0° C. 1-Fluoro-3-(dimethylphosphonato)but-4-en-2-one (12 mmol) was added and the solution was stirred at room temperature for 48 hours then evaporated in vacuo. The residue was flash chromatographed on silica gel eluted with 2% methanol:ethyl acetate to give 1.1 g, 23% yield of 4-(R,S)-(t-butoxycarbonylamino)-3-oxo-1-[1'-(fluoro)-3'-(dimethylphosphonato)butan-2'-oxo-4'-yl]-1,2-diazolidine.

EXAMPLE 92

2-(Allyl carboxylate)-3-(Monofluroacetyl)-7-(R,S)-(t-Butoxycarbonylamino)-8-Oxo-1,5-Diazabicyclo-[3.3.0]Octa-2-ene Under a nitrogen atmosphere, 4-(R,S)-(t-butoxycarbonylamino)-3-oxo-1-[1'-(fluoro)-3'-(dimethylphosphonato)butan-2'-oxo-4'-yl]-1,2-diazolidine (1.1 g, 2.8 mmol) was dissolved in methylene chloride and the solution was cooled to 0° C. Allyl oxalate acid chloride (416 mg, 2.8 mmol) was added in one portion followed by the dropwise addition of bis(iso-propyl)ethylamine (724 mg, 0.98 ml, 5.6 mmol) and the solution was stirred for 15 minutes at room temperature then evaporated to dryness. The residue was flash chromatographed on silica gel eluted with ethyl acetate. The resultant yellow oil crystallized on standing overnight. The material was recrystallized from diethyl ether to yield approximately 200 mg of 2-(allyl carboxylate)-3-(monofluoroacetyl)-7-(R,S)-(t-butoxycarbonylamino)-8-oxo-1,5-diazabicyclo[3.3.0]octa-2-ene. n.m.r. (300 MHz, CDCl$_3$): δ 1.46 (s, 9), 2.77–2.91 (m, 1), 4.03, 4.43 (ABq, 2, J=12), 4.09 (br. t, 1, J=9), 4.72–5.16 (m, 6), 5.36 (d, 1, J=12), 5.45

(d, 1, J=18), 5.91–6.08 (m, 1); i.r. (CHCl$_3$): 3020, 1740, 1717, 1375, 1346, 1287, 1161 cm$^{-1}$; u.v. (EtOH): $\lambda_{max}$=230 ($\epsilon$=7885), 379 ($\epsilon$=7589); f.d.m.s. (m/e): M$^+$=383; m.p. 134°–136° C.

Anal. Calcd for C$_{17}$H$_{22}$N$_3$O$_6$F: Theory: C, 53.26; H, 5.78; N, 10.96; Found: C, 53.57; H, 5.86; N, 10.74.

EXAMPLE 93

2-(Allyl Carboxylate)-3-(Monofluoroacetyl)-7-(R,S)-Amino-8-Oxo-1,5-Diazabicyclo[3.3.0]Octa-2-ene Hydrochloride Under a nitrogen atmosphere, 2-(allyl carboxylate)-3-(monofluoroacetyl)-7-(R,S)-(t-butoxycarbonylamino)-8-oxo-1,5-diazabicyclo3.3.0]octa-2-ene (190 mg, 0.5 mmol) was combined with a glacial acetic acid solution that was 3N in anhydrous hydrogen chloride (10 ml). The solution was stirred at room temperature for 10 minutes then concentrated in vacuo. The remaining volatiles on the concentrate were removed by azeotropic distillation with methylene chloride (2 x) to give 2-(allyl carboxylate)-3-(monofluoroacetyl)-7-(R,S)-amino-8-oxo-1,5-diazabicyclo3.3.0]octa-2-ene hydrochloride.

EXAMPLE 94

2-(Allyl carboxylate)-3-(Monofluoroacetyl)-7-(R,S)-[2-(2-(Allyloxycarbonylamino)thiazol-4-yl)-2-(Z)-Methoxyiminoacetamido]-8-Oxo-1,5-Diazabicyclo[3.3.0]-Octa-2-ene Under a nitrogen atmosphere, 2-[2-allyloxycarbonylamino)thiazol-4-yl]-2-(Z)-methoxyiminoacetic acid (142.5 mg, 0.5 mmol) was suspended in methylene chloride (5 ml) and the suspension was cooled to 0° C. 2-Chloro-4,6-dimethoxy-1,3,5-triazine (87.8 mg, 0.5 mmol) followed by N-methylmorpholine (0.054 ml, 0.5 mmol) was added and the solution was stirred at 0° C. for 30 minutes. A methylene chloride solution (10 ml) of 2-(allyl carboxylate)-3-(monofluoroacetyl)-7-(R,S)-amino-8-oxo-1,5-diazabicyclo[3.3.0]octa-2-ene hydrochloride (0.5 mmol) and additional N-methylmorpholine (0.054 ml, 0.5 mmol) were added. The resultant solution was allowed to warm gradually to room temperature, stirred for 1.5 hours then concentrated in vacuo. The residue was flash chromatographed on silica gel eluted with 10% hexane:ethyl acetate to yield 100 mg, 36% of 2-(allylcarboxylate)-3-(monofluoroacetyl)-7-(R,S)-[2-(2-(allyloxycarbonylamino)thiazol-4-yl)-2-(Z)-methoxyiminoacetamido]-8-oxo-1,5-diazabicyclo[3.3.0]octa-2-ene: n.m.r. (300 MHz, CDCl$_3$): $\delta$ 3.05 (dd, 1, J=6 and 12), 4.00 (s, 3), 3.90–4.10 (m, 2), 4.17 (t, 1, J=7.5), 4.45 ($\frac{1}{2}$ABq, 1, J=12), 4.66–5.18 (m, 6), 5.24–5.50 (m, 4), 5.88–6.07 (m, 2), 7.27 (s, 1), 7.83 (br. d, 1, J=6); 9.14 (br. s, 1); i.r. (CHCl$_3$): 3019, 1735, 1678, 1553, 1378, 1045 cm$^{-1}$; u.v. (EtOH): $\lambda_{max}$=374 ($\epsilon$=6110); f.d.m.s. (m/e): M$^+$+1=551; m.p. 178°–181° C.

Anal. Calcd for C$_{22}$H$_{23}$N$_6$O$_8$SF: Theory: C, 48.00; H, 4.21; N, 15.28; Found: C, 48.28; H, 4.23; N, 15.22.

PREPARATION 25

Methyl 2-(Diethylphosphonato)Prop-2-enoate

Under a nitrogen atmosphere, paraformaldehyde (9.6 g, 0.32 mol), methanol (250 ml), and pyrrolidine (2.28 g, 2.7 ml, 0.032 mmol) were combined and the mixture was heated to reflux for 2 hours. The solution was cooled and then methyl 2-(diethylphosphonato)acetate (50.0 g, 0.24 mol) was added and the solution was first heated to reflux for 7 hours then stirred at room temperature overnight. The reaction solution was concentrated in vacuo then dissolved in toluene and evaporated in vacuo several times. The residue was treated with phosphoric acid (86%, 2.5 ml) then distilled in vacuo. The fraction boiling from 115°–122° C. consisted of 12.32 g of a clear oil of methyl 2-(diethylphosphonato)prop-2-enoate. n.m.r. (90 MHz, CDCl$_3$): $\delta$ 1.36 (t, 6, J=7), 3.80 (s, 3), 4.00–4.36 (m, 4), 6.72 (dd, 1, J=22 and 1.8), 6.96 (dd, 1, J=41 and 1.8).

PREPARATION 26

4-(R,S)-(t-Butoxycarbonylamino)-3-Oxo-1-1'-(Methyl carboxylate)-1'-(Diethylphosphonato)eth-2'-yl]-1,2-Diazolidine Under a nitrogen atmosphere, 4-(R,S)-(t-butoxycarbonylamino)-3-oxo-1,2-diazolidine (1 g, 4.98 mmol) was dissolved in methanol (10 ml) with heating. The solution was cooled to 0° C. then a methanol solution (1 ml) of methyl 2-(diethylphosphonato)prop-2-enoate (1.1 g, 4.98 mmol) was added and the solution was stirred at room temperature overnight then concentrated in vacuo to give 1.9 g of an oil of 4-(R,S)-(t-butoxycarbonylamino)-3-oxo-1-[1'-(methyl carboxylate)-1'-(diethylphosphonato)eth- 2'-yl]-1,2-diazolidine: n.m.r. (90 MHz, CDCl$_3$): $\delta$ 1.28 (t, 6, J=7), 1.36 (s, 9), 2.68–4.64 (m, 10), 3.68 (s, 3), 5.48 (br. t, 1, J=7), 8.92 (br. s, 1).

PREPARATION 27

4-(R,S)-(t-Butoxycarbonylamino)-3-Oxo-1-[1'-(Methyl Carboxylate)-1'-(Diethyphosphonato)eth-2'-yl-2-[Allyl oxaloyl]-1,2-Diazolidine Under a nitrogen atmosphere, 4-(R,S)-(t-butoxycarbonylamino)-3-oxo-1-[1'-(methyl carboxylate)-1'-(diethylphosphonato)eth-2'-yl]-1,2-diazolidine (1.9 g, 4.5 mmol) was dissolved in methylene chloride (15 ml). The solution was cooled to −60° C. and then a methylene chloride solution (2 ml) of allyl oxalate acid chloride (668.25 mg, 4.5 mmol) followed by bis(iso-propyl)ethylamine (581.63 mg, 4.5 mmol, 0.78 ml) were added and the resultant solution was stirred at −60° C. for 1 hour and at room temperature for 2 hours. The reaction solution was poured into water, the layers were separated, and the organic layer was dried over magnesium sulfate, filtered and concentrated in vacuo to give 2.34 g of a yellow oil. The oil was flash chromatographed on silica gel eluted with ethyl acetate to give 830 mg of a yellow oil of 4-(R,S)-(t-butoxycarbonylamino)-3-oxo-1-[1'-(methyl carboxylate)-1'-(diethylphosphonato)eth-2'-yl]-2-[allyl oxaloyl]-1,2-diazolidine: n.m.r. (90 MHz, CDCl$_3$): $\delta$ 1.12–1.52 (m, 6), 1.44 (s, 9), 3.12–4.32 (m, 11), 3.76 (s, 3), 4.72 (br. d, 2, J=5), 5.12–6.16 (m, 3).

EXAMPLE 95

2-(Allyl Carboxylate)-3-(Methyl Carboxylate)-7-(R,S)-(t-Butoxycarbonylamino)-8-Oxo-1,5-Diazabicyclo-[3.3.0]Octa-2-ene Under a nitrogen atmosphere, 4-(R,S)-(t-butoxycarbonylamino)-3-oxo-1-[1'-(methyl carboxylate)-1'-diethylphosphonato)eth-2'-yl]-2-[allyl oxaloyl]-1,2-diazolidine (115 mg, 0.215 mmol) was dissolved in THF (5 ml). The solution was cooled to 0° C., sodium hydride (60% in oil, 17.2 mg of the oil, 0.43 mmol) was added, and the solution was stirred at 0° C. for 45 minutes. Saturated aqueous ammonium chloride solution then methylene chloride were added, the layers were separated, and the organic layer was dried over magnesium sulfate, filtered and concentrated in vacuo to give 78 mg of a yellow oil.

The oil was flash chromatographed on silica gel eluted with 50% ethyl acetate/hexane to yield 28.3 mg of a yellow oil which slowly crystallized on standing. The crystals were 2-(allyl carboxylate)3-(methyl carboxylate)-7-(R,S)-(t-butoxycarbonylamino)-8-oxo-1,5-diazabicyclo[3.3.0]octa-2-ene: n.m.r. (90 MHz, CDCl$_3$): δ 1.46 (s, 9), 2.90 (dd, 1, J=7 and 11), 3.68–4.20 (m, 2), 3.76 (s, 3); 3.92, 4.38 (ABq, 2, J=12.5); 4.80–5.00 (m, 2); 5.00–5.22 (br. d, 1, J=5); 5.22–5.60 (m, 2); 5.76–6.40 (m, 1).

PREPARATION 28

Ethyl 2-(Diethylphosphonato)prop-2-enoate

Under a nitrogen atmosphere, paraformaldehyde (9 g, 0.3 mol) and ethanol (250 ml, 3A) were combined. Pyrrolidine (2.13 g, 2.5 ml, 0.03 mol) was added and the solution was heated to reflux for 1.5 hours then cooled to room temperature, ethyl 2-(diethylphosphonato)acetate (50 g, 0.223 mol) was added and the solution was heated to reflux for 5 hours, stirred at room temperature overnight, reheated to reflux for 3.5 hours then cooled and evaporated in vacuo. The resultant light yellow oil was combined with phosphoric acid (86%, 2.5 ml) and the solution was distilled in vacuo. The fraction boiling between 120°–125° C. gave 22.74 g of ethyl 2-(diethylphosphonato)prop-2-enoate. n.m.r. (90 MHz, CDCl$_3$): δ 1.32 (t, 9, J=5.4); 4.00–4.40 (m, 6); 6.72 (dd, 1, J=20); 6.96 (dd, 1, J=41).

PREPARATION 29

4-(R,S)-(t-Butoxycarbonylamino)-3-Oxo-1-1'-(Ethyl Carboxylate)-1'-(Diethylphosphonato)eth-2'-yl]-1,2-Diazolidine Under a nitrogen atmosphere, 4-(R,S)-(t-butoxycarbonylamino)-3-oxo-1,2-diazolidine (5 g, 24.9 mmol) was dissolved in ethanol (3A, 50 ml) with heating. phosphonato)prop-2-enoate (5.87 g, 24.9 mmol) was rinsed into the solution with additional ethanol. The solution was stirred overnight at room temperature then concentrated in vacuo. The resultant oil was flash chromatographed on silica gel, eluted with 5% methanol/ethyl acetate to give 6.9 g of a yellow oil of 4-(R,S)-(t-butoxycarbonylamino)-3-oxo-1-[1'-ethyl carboxylate)-1'-(diethylphosphonato)eth-2'-yl]-1,2-diazolidine: n.m.r. (90 MHz, CDCl$_3$): δ 1.20–1.32 (m, 9); 1.36 (s, 9); 3.00–4.40 (m, 12); 5.08–5.36 (br. t, 1, J=5.4); 8.16–8.60 (br. d, 1); i.r. (CHCl$_3$): 3018, 3001, 1731, 1710, 1255, 1028 cm$^{-1}$; f.a.b.m.s. (m/e): M$^+$+1=438.

PREPARATION 30

4-(R,S)-(t-Butoxycarbonylamino)-3-Oxo-1-[1'-(Ethyl carboxylate)-1'-(Diethylphosphonato)eth-2'-yl-]2-[Allyl oxaloyl]-1,2-Diazolidine Under a nitrogen atmosphere, 4-(R,S)-(t-butoxycarbonylamino)-3-oxo-1-[1'-(ethyl carboxylate)-1'-(diethylphosphonato)eth-2'-yl]-1,2-diazolidine (6.5 g, 14.9 mmol) was dissolved in methylene chloride (50 ml) and the solution was cooled to −78° C. A methylene chloride solution (5 ml) of allyl oxalate acid chloride (2.21 g, 14.9 mmol) then bis(iso-propyl)ethylamine (1.93 g, 14.9 mmol) were added and the solution was stirred at −78° C. for 2.66 hours then at room temperature for 75 minutes. The solution was poured into water, the layers were separated and the organic phase was dried over magnesium sulfate, filtered and concentrated in vacuo to give 8.24 g of a golden oil. The oil was flash chromatographed on silica eluted with ethyl acetate to yield 3.87 g of a golden oil of 4-(R,S)-(t-butoxycarbonylamino)-3-oxo-1-[1'-(ethyl carboxylate)-1'-(diethylphosphonato)eth-2'-yl]-2-[allyl oxaloyl]-1,2-diazolidine: n.m.r. (90 MHz, CDCl$_3$): δ 1.20–1.36 (m, 9); 1.40 (s, 9); 3.20–4.40 (m, 13); 4.60–4.88 (br. d, 2, J=5.4); 5.12–5.52 (m, 2); 5.64–6.40 (m, 1).

EXAMPLE 96

2-(Allyl carboxylate)-3-(Ethyl carboxylate)-7-(R,S)-(t-Butoxycarbonylamino)-8-Oxo-1,5-Diazabicyclo-[3.3.0]Octa-2-ene Under a nitrogen atmosphere, 4-(R,S)-(t-butoxycarbonylamino)-3-oxo-1-[1'-(ethyl carboxylate)-1'-(diethylphosphonato)eth-2'-yl]-2-[allyl oxaloyl]-1,2-diazolidine (3.75 g, 6.83 mmol) was dissolved in THF (100 ml) and the solution was cooled to 0° C. Sodium hydride (60% in oil, 546.5 mg of the oil, 13.66 mmol) was added and the solution was stirred at 0° C. for 15 minutes, at room temperature for 30 minutes then cooled to 0° C. and additional THF (100 ml) was added. The solution was stirred at room temperature overnight, methylene chloride was added and saturated aqueous ammonium chloride solution (30 ml) was added. Water and additional methylene chloride was added, the layers were separated and the aqueous layer was washed with additional methylene chloride. The organic layers were combined, dried over magnesium sulfate, filtered and concentrated in vacuo to yield 2.56 g of a yellow oil. The oil was flash chromatographed on silica gel, eluted with 50% ethyl acetate/hexane as an oil which crystallized on standing to give 1.82 g, 67.5% of 2-(allyl carboxylate)-3-(ethyl carboxylate)-7-(R,S)-(t-butoxycarbonylamino)-8-oxo-1,5-diazabicyclo[3.3.0]octa-2-ene. n.m.r. (300 MHz, CDCl$_3$): δ 1.26 (t, 3, J=6), 1.46 (s, 9); 2.84 (m, 1), 3.91, 4.36 (ABq, 2, J=12), 4.02–4.12 (m, 1), 4.21 (q, 2, J=6), 4.66–4.92 (m, 3), 5.08 (br. s, 1), 5.32 (d, 1, J=9), 5.44 (d, 1, J=18), 5.90–6.06 (m, 1); i.r.: (CHCl$_3$) 3021, 2980, 1750, 1707, 1393, 1370, 1283, 1233, 1207, 1163 cm$^{-1}$; f.d.m.s. (m/e): M$^+$=395; u.v. (EtOH): λ$_{max}$=345 (ε=8825); m.p. 118°–121° C.

Anal. Calcd for C$_{18}$H$_{25}$N$_3$O$_7$: Theory: C, 54.68; H, 6.37; N, 10.63; Found: C, 54.99; H, 6.55; N, 10.36.

EXAMPLE 97

2-(Allyl carboxylate)-3-(Ethyl carboxylate)-7-(R,S)-Amino-8-Oxo-1,5-Diazabicyclo[3.3.0]Octa-2-ene Hydrochloride Under a nitrogen atmosphere, 2-(allyl carboxylate)-3-(ethyl carboxylate)-7-(R,S)-(t-butoxycarbonylamino)-8-oxo-1,5-diazabicyclo[3.3.0]octa-2-ene (120 mg, 0.304 mmol) was combined with a glacial acetic acid solution that was 3N in anhydrous hydrogen chloride (5 ml) and the solution was stirred for 5 minutes then concentrated in vacuo. The resultant oil was dried in vacuo for 1.6 hours to yield 2-(allyl carboxylate)-3-(ethyl carboxylate)-7-(R,S)-amino-8-oxo-1,5-diazabicyclo[3.3.0]-octa-2-ene hydrochloride.

EXAMPLE 98

2-(Alyl carboxylate)-3-(Ethyl carboxylate)-7-(R,S)-[2-(2-(allyloxycarbonylamino)Thiazol-4-yl)-2-(Z)-Methoxyiminoacetamido]-8-Oxo-1,5-Diazabicyclo[3.3.0]Octa-2-ene Under a nitrogen atmosphere, 2-[2'-(allyloxycarbonylamino)thiazol-4'-yl]-2-(Z)-methoxyiminoacetic acid (86.73 mg, 0.304 mmol) was slurried in methylene chloride (2 ml) and the slurry was cooled to 0° C. 2-Chloro-4,6-dimethoxy-1,3,5-triazine (53.38 mg, 0.304 mmol) then N-methylmorpholine (30.75 mg, 33.4 μl, 0.304 mmol) were added and the reaction solution was stirred for 40 minutes at 0° C. A methylene chloride solution (2.5 ml) of 2-(allyl carboxylate)-3-(ethyl carboxylate)-7-(R,S)-amino-8-oxo-1,5-diazabicyclo[3.3.-0]octa-2-ene hydrochloride (0.304 mmol) then additional N-methylmorpholine (33.4 μl) were added and the solution was stirred at 0° C. for 20 minutes and at room temperature for 2.33 hours then concentrated in vacuo. The residue was flash chromatographed on silica gel (15 mm × 11 inch column) eluted with ethyl acetate to give 89.5 mg of a yellow solid. The solid was taken up in a warm mixture of ethyl acetate and methylene chloride and the resultant crystals were collected by filtration to give 71.5 mg of 2-(allyl carboxylate)-3-(ethyl carboxylate)-7-(R,S)-[2-(2-(allyloxycarbonylamino)thiazol-4-yl)-2-(Z)-methoxyiminoacetamido]-8-oxo-1,5-diazabicyclo[3.3.0]octa-2-ene: n.m.r. (300 MHz, CDCl$_3$) δ 1.27 (t, 3, J=6), 3.07 (dd, 1, J=6 and 12), 3.99 (s, 3), 3.97, 4.41 (ABq, 2, J=12), 4.14 (t, 1, J=9), 4.23 (q, 2, J=6), 4.70–4.92 (m, 4), 5.28–5.52 (m, 5), 5.90–6.08 (m, 2), 7.28 (s, 1), 8.08 (br. s, 1), 9.40 (br. s, 1); i.r. (CHCl$_3$): 3021, 1750, 1730, 1701, 1554, 1226 cm$^{-1}$; f.d.m.s. (m/e): M$^+$=562; u.v. (EtOH): λ$_{max}$=209 (ε=24594), 264 (ε=13970), 343 (ε=9105); m.p. 204°–207° C. (d);

Anal. Calcd for C$_{23}$H$_{26}$N$_6$O$_9$S$_1$: Theory: C, 49.11; H, 4.66; N, 14.94; Found: C, 49.33; H, 4.64; N, 14.90.

EXAMPLE 99

2-(Carboxylic Acid)-3-(Ethyl Carboxylate)-7-(R,S)-[2-(2-Aminothiazol-4-yl)-2-(Z)-Methoxyiminoacetamido]-8-Oxo-1,5-Diazabicyclo[3.3.0]Octa-2-ene Under an argon atmosphere, 2-(allyl carboxylate)-3-(ethyl carboxylate)-7-(R,S)-[2-(2-(allyloxycarbonylamino)thiazol-4-yl)-2-(Z)-methoxyiminoacetamido]-8-oxo-1,5-diazabicyclo[3.3.0]octa-2-ene (71.5 mg, 0.127 mmol) was combined with acetonitrile (2 ml), diethyl ether (1 ml), palladium (II) acetate (1.43 mg, 0.00635 mmol) and triphenylphosphine (13.32 mg, 0.0508 mmol). The resultant yellow slurry was stirred and acetone was added (2 ml) to dissolve all the solids. The solution was stirred at room temperature for 40 minutes then cooled to 0° C. tri(n-Butyl)tin hydride (75.77 mg, 70.03 μl, 0.260 mmol) was added and the solution was stirred at room temperature for 1.66 hours. Hydrochloric acid (12N, 0.022 ml, 0.260 mmol) was added and the precipitate that formed was collected by filtration then washed with ether (10 ml), methylene chloride (5 ml), and diethyl ether (5 ml) to yield 42 mg of a yellow solid. The solid was dissolved in 10% acetonitrile/water with 1% ammonium acetate then chromatographed by medium pressure liquid chromatography using a C$_{18}$ reverse phase column eluted with 10% acetonitrile/water with 1% ammonium acetate. The product-containing fractions were combined and lyophilized overnight. The solid was redissolved in a small amount of water and lyophilized again to yield approximately 40 mg of 2-(carboxylic acid)-3-(ethyl carboxylate)-7-(R,S)-[2-(2-aminothiazol-4-yl)-2-(Z)-methoxyiminoacetamido]-8-oxo-1,5-diazabicyclo[3.3.-0]octa-2-ene. n.m.r. (300 MHz, DMSO-d$_6$): δ 1.13 (t, 3, J=7.5); 2.93 (dd, 1, J=9 and 12); 3.80 (s, 3); 3.20–3.85 (m, 3); 4.00–4.06 (m, 2); 4.85–5.00 (m, 1); 7.03 (s, 1); 7.10–7.60 (m, 2); 9.14 (d, 1, J=9); i.r. (KBr): 3210 (br), 1720, 1682, 1621, 1538, 1389, 1279, 1262 cm$^{-1}$; f.a.b.m.s. (m/e): M$^+$+1=439; u.v. (EtOH): λ$_{max}$=233 (ε=15001), 326 (ε=10781); m.p. d>168° C.;

PREPARATION 31

2-(Diethylphosphonato)Acrylonitrile

Under a nitrogen atmosphere, benzene (200 ml), acetic acid (glacial, 50 ml), paraformaldehyde (4.51 g, 0.150 mol), and pyrrolidine (1.07 g, 0.150 mol) were combined and the mixture was heated to reflux for 10 minutes then cooled to 0° C. 2-(Diethylphosphonato)acetonitrile (20 g, 0.113 mol) was added, and the solution was heated to reflux for 5 minutes. A Dean-Stark trap was added to the apparatus and the solution was heated to reflux for an additional 20 minutes then concentrated in vacuo. Three repetitions of first redissolution of the residue in toluene and then evaporation to dryness in vacuo of the resultant solution yielded 2-(diethylphosphonato)acrylonitrile; n.m.r. (90 MHz, CDCl$_3$): δ 1.44 (t, 6, J=7); 3.88–4.60 (m, 4); 6.36–7.00 (m, 2).

PREPARATION 32

4-(R,S)-(t-Butoxycarbonylamino)-3-Oxo-1-[1'-Cyano-1'-(Diethylphosphonato)eth-2'-yl]-1,2-Diazolidine Under a nitrogen atmosphere, 4-(R,S)-(t-butoxycarbonylamino)-3-oxo-1,2-diazolidine (22.7 g, 0.113 mol) was dissolved in methanol (200 ml) with heating and the solution was cooled to 0° C. 2-(Diethylphosphonato)acrylonitrile (0.113 mol) was washed into the solution with additional methanol (10 ml) and the solution was stirred at 0° C. for 1 hour then at room temperature overnight and concentrated in vacuo to an oil. The oil was flash chromatographed on silica gel eluted with 5% methanol/ethyl acetate to yield 15.83 g of 4-(R,S)-(t-butoxycarbonylamino)-3-oxo-1-[1'-cyano-1'-(diethylphosphonato)eth-2'-yl]-1,2-diazolidine: n.m.r. (90 MHz, CDCl$_3$): δ 1.16–1.40 (m, 6); 1.36 (s, 9); 3.08–4.80 (m, 10); 5.34 (br. s, 1); 8.72 (br. s, 1); i.r. (CHCl$_3$): 3021, 2250, 1712, 1264, 1023 cm$^{-1}$; f.a.b.m.s. (m/e): M$^+$+1=391.

EXAMPLE 100

2-(Allyl Carboxylate)-3-Cyano-7-(R,S)-(t-Butoxycarbonylamino)-8-Oxo-1,5-Diazabicyclo[3.3.0]Octa-2-ene Under a nitrogen atmosphere, 4-(R,S)-(t-butoxycarbonylamino)-3-oxo-1-[1'-cyano-1'-(diethylphosphonato)eth-2'-yl]-1,2-diazolidine (15.83 g, 0.041 mol) was dissolved in methylene chloride (250 ml) and the solution was cooled to 0° C. Allyl oxalate acid chloride (6.03 g, 0.041 mol) then bis(iso-propyl)ethylamine (10.49 g, 0.082 mol) were added, and the solution was stirred at 0° C. for 1.5 hours, washed with water (2 x), dried over magnesium sulfate, filtered and concentrated to a yellow oil (16.46 g). The oil was flash chromatographed on silica gel eluted with 50% hexane in ethyl acetate to yield 3.97 g of 2-(allyl carboxylate)-3-cyano-7-(R,S)-(t-butoxycarbonylamino)-8-oxo-1,5-diazabicyclo[3.3.0]octa-2-ene. (The following data was gathered on a small amount of this final product that had been triturated with diethyl ether.) n.m.r. (300 MHz, CDCl$_3$): δ 1.47 (s, 9); 2.93 (dd, 1, J=9 and 12); 3.93, 4.37 (ABq, 2, J=12); 4.09 (br. t, 1, J=9); 4.62–4.77 (m, 1); 4.78–4.96 (m, 2); 5.13 (br. s, 1); 5.36 (d, 1, J =12); 5.47 (d, 1, J=15); 5.92–6.06 (m, 1); i.r. (CHCl$_3$): 3040, 2990, 2220, 1753, 1742, 1716, 1501, 1407, 1370, 1160 cm$^{-1}$; f.d.m.s. (m/e): M$^+$=348; u.v. (EtOH): λ$_{max}$=212 (ε=8400), 365 (ε=5300); Anal. Calcd for C$_{16}$H$_{20}$N$_4$O$_5$: Theory: C, 55.17; H, 5.79; N, 16.08; Found: C, 55.46; H, 5.56; N, 15.95.

EXAMPLE 101

2-(Allyl Carboxylate)-3-Cyano-7-(R,S)-Amino-8-Oxo-1,5-Diazabicyclo[3.3.0]Octa-2-ene Hydrochloride Under a nitrogen atmosphere, 2-(allyl carboxylate)-3-cyano-7-(R,S)-(t-butoxycarbonylamino)-8-oxo-1,5-diazabicyclo[3.3.0]octa-2-ene (1.54 g, 4.43 mmol) was combined with a glacial acetic acid solution that had a 3N concentration of anhydrous hydrogen chloride (45 ml) and the mixture was stirred at room temperature until it was a solution (5 minutes), when it was evaporated in vacuo to dryness. The residue was redissolved in methylene chloride and the solution was taken to dryness in vacuo two times to yield 2-(allyl carboxylate)-3-cyano-7-(R,S)-amino-8-oxo-1,5-diazabicyclo[3.3.0]octa-2-ene hydrochloride.

EXAMPLE 102

2-(Allyl Carboxylate)-3-Cyano-7-(R,S)-[2-(2-Allyloxycarbonylaminothiazol-4-yl)-2-(Z)-Methoxyiminoacetamido]-8-Oxo-1,5-Diazabicyclo[3.3.0]Octa-2-ene Under a nitrogen atmosphere, 2-[2'-(allyloxycarbonylamino)thiazol-4'-yl]-2-(Z)-methoxyiminoacetic acid (1.26 g, 4.43 mmol) was slurried in methylene chloride (25 ml) and the slurry was cooled to 0° C. 2-Chloro-4,6-dimethoxy-1,3,5-triazine (777 mg, 4.43 mmol) then N-methylmorpholine (0.487 ml, 4.43 mmol) was added and the mixture was stirred at 0° C. for 70 minutes. 2-(allyl carboxylate)-3-cyano-7-(R,S)-amino-8-oxo-1,5-diazabicyclo[3.3.0]octa-2-ene hydrochloride (4.43 mmol) was dissolved in methylene chloride (20 ml) and was added followed by an additional amount of N-methylmorpholine (0.49 ml). The resultant mixture was stirred at 0° C. for 1.5 hours then at room temperature overnight and concentrated to dryness in vacuo. The residue was flash chromatographed on silica gel eluted with ethyl acetate to yield 630 mg of a yellow oil. The oil was taken up in a mixture of ethyl acetate/hexane and the resultant precipitate was isolated by filtration to yield approximately 180 mg of 2-(allyl carboxylate)-3-cyano-7-(R,S)-[ 2-(2-allyloxycarbonylaminothiazol-4-yl)-2-(Z)-methoxyiminoacetamido]-8-oxo-1,5-diazabicyclo[3.3.0]octa-2-ene: n.m.r. (300 MHz, DMSO-$d_6$): δ 3.20 (dd, 1, J=12 and 12); 3.82–3.94 (m, 1); 3.88 (s, 3); 4.13, 4.41 (ABq, 2, J=15); 4.70 (d, 2, J=6); 4.85 (d, 2, J=6); 5.02–5.15 (m, 1); 5.22–5.52 (m, 4); 5.86–6.04 (m, 2); 7.44 (s, 1); 9.29 (d, 1, J=6); 12.18 (s, 1); i.r. (CHCl$_3$); 3020, 3000, 2230, 1733, 1681, 1554, 1411, 1371, 1276, 1044 cm$^{-1}$; f d.m.s. (m/e): M+=515; u.v. (EtOH) $\lambda_{max}$=209 (ε=22387), 227 (ε=21822), 263 (ε=14291), 363 (ε=5800);

Anal. Calcd for $C_{21}H_{21}N_7O_7S_1$: Theory: C, 48.93; H, 4.11; N, 19.02; Found: C, 49.14; H, 4.23; N, 18.77.

EXAMPLE 103

2-(Carboxylic Acid)-3-Cyano-7-(R,S)-[2-(2-Aminothiazol-4-yl)-2-(Z)-Methoxyiminoacetamido]-8-Oxo-1,5-Diazabicyclo[3.3.0]Octa-2-ene 2-(Allyl carboxylate)-3-cyano-7-(R,S)-[2-(2-(allyloxycarbonylamino)thiazol-4-yl)-2-(Z)-methoxyiminoacetamido]-8-oxo-1,5-diazabicyclo[3.3.0]octa-2-ene (205 mg, 0.398 mmol) was dissolved in acetonitrile (10 ml) and the stirred solution was flushed with nitrogen. Triphenylphosphine (41.76 mg, 0.159 mmol) and palladium (II) acetate (4.47 mg, 0.0199 mmol) were added and the solution was stirred under nitrogen at room temperature for 20 minutes then cooled to 0° C. Tri(n-butyl)tin hydride (237.5 mg, 0.816 mmol, 0.22 ml) was added and the solution was stirred for ten minutes at 0° C. and then at room temperature for one hour. Diethyl ether was added (10 ml) and the resultant solution was stirred for an additional hour at room temperature then additional ether (approximately 7 ml) and acetonitrile (approximately 1 ml) were added. 12M hydrochloric acid (0.068 ml, 0.816 mmol) was added and the resultant yellow precipitate was collected by filtration, washed with diethyl ether (20 ml), dichloromethane (5 ml), and again with diethyl ether (10 ml) to yield 136 mg of a solid. The solid was chromatographed by medium pressure liquid chromatography on a $C_{18}$s reverse phase column eluted with 5% acetonitrile/1% acetic acid/water to yield approximately 15 mg of 2-(carboxylic acid)-3-cyano-7-(R,S)-[2-(2-aminothiazol-4-yl)-2-(Z)-methoxyiminoacetamido]-8-oxo-1,5-diazabicyclo[3.3.0]octa-2-ene: n.m.r. (300 MHz, DMSO-$d_6$): δ 3.00–4.00 (m, 1); 3.09 (dd, 1, J=9 and 12), 3.84 (s, 3), 3.96 (d, J=12, 1), 4.27 (½ ABq, 1, J=12), 4.92–5.06 (m, 1), 6.98 (s, 1), 7.24 (br. s, 2), 9.15 (d, 1, J=9); i.r. (KBr): 3320 (br), 2220, 1724, 1649, 1534, 1398, 1046 cm$^{-1}$; u.v. (EtOH): $\lambda_{max}$=227 ($\epsilon_{max}$=16225), 302 ($\epsilon_{max}$=9726); m.p.>225° C. (d).

PREPARATION 33

1-(Dimethylphosphonato)-1-(Methylsulfonato)Ethylene

Under a nitrogen atmosphere, benzene (50 ml), acetic acid (15 ml), paraformaldehyde (0.99 g, 0.033 mol), and pyrrolidine (0.234 g, 0.0033 mol) were combined and the mixture was warmed to reflux for 25 minutes then cooled to 0° C. 1-(Dimethylphosphonato)-1-(methylsulfonato)methane was added (5 g, 0.025 mol) and the solution was heated to reflux first for 10 minutes then a Dean-Stark trap was added to the apparatus and the solution was heated to reflux for 25 minutes. Toluene was added and the solution was concentrated in vacuo, followed by the addition of toluene and reconcentration in vacuo to yield 1-(dimethylphosphonato)-1-(methylsulfonato)ethylene: n.m.r. (90 MHz, CDCl$_3$): δ 3.08 (s, 3); 3.80 (d, 6, J=13); 6.80 (d, 1, J=18); 7.00 (d, 1, J=36).

PREPARATION 34

4-(R,S)-(t-Butoxycarbonylamino)-3-Oxo-1-[1'-(Dimethylphosphonato)-1'-(Methylsulfonato)Eth-2'-yl]-1,2-Diazolidine Under a nitrogen atmosphere, 4-(R,S)-(t-butoxycarbonylamino)-3-oxo-1,2-diazolidine (4.5 g, 22.4 mmol) was dissolved in methanol (40 ml) with warming then the solution was cooled to 0° C. 1-(Dimethylphosphonato)-1-(methylsulfonato)ethylene (25 mmol) was added and the solution was stirred for 1 hour at 0° C., for 1 hour and 50 minutes at room temperature then filtered. The solid collected by filtration was washed with methanol, dried in vacuo at room temperature overnight to give 3.25 g of 4-(R,S)-(t-butoxycarbonylamino)-3-oxo-1-[1'-(dimethylphosphonato)-1'-(methylsulfonato)eth-2'-yl]-1,2-diazolidine. n.m.r. (300 MHz, DMSO-$d_6$): δ 1.40 (s, 9); 2.80–3.00 (m, 1); 3.10–3.66 (m, 3); 3.20 (s, 3); 3.66–3.80 (m, 6); 4.20–4.54 (m, 2); 7.20 (br. d, 1, J=12); 9.70 (br. d, 1, J=6); i.r. (KBr): 3310, 3190, 1710, 1696, 1525, 1232, 1165, 1142, 1052, 1043 cm$^{-1}$; f.d.m.s. (m/e): M+=415, 215 (M-200), 201 (M-215); m.p. 141°–143° C.;

Anal. Calcd for $C_{13}H_{26}N_3O_8S_1P_1$: Theory: C, 37.59; H, 6.31, N, 10.12; Found: C, 37.85; H, 6.30; N, 9.99.

EXAMPLE 104

2-(Allyl Carboxylate)-3-(Methylsulfonyl)-7-(R,S)-(t-Butoxycarbonylamino)-8-Oxo-1,5-Diazabicyclo[3.3.0]Octa-2-ene Under a nitrogen atmosphere, 4-(R,S)-(t-butoxycarbonylamino)-3-oxo-1-[1'-(dimethylphosphonato)-1'-(methylsulfonato)eth-2'-yl]-1,2-diazolidine (2.75 g, 6.6 mmol) was slurried in methylene chloride (150 ml) and the resulting slurry was cooled to 0° C. Allyl oxalate acid chloride (0.98 g, 6.6 mmol) was rinsed into the solution with additional methylene chloride then bis-(iso-propyl)ethylamine (1.71 g, 13.2 mmol, 2.3 ml) was added and the mixture was stirred at 0° C. for 30 minutes then at room temperature for 3.25 hours. The solution was washed with water, dried over magnesium sulfate, filtered and concentrated to yield 3.89 g of a yellow oil. The oil was combined with crude product from a previous procedure paralleling that above and the combination was flash chromatographed on silica gel eluted with 25% hexane/75% ethyl acetate to yield 1.87 g of 2-(allyl carboxylate)-3-(methylsulfonato)-7-(R,S)-(t-butoxycarbonylamino)-8-oxo-1,5-diazabicyclo[3.3.0]-octa2-ene. n.m.r. (90 MHz, CDCl$_3$): δ 1.44 (s, 9); 2.94 (dd, 1, J=11 and 11); 3.10 (s, 3); 3.86–4.90 (m, 4); 3.97, 4.49 (ABq, 2, J=12.5); 4.96–5.18 (br. d, 1, J=5); 5.18–5.54 (m, 2); 5.68–6.18 (m, 1); i.r. (CHCl$_3$): 3021, 1741, 1717, 1326, 1142 cm$^{-1}$; f.d.m.s. (m/e): M$^+$=401; u.v. (EtOH): λ$_{max}$=329 (ε=6037); m.p. 80° C.

Anal. Calcd for $C_{16}H_{23}N_3O_7S_1$: Theory: C, 47.87; H, 5.78, N, 10.47; Found: C, 47.75; H, 5.74; N, 10.55.

PREPARATION 35

4-(R,S)-(t-Butoxycarbonylamino)-3-Oxo-1-(1'-(Thien-2''-yl)-1'-Oxoeth-2'-yl)-1,2-Diazolidine A DMF solution (150 ml) of 4-(R,S)-(t-butoxycarbonylamino)-3-oxo-1,2-diazolidine (12.06 g, 60 mmol) and sodium hydride (2.4 g, 60 mmol, 60% dispersion in mineral oil) were combined and the resultant mixture was stirred at room temperature for one hour then cooled to 0° C. A DMF solution (50 ml) of 2-(bromoacetyl)thiophene (12.9 g, 63 mmol) was added over a period of 15 minutes and the resultant mixture was stirred at 0° C. for approximately two to three hours, then stirred at room temperature for 18 hours. The reaction mixture was diluted with xylene (400 ml) and the solvents were removed in vacuo. The residue was dissolved in chloroform (400 ml) and water (200 ml). The chloroform layer was separated and the aqueous layer was extracted with chloroform (2 X, 200 ml). The chloroform layers were combined and washed with brine (3 X, 200 ml), dried over sodium sulfate, filtered and concentrated in vacuo to yield a red oil (26 g). The oil was chromatographed by preparatory-scale high performance liquid chromatography on a silica gel column eluted with a gradient of 1:1 toluene:ethyl acetate to 100% ethyl acetate to yield approximately 10 g of a yellow foam. The foam was recrystallized from diethyl ether to yield 5.53 g of a solid. The solid was slurried in diethyl ether, filtered, and the collected solid was washed with diethyl ether to yield 4.46 g of 4-(R,S)-(t-butoxycarbonylamino)-3-oxo-1-[1'-(thien-2''-yl)-1'-oxoeth-2'-yl]-1,2-diazolidine: n.m.r. (270 MHz, DMSO-d$_6$) δ 9.66 (s, 1), 8.06 (m, 2), 7.27 (d, 1), 7.14 (d, 1), 4.6 (m, 1), 4.28 (dd, 2), 3.5 (t, 1), 3.11 (t, 1), 1.37 (9); i.r. (KBr): 1719, 1685, 1657 cm$^{-1}$; f.d.m.s. (m/e): M$^+$=325.

PREPARATION 36

4-(R,S)-(t-Butoxycarbonylamino)-3-Oxo-2-(p-Nitrobenzyl Oxaloyl)-1-[1'-(Thien-2''-yl)-1'-Oxoeth-2'-yl]1,2-Diazolidine A methylene chloride solution (20 ml) of 4-(R,S)-(t-butoxycarbonylamino)-3-oxo-1-(1'-(thien2''-yl)-1'-oxoeth-2'-yl)-1,2-diazolidine (1.625 g, 5 mmol) was combined with diisopropylethylamine (0.645 g, 5 mmol) and the resultant mixture was cooled to 10° C. A methylene chloride solution (20 ml) of p-nitrobenzyl oxalate acid chloride (1.217 g, 5 mmol) was added over a period of 20 minutes and the resulting mixture was stirred at 10°–15° C. for 4.5 hours then refrigerated overnight. The cold methylene chloride solution was washed with water (50 ml), brine (2 X, 50 ml), dried over sodium sulfate, filtered and evaporated in vacuo. The residue was dissolved in chloroform (70 ml, ethanol-free) and used in the next step.

EXAMPLE 105

2-(p-Nitrobenzyl Carboxylate)-3-(Thien-2-yl)-7-(R,S)-(t-Butoxycarbonylamino)-8-Oxo-1,5-Diazabicyclo [3.3.0]Octa-2-ene A chloroform solution (70 ml) of 4-(R,S)-(t-butoxycarbamylamino)-3-oxo-2-(p-nitrobenzyl oxaloyl)1-[1'-(thien-2''-yl)-1'-oxoeth-2'-yl)-1,2-diazolidine (approximately 5 mmol) taken from Preparation 36 above was combined with triethylphosphite (8.3 g, 50 mmol) and the mixture was heated to reflux for 24 hours and evaporated to dryness in vacuo. The residue was dissolved in ethyl acetate (300 ml) and the solution was washed with saturated aqueous sodium bicarbonate solution (2 X, 100 ml), brine (2 X, 100 ml), dried over sodium sulfate, filtered then evaporated in vacuo. Xylene (300 ml) was added to the residue then removed in vacuo. The resultant yellow oil was flash chromatographed over silica gel (100 g) eluted with 4:1 toluene, ethyl acetate to yield 0.643 mg of a yellow solid. The solid was recrystallized from ethyl acetate/hexanes to yield 0.471 g of 2-(p-nitrobenzyl carboxylate)-3-(thien-2-yl))-7-(R,S)-(t-butoxycarbonylamino)-8-oxo-1,5-diazabicyclo[3.3.0]octa-2-ene: n.m.r. (270 MHz, DMSO-d$_6$): δ 8.23 (d, 2), 7.78 (d, 1), 7.73 (d, 2), 7.45 (d, 1), 7 38 (d, 1, J=8.5), 7.16 (m, 1), 5.48 (q, 2), 4.72 (m, 1), 4.64 (d, 1, J=12), 4.12 (d, 1, J=12), 3.85 (t, 1), 2.98 (t, 1), 1.40, 1.36 (s, 9); i.r. (KBr): 1719, 1679 cm$^{-1}$; m.p.186°–188° C.; u.v. (ethanol): λ$_{max}$=370 (ε$_{max}$=13,059), 264 (ε$_{max}$=18,327); f.d. m.s. (m/e): M$^+$=500.

EXAMPLE 106

2-(p-Nitrobenzyl Carboxylate)-3-(Thien-2-yl)-7-(R,S)-(Amino)-8-Oxo-1,5-Diazabicyclo[3.3.0]Octa-2-ene 2-(p-Nitrobenzyl carboxylate)-3-(thien-2-yl)-7-(R,S)-(t-butoxycarbonylamino)-8-oxo-1,5-diazabicyclo [3.3.0]octa-2-ene (1.0 g, 2 mmol) was combined with trifluoroacetic acid (100 g, 61 ml) and the resultant solution was stirred for three minutes then evaporated in vacuo. Ethyl acetate (250 ml) and water (100 ml) were added to the residue and the resultant mixture was cooled to 0° C. The pH of the solution was adjusted to approximately 8.8 with aqueous saturated sodium bicarbonate solution. The aqueous layer was separated and extracted with ethyl acetate (2 X, 125 ml). The ethyl acetate layers were combined, washed with brine (2 X, 125 ml), dried over sodium sulfate, filtered and evaporated in vacuo to give 0.797 g of 2-(p-nitrobenzyl carboxylate)-3-(thien-2-yl)-7-(R,S)-(amino)-8-oxo-1,5-diazabicyclo[3.3.0]octa-2-ene. The solid was dissolved in acetonitrile (60 ml) and used in the next step.

EXAMPLE 107

2-(p-Nitrobenzyl Carboxylate)-3-(Thien-2-yl)-7-(R,S)-[2-(2-Aminothiazol-4-yl)-2-(Z)-Methoxyiminoacetamido]-8-Oxo-1,5-Diazabicyclo[3.3.0]Octa-2-ene An acetonitrile solution (60 ml) of 2-(p-nitrobenzyl carboxylate)-3-(thien-2-yl)-7-(R,S)-(amino)-8-oxo-1,5-diazabicyclo[3.3.0]octa-2-ene (0.797 g, 2 mmol) was combined with diisopropylethylamine (0.2967 g, 2.3 mmol, 0.4 ml) and (1-hydroxy N-benzotriazolyl) 2-(2'-aminothiazol-4'-yl)-2-(Z)-methoximinoacetate (0.6678 g, 2.1 mmol) and the resultant mixture was stirred at room temperature for 20 hours and then evaporated in vacuo. The residue was dissolved in a mixture of ethyl acetate (600 ml) and aqueous saturated sodium bicarbonate solution (100 ml). The ethyl acetate layer was separated then extracted with aqueous saturated sodium bicarbonate solution (100 ml), brine (2 X, 150 ml), dried over sodium sulfate, filtered and evaporated to dryness in vacuo to yield a yellow solid. The solid was recrystallized from ethyl acetate to yield 0.57 g of 2-(p-nitrobenzyl carboxylate)-3-(thien2-yl)-7-(R,S)-[2-(2-aminothiazol-4-yl)-2-(Z)-methoxyimino-acetamido]-8-oxo-1,5-diazabicyclo[3.3.0]octa2-ene: n.m.r. (360 MHz, DMSO-d$_6$): δ 9.14 (d, 1, J = 8.5), 8.23 (d, 2), 7.80 (d, 1), 7.75 (d, 2), 7.48 (d, 1), 7.2 (br. s, 2), 7.17 (m, 1), 7.00 (s, 1), 5.50 (q, 2), 5.08 (m, 1), 4.65 (d, 1, J=12), 4.22 (d, 1, J=12), 3.94 (t, 1), 3.83 (s, 3), 3.14 (t, 1); i.r. (KBr): 1709 cm$^{-1}$; u.v. (ethanol): $\lambda_{max}$=370 ($\epsilon_{max}$=12,692), 260 ($\epsilon_{max}$=25,332); f.d. m.s. (m/e): M+ =584.

EXAMPLE 108

2-(Carboxylic Acid)-3-(Thien-2-yl)-7-(R,S)-[2-(2-Aminothiazol-4-yl)-2-(Z)-Methoxyiminoacetamido]-8-Oxo-1,5-Diazabicyclo[3.3.0]Octa-2-ene 2-(p-Nitrobenzyl carboxylate)-3-(thien-2-yl)-7-(R,S)-[2-(2-aminothiazol-4-yl)-2-(Z)-methoxyiminoacetamido]-8-oxo-1,5-diazabicyclo[3.3.0]octa-2-ene (0.618 g, 1.048 mmol) was electrolytically reduced under the following conditions:

The electrochemical cell had the cathode and the anode compartments separated by a fritted glass disc. The cathode was a mercury pool with 14 cm$^2$ surface area immersed in a catholyte of 9:1 DMF:12N sulfuric acid (total volume of 40 ml). The cathode compartment was fitted with a deaerating frit and an SCE reference electrode. Both compartments were purged with argon before the electrolysis. The anode was a platinum wire ring and the anolyte was the same as the catholyte. The temperature of the cell was maintained at 25° C. for the electrolysis. A constant potential of −0.5 V was maintained and the progress of the reduction was monitored by HPLC. The reduction was stopped at approximately 91% completion (370 q).

The catholyte was chromatographed by preparatory-scale high performance liquid chromatography on a C$_{18}$ reverse phase column eluted with a gradient of 0–15% acetonitrile/1% acetic acid/water. The product-containing fractions were combined and lyophilized to yield 88.7 mg of 2-(carboxylic acid)-3-(thien-2-yl)-7-(R,S)-[2-(2-aminothiazol-4-yl)-2-(Z)-methoxyiminoacetamido]-8-oxo-1,5-diazabicyclo[3.3.0]octa-2-ene: δ 9.12 (d, 1, J=9), 7.7 (d, 1), 7.37 (d, 1), 7.22 (br. s, 2), 7.13 (m, 1), 7.06 (s, 1), 5.04 (t, 1), 4.54 (d, 1, J=12), 4.09 (d, 2, J=12), 3.9 (t, 1), 3.86 (s, 3), 3.07 (t, 1); i.r. (KBr): 1685, 1676, 1628 cm$^{-1}$; u.v. (ethanol): $\lambda_{max}$=344 ($\epsilon_{max}$=15,727), 292 ($\epsilon_{max}$=10,516), 236 ($\epsilon_{max}$=18,645) f.d. m.s. (m/e): M+ =448.

PREPARATION 37

N-(t-Butoxycaronyl) (L)-Serine Trifluoroacetyl Acyl Hydrazide

N-(t-Butoxycarbonyl) (L)-serine acyl hydrazide (32.85 g, 150 mmol) was suspended in ethanol (400 ml). Ethylthio trifluorothioacetate (30 ml, 37.02 g, 234.3 mmol) was added to the suspension and the resultant mixture was stirred at room temperature for 65 hours. The solvent was removed in vacuo and the residue was dissolved in diethyl ether (160 ml). A seed crystal was added to the diethyl ether solution and the resultant crystals were collected by filtration (approx. 27 g). The filtrate was evaporated in vacuo and diethyl ether (50 ml) was added to the residue. The solids that formed on standing were removed by filtration to yield approximately 16.5 g of additional product. The two batches of solids collected by filtration were combined and recrystallized from diethyl ether (3 liters). After effecting solution, the solution was reduced to approximately 450 ml to yield (after a second crop) 41.04 g, 87% yield of N-(t-butoxycarbonyl) (L)-serine trifluoroacetyl acyl hydrazide: n.m.r. (300 MHz, DMSO-d$_6$): δ 11.5 (br. s, 1), 10.33 (s, 1), 6.84 (d, 1, J=9), 4.9 (t, 1, J=7, (OH), 4.1 (m, 1), 3.59 (br. m, 2), 1.4 (s, 9); specific rotation: $[\alpha]_D^{25}$=−25.87° (10.05 mg/ml, methanol); m.p.: 143°–144° C. (first crop), 142°14 144° C. (second crop).

Anal Calcd for C$_{10}$H$_{16}$N$_3$O$_5$F$_3$: Theory: C, 38.10; H, 5.12; N, 13.33; Found: C, 38.34: H, 4.89; N, 13.16.

PREPARATION 38

4-(S)-(t-Butoxycarbonylamino)-1-(Trifluoroacetyl)-3-Oxo-1,2-Diazolidine

N-(t-Butoxycarbonyl) (L)-serine trifluoroacetyl acyl hydrazide (3.78 g, 12 mmol) and triphenylphosphine (3.46 g, 13.2 mmol) were dissolved in THF (50 ml). To the solution was added a THF solution (10 ml) of 95% diethyl azodicarboxylate (2.42 g, 2.19 ml, 13.2 mmol). The resultant mixture was stirred at room temperature for six hours and then the solvent was removed in vacuo. The residue was dissolved in ethyl acetate (100 ml) and then the solution was washed with aqueous sodium bicarbonate solution (33 ml, 3X). The sodium bicarbonate extracts were combined, aqueous saturated brine solution (70 ml) was added and the resultant mixture was extracted with ethyl acetate (120 ml, 3X). The sodium bicarbonate solution was then layered with additional ethyl acetate (200 ml) and 1N hydrochloric acid (approx. 80 ml) was added until the sodium bicarbonate solution had a pH of 2.5. The ethyl acetate layer was separated and the aqueous layer was extracted with additional ethyl acetate (4X, 125 ml). The ethyl acetate extracts were combined, washed with saturated aqueous brine (125 ml, 2X), dried over sodium sulfate, filtered, and taken to dryness in vacuo. The resultant residue was dissolved in acetonitrile (100 ml) then the acetonitrile was removed in vacuo. Treatment of the residue with acetonitrile was repeated to yield 3.06 g, 96% yield of 4-(S)-(t-butoxycarbonylamino)-1-(trifluoroacetyl)-3-oxo-1,2-diazolidine: n.m.r. (300 MHz, CDCl$_3$): δ 5.25 (d, 1, J=6), 4.81 (t, 1), 4.6 (m, 1), 4.06 (t, 1), 1.46 (s, 9); i.r. (CHCl$_3$): 1722, 1682, 1518 cm$^{-1}$;

f.d.m.s. (m/e): M+ = 297; specific rotation: $[\alpha]_D^{25} = -88.14°$ (10.03 mg/ml in methanol);

Anal. Calcd for $C_{10}H_{14}N_3O_4F_3$: Theory: C, 40.41; H, 4.75; N, 14.14; Found: C, 40.58; H, 5.01; N, 13.92.

PREPARATION 39

4-(S)-(t-Butoxycarbonylamino)-3-Oxo-1,2-Diazolidine 4-(S)-(t-butoxycarbonylamino)-1-(trifluoroacetyl)3-oxo-1,2-diazolidine (2.97 g, 10 mmol) was suspended in water (30 ml), 1N sodium hydroxide solution (20 ml, 0.8 g, 20 mmol) was added to raise the pH of the solution to 12.2 and the resultant mixture was stirred for one hour at room temperature. The pH of the mixture was adjusted to 7.2 by the addition of 1N hydrochloric acid (10 ml). Sodium chloride (13 g) was added to the solution and the mixture was extracted with chloroform (50 ml, 8X). The chloroform extracts were combined, washed with saturated aqueous sodium chloride solution (75 ml), dried over sodium sulfate, filtered, and evaporated to dryness in vacuo. Diethyl ether (100 ml) was added to the residue and then the ether was removed in vacuo to yield 0.798 g of a white solid of 4-(S)-(t-butoxycarbonylamino)-3-oxo-1,2-diazolidine: n.m.r. (300 MHz, DMSO-d$_6$): δ 9.23 (s, 1), 7.04 (d, 1, J=9), 5.24 (br. s, 1,), 4.24 (m, 1), 3.41 (t, 1), 2.88 (t, 1). 1.38 (s, 9); specific rotation: $[\alpha]_D^{25} = -74.16°$ (10.06 mg/ml in methanol); (the compound was dried overnight at 80° C. before analysis):

Anal. Calcd for $C_8H_{15}N_3O_3$: Theory: C, 47.75; H, 7.51; N, 20.88; Found: C, 47.75; H, 7.46; N, 20.62.

EXAMPLE 109

2-(Allyl Carboxylate)-3-(Methyl Carboxylate)-7-(S)-(t-Butoxycarbonylamino)-8-Oxo-1,5-Diazabicyclo[3.3.0]Octa-2-ene

Step 1

Formation of Pyrazolidinium Ylide 4-(S)-(t-Butoxycarbonylamino)-3-oxo-1,2-diazolidine (20.1 g, 100 mmol) was suspended in 1,2-dichloroethane (400 ml), 37% aqueous formaldehyde solution (0.51 ml, 3.15 g, 105 mmol) was added and the resultant mixture was stirred at room temperature for 1.5 hours to give 4-(S)-(t-butoxycarbonylamino)-3-oxo-1-(methylene)-1,2-pyrazolidinium ylide.

Step 2

Cycloaddition of Acetylene

Allyl methyl butynedioate (18.48 g, 110 mmol) was added to the mixture from Step 1 and the resultant mixture was refluxed for 6.5 hours. The volume of the reaction mixture was reduced by half in a flask fitted with a Dean-Stark trap. Hexane (200 ml) was added and the mixture was allowed to stand until an oil formed. The solvent was decanted, the oil was dissolved in ethyl acetate (300 ml) and the solution was taken to dryness in vacuo to yield 17.3 g of a foam. The foam was chromatographed using preparatory-scale high performance liquid chromatography using a silica column eluted with a gradient of 0 to 40% ethyl acetate in isooctane (8 liters). The product-containing fractions were combined to yield 1.456 g of a yellow solid. The solid was recrystallized from a mixture of ethyl acetate and hexane to yield 0.55 g of 2-(allyl carboxylate)-3-(methyl carboxylate)-7-(S)-(t-butoxycarbonylamino-)8-oxo-1,5-diazabicyclo[3.3.0]octa-2-ene: n.m.r. (300 MHz, CDCl$_3$) δ 6.00 (m, 1), 5.38 (m, 2), 5.1 (br. d, J=6), 4.86 (d, 2), 4.74 (m, 1), 4.37 (d, 1, J=13), 4.08 (t, 1), 3.91 (d, 1, J=13), 3.77 (s, 3), 2.86 (t, 1), 1.46 (s, 9); i.r. (KBr): 1751, 1710, 1687 cm$^{-1}$; u.v. (ethanol : $\lambda_{max}$=346 ($\epsilon_{max}$=8489); f.d.m.s. (m/e): M+ =381; specific rotation: $[\alpha]_D^{25} = -481.92°$ (10.01 mg/ml in methanol); m.p.: 111°-113° C.;

Anal. Calcd for $C_{17}H_{23}N_3O_7$: Theory: C, 53.54; H, 6.08; N, 11.02; Found: C, 53.83; H, 6.06; N, 10.77.

EXAMPLE 110

2-(Allyl Carboxylate)-3-(Methyl Carboxylate)-7-(S)-Amino-8-Oxo-1,5-Diazabicyclo[3.3.0]Octa-2-ene Hydrochloride Salt 2-(Allyl carboxylate)-3-(methyl carboxylate)-7(S)-(t-butoxycarbonylamino)-8-oxo-1,5-diazabicyclo[3.3.0]octa-2-ene (0.1905 g, 0.5 mmol) was added to a solution of glacial acetic acid with a 3N concentration of anhydrous hydrochloric acid (7 ml) and the resultant mixture was stirred at room temperature for five minutes and then taken to dryness in vacuo. The resultant yellow solid was dissolved in methylene chloride (20 ml) and the mixture was sonicated and evaporated in vacuo. The methylene chloride/sonication procedure was repeated two more times. The solid was dried in vacuo for 1.5 hours to yield to 2-(allyl carboxylate)-3-(methyl carboxylate)-7-(S)-amino-8-oxo-1,5-diazabicyclo[3.3.0]octa-2-ene hydrochloride salt.

EXAMPLE 111

2-(Allyl Carboxylate)-3-(Methyl Carboxylate)-7-(S)-[2-(2-(Allyloxycarbonylamino)-Thiazol-4-yl)-2-(Z)-Methoxyiminoacetamido]-8-Oxo-1,5-Diazabicyclo[3.3.0]Octa-2-ene Under a nitrogen atmosphere, 2-[2-(N-allyloxy carbonylamino)thiazolo-4-yl]-2-(Z)-methoxyimioacetic acid (0.1425 g, 0.5 mmol) was suspended in dried methylene chloride (5 ml). The suspension was cooled to 0° C. then 6-chloro-2,4-dimethoxy-1,3,5-triazine (0.088 g, 0.5 mmol) and N-methylmorpholine (0.0505 g, 0.5 mmol) were added. The resultant solution was stirred at 0° C. for forty minutes. Additional N-methylmorpholine (0.0505 g, 0.5 mmol) and a methylene chloride suspension (5 ml) of 2-(allyl carboxylate)-3-(methyl carboxylate)-7-(S)-amino-8-oxo-1,5-diazabicyclo[3.3.0]octa-2-ene hydrochloride salt (0.5 mmol) were added. After all the solid dissolved, the solution was stirred at room temperature for 20 hours then evaporated to dryness in vacuo. The residue was dissolved in ethyl acetate (70 ml) and water (15 ml), the layers were separated, and the ethyl acetate was extracted sequentially with 0.1N hydrochloric acid (10 ml, 3X), saturated aqueous sodium bicarbonate solution (20 ml, 3X), brine solution (20 ml, 3X), dried over sodium sulfate, filtered, and evaporated to dryness in vacuo to yield 280 mg of a yellow solid. The solid was recrystallized from a mixture of methylene chloride and di(isopropyl) ether to yield 136 mg of the 2-(allyl carboxylate)-3-(methyl carboxylate)-7-(S)-[2-(2-(allyloxycarbonylamino)thiazol-4-yl-2-(Z)-methoxyiminoacetamido] -8-oxo-1,5-diazabicyclo[3.3.0]octa-2-ene: n.m.r. (300 MHz, DMSO-d$_6$): δ 12.1 (s, 1), 9.32 (d, 1, J=9), 7.43 (s, 1), 5.94 (m, 2), 5.34 (m, 4), 5.09 (m, 1), 4.83 (d, 2, J=6), 4.7 (d, 2, J=6), 4.31 (d, 1, J=13), 4.02 (d, 1, J=13), 3.88 (overlapping s and t, 4), 3.69 (s, 3), 3.18 (t, 1); u.v. (ethanol); $\lambda_{max}$=342 ($\epsilon_{max}$=8680), 264 (13,626), 209 (25,137); f.d.m.s. (m/e): M+ =548, 490; specific rotation: $[\alpha]_D^{25} = -351.45°$ (10.01 mg/ml in methanol).

Anal. Calcd for $C_{22}H_{24}N_6O_9S$: Theory: C, 48.17; H, 4.41; N, 15.32; Found: C, 48.09; H, 4.41; N, 15.02.

EXAMPLE 112

2-(Carboxylic Acid)-3-(Methyl Carboxylate)-7-(S)-[2-2-Aminothiazol-4-yl)-2-(Z)-Methoxyiminoacetamido]-8-Oxo-1,5-Diazabioyclo[3.3.0]Octa-2-ene Hydrate Palladium (II) acetate (18 mg, 0.08 mmol) was suspended in acetone (4 ml). Triphenylphosphine (105 mg, 0.4 mmol) was washed into the suspension with additional acetone (2 ml) and the resultant mixture was stirred at room temperature for 20 minutes. 2-(Allyl carboxylate)-3-(methyl carboxylate)-7-(S)-[2-(2-(allyloxycarbonylamino)thiazol-4-yl)-2-(Z)-methoxyiminoacetimido]-8-oxo-1,5-diazabicyclo[3.3.0]octa-2-ene (0.497 g, 0.9096 mmol) was suspended in a mixture of acetone (45 ml) and acetonitrile (15 ml) was added to the reaction suspension. This suspension was stirred at room temperature for 35 minutes then cooled to 0° C. Tri(n-butyl)tin hydride (0.548 g, 1.81 mmol, 0.506 ml) was slowly added to the cooled suspension and the mixture was stirred at 0° C. for 30 minutes then at room temperature for 50 minutes. The mixture was cooled to 0° C. then 1N hydrochloric acid (1.82 ml, 1.81 mmol) was added. The resultant mixture was stirred at 0° C. for 10 minutes then at room temperature for 5 minutes. The mixture was filtered, water (130 ml) was added to the filtrate, and the resultant mixture was filtered through a pad of Celite ™. The filtrate was extracted with hexane (4X, 40 ml), and the aqueous layer was filtered through a pad of Celite ™ then reduced in vacuo to about 75% volume. The resultant yellow solid was removed by filtration through a pad of Celite ™ and the filtrate was extracted with ether (2X, 75 ml), concentrated in vacuo to remove any residual ether and then the resultant yellow solution was lyophilized. The lyophilized solid was dissolved in water (75 ml), filtered and then chromatographed on a preparatory-scale high performance liquid chromatograph using a $C_{18}$ reverse phase column eluted with a gradient of 0 to 10% methanol/0.5% acetic acid/water (8 liters) then a gradient of 10% to 25% methanol/0.5% acetic acid/water (8 liters) to yield 91.5 mg of 2-(carboxylic acid)-3-(methyl carboxylate)-7-[2-(2-aminothiazol-4-yl)-2-(Z)-methoxyiminoacetamido]-8-oxo-1,5-diazabicyclo[3.3.0]octa-2-ene: n.m.r. (300 MHz, DMSO-$d_6$): δ 9.18 (d, 1, J=10), 7.24 (br. s, 2), 6.94 (s, 1), 5.02 (m, 1), 4.23 (d, 1, J=13), 3.9 (d, 1, J=13), 3.8 (overlapping t and s, 4), 3.1 (t, 1); i.r. (KBr): 1726, 1688, 1670.5 cm$^{-1}$; u.v. (ethanol): $\lambda_{max}$=328 ($\epsilon_{max}$10, 950), 233 (16,013); f.d.m.s. (m/e): M+=425; specific rotation: $[\alpha]_D^{25}$=−326.35° (9.83 mg/ml in methanol);

Anal. Calcd for $C_{15}H_{16}O_7S \cdot H_2O$: Theory: C, 40.72; H, 4.10; N, 19.00; Found: C, 40.81; H, 3.70; N, 19.03.

PREPARATION 40

(Phenylsulfonyl)acetone

Sodium benzenesulfinate (50 g, 304.6 mmol) was dissolved in water (200 ml). A dioxane solution (200 ml) of chloroacetone (29.6 g, 319.9 mmol) was added and the solution was stirred and heated to 50° C. for 22 hours then cooled to approximately 25° C. The solution was extracted with methylene chloride (2X, 250 ml), the methylene chloride layers were combined and washed with saturated aqueous sodium bicarbonate solution (1X, 250 ml) and water (1X, 250 ml) then the aqueous wash solutions were combined and extracted with methylene chloride (2X, 100 ml). All of the methylene chloride layers were combined and washed with saturated aqueous sodium chloride solution (1X, 150 ml), dried over sodium sulfate, filtered and concentrated in vacuo to a solid. The solid was dissolved in diethyl ether (800 ml) with gentle heating and then the solution was stirred and allowed to cool to room temperature. The solution was slowly cooled to 0° C. with stirring, causing the product to crystallize. The resulting crystals were collected by filtration, washed with cold diethyl ether, and dried in vacuo at 35° C. for 4 hours to yield 36.43 g of (phenylsulfonyl)acetone. The filtrate was concentrated to approximately one-eighth of its volume in vacuo and was gradually cooled below room temperature to induce crystallization, then stirred overnight at room temperature. The resulting crystals were collected by filtration, washed with cold diethyl ether, and dried in vacuo at 35° C. for 8 hours to yield an additional 14 g of the (phenylsulfonyl)acetone: n.m.r. (90 MHz, CDCl$_3$): δ 2.39 (s, 3), 4.17 (s, 2), 7.55–7.95 (m, 5); m.p. 56°–58° C.

PREPARATION 41

Allyl 3-(Phenylsulfonyl)-4-Oxopentanoate

Under a nitrogen atmosphere, sodium hydride (6.41 g, 0.267 mol) and THF (125 ml) were combined and the suspension was cooled to −15° C. A THF solution (150 ml) of (phenylsulfonyl)acetone (50 g, 0.253 mol) was added to the suspension in a dropwise fashion over an hour. The resultant mixture was stirred for an additional 20 minutes at −15° C. Allyl bromoacetate (47.5 g, 0.265 mol) dissolved in THF (100 ml) was added in a dropwise fashion to the mixture over a period of 30 minutes while maintaining the temperature of the solution below 0° C. The resultant solution was stirred at −5° C. for 15 minutes, allowed to warm to room temperature over a period of an hour, and stirred overnight at room temperature. The reaction solution was poured into saturated aqueous ammonium chloride solution (800 ml) and chloroform (500 ml) and the aqueous layer was separated and extracted with chloroform (2X, 200 ml). The chloroform layers were combined and washed with saturated aqueous sodium chloride (1X, 350 ml), dried over sodium sulfate, filtered and concentrated in vacuo to an oil. The oil was crystallized from a mixture of ethyl acetate and hexane. The collected solid was washed with cold 1:3 ethyl acetate: hexane and dried in vacuo, yielding 52.9 g of the allyl 3-(phenylsulfonyl)-4-oxopentanoate: n.m.r. (90 MHz, CDCl$_3$): δ 2.51 (s, 3), 2.97 (n, 2,), 4.51 (dm, 2, J=6), 4.65 (m, 1), 5.1–5.19 (m,2), 5.58–6.00 (m, 1), 7.4–7.8 (m, 5); m.p. 62–64° C.

PREPARATION 42

Allyl 3-(Phenylsulfonyl)-4-Oxopent-2-(E)-Enoate

Allyl 3-(phenylsulfonyl)-4-oxopentanoate (42 g, 141.9 mmol) was combined with chloroform (400 ml). Upon dissolution the solution was cooled to −20° C. and then triethylamine (39.4 ml, 282.8 mmol) was added while maintaining the temperature between −25° C. to −20° C. A chloroform solution of bromine (238 ml, 0.594M, 141.4 mmol) was added in a dropwise fashion over a 1 hour period. The solution was stirred at −20° C. for 30 minutes then at room temperature overnight. The reaction mixture was washed with water (2X, 200 ml), 0.5N hydrochloric acid (1X, 200 ml), saturated aqueous sodium bicarbonate solution (1X, 200 ml), saturated sodium chloride solution (1X, 250 ml), dried over sodium sulfate, filtered and concentrated in vacuo to yield 41.76 g of allyl 3-(phenylsulfonyl)-4-oxopent-2-(E)-enoate as an oil: n.m.r. (90 MHz, CDCl$_3$): δ 2.50 (s, 3), 4.65 (dm, J=6), 5.20 –5.44 (m, 2), 5.65–6.10, (m, 1), 6.86 (s, 1), 7.42–7.85 (m, 5).

EXAMPLE 113

2-(Allyl Carboxylate)-3-(Acetyl)-7-(S)-(t-Butoxycarbonylamino)-8-Oxo-1,5-Diazabicyclo[3.3.0]-Octa-2-ene

Step A 4-(S)-(t-Butoxycarbonylamino)-3-Oxo-1-Methylene-1,2-Pyridazolinium Ylide 4-(S)-(t-Butoxycarbonylamino)-3-oxo-1,2-diazolidine (22.7 g, 113 mmol), formalin (37%, 10.1 g, 124.6 mmol) and 1,2-dichloroethane (450 ml) were combined and stirred at room temperature for 2 hours. The solution was evaporated in vacuo to a solid that was taken up in toluene (200 ml) and concentrated again in vacuo.

Step B

Cycloaddition

Allyl 3-(phenylsulfonyl)-4-oxopent-2-(E)-enoate (40 g, 136 mmol) was washed into a flask with 1,2-dichloroethane (150 ml). The solution was heated to 70° C. and then a 1,2-dichloroethane solution (300 ml) of the ylide of Step A was added over a period of two hours while maintaining the temperature of the solution between 70° to 75° C. The solution was heated to reflux then allowed to cool to 24° C. The solution contained 2-(R,S)-(allyl carboxylate)-3-(R,S)-acetyl-3-(R,S)-phenylsulfonyl)-7-(S)-(t-butoxycarbonylamino)-8-oxo-1, 5-diazabicyclo[3.3.0]octane.

Step C

Elimination

N-methylmorpholine (12.5 ml, 113.6 mmol) was added to the solution of Step B over a period of one minute, and the resultant solution was stirred overnight at room temperature. The solvent was evaporated in vacuo and the resultant oily product was taken up in ethyl acetate (1 liter). The solution was washed with 0.2N hydrochloric acid (2X, 250 ml), water (1X, 250 ml), saturated aqueous sodium bicarbonate solution (1X, 250 ml) and saturated aqueous sodium chloride solution (1X, 250 ml), dried over sodium sulfate, filtered and concentrated in vacuo to a volume of approximately 165 ml. Additional ethyl acetate (50 ml) was added and the solution was heated until all solids dissolved. Hexane (100 ml) was slowly added, the solution was first stirred at room temperature for 1.5 hours then at 0° C. for one hour and filtered. The collected solid was washed with a 0° C. mixture of 30% ethyl acetate/70% hexane (2X, 100 ml) to yield a yellow crystalline solid. The solid was dried in vacuo at 40° C. for 3 hours to give 25.3 g, 61.4% of the 2-(allyl carboxylate)-3-(acetyl)-7-(S)-(t-butoxycarbonylamino)-8-oxo-1,5-diazabicyclo[3.3.0]octa-2-ene: n.m.r. (90 MHz, CDCl$_3$): δ 1.45 (s, 9), 2.27 (s, 3), 2.83 (dd, J=11 and 8, 1), 4.02 (br. t, 1), 3.91 (d, J=12.5,1), 4.39 (d, J=12.5,1) 4.68 (m, 1), 4.87 (dm, 2, J=6), 5.15 (br. d, 1), 5.3–5.5 (m, 2), 5.8–6.2 (m, 1); i.r. (CHCl$_3$): 3440, 1750, 1717 cm$^{-1}$; u.v. (methanol): λ$_{max}$=225 (ε$_{max}$=8,927), 364 (8667); f.d.m.s. (m/e): M$^+$=365; m.p. 136°–137° C.; [α]$_D^{25}$= −644° (c 1, methanol).

EXAMPLE 114

2-(Allyl Carboxylate)-3-Acetyl-7-(S)-[2-(2-(Allyloxycarbonylamino)thiazol-4-yl)-2-(Z)-Methoximinoacetamido]-8-Oxo-1,5-Diazabicyclo[3.3.0]Octa-2-ene

Step A

Formation of Acid Chloride

Under a nitrogen atmosphere, ethyl acetate (55 ml) and DMF (2.2 ml, 28.4 mmol) were combined and cooled to 0° C. Phosphoryl chloride (1.8 ml, 19.3 mmol) was added and the solution was stirred at 0° C. for 75 minutes. 2-(2-(N-allyloxycarbonylamino)thiazol-4-yl)-2-(Z)-methoxyiminoacetic acid (5.5 g, 19.3 mmol) was added and the solution was stirred at 0° C. for two hours.

Step B

Synthesis of 2-(Allyl Carboxylate)-3-Acetyl-7-(S)-Amino-1,5-Diazabicyclo[3.3.0]Octa-2-ene Hydrochloride 2-(Allyl carboxylate)-3-(acetyl)-7-(S)-(t-butoxycarbonylamino)-8-oxo-1,5-diazabicycl[3.3.0]octa-2-ene (7.0 g, 19.2 mmol) was stirred with a glacial acetic acid solution that was 3N in anhydrous hydrogen chloride (50 ml) for twenty minutes at room temperature. The acetic acid was removed in vacuo, and methylene chloride was added to the residue and the mixture evaporated in vacuo. Methylene chloride was again added and the solution taken to dryness in vacuo, affording a thick, orange oil.

Step C

Acylation

The hydrochloride nucleus from Step B above was dissolved in a mixture of acetonitrile (250 ml) and water (250 ml) and the solution was cooled to 5° C. The pH of the solution was raised from 1.9 to 7.25 by the addition of 1M K$_2$HPO$_4$ solution. The solution containing the acid chloride from Step A above was added to this cooled solution over a period of 15 minutes while maintaining the temperature of the solution below 5° C. and the pH of the solution at approximately 7. The resultant solution was stirred for 30 minutes at 3° C. then at room temperature for 1.5 hours. Ethyl acetate (250 ml) was added, the aqueous layer was separated and extracted with additional ethyl acetate (1X, 250 ml). The ethyl acetate layers were combined, washed with water (1X, 250 ml), saturated aqueous sodium bicarbonate solution (1X, 250 ml), water (1X, 250 ml), saturated sodium chloride solution (1X, 250 ml), dried over sodium sulfate, filtered and evaporated to dryness in vacuo to give 6.96 g, 68% yield of a yellow solid of the 2-(allyl carboxylate)-3-acetyl-7-(S)-[2-(2-(allyloxycarbonylamino)-thiazol-4-yl)-2-(Z)-methoximinoacetamido]-8-oxo-1,5-diazabicyclo[3.3.0]octa-2-ene: n.m.r. (90 MHz, CDCl$_3$): δ 2.28 (s, 3), 3.0 (m, 1), 3.95 (s, 3), 3.96 (d, J=12.5, 1), 4.08 (t, 1, partially observed), 4.39 (d, 5=12.5, 1), 4.69 (dm, 2, J=5.4), 4.78 (d, 2, J=3.6), 5.28–5.44 (m, 4), 5.7–6.2 (2), 7.14 (s, 1), 8.18 (br. d, 1).

EXAMPLE 115

2-(Carboxylic Acid)-3-Acetyl-7-(S)-[2-(2-Aminothiazol-4-yl)-2-(Z)-Methoximinoacetamido]-8-Oxo-1,5-Diazabicyclo[3.3.0]Octa-2-ene Under a nitrogen atmosphere, palladium (II) acetate (26 mg) was combined with acetone (5 ml) then triphenylphosphine (131 mg) was washed into the solution with acetone (5 ml). The solution was stirred for 10 minutes at room temperature than 2-(allyl carboxylate)-3-acetyl-7-(S)-[2-(2-(allyloxycarbonylamino)thiazol-4-yl)-2-(Z)-methoximinoaoetamido]-8-oxo-1,5-diazabicyclo-[3.3.0]octa-2-ene (0.8 g) as an acetone solution (20 ml) was added. The resultant solution was stirred first for 40 minutes at room temperature then cooled to 2° C. Tri(n-butyl)tin hydride (0.81 ml) was added and the solution was stirred at 0° C. for 30 minutes then at room temperature for approximately two hours. The solution was cooled to approximately 2° C. and 1N hydrochloric acid (3.0 ml) was added. The cooling bath was removed and the solution was stirred for 10 minutes then filtered. Water (200 ml) was added to the filtrate. Acetonitrile (40 ml) was added to redissolve the orange oil that formed. The resulting solution was washed with hexane (2X, 50 ml), filtered through Hy-Flo ™ and the resultant filtrate was washed with diethyl ether (2X, 50 ml) and hexane (1X, 50 ml), concentrated in vacuo at 40° C. then lyophilized. The lyophilized material was chromatographed on a preparatory-scale high performance liquid chromatography apparatus using a reverse phase C-18 column eluted with a gradient of 0% to 20% methanol in water. The product-containing fractions were combined and lyophilized to give 0.155 g of the 2-(carboxylic acid)-3-acetyl-7-(S)-[2-(2-aminothiazol-4-yl)-2-(Z)-methoximinoacetamido]-8-oxo-1,5-diazabicyclo[3.3.0]octa-2-ene: n.m.r.(90 MHz, $D_2O$): δ 2.34 (s, 3), 3.23 (dd, 1, J=11 and 9), 3.97 (s, 3), 3.84–4.10 (m, 2), 4.29 (d, J=12.5, 1), 5.21 (dd, 1, J=13.5 and 8), 7.06 (s, 1); $[α]_D^{25}$=−347° (c=0.4 methanol).

PREPARATION 43

2-(R,S)-(Allyl Carboxylate)-3-(R,S)-Chloro-3-(R,S)-Phenylthio-7-(S)-(t-Butoxycarbonylamino)-8-Oxo-1,5-Diazabicyclo[3.3.0]Octane 2-(R,S)-(Allyl carboxylate)-3-(R,S)-phenylthio-7-(S)-(t-butoxycarbonylamino)-8-oxo-1,5-diazabicyclo[3.3.0]octane (433 mg, 1 mmol) is dissolved in carbon tetrachloride (5 ml). N-chlorosuccinimide (134 mg, 1 mmol) is added and the mixture is heated to reflux for 1 hour. The mixture is cooled, filtered, and is evaporated to dryness in vacuo to give 2-(R,S)-(allyl carboxylate)-3-(R,S)-chloro-3-(R,S)-phenylthio-7-(S)-(t-butoxycarbonylamino)-8-oxo-1,5-diazabicyclo[3.3.0]octane.

PREPARATION 44

2-(R,S)-(Allyl Carboxylate)-3-Hydroxy-7-(S)-(t-Butoxycarbonylamino)-8-Oxo-1,5-Diazabicyclo[3.3.0]-Octa-2-ene 2-(R,S)-(Allyl carboxylate)-3-(R,S)-chloro-3-(R,S)-phenylthio-7-(S)-(t-butoxycarbonylamino)-8-oxo- 1,5-diazabicyclo[3.3.0]octane (468 mg, 1 mmol) is dissolved in acetone (10 ml) containing 0.2 ml of water. Copper-(II) oxide (450 mg) and copper(II) chloride dihydrate (450 mg) is added and the mixture is heated to reflux for 15 minutes, cooled rapidly and then is diluted with toluene (50 ml). The mixture is filtered, dried over sodium sulfate, filtered and is concentrated in vacuo to give 2-(R,S)-(allyl carboxylate)-3-hydroxy-7-(S)-(t-butoxycarbonylamino)-8-oxo-1,5-diazabicyclo[3.3.0]octa-2-ene.

EXAMPLE 116

2-(Allyl Carboxylate)-3-Methoxy-7-(S)-(t-Butoxycarbonylamino)-8-Oxo-1,5-Diazabicyclo[3.3.0]-Octa-2-ene 2-(R,S)-(Allyl carboxylate)-3-hydroxy-7-(S)-(t-butoxycarbonylamino)-8-oxo-1,5-diazabicyclo[3.3.0]octa-2-ene (339 mg, 1 mmol) is dissolved in THF (5 ml) and the solution is cooled to 0° C. A diethyl ether solution of diazomethane (1.1 mmol) is added and the mixture is stirred at 0° C. for 30 minutes, and then glacial acetic acid is added. The mixture is diluted with methylene chloride, washed with saturated aqueous sodium bicarbonate solution and brine, is dried over magnesium sulfate, filtered and is concentrated in vacuo. The concentrate is flash chromatographed on silica gel eluted with a mixture of hexane/ethyl acetate to give 2-(allyl carboxylate)-3-methoxy-7-(S)-(t-butoxycarbonylamino)- 8-oxo-1,5-diazabicyclo[3.3.0]-octa-2-ene.

EXAMPLE 117

2-(Allyl Carboxylate)-3-Amino-7-(S)-(t-Butoxycarbonylamino)-8-Oxo-1,5-Diazabicyclo[3.3.0]Octa-2-ene 2-(R,S)-(Allyl carboxylate)-3-hydroxy-7-(S)-(t-butoxycarbonylamino)-8-oxo-1,5-diazabicyclo[3.3.0]-octa-2-ene (339 mg, 1 mmol) is dissolved in anhydrous ethanol (10 ml). Ammonium chloride (4 mmol) and pyridine (0.5 ml) are added and the mixture is heated to 50° C. for 24 hours. The solution is filtered and is concentrated in vacuo. The residue is dissolved in methylene chloride, dried over sodium sulfate, filtered and concentrated in vacuo to give 2-(allyl carboxylate)-3-amino-7-(S)-(t-butoxycarbonylamino)-8-oxo-1,5-diazabicyclo[3.3.0]octa-2-ene.

EXAMPLE 118

2-(Allyl Carboxylate)-3-(Dibenzylamino)-7-(S)-(t-Butoxycarbonylamino)-8-Oxo-1,5-Diazabicyclo[3.3.0]Octa-2-ene 2-(R,S)-(Allyl carboxylate)-3-hydroxy-7-(S)-(t-butoxycarbonylamino)-8-oxo-1,5-diazabicyclo[3.3.0]-octa-2-ene (339 mg, 1 mmol) is dissolved in benzene (10 ml). Dibenzylamine (1 mmol), d-10-camphorsulfonic acid (10 mg) and 4A molecular sieves (5 g) are added and the mixture is stirred at room temperature for 24 hours. The mixture is filtered, concentrated in vacuo and the residue is flash chromatographed on silica gel that is eluted with a mixture of hexane/ethyl acetate to give 2-(allyl carboxylate)-3-(dibenzylamino)-7-(S)-(t-butoxycarbonylamino)-8-oxo-1,5-diazabicyclo[3.3.0]-octa-2-ene.

PREPARATION 45

2-(allyl carboxylate)-3-(R,S)-chloro-3-(R,S)-phenysulfoxide-7-(S)-(t-butoxycarbonylamino)-8-oxo-1,5-diazabicyclo[3.3.0]octane 2-(R,S)-(allyl carboxylate)-3-(R,S)-chloro-3-(R,S)-phenylthio-7-(S)-(t-butoxycarbonylamino)-8-oxo-1,5-diazabicyclo[3.3.0]octane (468 mg, 1 mmol) is dissolved in methylene chloride (5 ml). m-Chloroperbenzoic acid (1 mmol) is added and the mixture is stirred at −78° C. for 15 minutes and then poured into methylene chloride (20 ml). The methylene chloride solution is washed with 5% aqueous potassium carbonate solution and brine, dried over magnesium sulfate, filtered, and is concentrated in vacuo to give 2-(allyl carboxylate)-3-(R,S)-chloro-3-(R,S)-phenylsulfoxide-7-(S)-(t-butoxycarbonylamino)-8-oxo-1,5-diazabicyclo[3.3.0]octane.

EXAMPLE 119

2-(Allyl Carboxylate)-3-Chloro-7-(S)-(t-Butoxycarbonylamino)-8-Oxo-1,5-Diazabicyclo[3.3.0]-Octa-2-ene

2-(Allyl carboxylate)-3-(R,S)-chloro-3-(R,S)-phenylsulfoxide-7-(S)-(t-butoxycarbonylamino)-8-oxo-1,5-diazabicyclo[3.3.0]octane (484 mg, 1 mmol) is dissolved in carbon tetrachloride (15 ml). Triphenylphosphite (2 mmol) is added and the mixture is heated to reflux for 6 hours, cooled, and is concentrated in vacuo. The residue is flash chromatographed on silica gel that is eluted with a mixture of hexane/ethyl acetate to give 2-(allyl carboxylate)-3-chloro-7-(S)-(t-butoxycarbonylamino)-8-oxo-1,5-diazabicyclo[3.3.0]-octa-2-ene.

EXAMPLE 120

2-(t-Butyl Carboxylate)-3-(N-(Methoxycarbonylamino))-7-(R,S)-(t-Butoxycarbonylamino)-8-Oxo-1,5-Diazabicyclo[3.3.0]Octa-2-ene

2-(t-Butyl carboxylate)-3-(carboxylic acid)-7-(R,S)-(t-butoxycarbonylamino)-8-oxo-1,5-diazabicyclo[3.3.0]octa-2-ene (1 mmol) is dissolved in benzene (5 ml). Diphenylphosphoryl azide (1 mmol) is added and the solution is refluxed for 1 hour, methanol (2 mmol) is added and the solution is refluxed for an additional 15 hours. The solution is cooled, washed with 1N hydrochloric acid, saturated aqueous sodium bicarbonate solution, and brine, dried over magnesium sulfate, filtered and concentrated in vacuo. The residue is flash chromatographed on silica gel eluted with hexane/ethyl acetate to give 2-(t-butyl carboxylate)-3-(N-(methoxycarbonylamino))-7-(R,S)-(t-butoxycarbonylamino)-8-oxo-1,5-diazabicyclo[3.3.0]-octa-2-ene.

EXAMPLE 121

2-(Carboxylic Acid)-3-Cyano-7-(S)-[2-(2-Aminothiazol-4-yl)-2-(Z)-Methoxyiminoacetamido]-8-Oxo-1,5-Diazabicycli[3.3.0]Octa-2-ene

In a manner similar to the synthesis of the corresponding 7-(R,S) compound (Example 103, and the intermediates thereto, Examples 102, 101 and 100, and Preparations 32, 31 and 2), except that the 4-(S) (chiral) substituted diazolidinone of Preparation 39 was used as the starting material, the (chiral) title product was synthesized: n.m.r. (300 MHz, DMSO-d$_6$) δ 3.13 (dd, 1, J=9 and 12), 3.85 (s, 3), 3.60–4.00 (m, 1); 4.03 and 4.34 (ABq, 2, J=12), 4.94–5.10 (m, 1); 6.96 (s, 1), 7.25 (br. s, 2), 9.17 (d, 1, J=9); i.r. (KBr): 3320 (br), 2220, 1724, 1642, 1534, 1399, 1047 cm$^{-1}$; u.v. (ethanol) $\lambda_{max}$=230 ($\epsilon_{max}$=16,345), 303 ($\epsilon_{max}$=9307); $[\alpha]_D^{25}$= −383.1 (in methanol); m.p. >225° (decompose).

EXAMPLE 122

2-(Allyl Carboxylate)-3-(Methylsulfonyl)-7-(R,S)-Amino-8-Oxo-1,5-Diazabicyclo[3.3.0]Octa-2-ene Hydrochloride

Under a nitrogen atmosphere, 2-(allyl carboxylate)-3-(methylsulfonyl)-7-(R,S)-(t-butoxycarbonylamino)-8-oxo-1,5-diazabicyclo[3.3.0]octa-2-ene (1.54 g, 4.43 mmol) was combined with a cold glacial acetic acid solution that had a 3N concentration of anhydrous hydrogen chloride (50 ml) and the mixture was stirred at room temperature until it was a solution (2 minutes), when it was evaporated in vacuo to dryness. The volatiles on the residue were removed by azeotropic distillation with methylene chloride (7X) then dried in vacuo at room temperature for 2.5 hours to yield 3.5 g of The residue was redissolved in methylene chloride and the solution was taken to dryness in vacuo two times to yield 2-(allyl carboxylate)-3-(methylsulfonyl)-7-(R,S)-amino-8-oxo-1,5-diazabicyclo[3.3.0]octa-2-ene hydrochloride.

EXAMPLE 123

2-(Allyl Carboxylate)-3-(Methylsulfonyl)-7-(R,S)-[2-(2-Allyloxycarbonylaminothiazol-4-yl)-2-(Z)-Methoxyiminoacetamido]-8-Oxo-1,5-Diazabicyclo[3.3.0]Octa-2-ene

Under a nitrogen atmosphere, 2-[2'-(allyloxy(carbonylamino)thiazol-4'-yl]-2-(Z)-methoxyiminoacetic acid 2.7 g, 9.5 mmol) was suspended in methylene chloride (100 ml) and the suspension was cooled to 0° C. 2-Chloro-4,6-dimethoxy-1,3,5-triazine (1.7 g, 9.5 mmol) then N-methylmorpholine (1.0 ml, 9.5 mmol) was added and the mixture was stirred at 0° C. for 45 minutes. 2-(allyl carboxylate)-3-(methylsulfonyl)-7-(R,S)-amino-8-oxo-1,5-diazabicyclo[3.3.0]octa-2-ene hydrochloride (3.2 g, 9.5 mmol) was added followed by an additional amount of N-methylmorpholine (1.0 ml, 9.5 mmol). The resultant mixture was stirred overnight first at 0° C. then gradually warmed to room temperature and concentrated to dryness in vacuo. The residue was dissolved in a solution of ethyl acetate containing a 0.1N concentration of hydrochloric acid. The layers were separated and the organic layer was washed with saturated aqueous sodium bicarbonate solution and saturated aqueous sodium chloride solution, dried over magnesium sulfate, filtered and evaporated to dryness. The residue was flash chromatographed on silica gel eluted with ethyl acetate to yield 1.27 g, 23.5% of 2-(allyl carboxylate)-3-(methylsulfonyl)-7-(R,S)-[2-(2-allyloxycarbonylaminothiazol-4-yl)-2-(Z)-methoxyiminoacetamido]-8-oxo-1,5-diazabicyclo[3.3.0]octa-2-ene: n.m.r. (300 MHz, DMSO-d$_6$): δ 3.26 (s, 3); 3.20–3.30 (m, 1); 3.80–3.96 (m, 1); 3.90 (s, 3); 4.23 and 4.42 (ABq, 2, J=12); 4.60–4.92 (m, 4); 5.04–5.20 (m, 1); 5.20–5.54 (m, 4); 5.86–6.06 (m, 2); 7.43 (s, 1); 9.31 (d, 1, J=6) 12.20 (s, 1); i.r. (CHCl$_3$); 3240, 3019, 1748, 1732, 1704, 1554, 1423, 1321, 1144 cm$^{-1}$; f.d.m.s. (m/e): M$^+$+1 =569; u.v. (EtOH) $\lambda_{max}$=206 ($\epsilon$=22059), 264 ($\epsilon$=13351);

Anal. Calcd for C$_{21}$H$_{24}$N$_6$O$_9$S$_2$: Theory: C, 44.36; H, 4.25; N, 14.78; Found: C, 44.56; H, 4.25; N, 14.50.

EXAMPLE 124

2-(Carboxylic Acid)-3-(Methylsulfonyl)-7-(R,S)-[2-(2-Aminothiazol-4-yl)-2-(Z)-Methoxyiminoacetamido]-8-Oxo-1,5-Diazabicyclo[3.3.0]Octa-2-ene

Under a nitrogen atmosphere, palladium (II) acetate (54 mg, 0.24 mmol) was dissolved in acetone (13 ml), then triphenylphosine (316 mg, 1.2 mmol) was added. The resultant suspension was stirred at room temperature for 30 minutes. 2-(Allyl carboxylate)-3-(methylsulfonyl)-7-(R,S)-[2-(2-(allyloxycarbonylamino)-thiazol-4-yl)-2-(Z)-methoxyimino-acetamido]-8-oxo-1,5-diazabicyclo[3.3.0]octa-2-ene (1.23 g, 2.17 mmol) was dissolved in acetone (85 ml) and added to the above suspension. The resultant solution was stirred under nitrogen at room temperature for 40 minutes then cooled to −10° C. for 10 minutes. Tri(n-butyl)tin hydride (1.26 g, 4.34 mmol, 1.17 ml) was added and the suspension was stirred for 75 minutes at −10° C. and then at room temperature for 1.75 hours. (Over the course of the 1.75 hours, additional diethyl ether (40 ml) was added to the suspension). The suspension was cooled to −10° C. and 1N hydrochloric acid (4.34 ml, 2 mmol) was added. The suspension was stirred at −10° C. for 10 minutes then at room temperature for 10 minutes.

The resultant yellow precipitate was collected by filtration through a Celite® pad. The collected solid was washed with water (400 ml), and the wash was added to the acetone filtrate. The resultant cloudy yellow solution was filtered through a Celite pad and the filtrate was extracted with hexanes (4x, 150 ml). The filtrate was again filtered through a pad of Celite® then reduced to three-fourths volume in vacuo. The filtrate was again filtered through a Celite® pad then washed with diethyl ether (2x, 200 ml). The filtrate was concentrated in vacuo then lyophilized to give 1.0 g of a solid. A portion of the solid (100 mg) was chromatographed by medium pressure liquid chromatography on a silica gel column eluted with 5% methanol/0.5% acetic acid/water to give 30 mg of the title product. The remaining portion of the solid was chromatographed by medium pressure liquid chromatography on a (45 mm diameter × 12 inch length) silica gel column eluted with 2% methanol/0.5% acetic acid/water to give 2-(carboxylic acid)-3-(methylsulfonyl)-7-(R,S)-[2-(2-aminothiazol-4-yl)-2-(Z)-methoxyiminoacetamido]-8-oxo-1,5-diazabicyclo-[3.3.0]octa-2-ene: n.m.r. (300 MHz, DMSO-$d_6$): 3.00–3.26 (m, 1), 3.22 (s, 3), 3.70–4.04 (m, 1), 3.84 (s, 3), 4.12 and 4.34 (ABq, 2, J=12), 4.94–5.10 (m, 1), 6.94 (s, 1); 7.24 (br. s, 2), 9.18 (d, 1, J=9); i.r. (KBr): 3340 (br), 1721, 1644, 1534, 1403, 1304, 1134, 1047 cm$^{-1}$; u.v. (EtOH): $\lambda_{max}$=232 ($\epsilon_{max}$=14681), 303 ($\epsilon_{max}$=11495); f.a.b. m.s. (m/e): M$^+$+1=445; m.p.>200° C.

Anal. Calc'd for $C_{13}H_{16}N_6O_7S_2$:
Theory: C, 37.83; H, 3.63; N, 18.91
Found : C, 37.57; H, 3.73; N, 18.68

EXAMPLE 125

2-(Carboxylic Acid)-3-(Methylsulfonyl)-7-(S)-[2-(2-Aminothiazol-4-yl)-2-(Z)-Methoximinoacetamido]-8-Oxo-1,5-Diazabicyclo[3.3.0]Octa-2-ene In a manner similar to that of Examples 124, 123, 122, and 104, and Preparations 33 and 34, (except that the 4-(S)-diazolidinone is used as the starting material), the title product is synthesized: n.m.r. (300 MHz, DMSO-$d_6$): δ 3.13 (dd, J=9, 12 Hz, 1H); 3.20 (s, 3H); 3.74–3.90 (m, 1H); 3.85 (s, 3H); 4.00 and 4.37 (ABq, J=12 Hz, 2H); 4.93–5.05 (m, 1H); 6.95 (s, 1H); 7.23 (br s, 2H); 9.15 (d, J=9 Hz, 1H); i.r. (KBr): 3320, 1722, 1652, 1534, 1402, 1383, 1304, 1133, 1046 cm$^{-1}$; m.s.: FAB m/e=445 (m+1); u.v.: (ethanol) $\lambda_{max}$=302 nm ($\epsilon$=10,022; 229 nm ($\epsilon$=17,163); o.r.: (DMSO) −88.84° at 589 nm;

Analysis Calc'd for $C_{13}H_{16}N_6O_7S_2 \cdot \frac{1}{2} H_2O$:
Theory: C, 37.08; H, 3.78; N, 18.53. Found: C, 37.00; H, 3.64; N, 18.31.

EXAMPLE 126 TO 155

In a manner similar to that of Examples 104, 122, 123, 124, 125 and Preparations 33 and 34 (except that the 4-(S)-diazolidinone was used as the starting material), the following compounds were synthesized. The $R_2$ substituent,

was varied by simply starting with the desired $R_7$ group as per Scheme 4, step 4 above.

The $R_{26}$ substituent was inserted by an alkylation of the free oxime (i.e., $R_{26}$=hydrogen). Protection of the 2-amino group of the 2-aminothiazole ring ($R_{24}$) was protected throughout the synthesis with the triphenylmethyl group (trityl). The trityl group was then removed by the triethylsilane/trifluoroacetic acid method. The 2-carboxyl group was protected throughout the synthesis as its allyl ester and eventually removed last by the palladium acetate/triphenylphosphine/triethylsilane method.

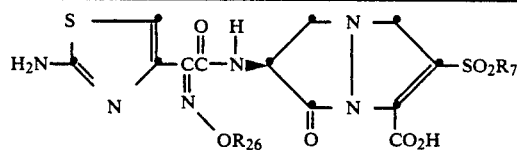

| Example | $R_{26}$ | $R_7$ | Physical Data |
|---|---|---|---|
| 126 | —CH$_2$—CH=C(CH$_3$)$_2$ | —CH$_3$ | 300 MHz (DMSOd$_6$): δ 1.65 (s, 3H); 1.72 (s, 3H); 2.95 (dd, 1H, J=10, 12 Hz); 3.18 (s, 3H); 3.72–3.80 (m, 1H); 3.81 and 4.13 (ABq, 2H, J=12 Hz); 4.55 (d, 2H, J=6 Hz); 4.89–5.01 (m, 1H); 5.35 (t, 1H, J=6 Hz); 7.06 (s, 1H); 7.22 (s, 2H); 9.04 (d, 1H, J=10 Hz); i.r. (KBr): 3541, 3335, 1715, 1649, 1536, 1412, 1383, 1321, 1302, 1230, 1135, 1001, 980 (cm$^{-1}$); ms: FAB m/e=499 (M$^+$); u.v.: (EtOH) λ=232 nm (ε=15,100); 302 nm (ε=11,700). |
| 127 | —CH$_2$—CO$_2$H | —CH$_3$ | 300 MHz (DMSOd$_6$): δ 2.93 (dd, 1H, J=10, 12 Hz); 3.14 (s, 3H); 3.69 (t, 1H, J=9 Hz); 3.77 and 4.08 (ABq, 2H, J=12 Hz); 4.22 (s, 2H); 4.80–4.94 (m, 1H); 6.85 (s, 1H); 7.14 (s, 2H); i.r. (KBr): 3390, 2980, 1756, 1719, 1395, 1369, 1320, 1143, 1116 (cm$^{-1}$); ms: FAB m/e=489 (M$^+$ 1); u.v. (EtOH) λ=305 nm (ε=2400); o.r.: −133.127 at 589 nm (DMSO). |
| 128 | —CH$_3$ | —CH$_2$CH$_3$ | 300 MHz (DMSOd$_6$): δ 1.22 (t, 3H, J=10 Hz); 3.10–3.77 (m, 3H); 3.84 (s, 3H); 3.94 (t, 1H, J=12 Hz); 4.05 and 4.33 (ABq, 2H, |

-continued

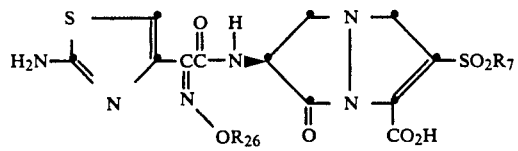

| Example | $R_{26}$ | $R_7$ | Physical Data |
|---|---|---|---|
| | | | J=12 Hz); 4.94–5.10 (m, 1H); 6.92 (s, 1H); 7.23 (br s, 2H); 9.16 (d, 1H, J=10 Hz); i.r. (KBr): 3320, 2940, 1725, 1705, 1530, 1410, 1380, 1310, 1125, 1040 cm$^{-1}$; ms: FAB m/e= 459 (M$^+$ 1); u.v. (EtOH) λ=304 nm (ε=11717); λ=232 nm (ε=14870); o.r.: (DMSO) −211.6° at 589 nm. |
| 129 | —CH$_3$ | phenyl | 300 MHz (DMSOd$_6$): δ 3.06 (dd, 1H, J=15, 10Hz); 3.75 (t, 1H, J=10 Hz); 3.82 and 4.12 (ABq, 2H, J=12 Hz); 3.83 (s, 3H); 4.90–5.02 (m, 1H); 6.91 (s, 1H); 7.21 (br s, 2H); 7.60–8.05 (m, 5H); 9.09 (d, 1H, J=10 Hz); i.r. (KBr): 3330, 1725, 1645, 1530, 1205, 1150 cm ; ms: FAB m/e=507 (M+); u.v. (EtOH) λ=316 nm (ε=11587); λ=228 nm (ε=22315); o.r.: (DMSO) −82.7° at 589 nm. |
| 130 | —CH$_2$CH$_2$CH$_2$CH=CH$_2$ | —CH$_3$ | 300 MHz (DMSOd$_6$): δ 1.56–1.73 (m, 2H) 1.96–2.10 (m, 2H); 2.94 (dd, 1H, J=10 and 15 Hz); 3.00–3.46 (m, 1H); 3.14 (s, 3H); 3.72 (t, 1H, J=5 Hz); 4.00 (t, 2H, J=5 Hz); 4.12 and 3.88 (ABq, 2H, J=10 Hz); 4.86– 5.06 (m, 2H); 5.70–5.90 (m, 1H); 700 (s, 1H); 7.19 (br s, 2H); 9.20 (d, 1H, J=10 Hz); i.r. (KBr): 3323, 1718, 1651, 1533, 1401, 1321, 1303, 1135 cm$^{-1}$; m.s. (FD): m/e=455 (M$^+$ 1-CO$_2$(44)); u.v.: (EtOH)=303 nm, 235 nm; o.r.: (DMSO) −141.6° at 589 nm |
| 131 | CH$_2$CH$_2$Br | —CH$_2$CH$_3$ | 300 MHz (DMSOd$_6$): δ 0.93 (t, 3H, J=10 Hz); 1.63 (q, 2H, J=10 Hz); 2.88–3.00 (m, 1H); 3.20–3.38 (m, 2H); 3.60 (t,2H, J=7.5 Hz); 3.72 and 4.10 (ABq, 2H, J=10 Hz); 3.70–3.77 (m, 1H); 4.28 (t, 2H, J=7.5 Hz); 4.87–5.00 (m, 1H); 7.08 (s, 1H); 7.23 (br s, 2H; 9.08 (d, 1H, J=10 Hz); i.r. (KBr): 3390, 1730, 1661, 1532, 1406, 1318, 1288, 1130 cm$^{-1}$; m.s. (FAB): m/e=589 (M + 1 + 23 (Na)); u.v.: (EtOH) λ=305 nm (ε=11559); λ=231 nm ε=15361); o.r.: (DMSO) −153.2° at 589 nm. Elem. Anal.: Calc'd: C, 36.11; H, 3.74; N, 14.86 Obs'd: C, 35.84; H, 3.61; N, 14.62 |
| 132 | —CH$_2$CH$_2$Cl | CH$_2$CH$_3$ | 300 MHz (DMSOd$_6$): δ 1.13 (t, 3H, J=10 Hz); 2.92 (dd, 1H, J=15, 10 Hz); 3.72 and 4.08 (ABq, 2H, J=10 Hz; 3.20–3.60 (m, 3H); 3.75 (t, 2H, J=7.5 Hz); 4.22 (t, 2H, J=7.5 Hz); 4.87–4.98 (m, 1H); 7.07 (s, 1H); 7.27 (br s, 2H); 9.10 (d, 1H, J=10 Hz); i.r. (KBr): 3440, 3000, 1720, 1655, 1575, 1420, 1135, 1025 cm$^{-1}$; m.s. (FAB): m/e=507 (M+); u.v.: (EtOH) λ= 301 nm (ε=3471); λ=231 nm (68 =4808); o.r.: (DMSO) −32.0° at 589 nm. |
| 133 | —CH$_2$CH$_2$Cl | —CH$_3$ | 300 MHz (DMSOd$_6$): δ 2.97 (dd, 1H, J=15, 10 Hz); 3.16 (s, 3H); 3.70–3.85 (m, 1H); 3.78 (t, 2H, J=7.5 Hz); 3.75 and 4.12 (ABq, 2H, J=10 Hz); 4.25 (t, 2H, J=7.5 Hz); 4.87–5.00 (m, 1H); 7.10 (s, 1H); 7.27 (br s, 2H); 9.12 (d, 1H, J=10 Hz); i.r. (KBr): 3430, 1720, 1615, 1570, 1540, 1140, 1025 cm$^{-1}$; m.s. (FAB): m/e=493 (M+); u.v.: (EtOH) λ=303 nm (ε=4901); λ=231 nm (ε=6546); o.r.: (DMSO) −30.7° at 589 nm. |
| 134 | —CH$_2$CH$_2$Cl | phenyl | 300 MHz (DMSOd$_6$): δ 2.55 (dd, 1H, J=15, 10 Hz); 3.10–3.70 (ABq, 2H, J=10 Hz); 3.38 (t, 1H, J=10 Hz); 3.47 (t, 2H, J=7.5 Hz); 3.95 (t, 2H, J=7.5 Hz); 4.58–4.70 (m, 1H); 6.77 (s, 1H); 6.97 (br s, 2H); 7.24–7.80 (m, 5H); 8.75 (d, 1H, J=10 Hz); i.r. (KBr): 3340, 3200, 1735, 1655, 1540, 1405, 1320, 1305, 1155, 1105, 1090, 1025 cm$^{-1}$; m.s. (FAB): m/e=577 (M+Na); u.v.: (EtOH) λ=316 nm (ε= 10270); λ=227 nm (ε=23148); o.r.: (DMSO) −76° at 589 nm. |
| 135 | —CH$_2$CH$_2$Cl | —CH$_2$CH$_2$CH$_3$ | 300 MHz (DMSOd$_6$): δ 0.67 (t, 3H, J=10 Hz); 1.37 (q, 2H, J=10 Hz); 2.67 (dd, 1H, J=15, |

-continued

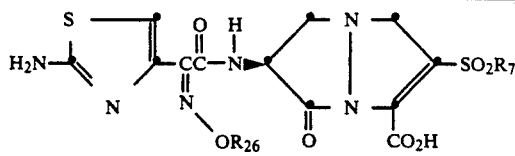

| Example | R$_{26}$ | R$_7$ | Physical Data |
|---|---|---|---|
| | | | 10 Hz); 2.90-3.20 (m, 2H); 3.44-3.52 (m, 1H); 3.45 and 3.85 (ABq, 2H, J=10 Hz); 3.50 (t, 2H, J=7.5 Hz); 3.97 (t, 2H, J=7.5 Hz); 4.60-4.70 (m, 1H); 6.82 (s, 1H); 6.97 (br s, 2H); 8.82 (d, 1H, J=10 Hz); i.r. (KBr): 3320, 2980, 1720, 1660, 1535, 1410, 1385, 1315, 1290, 1230, 1130, 1025 cm$^{-1}$; m.s. (FAB): m/e=521 (M+); u.v.: (etOH) λ=305 nm (ε=11581); λ=230 nm (ε=14940); o.r.: (DMSO) −125.7° at 589 nm. |
| 136 | —CH$_2$CH$_2$Br | —CH$_3$ | 300 MHz (DMSOd$_6$): δ 2.70 (dd, 1H, J=15, 10 Hz); 2.87 (s, 3H); 3.33 (t, 2H, J=7.5 Hz); 3.47 (t, 1H, J=10 Hz); 3.52 and 3.83 (ABq, 2H, J=10 Hz); 4.02 (t, 2H, J=7.5 Hz); 4.62-4.73 (m, 1H); 6.82 (s, 1H); 6.97 (br s, 2H); 8.81 (d, 1H, J=10 Hz); i.r. (CHCl$_3$): 3420, 3350, 1720, 1655, 1530, 1415, 1380, 1320, 1305, 1135, 1010 cm$^{-1}$; m.s. (FAB): m/e=561 (M+1 +23 (Na)); u.v.: (etOH) λ=304 nm (ε=11292); λ=231 nm (ε=14932); o.r.: (DMSO) −54.6° at 589 nm. |
| 137 | —CH$_2$CH$_2$Cl | —CH$_2$CH$_2$CH$_2$CH$_3$ | 300 MHz (DMSOd$_6$): δ 0.60 (t, 3H, J=10 Hz); 1.08 (q, 2H, J=10 Hz); 1.25-1.37 (m, 2H); 2.68 (dd, 1H, J=15, 10 Hz); 3.00-3.20 (m, 2H); 3.44-3.50 (m, 1H); 3.47 and 3.85 (ABq, 2H, J=10 Hz); 3.50 (t, 2H, J=7.5 Hz); 3.97 (t, 2H, J=7.5 Hz); 4.60-4.73 (m, 1H); 6.82 (s, 1H); 6.98 (br s, 2H); 8.82 (d, 1H, J=10 Hz); i.r. (KBr): 3370, 2950, 1685, 1660, 1530, 1425, 1385, 1325, 1210, 1135, 1025 cm$^{-1}$; m.s. (FAB): m/e=557 (M+23 (Na)); u.v.: (etOH) λ=305 nm (ε=9084); λ=230 nm (ε=12210); o.r.: (DMSO) −82.6° at 589 nm. |
| 138 | —CH$_2$CH$_2$Cl | benzyl | 300 MHz (DMSOd$_6$): δ 2.57-2.70 (m, 1H); 3.57 (t, 1H, J=10 Hz); 3.70-3.80 (m, 4H); 4.25 (t, 2H, J=7.5 Hz); 4.40 and 5.05 (ABq, 2H, J=10 Hz); 4.78-4.90 (m, 1H); 7.07 (s, 1H); 7.25 (br s, 2H); 7.30-7.45 (m, 5H); 9.18 (d, 1H, J=10 Hz); i.r. (KBr); 3340, 3200, 1720, 1660, 1540, 1410, 1325, 1210, 1150, 1115, 1025 cm$^{-1}$; m.s. (FAB): m/e= 591 (M+23 (Na)); u.v.: (etOH) λ=304 nm (ε=10142); o.r.: (DMSO) −181.5° at 589 nm. |
| 139 | —CH$_2$—CH$_2$CH$_2$CH$_2$Cl | —CH$_3$ | 300 MHz (DMSOd$_6$): δ 2.92 (dd, 1H J=9, 10 Hz); 3.13 (s, 3H); 3.30-3.75 (m, 5H); 3.62 (t, 2H, J=7.5 Hz); 3.75 and 4.10 (ABq, 2H, J=10 Hz); 4.03 (t, 2H, J=7.5 Hz); 4.85-4.98 (m, 1H); 7.00 (s, 1H); 7.22 (br s, 2H); 9.03 (d, 1H, J=10 Hz); i.r. (KBr): 3420, 1715, 1690, 1655, 1580, 1550, 1420, 1305, 1210, 1140, 1025 cm$^{-1}$; u.v.: (etOH) λ=302 nm (ε=5990); λ=232 nm (ε=7767); o.r.: (DMSO) −28.3° at 589 nm. |
| 140 | —CH$_2$CH$_2$Br | —CH$_2$CH$_3$ | 300 MHz (DMSOd$_6$): δ 1.17 (t, 3H, J=Hz); 2.95-3.03 (m, 1H); 3.20-3.43 (m, 2H), 3.62 (t, 2H, J=7.5 Hz); 3.73 (t, 1H, J=10 Hz); 3.77 and 4.15 (ABq, 2H, J=10 Hz); 4.28 (t, 2H, J=7.5 Hz); 4.88-5.00 (m, 1H); 7.05 (s, 1H); 7.23 (br s, 2H); 9.08 (d, 1H, J=10 Hz); i.r. (KBr): 3360, 1717, 1653, 1533, 1407, 1307, 1129, 1011, cm$^{-1}$; m.s. (FAB): m/e=551 (M+); u.v.: (etOH)λ=305 nm (ε=12828), λ= 213 nm (ε=17092); o.r.: (DMSO) −136.6° at 589 nm. |
| 141 | -allyl | —CH$_3$ | 300 MHz (DMSOd$_6$): δ 2.95 (dd, 1H, J=15, 10 Hz); 3.15 (s, 3H); 3.75 (t, 1H, J=10 Hz); 3.80 and 4.12 (ABq, 2H, J=10 Hz); 4.55 (d, 2H, J=5 Hz); 4.87-5.00 (m, 1H); 5.15 (d, 1H, J= 10 Hz); 5.28 (d, 1H, J=12 Hz); 5.83-5.98 (m, 1H); 7.05 (s, 1H); 7.22 (br s, 2H); 9.08 (d, 1H, J=10 Hz); i.r. (KBr): 3410, 2920, 1730, 1717, 1533, 1413, 1303, 1135, cm$^{-1}$; m.s. (FAB): m/e=471 (M$^+$1); u.v.: |

-continued

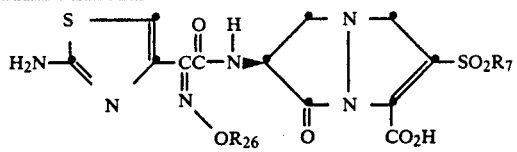

| Example | R$_{26}$ | R$_7$ | Physical Data |
|---|---|---|---|
| 142 | —CH$_2$CH$_2$F | —CH$_3$ | (EtOH) λ=302 nm (ε=11797), λ=232 nm (ε=15342); o.r.: (DMSO) −62.8° at 589 nm. 300 MHz (DMSOd$_6$): δ 2.92 (dd, 1H J=15, 10 Hz); 3.13 (s, 3H); 3.72 (t, 1H, J=10 Hz); 3.77 and 4.08 (ABq, 2H, J=10 Hz); 4.18 (t, 1H, J=5 Hz); 4.28 (t, 1H, J=5Hz); 4.52 (t, 1H, J=5 Hz); 4.67 (t, 1H, J=5 Hz); 4.85-5.00 (m, 1H); 7.07 (s, 1H); 7.22 (KBr s, 2H); 9.08 (d, 1H, J=10 Hz); i.r. (KBR): 3410, 1717, 1652, 1534, 1414, 1302, 1135 cm$^{-1}$; m.s. (FAB); m/e=499 (M+23 (Na)); u.v.: (etOH) λ=305 nm (ε=10800), λ=230 nm (ε=13800); o.r.: (DMSO) −173.1° at 589 nm. |
| 143 | —CH$_2$CH$_2$CH$_3$ | —CH$_3$ | 300 MHz (DMSOd$_6$): δ 0.85 (t, 3H, J=7.5 Hz); 1.57 (q, 2H, J=7.5 Hz); 2.95 (dd, 1H, J=15, 10 Hz); 3.17 (s, 3H); 3.72 (t, 1H, J=10 Hz); 3.82 and 4.12 (ABq, 2H, J=10 Hz); 3.97 t, 2H, J=7.5 Hz); 4.87-5.00 (m, 1H); 7.00 (s, 1H); 7.20 (br s, 2H); 9.02 (d, 1H, J=10 Hz); i.r. (KBr): 3380, 3000, 1735, 1659, 1532, 1386, 1320, 1305, 1135, cm$^{-1}$; m.s. (FAB): m/e=473 (M+1); u.v.: (etOH) λ=302 nm (ε=12000); λ=234 nm (ε=14900); o.r.: (DMSO) −75° at 589 nm. |
| 144 | —CH$_2$CH$_2$F | —CH$_2$CH$_3$ | 300 MHz (DMSOd$_6$): δ 1.13 (t, 3H, J=7.5 Hz); 2.93 (dd, 1H, J=15, 10 Hz); 3.20-3.50 (m, 2H): 3.73 (t, 1H, J=5 Hz); 3.73 and 4.12 (ABq, 2H, J=10 Hz); 4.18 (t, 1H, J=5 Hz); 4.28 (t, 1H, J=5 Hz); 4.50 (t, 1H, J=5 Hz); 4.67 (t, 1H, J=5 Hz); 4.88-5.00 (m, 1H); 7.05 (s, 1H); 7.22 (br s, 2H); 9.08 (d, 1H, J=10 Hz); i.r. (KBr): 3460, 3350, 3207, 1730, 1658, 1533, 1410, 1306, 1129 cm$^{-1}$; m.s. (FAB): m/e=513 (M+23 (Na)); u.v.: (etOH) λ=305 nm (ε=11300), λ=230 nm (ε=14700); o.r.: (DMSO) −1.4° at 589 nm. |
| 145 | —CH$_2$—C≡CH | —CH$_3$ | 300 MHz (DMSOd$_6$): δ 2.93 (dd, 1H, J=15, 10 Hz); 3.13 (s, 3H); 3.45 (t, 1H, J=2.5 Hz); 3.75 (t, 1H, J=10 Hz); 3.77 and 4.08 (ABq, 2 Hz, J=10 Hz); 4.65 (d, 2H, J=2.5 Hz); 4.85-4.97 (m, 1H); 7.12 (s, 1H); 7.25 (br s, 2H); 9.12 (d, 1H, J=10 Hz); i.r. (KBr): 3390, 2140, 1730, 1675, 1610, 1564, 1537, 1449, 1421, 1310 cm$^{-1}$; u.v.: (etOH) λ=299 nm (ε=4170), λ=230 nm (ε=8020). |
| 146 | —CH$_2$CH$_2$CH$_2$CH$_3$ | —CH$_3$ | 300 MHz (DMSOd$_6$): δ 0.85 (t, 3H, J=10 Hz): 1.30 (q, 2H, J=10 Hz); 1.48-1.58 (m, 2H); 2.95 (dd, 1H, J=15, 10 Hz); 3.15 (s, 3H): 3.72 (t, 1H, J=10 Hz); 3.78 and 4.12 (ABq, 2H, J=10 Hz); 3.98 (t, 2H, J=7.5 Hz); 4.87-4.98 (m, 1H); 6.98 (s, 1H); 7.18 (br s, 2H); 9.02 (d, 1H, J=10 Hz); i.r. (mull): 3520, 2918, 2870, 1653, 1462, 1377, 1319 cm$^{-1}$, m.s. (FAB): m/e=487 (M+); u.v.: (etOH) λ=302 nm (ε=11700), λ=233 nm (ε=14600); o.r.: (DMSO) −84.2105° at 589 nm. |
| 147 | —CH$_2$CH$_2$F | —CH$_2$CH$_2$CH$_3$ | 300 MHz (DMSOd$_6$): δ 0.93 (t,3H, J=10 Hz); 1.63 (q, 2H, J=10 Hz); 2.93 (dd, 1H, J=15, 10 Hz); 3.12-3.45 (m, 2H); 3.72 (t, 1H, J=10 Hz); 3.72 and 4.12 (ABq, 2H, J=10 Hz); 4.18 (t, 1H, J=5 Hz); 4.28 (t, 1H, J=5 Hz); 4.50 (t, 1H, J=5 Hz); 4.67 (t, 1H, J=5 Hz); 4.87-5.02 (m, 1H); 7.07 (s, 1H); 7.22 (br s, 2H); 9.08 (d, 1H, J=10 Hz); i.r. (KBr): 3420, 3020, 1717, 1657, 1534, 1409, 1289, 1129 cm$^{-1}$; m.s. (FAB): m/e=505 (M+); u.v.: (etOH) λ=305 nm (ε=12200), λ=230 nm (ε=15700); o.r.: (DMSO) −12.2° at 589 nm. |
| 148 | —CH$_2$CH$_2$CH$_3$ | —CH$_2$CH$_2$CH$_3$ | 300 MHz (DMSOd$_6$): δ 0.85 (t, 3H, J=10 Hz); |

-continued

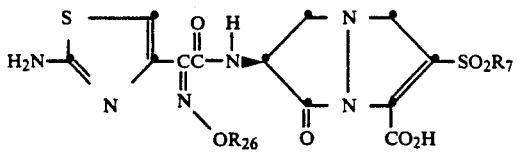

| Example | R_{26} | R_7 | Physical Data |
|---|---|---|---|
|  |  |  | 0.93 (t, 3H, J=10 Hz); 1.55 (q, 2H, J=10 Hz); 1.62 (q, 2H, J=10 Hz); 2.93 (dd, 1H, J=15, 10 Hz); 3.13–3.43 (m, 2H); 3.68 (t, 1H, J=10 Hz); 3.72 and 4.10 (ABq, 2H, J=10 Hz); 3.95 (t, 2H, J=7.5 Hz); 4.87–4.98 (m, 1H); 7.00 (s, 1H); 7.20 (br s, 2H); 9.02 (d, 1H, J=10 Hz); i.r. (KBr): 3330, 2970, 1730, 1657, 1534, 1407, 1386, 1320, 1289, 1130 cm$^{-1}$; m.s. (FAB): m/e=501 (M+); u.v.: (etOH) $\lambda$=303 nm ($\epsilon$=11800); 232 nm ($\epsilon$=15000); o.r.: (DMSO) −20.6° at 589 nm. |
| 149 | -allyl | —CH$_2$CH$_2$CH$_3$ | 300 MHz (DMSOd$_6$): $\delta$ 0.93 (t, 3H, J=10 Hz); 1.61 (q, 2H, J=10 Hz); 2.93 (dd, 1H, J=15, 10 Hz); 3.15–3.43 (m, 2H); 3.72 and 4.10 (ABq, 2H, J=10 Hz); 3.72 (t, 1H, J=6 Hz); 4.53 (d, 2H, J=5 Hz); 4.85–5.00 (m, 1H); 5.13 (d, 1H, J=10 Hz); 5.27 (d, 1H, J=20 Hz); 5.83–5.98 (m, 1H); 7.03 (s, 1H); 7.20 (br s, 2H); 9.07 (d, 1H, J=10 Hz); i.r. (KBr); 3420, 2980, 1717, 1658, 1534, 1411, 1380, 1280, 1129 cm$^{-1}$; m.s. (FAB): m/e=499 (M+); u.v.: (etOH) $\lambda$=304 nm ($\epsilon$=12100), $\lambda$=233 nm ($\epsilon$=15300); o.r.: (DMSO) −17.8° at 589 nm. |
| 150 | —CH$_2$CF$_3$ | —CH$_2$CH$_2$CH$_3$ | 300 MHz (DMSOd$_6$): $\delta$0.92 (t, 3H, J=10 Hz): 1.62 (q, 2H, J=10 Hz); 1.62 (q, 2H, J=10 Hz); 2.93 (dd, 1H, J=15, 10 Hz); 3.17–3.45 (m, 2H); 3.72 (t, 1H, J=10 Hz); 3.70 and 4.10 (ABq, 2H, J=10 Hz); 4.67 (q, 2H, J=10 Hz); 4.88–5.02 (m, 1H); 7.17 (s, 1H); 7.28 (br s, 2H); 9.20 (d, 1H); i.r. (KBr): 3490, 3390, 1717, 1657, 1535, 1409, 1280, 1163, 1130 cm$^{-1}$; m.s. (FAB): m/e=541 (M+); u.v.: (etOH) $\lambda$=307 nm ($\epsilon$=12300), $\lambda$=227 nm ($\epsilon$=16800); o.r.: (DMSO) −15.1° at 589 nm. |
| 151 | -cyclopropylmethyl- | —CH$_2$CH$_3$ | 300 MHz (DMSOd$_6$): $\delta$0.22–0.30 (m, 1H); 0.43–0.55 (m, 2H); 1.03–1.17 (m, 1H); 1.17 (t, 3H, J=10 Hz); 2.97 (dd, 1H, J=15, 10 Hz); 3.18–3.53 (m, 2H); 3.73 and 4.15 (ABq, 2H, J=10 Hz); 3.77 (t, 1H, J=10 Hz); 3.83–3.92 (m, 2H); 4.93–5.03 (m, 1H); 7.05 (s, 1H); 7.23 (br s, 2H); 9.05 (d, 1H, J=10 Hz); m.s. (FAB): m/e=499 (M+1); u.v.: (etOH) $\lambda$=300 nm ($\epsilon$=8230), $\lambda$=232 nm ($\epsilon$=10800). |
| 152 | —CH$_2$—S—CH$_3$ | —CH$_2$CH$_3$ | 300 MHz (DMSOd$_6$): $\delta$1.18 (t, 3H, J=10 Hz); 1.65 (s, 3H); 2.98 (dd, 1H, J=15, 10 Hz); 3.23–3.50 (m, 2H); 3.75 and 4.15 (ABq, 2H, J=10 Hz); 3.77 (t, 1H, J=10 Hz); 4.92–5.03 (m, 1H); 5.20 (s, 2H); 7.15 (s, 1H); 7.28 (br s, 2H); 9.13 (d, 1H, J=10 Hz); i.r. (KBr): 3430, 2900, 1730, 1653, 1576, 1537, 1413, 1304, 1132 cm$^{-1}$; m.s. (FAB): m/e=505 (M+); u.v.: (etOH) $\lambda$=303 nm ($\epsilon$=8930), $\lambda$=229 nm ($\epsilon$=12200); o.r.: (DMSO) −61.4° at 589 nm. |
| 153 | -allyl | -allyl | 300 MHz (DMSOd$_6$): $\delta$2.92 (dd, 1H, J=15, 10 Hz); 3.70 and 4.13 (ABq, 2H, J=10 Hz); 3.75 (t, 1H, J=10Hz); 4.02–4.23 (m, 2H); 4.58 (d, 2H, J=7.5 Hz); 4.90–5.02 (m, 1H); 5.13–5.47 (m, 4H); 5.70–5.85 (m, 1H); 5.85–6.03 (m, 1H); 7.07 (s, 1H); 7.25 (br s, 2H); 9.13 (d, 1H, J=10 Hz); i.r. (KBr): 3450, 1735, 1653, 1534, 1440, 1410, 1321, 1130 cm$^{-1}$; m.s. (FAB): m/e=497 (M+); u.v.: (etOH) $\lambda$=306 nm ($\epsilon$=11600), $\lambda$=232 nm ($\epsilon$=16100); o.r.: (DMSO) −149.6° at 589 nm. |
| 154 | —C(CH$_3$)$_2$—CO$_2$H | —CH$_3$ | 300 MHz (DMSOd$_6$): $\delta$1.35 (s, 3H); 1.42 (s, 3H); 2.95 (dd, 1H, J=15, 10 Hz); 3.18 (s, 3H); 3.72 (t, 1H, J=10 Hz); 3.80 and 4.12 (ABq, 2H, J=10 Hz); 4.88–5.03 (m, 1H); 6.80 (s, 1H); 7.20 (br s, 2H). |
| 155 | —CH$_2$CH$_2$CH=CH$_2$ | —CH$_3$ | 300 MHz (DMSOd$_6$): $\delta$2.27–2.38 (m, 2H); |

-continued

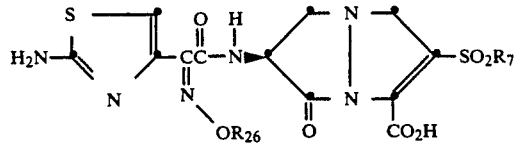

| Example | R26 | R7 | Physical Data |
|---|---|---|---|
|  |  |  | 2.90–3.00 (m, 1H); 3.15 (s, 3H); 3.72 (t, 1H, J=10 Hz); 3.82 and 4.10 (ABq, 2H, J=10 Hz); 4.03 (t, 2H, J=7.5 Hz); 4.87–5.13 (m, 3H); 5.68–5.88 (m, 1H); 7.00 (s, 1H); 7.22 (br s, 2H); 9.02 (d, 1H, J=10 Hz); i.r. (KBr): 3360, 1717, 1645, 1533, 1413, 1406, 1303, 1135 cm$^{-1}$; m.s. (FAB): m/e=485 (M+); u.v.: (etOH) λ=303 nm (ε=11800), λ=233 nm (ε14900); o.r.: (DMSO) −163.4° at 589 nm. |
| 156 | —C(CH$_3$)$_2$CO$_2$H | —CH$_3$ | 300 MHz (DMSOd$_6$): δ1.35 (s, 6H); 2.90–3.00 (m, 1H); 3.18 (s, 3H); 3.72 (t, J=6 Hz, 1H); 4.12 and 3.79 (ABq, J=10 Hz, 2H); 4.87–4.98 (m, 1H); 6.97 (s, 1H); 7.28 (br s, 2H); 8.90–9.00 (m, 1H); i.r. (KBr): 3340, 1718, 1645, 1534, 1403, 1384, 1320, 1302, 1137 cm$^{-1}$; m.s. (FAB): m/e= 539 (M+); u.v.: (etOH) λ$_{max}$=303 nm (ε=10,600), 210 nm (ε=15,800); o.r.: (DMSO) −94.8° at 589 nm. (Sodium salt by mass spectra). |

EXAMPLES 157 TO 170

In a manner similar to that of Examples 100, 101, 102, 103, 121, and Preparation 39 (for the synthesis of the chiral (S) diazolidinone of Preparation 39), the following compounds were synthesized. The same amino and carboxy protecting groups were utilized as described in Examples 126 to 155.

EXAMPLE 157

7-(S)-(Phenylthio)acetyl-3-cyano-8-oxo-1,5-diazabicyclo[3.3.0]octa-2-ene-2-carboxylic acid
m.p. (dec.) 75° C.

NMR: 300 MHz(DMSO d$_6$): δ 3.00 (dd, 1H, J=6, 12 Hz), 3.20–3.90 (m, 1H); 3.74 (s, 2H); 3.95 and 4.29 (ABq, 2H, J=12 Hz); 4.84–4.97 (m, 1H); 7.15–7.40 (m, 5H); 8.70 (d, 1H, J=9 Hz).

IR (KBr): 3360, 2220, 1740, 1665, 1530, 1440 cm$^{-1}$.
Mass Spectra (FD): m/e=358 (M+)
UV: (Ethanol) λ=333 nm (ε=7262)
OR: −377.4° at 589 nm (DMSO)
Elem. Anal.: (%) Calc'd: C, 53.62; H, 3.94; N, 15.63
Obs'd: C, 53.42; H, 4.16; N, 15.35

EXAMPLE 158

7-(S)-(2-aminothiazol-4-yl)acetyl-3-cyano-8-oxo-1,5-diazabicyclo[3.3.0]octa-2-ene-2-carboxylic acid NMR: 300 MHz (DMSO d$_6$): δ 3.00 (dd, 1H, J=9, 12 Hz); 3.37 (s, 2H); 3.74 (t, 1H, J=6 Hz); 4.24 and 3.93 (ABq, 2H, J=12 Hz); 4.81–4.96 (m, 1H); 6.33 (s, 1H); 7.07 (br s, 2H); 8.47 (d, 1H, J=9 Hz).

IR (KBr): 3292, 2220, 1720, 1640, 1561, 1404 cm$^{-1}$.
Mass Spectra (FAB): m/e=349 (M+1)
UV: (Ethanol) λ=330 nm (ε=5387); 252 nm (ε=5667)
OR: −77.7° at 589 nm (methanol)

EXAMPLE 159

7-(S)-[2-(2-Aminothiazol-4-yl)-2-(Z)-n-butyl-oxyiminoacetamido]-3-cyano-8-oxo-1,5-diazabicyclo[3.3.0]-octa-2-ene-2-carboxylic acid 300 MHz (DMSO d$_6$): δ 0.87 (t, 3H, J=10 Hz); 1.22–1.40 (m, 2H); 1.48–1.63 (m, 2H); 3.12 (dd, 1H, J=15, 10 Hz); 3.80 (t, 1H, J=10 Hz); 3.92–4.07 (m, 2H); 3.98 and 4.30 (ABq, 2H, J=12 Hz); 4.92–5.10 (m, 1H); 6.92 (s, 1H); 7.23 (br s, 2H); 9.10 (d, 1H, J=10 Hz).

IR (KBr): 3380, 2970, 2220, 1717, 1674, 1640, 1400, 1203, 1145 cm$^{-1}$.
Mass Spectra (FAB): m/e=434 (M+1)
UV: (Ethanol) λ=302 nm (ε=8290); λ=231 nm (ε=14866)
OR: −324.8° at 589 nm (DMSO)

EXAMPLE 160

7-(S)-[2-(2-Aminothiazol-4-yl)-2-(Z)-benzyl-oxyiminoacetamido]-3-cyano-8-oxo-1,5-diazabicyclo[3.3.0]-octa-2-ene-2-carboxylic acid NMR: 300 MHz (DMSO d$_6$): δ 3.10 (dd, 1H, J=15, 10 Hz); 3.80 (t, 1H, J=10 Hz); 3.95 and 4.27 (ABq, 2H, J=12 Hz); 4.97–5.10 (m, 1H); 5.13 (s, 2H); 6.98 (s, 1H); 7.23 (br s, 2H); 7.23–7.40 (m, 5H); 9.22 (d, 1H, J=10 Hz).

IR (KBR): 3340, 2230, 1677, 1608, 1534, 1409, 1205, 1136, 1015 cm$^{-1}$.
Mass Spectra (FAB): m/e=490 (M+23 (Na))
UV: (Ethanol) λ=304 nm (ε=8322)
OR: −317.0° at 589 nm (DMSO)

EXAMPLE 161

7-(S)(2,5-Dichlorophenyl)acetylamino-3-cyano-8-oxo-1,5-diazabicyclo[3.3.0octa-2-ene-2-carboxylic acid NMR: 300 MHz (DMSO d$_6$): δ 2.93 (dd, 1H, J=15, 10 Hz); 3.73 (t, 1H, J=8 Hz); 3.83 and 4.16 (ABq, 2H, J=12 Hz); 3.92 (d, 2H, J=3 Hz); 4.81–4.94 (m, 1H); 7.20–7.30 (m, 1H); 7.40–7.51 (m; 1H); 7.72–7.83 (m, 1H); 8.50 (d, 1H, J=10 Hz).

IR (KBr): 3340, 2220, 1725, 1675, 1609, 1450, 1410, 1035 cm$^{-1}$.
UV: (Ethanol) λ=332 nm (ε=7456); λ=255 nm (ε=9245); λ=220 nm (ε=28647)
OR: −164.7° at 589 nm (DMSO)

EXAMPLE 162

7-(S)-[2-(2-Aminothiazol-4-yl)-2-(Z)(2-chloro-eth-1-yl)oximinoacetamido]-3-cyano-8-oxo-1,5-diazabicyclo[e3.3.0]octa-2-ene-2-carboxylic acid NMR: 300 MHz (DMSO d$_6$): δ 2.98 (dd, 1H, J=10, 12 Hz); 3.73-3.80 (m, 1H); 3.77 (t, 2H, J=6 Hz); 3.73 and 4.09 (ABq, 2H, J=12 Hz); 4.26 (t, 2H, J=6 Hz); 4.90-5.03 (m, 1H); 7.10 (s, 1H); 7.26 (s, 2H); 9.12 (d, 1H, J=10 Hz).

IR (KBR): 3418, 2225, 1718, 1652, 1606, 1418, 1025, 673, 661 cm$^{-1}$.

Mass Spectra (FAB): m/e=400 (M+1)

UV: (Ethanol) λ=300 nm (ε=3990); λ=229 nm (ε=6930)

OR: −90.0783° at 589 nm (DMSO)

EXAMPLE 163

7-[[[(4-Ethyl-2,3-dioxo-1-piperazinyl)-carbonyl]amino]phenylacetyl]-(D)-amino-3-cyano-1,5-diazabicyclo[3.3.0]octa-2-ene-2-carboxylic acid NMR: 300 MHz (DMSO d$_6$): δ 1.08 (t, 3H, J=6 Hz); 2.75 (dd, 1H, J=10, 12 Hz); 3.39 (t, 1H, J=6 Hz); 3.52-3.60 (m, 2H); 3.61 (q, 2H, J=9 Hz); 3.72-4.02 (ABq, 2H, J=10 Hz); 3.83-3.96 (m, 2H); 4.76-4.91 (m, 1H); 5.54 (d, 1H, J=7 Hz); 7.24-7.52 (m, 5H); 9.10 (d, 1H, J=7 Hz); 9.84 (d, 1H, J=6 Hz).

IR (KBr): 3290, 2240, 1716, 1677, 1516, 1397, 1368, 1187 cm$^{-1}$.

Mass Spectra (FD): m/e=465 (M+−44) (CO$_2$)

UV: (Ethanol) λ=327 nm (ε=6224)

OR: −208.1° at 589 nm (DMSO)

EXAMPLE 164

7-(S)-Thienylacetyl)amino-3-cyano-8-oxo-1,5-diazabicyclo[3.3.0]octa-2-ene-2-carboxylic acid NMR: 300 MHz (DMSO d$_6$): δ 3.04 (dd, 1H, J=10 12 Hz); 3.75 (s, 2H); 3.77 (t, 1H, J=8 Hz); 4.02 and 4.31 (ABq, 2H, J=12 Hz); 4.82-4.98 (m, 1H); 6.88-7.00 (m, 2H); 7.32-7.42 (m, 1H); 8.66 (d, 1H, J=8 Hz).

IR (KBr): 3395, 2225, 1671, 1624, 1512, 1455, 1372, 1288, 1126, 943 cm$^{-1}$.

Mass Spectra (FD): 332 (M+)

UV: (Ethanol) λ=333 nm (ε=7804); 232 nm (ε=13,115)

OR: −753.0° at 589 nm (DMSO)

Elem. Anal.: Calc'd: C, 50.60; H, 3.64; N, 16.86 Obs'd : C, 50.84; H, 3.77; N, 16.58

EXAMPLE 165

7-(S)(Tetrazol-1-yl)acetylamino-3-cyano-8-oxo-1,5-diazabicyclo[3.3.0]octa-2-ene-2-carboxylic acid NMR: 300 MHz (DMSOd$_6$): δ 3.02 (dd, 1H, J=10, 12 Hz); 3.77 (t, 1H, J=9); 3.92 and 4.13 (ABq, 2H, J=12); 4.87-5.00 (m, 1H); 5.33 and 5.41 (ABq, J=16 Hz); 8.12 (s, 1H); 9.11 (d, 1H, J=8 Hz); 9.39 (s, 1H).

IR (KBr): 3288, 3150, 3090, 2225, 1700, 1674, 1605, 1559, 1431, 1211, 1170, 1104 cm$^{-1}$.

Mass Spectra (FD): m/e=274 (M+−44) (CO$_2$)

UV: (Ethanol) λ=329 nm (ε=11,485)

OR: −646.6 at 589 nm (DMSO)

EXAMPLE 166

7-(S)[2-(2-Aminothiazol-4-yl)-2-(Z)-(2-fluoroeth-1-yl)oximinoacetamido]-3-cyano-8-oxo-1,5-diazabicyclo[3.3.0]octa-2-ene-2-carboxylic acid NMR: 300 MHz (DMSO d$_6$): δ 2.98 (dd, 1H, J=10, 12); 3.73-3.79 (m, 1H); 3.72 and 4.09 (ABq, 2H, J=12 Hz); 4.27 (dt, 2H, J=30, 4); 4.62 (dt, 2H, J=48, 5 Hz); 4.90-5.03 (m, 1H); 7.09 (s, 1H); 7.25 (s, 2H); 9.12 (d, 1H, J=10 Hz).

IR (KBr): 3418, 2218, 1718, 1650, 1612, 1531, 1406, 1325, 1250, 1043 cm$^{-1}$.

Mass Spectra (FAB): m/e=424 (M+1)

UV: (Ethanol) λ=228 nm (ε=15,300); λ=302 nm (ε=8.800)

EXAMPLE 167

7-(S)-Phenylacetylamino-3-cyano-8-oxo-1,5-diazabicyclo[3.3.0]octa-2-ene-2-carboxylic acid NMR: 300 MHz (DMSO d$_6$): δ 2.98 (dd, 1H, J=10, 12 Hz); 3.51 (s, 2H); 3.70 (t, 1H, J=7 Hz); 3.90 and 4.13 (ABq, 2H, J=12 Hz); 4.76-4.94 (m, 1H); 7.10-7.40 (m, 5H); 8.64 (d, 1H, J=10 Hz).

IR (KBr): 3340, 3044, 3032, 2920, 2247, 1711, 1653, 1538, 1214, 730, 698 cm$^{-1}$.

Mass Spectra (FD): m/e=326 (M+)

UV: (Ethanol) λ=330 nm (ε=6980)

OR: −509.2° at 589 nm (DMSO)

Elem. Anal. Calc'd: C, 55.81; H, 4.68; N, 16.27 Obs'd : C, 55.66; H, 4.72; N, 16.30

EXAMPLE 168

7-(S)-[2-(2-Aminothiazol-4-yl)-2-(Z)-(2-bromoeth-1-yl)oximinoacetamido]-3-cyano-8-oxo-1,5-diazabicyclo[3.3.0]octa-2-ene-2-carboxylic acid NMR: 300 MHz (DMSO d$_6$): δ 3.01 (dd, 1H, J=10, 12 Hz); 3.63 (t, 2H, J=6 Hz); 3.73-3.80 (m, 1H); 3.73 and 4.09 (ABq, 2H, J=12 Hz); 4.31 (t, 2H, J=6 Hz); 4.90-5.03 (m, 1H); 7.10 (s, 1H); 7.26 (s, 2H); 9.11 (d, 1H, J=10 Hz).

IR (KBr): 3425, 2218, 1718, 1650, 1612, 1531, 1393, 1012 cm$^{-1}$.

Mass Spectra (FAB): m/e=484 (M$^+$+1), 486 (M$^+$+3)

UV: (Ethanol) λ=228 nm (ε=16,500); 340 nm (ε=9,400)

EXAMPLE 169

7-(S)-[2-(2-Aminothiazol-4-yl)-2-(Z)-(allyl)-oximinoacetamido]-3-cyano-8-oxo-1,5-diazabicyclo[3.3.0]-octa-2-ene-2-carboxylic acid NMR: 300 MHz (DMSO d$_6$): δ 2.99 (dd, 1H, J=10, 12 Hz); 3.76 (t, 1H, J=10 Hz); 4.09 and 3.72 (ABq, 2H, J=10 Hz); 4.57 (d, 2H, J=6 Hz); 4.86-5.06 (m, 1H); 5.17 (d, 1H, J=9 Hz); 5.23 (d, 1H, J=18 Hz); 5.96-6.02 (m, 1H); 7.06 (s, 1H); 7.23 (s, 2H); 9.12 (d, 1H, J=8 Hz).

IR (KBr): 3410, 2220, 1720, 1652, 1609, 1534, 1407, 1322, 1247, 1205, 1,120, 1019, 934 cm$^{-1}$.

Mass Spectra (FAB): m/e=418 (M$^+$+1)

UV: (Ethanol) λ=232 nm (ε=14,400); 301 nm (ε=8670)

OR: −240° at 589 nm (DMSO)

EXAMPLE 170

7-(S)-[2-(2-Aminothiazol-4-yl)-2-(Z)-(2-carboxyprop-2-yl)oximinoacetamido]-3-cyano-8-oxo-1,5-diazabicyclo[3.3.0]octa-3-ene-2-carboxylic acid NMR: 300 MHz (DMSO d$_6$): δ 1.34 (s, 3H); 1.38 (s, 3H); 3.13 (dd, 1H, J=10, 12 Hz); 3.63-3.76 (m, 1H); 3.69 and 4.05 (ABq, 2H, J=12 Hz); 4.86-5.00 (m, 1H); 6.80 (s, 1H); 7.15 (s, 1H).

UV (Ethanol) λ=215 nm (ε=16,600); 305 nm (ε=8290)

OR: −175.299° at 589 nm (DMSO)

EXAMPLE 171 t-Butyl-7-(S)-(t-butoxycarbonylamino)-3-carboxy-8-oxo-1,5-diazabicyclo[.3.3.0]octa-2-ene-2-carboxylate A 7.64 g (38 mMol) sample of 4-(S)-(t-butoxycarbonylamino)-1,2-diazolidine-3-one was suspended in 350 ml of $CH_2Cl_2$, cooled in an ice bath under $N_2$, and treated with 14.03 g of a crude mixture containing approximately 9.26 g (42 mMol) of 1-(allyloxycarbonyl)-1-dimethylphosphonato-ethene.

The reaction mixture was stirred overnight and allowed to warm to room temperature. The reaction mixture was then cooled in an ice bath and treated with 7.60 g (46 mMol) of oxalyl chloride and 9.6 ml of diisopropylethylamine (dropwise addition) in 40 ml of $CH_2Cl_2$. After about 30 minutes, an additional 8.5 ml of diisopropylethylamine was dissolved in 40 ml of $CH_2Cl_2$ and added dropwise. After stirring for an additional 5 h at room temperature, the $CH_2Cl_2$ was removed in vacuo and the crude product redissolved in 300 ml of ethyl acetate.

The ethyl acetate solution was then washed sequentially with 150 ml saturated $NaHCO_3$, 1N HCl (2× 150 ml), brine (3×150 ml) and dried over anhydrous $Na_2SO_4$. Removal of solvent in vacuo and preparativescale liquid chromatography (normal phase silica gel) provided 9.27 g (58% of t-butyl-7-(S)-(t-butoxycarbonylamino)-3-allyloxycarbonyl-8-oxo-1,5-diazabicyclo[3.3.0]-octa-2-ene-3-carboxylate.

OR: −387.1° (methanol) 589 nm
Mass Spectra (FD): m/e=423
NMR: 90 MHz ($CDCl_3$): δ 5.9, m, 1H; 5.2, bd, 2H, J=7 Hz; 5.08, m, 3H; 4.8, m, 3H; 4.3, d, 1H, J=13; 3.98, t, 1H, J=8; 3.94, d, 1H, J=13; 2.8, dd, 1H, J=7, J=10; 1.58, s, 9H; 1.44, s, 9H.

Under a nitrogen atmosphere, a 0.87 g (3.9 mM) sample of palladium acetate and 5.06 g (19.3 mM) sample of triphenylphosphine was combined in 250 ml of $CH_3CN$ and stirred for 20 min. A 20.51 g (48.5 mMol) sample of the 3-allyl carboxylate prepared above was dissolved in 350 ml of $CH_3CN$ and added to the reaction mixture and stirred for 35 min. The reaction mixture was then cooled to about 0° C. and treated with 8.5 ml (53.3 mM) of triethylsilane. Stirring was continued for 40 min. and the reaction mixture was allowed to warm to room temperature over a 5½ h period. The reaction mixture was then cooled in an ice bath and treated with 245 ml of 0.2N HCl and stirred for 5 min. The crude mixture was then diluted with 1.5 l of ethyl acetate and washed with 500 ml $H_2O$ (and brine). The aqueous washes were back-extracted with ethyl acetate and the combined organics washed with brine (2×500 ml), dried over anhydrous $MgSO_4$, and evaporated to provide 26 g of crude product. Preparative-scale liquid chromatography yielded 15.46 g of the title compound (83%).

OR: −319.0° at 589 nm (methanol)
NMR: 90 MHz ($CDCl_3$): δ 5.15, d, 1H, J=6 Hz; 4.7, m, 1H; 4.36, d, 1H, J=12 Hz; 4.01, dd, 1H, J=7 Hz, J=9 Hz; 3.84, d, 1H, J=12 Hz; 2.84, dd, 1H, J=9 H, J=11 Hz; 1.56, s, 9H; 1.44, s, 9H.

EXAMPLE 172 t-Butyl-7-(S)-(t-butoxycarbonylamino)-3-amino-8-oxo-1,5-diazabicyclo[3.3.0]octa-2-ene-2-carboxylate A. Under a nitrogen atmosphere, a 14.31 g (37.4 mMol) sample of the 3-carboxy nucleus synthesized in Example 171 was dissolved in 150 ml of $CH_2Cl_2$ and 1 l of benzene. The solution was then treated with 8.9 ml (1.1 molar equivalents) of diphenylphosphoryl azide and 7.2 ml (1.1 molar equivalents) of diisopropylethylamine and refluxed for 1 h. The reaction mixture was then treated with 5.4 ml (1.4 molar equivalents) of benzyl alcohol and refluxed for 3 h.

The volume was reduced in vacuo to remove the $CH_2Cl_2$ and washed sequentially with $H_2O$ (2×800 ml), saturated $NaHCO_3$ (500 ml), 0.2NHCl (2×500 ml) and brine (2×500 ml) and dried over anhydrous $MgSO_4$. The crude product solution was filtered and the solvent removed in vacuo to provide 20.4 g of crude product. Preparative scale liquid chromatography provided 7.59 g (42%) of t-butyl-7-(S)-(t-butoxycarbonylamino)-3-benzyloxycarbonylamino-8-oxo-1,5-diazabicyclo[3.3.0]octa-2-ene-3-carboxylate.

NMR: 90 MHz ($CDCl_3$): δ 9.05, bs, 1H; 7.28, s, 5H; 5.1, m, 1H; 5.08, s, 2H; 4.8, d, 1H, J=14 Hz; 4.55, m, 1H; 4.02, dd, 1H, J=9 Hz, J=11 Hz; 3.96, d, 1H, J=14 Hz; 2.66, dd, 1H, J=8 Hz, J=11 Hz; 1.5, s, 9H; 1.4, s, 9H.

B. A 3.94 g (8.07 mMol) sample of the compound prepared above in Part A was dissolved in 70 ml of ethyl acetate and hydrogenated for 90 min. at 48 psi of $H_2$ using 3.0 g of 5% Pd/C as catalyst. The catalyst was filtered off and the solvent removed in vacuo to provide 2.72 g (95% yield) of the title compound.

NMR: 90 MHz ($CDCl_3$): δ 5.48, bs, 2H, 5.24, m, 1H; 4.5, m, 1H; 4.04, t, J=7 Hz; 3.92, d, 1H, J=14 Hz; 3.56, d, 1H, J=14 Hz; 2.6, dd, 1H, J=9 Hz, J=11 Hz; 1.5, s, 9H; 1.4, s, 9H.

OR: +10.7° at 589 nm (methanol)

EXAMPLE 173 t-Butyl-7-(S)-(t-butoxycarbonylamino)-3,8-dioxo-1,5-diazabicyclo[3.3.0]octane-2-carboxylate A 790 mg (2.2 mMol) sample of the 3-amino nucleus prepared in Example 172 was dissolved in 27 ml of tetrahydrofuran, cooled in an ice bath and treated with 54 ml of 0.01N HCl. The pH of the solution was adjusted to pH 2.3 with 1N HCl. After about 12 min. the pH was adjusted to 5.3 with $NaHCO_3$, diluted with brine and extracted with $CHCl_3$ (5×100 ml). The combined organics were washed with $NaHCO_3$ (150 ml), 0.2N HCl (2×150 ml), brine (3×150 ml), dried over $MgSO_4$ and filtered and the solvent was removed in vacuo to provide 539 mg of the title compound.

Elemental Analysis: Theory: C, 54.07; H, 7.09; N, 11.82 Found: C, 54.31; H, 7.26; N, 11.78
Mass Spectra (FD): m/e=355
NMR: 90 MHz ($CDCl_3$): δ 5.12, bd, 1H; 4.8, s, 1H; 4.64, m, 1H; 4.64, m, 1H; 4.32, T, 1H, J=9 Hz; 3.82, d, 1H, J=15 Hz; 3.16, d, 1H, J=15 Hz; 2.86, T, 1H, J=9 Hz; 1.5, s, 9H; 1.46, s, 9H.
OR: +76.4° at 589 nm (methanol)

EXAMPLE 174 t-Butyl-7-S-(t-butoxycarbonylamino)-3-methoxy-carbonylamino-8-oxo-1,5-diazabicyclo[3.3.0]octa-2-ene-2-carboxylate Under a nitrogen atmosphere, a 1.15 g (3 mMol) sample of the 3-carboxy nucleus prepared in Example 171 was dissolved in 12 ml of $CH_2Cl_2$ and 120 ml of benzene. The solution was then treated with 0.72 ml (1.1 molar equivalents) of diphenylphosphoryl azide and 0.46 (1.1 molar equivalents) of triethylamine.

The reaction mixture was refluxed for 50 min. and then treated with 0.6 ml of methanol. After 70 min., an additional 0.6 ml of methanol was added and refluxing continued for 2 h. The reaction mixture was then diluted with ethyl acetate and washed with saturated NaHCO$_3$ solution (2×100 ml). The aqueous portion was back-extracted with ethyl acetate and the combined organics washed with H$_2$O (1,×100 ml) and brine (2×100 ml). The organic layer was then dried over anhydrous Na$_2$SO$_4$, filtered, and concentrated to provide 1.55 g of crude product. Liquid chromatography (1:1/ethyl acetate/hexane) provided 794 mg (64%) of the title compound.

OR: −74.1° at 589 nm (methanol)
Elemental Analysis:
Theory: C, 52.42; H, 6.84; N, 13.58
Found: C, 52.14; H, 6.72; N, 13.45
Mass Spectra (FD): m/e412
UV: max at 327 and 236
NMR: 300 MHz (CDCl$_3$): δ 9.1, bs, 1H; 4.98, m, 1H; 4.86, d, 1H; J=14 Hz; 4.66, m, 1H; 4.13, T, J=9 Hz; 3.96, d, 1H, J=14 Hz; 3.76, s, 3H; 2.69, dd, 1H, J=9 Hz, J=11 Hz; 1.54, s, 9H; 1.45, s, 9H.

EXAMPLE 175

7-(S)-[2-(2-Aminothiazol-4-yl)methoxyiminoacetamido]-3-methoxycarbonylamino-8-oxo-1,5-diazabicyclo[3.3.0]octa-2-ene-2-carboxylic acid The protected 3-methoxycarbonylamino nucleus prepared in Example 174 was treated with acetic acid/HCl (3.4 Mol) to provide the zwitterion.

Under a nitrogen atmosphere, a 0.64 mMol sample of 7-(S)-amino-3-methoxycarbonylamino-8-oxo-1,5-diazabicyclo[3.3.0]octa-2-ene-2-carboxylic acid was suspended in 10 ml of CH$_3$CN and cooled in an ice bath. The nucleus suspension was then treated with 0.15 ml of diisopropylethylamine followed by 0.24 ml of MSTFA. The reaction solution was then treated with 224 mg of the hydroxybenzotriazole ester of 2-(2-aminothiazol-4-yl)-oximinoacetic acid. Another 0.24 ml of MSTFA was added along with an additional 0.18 ml of diisopropylethylamine and the solution was allowed to warm to room temperature and stirred for 16 h.

The reaction mixture was then treated with 0.5 ml methanol and concentrated in vacuo and then triturated with ether/hexane to provide 477 mg of a brown solid. Reverse-phase (0–20% CH$_3$CN/H$_2$O gradient) liquid chromatography provided 61 mg of the title compound.

Elemental Analysis:
Theory: C, 41.00; H, 3.90; N, 22.31
Found: C, 39.50; H, 3.86, N, 21.40
Mass Spectra (FD): m/e=440
NMR: 300 MHz (CDCl$_3$): 6 9.5, bs, 1H; 9.07, d, 1H, J=9 Hz; 7.17, bs, 2H (NHz); 6.97, s, 1H; 4.94, m, 1H; 4.57, 1H, J=15 Hz; 4.11, d, 1H, J=15 Hz; 3.78, s, 3H; 3.66, s, 3H; 3.11, T, 1H, J=9 Hz.

EXAMPLE 176 t-Butyl-7-(S)-(t-butoxycarbonylamino)-3-methylaminocarbonylamino-8-oxo-1,5-diazabicyclo[3.3.0]-octa-2-ene-2-carboxylate Under a nitrogen atmosphere, a 766 mg (2 mM) sample of the 3-carboxy nucleus prepared in Example 171 was dissolved in 8 ml of CH$_2$Cl$_2$ and treated with 0.47 ml (2.2 mM) of diphenylphosphorylazide followed by 0.24 ml (2.2 mM) of N-methyl morpholine. The reaction mixture was diluted with 80 ml of benzene and refluxed for 3 h. The reaction mixture was allowed to cool to room temperature over a 1 h period and treated with a solution composed of 0.35 ml of diisopropylethylamine (dissolved in 10 ml CH$_2$Cl$_2$) and 135 mg (2 mM) of methylamine hydrochloride.

The reaction mixture was stirred for 16 h, concentrated in vacuo and diluted with ethyl acetate. The crude product solution was then washed with 50 ml of saturated NaHCO$_3$ solution, which was, in turn, back extracted with ethyl acetate. The combined organics were washed with H$_2$O (1×50 ml), 0.2 N HCl (2×50 ml), and brine (2×50 ml). The organic layer was then dried over anhydrous Na$_2$SO$_4$, filtered, and concentrated in vacuo to provide 866 mg of a yellow oil. Purification by liquid chromatography (5:1/ethyl acetate/hexane) provided 139 mg (17% yield) of the compound.

Elemental Analysis:
Theory: C, 52.54; H, 7.10; N, 17.02
Found: C, 52.36; H, 6.83; N, 16.95
Mass Spectra (FD): m/e=411
NMR: 90 MHz (CDCl$_3$): δ 9.04, s, 1H; 5.25, m, 2H; 4.28, d, 1H, J=14 Hz; 4.8 m, 1H; 4.00, m, 1H; 3.88, d, 1H, J=14 Hz; 2.8, d, 3H, J=6 Hz; 2.04, dd, 1H, J=9 Hz, J=11 Hz; 1.52, s, 9H; 1.44, s, 9H.
OR: −113.4° at 589 nm (methanol)

EXAMPLE 177 t-Butyl-7-(S)-(t-butoxycarbonylamino)-3-methylthiocarbonylamino-8-oxo-1,5-diazabicyclo[3.3.0]-octa-2-ene-2-carboxylate A 766 mg (2 mM) sample of the 3-carboxy nucleus prepared by the method of Example 171 was dissolved in 8 ml of CH$_2$Cl$_2$ and treated with 0.47 ml (2 mM) of diphenylphosphoryl azide followed by 0.24 ml of N-methyl morpholine. The reaction mixture was diluted with 80 ml of benzene and refluxed for about 4 h. The reaction mixture was then cooled to room temperature and treated with an excess of methanethiol and stirred for 16 h.

The reaction mixture was then concentrated in vacuo and redissolved in 100 ml of ethyl acetate. The ethyl acetate solution was then washed sequentially with saturated NaHCO$_3$ solution (2×50 ml), H$_2$O (1×50 ml), 0.2N HCl (2×50 ml), and brine (2×50 ml), dried over anhydrous Na$_2$SO$_4$, filtered and concentrated in vacuo to provide 2.36 g of a yellow oil. The crude product was purified by liquid chromatography using 95% CH$_2$Cl$_2$/5% acetone as eluent to provide 95 mg of the title compound.

Mass Spectra (FD): m/e=428
NMR: 90 MHz (CDCl$_3$): δ 9.56, bs, 1H; 5.08, m, 1H; 5.8, d, 1H; J=14 Hz, 4.56, m, 1H; 4.01, dd, J=8 Hz, J=10 Hz; 3.96, 1H, J=14 Hz; 2.62, dd, 1H, J=9 Hz, J=11 Hz; 2.36, s, 3H; 1.5, s, 9H, 1.4, s, 9H.

EXAMPLE 178 t-Butyl-7-(S)-t-butoxycarbonylamino)-3-2-tetrazolo-8-oxo-1,5-diazabicyclo[3.3.0]octa-3-ene-2-carboxylate Under a nitrogen atmosphere, an 88 mg sample (0.25 mM) of the 3-keto nucleus prepared by the procedure in Example 173 was dissolved in 10 ml of dry CH$_2$Cl$_2$, cooled in an ice bath and treated with 0.109 ml (0.625 mM) of diisopropylethylamine followed by 0.046 ml (0.275 mM) of triflic anhydride. The reaction mixture was allowed to stir for about 30 min. and allowed to warm to room temperature.

The reaction mixture was then treated with 19 mg (0.25 mM) of 1H-tetrazole and allowed to stir for 64 h.

The reaction mixture was then concentrated in vacuo and redissolved in ethyl acetate. The ethyl acetate solution was washed sequentially with 0.1N HCl (2×10 ml), H$_2$O (1×10 ml), and brine (1×10 ml). The ethyl acetate solution was then dried over anhydrous Na$_2$SO$_4$, filtered and concentrated in vacuo to provide 87 mg of crude product. Purification by liquid chromatography (3:2/ethyl acetate/hexane) provided 8 mg of the title compound.

Mass Spectra (FD): m/e=407

NMR: 90 MHz (CDCl$_3$): δ 9.68, s, 1H; 5.08, m, 1H; 4.96, d, 1H, J=14; 4.66, 1H; 4.16, d, 1H, J=14; 4.14, dd, 1H, J=7 Hz, J=10 Hz; 2.86, dd, 1H, J=7 Hz, J=10 Hz; 1.56, s, 9H; 1.44, s, 9H.

EXAMPLE 179 t-Butyl-7-(S)-(t-butoxycarbonylamino)-3-phenylsulfonyl-3-oxo-1,5-diazabicyclo[3.3.0]octa-3-ene-2-carboxylate Under a nitrogen atmosphere, a 104 mg (0.3 mM) sample of the 3-keto nucleus prepared in Example 173 was dissolved in 10 ml of dry CH$_2$Cl$_2$, cooled in an ice bath, and treated with 0.68 ml (0.39 mM) of diisopropylethylamine followed by 0.055 (0.33 mM) triflic anhydride and stirred for about 45 min. The CH$_2$Cl$_2$ was removed in vacuo and the residue was dissolved in 10 ml of dry DMF.

The reaction mixture was then treated with 56 mg (0.33 mM) of sodium benzyl sulfinate and stirred for about 5 h at room temperature. An additional 20 mg of sodium benzenesulfinate was added and the reaction mixture stirred for 16 h.

The reaction mixture was concentrated in vacuo and redissolved in ethyl acetate (50 ml), the ethyl acetate solution was washed with H$_2$O w (2×30 ml) (+50 ml of brine). The H$_2$O washes were backextracted and the combined organics washed with 0.1N HCl, brine, and dried over anhydrous MgSO$_4$. Filtration and concentration in vacuo provided 140 mg of crude product. Purification by liquid chromatography (1:1/hexane/ethyl acetate) provided 53 mg of the title compound.

Mass Spectra (FD): m/e=479

NMR: 90 MHz (CDCl$_3$)δ 7.9, m, 2H; 7.5, m, 3H; 4.96, d, 1H, J=5 Hz; 4.6, m, 1H; 4.24, d, 1H, J=14 Hz; 3.9, dd, 1H, J=7 Hz, J=9 Hz; 3.7, d, 1H, J=14 Hz; 2.76, dd, 1H, J=7 Hz, J=10 Hz; 1.64, s, gH; 1.4, s, 9H.

EXAMPLE 180 t-Butyl-7-(S)-(t-butoxycarbonylamino)-3-chloro-8-oxo-1,5-diazabicyclo[3.3.0]octa-3-ene-2-carboxylate Under a nitrogen atmosphere, a 0.25 mMol sample of the 3-keto nucleus prepared by the procedure of Example 173 was dissolved in 10 ml of dry CH$_2$CH$_2$ and cooled in an ice bath. The CH$_2$Cl$_2$ solution was treated with 0.057 ml (0.325 mM) of diisopropylethylamine followed by 0.044 ml (0.26 mM) of triflic anhydride. After 45 min., the reaction mixture was treated with 76 mg (0.275 mM) of tetrabutyl ammonium chloride and allowed to warm to room temperature. After 1 h, another 76 mg (0.275 mM) of tetrabutyl ammonium chloride was added and the reaction mixture stirred for 3 days.

The reaction mixture was then concentrated in vacuo and redissolved in 15 ml of ethyl acetate. The ethyl acetate solution was washed with H$_2$O (2×10 ml) and brine (2×10 ml), dried over anhydrous MgSO$_4$, filtered and concentrated in vacuo to provide 186 mg of crude product. Purification by liquid chromatography using 2:1 hexane/ethyl acetate as eluent provided 10 mg of the title compound.

Mass Spectra (FD): 373 and 390

Elemental Analysis:

Theory: Cl, 9.48

Found : Cl, 9.65

NMR: 90 MHz (CDCl$_3$):δ 5.1, 1, d, 1H, J=5 Hz; 4.56,m, 1H; 4.12, d, 1H, J=13 Hz; 4.04, T, 1H, J=8 Hz; 3.76, d, 1H, J=13 Hz; 2.7, dd, J=7 Hz, J=9 Hz; 1.52, s, 9H; 1.4, s, 9H.

EXAMPLE 181 t-Butyl-7-(S)-(t-butoxycarbonylamino)-3-(5-methyl-1,3,4-thiadiazol-2-yl)thiol-8-oxo-1,5-diazabicyclo[3.3.0]octa-3-ene-2-carboxylate Under a nitrogen atmosphere, a 710 mg (2 mM) sample of the 3-keto nucleus prepared by the procedure of Example 173 was dissolved in 80 ml of dry CH$_2$Cl$_2$ (cooled in an ice bath) and treated with 0.87 ml (5 mM) of diisopropylethylamine followed by 0.37 ml (2.2 mM) of triflic anhydride. The reaction mixture was stirred for 45 minutes in an ice bath and treated with 290 mg of 2-methylthia-3,4-diazol-5-thiol and stirred for an additional 30 min. The reaction mixture was then allowed to warm to room temperature and stirred for 4 h.

The reaction mixture was then concentrated in vacuo and redissolved in 100 ml of ethyl acetate. The ethyl acetate solution was washed with H$_2$O (2×50 ml), saturated NaHCO$_3$ solution (1×50 ml), 0.1 N HCl (2×50 ml), and brine (2×50 ml).

The ethyl acetate solution was then dried over anhydrous Na$_2$SO$_4$, filtered, and concentrated to provide 0.84 g of crude product. Purification by liquid chromatogjraphy using 4:1 ethyl acetate/hexane as eluent provided 460 mg (49% yield) of the title compound.

Elemental Analysis: Theory: C, 48.60; H, 5.80; N, 14.91 Found : C, 47.65; H, 5.37; N, 14.15

Mass Spectra (FD): m/e=469

NMR: 90 MHz (CDCl$_3$):δ 5.1, d, 1H, J=6 Hz; 4.64, m, 1H; 4.18, d, 1H, J=14 Hz; 4.02, dd, 1H, J=7 Hz, J=9 Hz; 3.8, d, 1H, J=14 Hz; 2.98, s, 3H; 2.7, dd, 1H, J=7 Hz, J=9 Hz; 1.56, s, 9H; 1.44, s, 9H.

EXAMPLE 182

7-(S)-[2-(2-Aminothiazol-4-yl)methoxyiminoacetamido]-3-(-methyl-13,4-thiadiazol-2-yl)thiol-8-oxo-1,5-diazabicyclo[3.3.0]octa-3-ene-2-carboxylic acid The nucleus prepared in Example 181 was deprotected and acylated according to the procedure outlined in Example 175 to provide the title compound.

NMR: 300 MHz (DMSO d$_6$):δ 9.05, d, 1H, J=9 Hz; 7.17, bs, 2H (NHz); 6.93, s, 1H; 4.95, m, 1H; 4.02, d, 1H, J=12 Hz; 3.82, d, 1H, J=12 Hz; 3.82, dd, 1H, J=7Hz, J=9 Hz; 3.77, s, 3H; 2.98, dd, 1H, J=7 Hz, J=9 Hz; 2.70, s, 3H.

EXAMPLE 183

Allyl-7-(R,S)-(t-butoxycarbonylamino)-3-dimethylaminosulfonyl-8-oxo-1,5-diazabicyclo[3.3.0]octa-3-ene-2-carboxylate A. Preparation of 1,1-diethylphosphonato, dimethylaminosulfonyl-ethene Under a nitrogen atmosphere, a solution of 9.84 g of dimethylaminomethanesulfonamide in 75 ml of tetrahydrofuran was cooled to −78° C. and treated with 50 ml of a 1.6N solution of n-butyl lithium and the resulting mixture stirred for 1 h. The resultant solution was slowly added to a solution of 13.8 g of diethylchlorophosphate dissolved in 50 ml of tetrahydrofuran. The reaction was maintained at −78° C. for 2 h and the allowed to warm to room temperature over a 2 h period. The solvent was removed in vacuo and the residue triturated with 3×75 ml of hexane. The resulting crude product was purified by preparative scale HPLC using a gradient elution of 50/50 toluene/ethyl acetate to 100% ethyl acetate to provide 2.9 g of diethylphosphonato, dimethylamino sulfonyl methane.

Elemental Analysis: Theory: C, 32.43; H, 7.00; N, 5.40 Found : C, 32.18; H, 6.89, N, 5.19

IR (cm$^{-1}$) (CHCl$_3$): 1052, 1160.7, 1258, 1345

NMR: 300 MHz (CDCl$_3$):δ 4.24, m, 4H; 4.34, d, 2H, J=17 Hz; 3.96, s, 6H; 1.38, T, 3H, J=6 Hz.

A mixture of 0.400 g of paraformaldehyde, 0.094 g of pyrrolidine in a mixture of 20 ml of benzene and 10 ml of glacial acetic acid was refluxed for 20 min. Next, a 2.59 g sample of diethylphosphonato dimethylsulfonylaminomethane was added and refluxing continued for 5 h.

The reaction mixture was then concentrated in vacuo and the product determined to contain 70-80% of vinyl phosphonate by NMR. The crude product was purified by liquid chromatography using ethyl acetate as eluent to provide the title compound for Part A.

Elemental Analysis: Theory: C, 35.42; H, 6.69; N, 5.16 Found : C, 35.20; H, 6.70; N, 5.09

NMR: 300 MHz (CDCl$_3$):δ 6.76-6.88, m, 2H; 4.22, m, 4H; 3.9, s, 6H (N—(CH$_3$)$_2$); 1.97, T, 3H, J=6 Hz.

B. Synthesis of 3-dimethylaminosulfonyl nucleus

A 0.43 g sample of 4-(S)-(t-butoxycarbonylamino)-3-oxo-1,2-pyrazolidine was suspended in 25 ml of CH$_2$Cl$_2$, cooled in an ice bath, and treated with a 0.592 g sample of the vinyl phosphonate prepared in Part A above, dissolved in 5 ml of CH$_2$Cl$_2$ and stirred at 0° for 2.5 hr. The reaction mixture was then treated with 0.357 g of allyl oxallyl chloride dissolved in 3 ml of CH$_2$Cl$_2$ followed by 0.765 ml of diisopropylethylamine and stirred at 0° C for 2.5 h. The reaction mixture was then cooled to −20° C and treated with 0.329 ml of DBU and stirred for 20 min. At this time, another 0.329 ml of DBU was added and the reaction allowed to warm to about 0° C over 50 min.

The reaction mixture was concentrated in vacuo and redissolved in 75 ml of ethyl acetate. The ethyl acetate solution was washed sequentially with 0.2N HCl (3×40 ml), saturated NaHCO$_3$ solution (2×40 ml), and brine (2×50). The ethyl acetate solution was then dried over anhydrous Na$_2$SO$_4$, filtered, and concentrated in vacuo to provide 1.05 g of crude product. Purification by liquid chromatography (1:1/ethylacetate/hexane) provided 0.442 g of the title compound.

Elemental Analysis: Theory: C, 47.43; H, 6.09; N, 13.02 Found : C, 47.30; H, 5.83; N, 12.89

Mass Spectra (FD): m/e=430, 431

NMR: 300 MHz (CDCl$_3$):67 5.98, m, 1H; 5.38, dd, 2H, J=15 Hz, J=11 Hz; 5.14, d, 1H, J=8 Hz; 4.94, d, 2, J=8 Hz; 4.74, m, 1H; 4.37, d, 1H, J=12 Hz; 4.06, T, 1H, J=9 Hz; 3.95, d, 1H, J=12 Hz; 2.93, m, 1H; 2.9, s, 6H; 1.47, s, 9H.

EXAMPLE 184

7-(R,S)-[2-Aminothiazol-4-yl)-2-(Z and E)-methoxyiminoacetamido]-3-dimethylaminosulfonyl-8-oxo-1,5-diazabicyclo[3.3.0]octa-3-ene-2-carboxylic acid A. Deprotection of 7-amino group A 0.345 g sample of the protected nucleus prepared by the method in Example 183 was deprotected by treatment with 15 ml of 3M HCl (in glacial acetic acid). Removal of solvent in vacuo provided the 7-(R,S)-amine hydrochloride to be used directly in Step B below.

B. Acylation

Under a hydrogen atmosphere, a 29% mg sample of 2-(2-allyloxycarbonylaminothiazol-4-yl)methoximino acetic acid was suspended in 10 ml of CH$_2$Cl$_2$ and treated with 0.105 ml of N-methyl morpholine and cooled to 0° C. The resulting solution was treated with 90 ψ1 of POCl$_3$ and stirred for 7 min. The reaction mixture was then treated with 294 mg of the nucleus hydrochloride (prepared in Part A), dissolved in 3 ml of CH$_2$Cl$_2$, followed by 0.292 g of N-methylmorpholine and stirring was continued for 2 h at 0° C. The CH$_2$Cl$_2$ was removed in vacuo and the residue redissolved in 75 ml of ethyl acetate. The ethyl acetate solution was then washed sequentially with 0.2N HCl, 0.1N HCl (2×25 ml), saturated NaHCO$_3$ solution (2×25 ml), and brine (2×25 ml). The ethyl acetate solution was then dried over anhydrous Na$_2$SO$_4$, filtered, and concentrated in vacuo to provide 420 g of crude product. Purification by liquid chromatography using ethyl acetate as eluent provided 326 mg of allyl-7-(R,S)-[2-(2-allyloxycarbonylaminothiazol-4-yl]methoxyimino-8-oxo-3-methylsulfonylamino-1,5-diazabicyclo[3.3.0]octa-3-ene-2-carboxylate.

Elemental Analysis: Theory: C, 44.22; H, 4.55; N, 16.41 Found : C, 44.14; H, 4.49; N, 16.48

Mass Spectra (FD): m/e=597, 598

NMR 300 MHz (DMSO d$_6$):δ 9.35, d, 1H, J=9 Hz; 7.42, s, 1H; 5.94, m, 2H, 5.46, bd, 2H, J=14 Hz; 5.3, m, 3H; 5.1, m, 1H; 4.78, T, 2H, J=6 Hz; 4.68, d, 2H, J=6 Hz; 4.32, d, 1H, J=12 Hz, 4.12, d, 1H, J=12 Hz; 3.88, s, 3H (OCH$_3$); 3.86, m, 1H; 3.25, T, 1H, J=9 Hz; 2.83, s, 6H (N(CH$_3$)$_2$).

C. Final deprotection

Under a nitrogen atmosphere, a 15 mg sample of palladium acetate was suspended in 3 ml of acetone and treated with 93.5 mg of triphenylphosphine and an additional 3 ml of acetone and stirred for 30 min. The reaction mixture was then treated with a 300 mg sample of the diprotected product from Part B above, dissolved in 20 ml of acetone. After stirring for 35 min., the reaction mixture was cooled in an ice/ethanol bath and treated with 0.279 ml of tri-butyl tin hydride and stirred at 0° C for 2 h, followed by stirring at room temperature for 2 h.

The reaction mixture was then cooled to 0° C. and treated with 1.005 ml of 1N HCl and stirred for 10 min. at 0° C. After an additional 15 min. at room temperature, the reaction mixture was diluted with 100 ml of H$_2$O, filtered through Celite ™, and extracted (3×50 ml) with hexane. The aqueous portion was again filtered through Celite and concentrated in vacuo. The aqueous solution was then extracted with diethyl ether (2×70 ml). The aqueous portion was then freeze-dried to provide 175 mg of crude product. Purification by liquid chromatography using 92:8:1 of acetonitrile/H$_2$O/acetic acid provided 109 mg of the title compound.

Elemental Analysis: Theory: C, 38.05; H, 4.04; N, 20.7 Found : C, 34.25; H, 3.81; N, 15.77

NMR: 300 MHz (D$_2$O):δ 7.08, s, 1H; 5.15, dd, 1H, J=8 Hz, J=12 Hz; 4.35, d, 1H, J=12 Hz; 4.05, d, 1H, J=12 Hz; 4.03, m, 1H; 3.99, s, 3H; 3.33, T, J=9; 2.9, s, 6H (N-(CH$_3$)$_2$).

EXAMPLE 185

Sodium 7(R,S)-[2-(2-aminothiazol-4-yl)-2-(Z)-(methoximinoacetyl)amino]-8-oxo-3-(2-methoximino)methyl-1,5-diazabicyclo[3.3.0]octa-2-ene-2-carboxylate A. Preparation of 2-(diethylphosphonato)-3-methoximino)-2-propene A 1.1 g sample of 1-(diethylphosphonato)-acetaldehyde was dissolved in 5 ml of methanol containing 0.84 g of granular potassium carbonate. A 0.5 g sample of methoxyamine hydrochloride was added and the reaction mixture refrigerated for 3 days. The methanol layer was decanted, concentrated in vacuo and the residue purified by liquid chromatography (3% methanol/$CH_2Cl_2$) to provide 0.75 g of a yellow oil.

A solution of 1.6 ml of glacial acetic acid, 10 ml of benzene, 0.14 g of paraformaldehyde, and 0.39 ml of pyrrolidine was refluxed for 10 min. The mixture was then cooled to 0° C and treated with 0.75 g of the yellow oil (oxime) prepared above. The reaction mixture was then refluxed for 20 min. utilizing a Dean-Stark trap. Removal of solvent in vacuo provided 1.8 g which was used directly in Part B.

B. (4-t-Butoxycarbonylamino)-1,2-diazolidin-3-one-1-(3'-methoximino-2'-diethylphosphonato-1-yl)

A 0.9 g sample of (4-t-butoxycarbonylamino)-1,2-diazolidine-3-one and the vinyl phosphonate prepared in Part A above was dissolved in 20 ml of methanol and stirred for approximately 16 h under nitrogen. Methanol was removed in vacuo and the residue purified by flash chromatography (10% methanol ($CH_2Cl_2$)) to provide 0.62 g of the title compound.

C. Allyl 7-(R,S)-(t-butoxycarbonylamino-3-methoximinomethyl-8-oxo-1,5-diazabicyclo[3.3.0]octa-2-ene-2-carboxylate A 0.36 g sample of the compound prepared in Part B above was dissolved in 9 ml of $CH_2Cl_2$ and cooled to 0° C under $N_2$. The reaction mixture was then treated with a 0.13 g sample of allyloxallyl chloride followed by 0.28 g of diisopropylethylamine. The mixture was then allowed to warm to room temperature after 45 min.

The reaction mixture was then cooled to 0° C. and treated with 0.2 ml of DBU and stirred at room temperature overnight. Purification by liquid chromatography (95% ethyl acetate/5% $CH_2Cl_2$)) provided 60 mg of the bicyclic pyrazolidinone.

NMR: 300 MHz ($CDCl_3$):δ 1.42 (s, 9H); 2.76 (dd, 1H, J=9, 12 Hz); 3.80 (d, 1H, 15 Hz); 3.91 (s, 3H); 4.10 (t, 1H); 4.38 (d, 1H, J=12 Hz); 4.78 (m, 3H); 5.30 (m, 3H); 5.94 (m, 1H); 8.30 (s, 1H).

MS: M+ =381

UV: 247 (δ=9120); 359 (δ=6670)

D. Deprotection, acylation, and deesterification

The "nucleus" prepared in Part C was treated with trifluoroacetic acid, acylated with the hydroxybenztriazole active ester of 2-(2-aminotriazol-4-yl)-2-(Z)-methoximinoacetic acid in the presence of diisopropylethylamine to provide the allyl ester of the title compound.

A 4.5 mg sample of triphenylphosphine, 1.0 mg of palladium acetate, and 15 mg of sodium-2-ethylhexanoate was dissolved in 0.5 ml of acetone. The reaction mixture was then treated with a 40 mg sample of the allyl ester prepared above, dissolved in 1 ml of acetone and stirred for 1 h at room temperature.

The reaction mixture was then centrifuged and the organics decanted. The solids were washed with acetone, centrifuged and again decanted. The combined acetone portions were concentrated in vacuo to provide 40 mg of the title compound.

NMR: 300 MHz ($D_2O$):δ 3.25 (t, 1H); 3.83-4.12 (m, 2H) with 3.92 (s, 3H) and 3.99 (s, 3H) superimposed; 4.31 (d, 1H); 5.27 (dd, 1H, J=9, 12 Hz); 7.11 (s, 1H); 8.26 (s, 1H).

UV: 234 (ε=18,800); 336 (ε=12,500)

EXAMPLE 186

Sodium 7-(R,S)-[2-(2-aminothiazol-4-yl)-methoximinoacetyl]amino]-8-oxo-3-benzyloximinomethyl-1,5-diazabicyclo[3.3.0]octa-2-ene-2-carboxylate In a manner analogous to Example 185 above, the title compound was prepared.

NMR: 300 MHz ($D_2O$):δ 3.23 (t, 1H); 4.03 (m, 1H) with 3.98 (s, 3H) superimposed; 4.27 (d, 1H); 4.7–4.9 (m, 4); 5.18 (s, 2H); 5.25 (dd, 1H); 7.09 (s, 1H); 7.45 (s, 5H); 8.31 (s, 1H).

IR: 3500 $cm^{-1}$, 1700, 1630, 1535

Mass Spectra (FD): 456, 455, 108, 93 (100)

UV: 234 (ε=19,700); 338 (ε=13,100)

EXAMPLE 187

Sodium 7-(R,S)-[2-(2-aminothiazol-4-yl)-2-(Z)-methoximinoacetyl]amino-3-(2-pyridyl)-8-oxo-1,5-diazabicyclo[3.3.0]octa-2-ene-2-carboxylate The title compound was prepared by the general methodology of Examples 185 and 186 above, while instead utilizing a (2-pyridyl)phosphonate as starting material rather than an oximinophosphonate.

NMR: 300 MHz ($D_2O$):δ 8.60 (d, 1H, J=6 Hz); 8.12 (t, 1H, J=8 Hz); 7.70 (d, 1H, J=8); 7.60 (m, 1H); 5.27 (dd, 1H, J=9 Hz, 12 Hz); 4.60 (d, 1H, J=12 Hz); 4.27 (d, 1H, J=12 Hz); 4.12 (t, 1H, J=9 Hz); 3.98 (s, 3 H); 3.39 (br t, 1H, J=10 Hz).

IR (KBr): 3364, 1699, 1663, 1619 $cm^{-1}$

UV: (Ethanol) 346 (ε=17,300); 232 (ε=18,800)

Mass Spectra (FD): 400 (m+2 less $CO_2$)

Elemental Analysis (hydrate (0.1$H_2O$)) (%) Theory: C, 44.81; H, 3.55; N, 2032 Found : C, 44.27; H, 3.79; N, 19.85

EXAMPLE 188

Allyl-7-(S)-(t-butoxycarbonylamino)-3-(ethyl-oxallyl)-1,5-diazabicyclo[3.3.0]octa-2-ene-2-carboxylate The title compound was synthesized using the general methodology of Example 49, Procedure B, utilizing ethyl (E)-2-oxo-3-phenylsulfonyl-4-carboallyloxybut-3-enoate as the starting material.

NMR:300 MHz ($CDCl_3$):δ 1.34 (t, 3H, J=8); 1.43 (s, 9H); 2.87 (t, 1H, J=9); 4.03 (m, 1H); 4.06 (d, 1H, J=12); 4.31 (m, 2H); 4.47 (d, 1H, J=12); 4.80 (m, 3H); 5.10 (bs, N-H); 5.29 (m, 2H); 5.98 (m, 1H).

Mass Spectra (FD): M+ =423

UV: 392 nm (ε=2521); 216 nm (ε=9880)

We claim:

1. A compound of the formula:

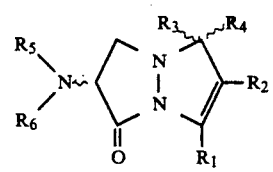

wherein:
either $R_1$ or $R_2$ is hydrogen, halo, $C_1$ to $C_6$ alkyl, $C_1$ to $C_6$ substituted alkyl, perfluoro $C_2$ to $C_4$ alkyl, $C_7$ to $C_{12}$ phenylalkyl, $C_7$ to $C_{12}$ substituted phenylalkyl, phenyl, substituted phenyl, nitro or cyano; a group of the formula

—CX₃ wherein
X is fluoro, chloro, bromo or iodo; a group of the formula

wherein
Z is 0, 1 or 2 and R₇ is C₁ to C₆ alkyl, C₁ to C₆ substituted alkyl, C₂ to C₇ alkenyl, C₂ to C₇ alkynyl, phenyl, substituted phenyl, C₇ to C₁₂ phenylalkyl, C₇ to C₁₂ substituted phenylalkyl, or (disubstituted)amino; a group of the formula

—COR₈ wherein
R₈ is hydrogen, C₁ to C₆ alkyl, C₁ to C₆ substituted alkyl, perfluoro C₂ to C₄ alkyl, trihalomethyl, C₇ to C₁₂ arylalkyl, C₇ to C₁₂ substituted arylalkyl, phenyl, substituted phenyl, amino, (monosubstituted)amino, or (disubstituted)amino; a group of the formula

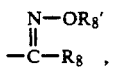

wherein
R₈ is as defined above and R₈' is hydrogen, C₁ to C₆ alkyl, C₂ to C₇ alkenyl, C₂ to C₇ alkynyl, phenyl, substituted phenyl, C₇ to C₁₂ phenylalkyl, C₇ to C₁₂ substituted phenylalkyl; a group of the formula

—COOR₉ wherein
R₉ is hydrogen, an organic or inorganic cation, C₁ to C₆ alkyl, C₁ to C₆ substituted alkyl, C₇ to C₁₂ arylalkyl, C₇ to C₁₂ substituted arylalkyl, phenyl, substituted phenyl, a carboxy-protecting group, or a non-toxic, metabolically-labile, ester-forming group; a group of formula

—PO₃(R₁₀)₂ wherein
R₁₀ is hydrogen, an organic or inorganic cation, C₁ to C₆ alkyl, C₁ to C₆ substituted alkyl, C₇ to C₁₂ arylalkyl, C₇ to C₁₂ substituted arylalkyl, phenyl, or substituted phenyl; a group of the formula

—OR₁₁ wherein
R₁₁ is hydrogen, C₁ to C₆ alkyl, C₁ to C₆ substituted alkyl, C₇ to C₁₂ phenylalkyl, C₇ to C₁₂ substituted phenylalkyl, phenyl, substituted phenyl, or C₁ to C₇ acyl; or a group of the formula

—NR₁₂R₁₃ wherein
R₁₂ and R₁₃ are the same or different and are hydrogen, C₁ to C₆ alkyl, C₁ to C₆ substituted alkyl, C₇ to C₁₂ phenylalkyl, C₇ to C₁₂ substituted phenylalkyl, phenyl, substituted phenyl, C₁ to C₇ acyl, or a group of the formula

wherein
R_q is C₁ to C₆ alkyl, C₇ to C₁₂ phenylalkyl or phenyl; or one of R₁₂ and R₁₃ is hydrogen and the other is a group of the formula

wherein
Nu is (monosubstituted)amino, (disubstituted)amino, C₁ to C₆ alkylthio, C₂ to C₇ alkenylthio, C₁ to C₆ substituted alkylthio, phenylalkylthio, C₇ to C₁ phenylalkylthio, or C₇ to C₁₂ substituted phenylalkylthio, C₁ to C₆ alkyl alcohol, C₁ to C₆ substituted alkyl alcohol, phenyl alcohol, substituted phenyl alcohol, C₇ to C₁₂ phenylalkyl alcohol, or C₇ to C₁₂ substituted phenylalkyl alcohol;
and the other of R₁ or R₂ is a group of the formula

—COOR₁₄ wherein
R₁₄ is hydrogen, an organic or inorganic cation, a carboxy-protecting group or a non-toxic, metabolicallylabile ester-forming group; and
R₃ and R₄ are the same or different and are hydrogen, C₁ to C₆ alkyl, C₁ to C₆ substituted alkyl, C₇ to C₁₂ arylalkyl, C₇ to C₁₂ substituted arylalkyl, phenyl, substituted phenyl or a group of the formula

—COOR₁₅ wherein
R₁₅ has the same definition as R₉;
R₅ and R₆ are:
(1) each hydrogen; or
(2) different and are either hydrogen or an amino-protecting group.

2. A compound of claim 1, wherein the R⁵R⁶N-group is in the S-configuration.

3. A compound of claim 1, wherein: either R₁ or R₂ is a group of the formula

—COOR₁₄;

while the other is:
(A) a group of the formula

(B) a group of the formula

—PO₃(R₁₀)₂;

(C) hydrogen;
(D) a group of the formula

—COR$_8$;

(E) a group of the formula

—CX$_3$;

(F) a group of the formula

—COOR$_9$;

(G) C$_1$ to C$_6$ substituted alkyl;
(H) phenyl or substituted phenyl; or
(I) cyano.

4. A compound of claim 3, wherein R$_3$ and R$_4$ are hydrogen.

5. A compound of claim 4, wherein R$_1$ is a group of the formula

—COOR$_{14}$;

and R$_2$ is:
(A) a group of the formula

(B) a group of the formula

—PO$_3$(R$_{10}$)$_2$;

(C) hydrogen;
(D) a group of the formula

—COR$_8$;

(E) a group of the formula

—CX$_3$;

(F) a group of the formula

—COOR$_9$;

(G) substituted methyl; or
(H) cyano.

6. A compound of claim 5, wherein R$_2$ is cyano or a group of the formula

wherein Z is 0, 1, or 2, and R$_7$ is C$_1$ to C$_6$ alkyl, C$_1$ to C$_6$ substituted alkyl, C$_2$-C$_7$ alkenyl, C$_2$ to C$_7$ alkynyl, phenyl, substituted phenyl, C$_7$ to C$_{12}$ phenylalkyl, C$_7$ to C$_{12}$ substituted phenylalkyl, or (disubstituted)amino.

7. A compound of claim 5, wherein R$_5$ and R$_6$ are hydrogen.

8. A compound of claim 1 wherein R$_3$ and R$_4$ are hydrogen, R$_1$ is —COOH and R$_2$ is cyano.

9. A compound of claim 1 wherein R$_3$ and R$_4$ are hydrogen, R$_1$ is —COOH, and R$_2$ is —SO$_2$—R$_7$ and R7 is C$_1$ to C$_6$ alkyl.

10. A compound of claim 9 wherein R$_7$ is methyl.

* * * * *